(12) United States Patent
Tsukamoto et al.

(10) Patent No.: US 8,288,390 B2
(45) Date of Patent: Oct. 16, 2012

(54) BENZOFURAN DERIVATIVES

(75) Inventors: Tetsuya Tsukamoto, Osaka (JP); Takeshi Wakabayashi, Guilderland, NY (US); Taiichi Ohra, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 386 days.

(21) Appl. No.: 12/659,447

(22) Filed: Mar. 9, 2010

(65) Prior Publication Data

US 2010/0234357 A1 Sep. 16, 2010

(30) Foreign Application Priority Data

Mar. 10, 2009 (JP) .................................. 2009-56719

(51) Int. Cl.
A61K 31/496 (2006.01)
C07D 405/02 (2006.01)
(52) U.S. Cl. .................................. 514/254.11; 544/376
(58) Field of Classification Search ............. 514/254.11; 544/376
See application file for complete search history.

(56) References Cited

U.S. PATENT DOCUMENTS

| | | | |
|---|---|---|---|
| 4,558,043 | A | 12/1985 | Wenk et al. |
| 5,532,241 | A | 7/1996 | Böttcher et al. |
| 5,681,954 | A | 10/1997 | Yamamoto et al. |
| 2004/0034049 | A1 | 2/2004 | Okawa et al. |
| 2004/0167171 | A1 | 8/2004 | Ohkawa et al. |
| 2007/0099933 | A1 | 5/2007 | Heinrich et al. |
| 2008/0194539 | A1 | 8/2008 | Gmeiner et al. |
| 2009/0286766 | A1 | 11/2009 | Sugasawa et al. |

FOREIGN PATENT DOCUMENTS

| | | |
|---|---|---|
| EP | 0 648 767 | 4/1995 |
| EP | 1 136 477 | 9/2001 |
| EP | 1 411 052 | 4/2004 |
| EP | 1 481 679 | 12/2004 |
| EP | 1 637 527 | 2/2006 |
| JP | 4-149546 | 5/1992 |
| JP | 7-149762 | 6/1995 |
| WO | 98/55454 | 12/1998 |
| WO | 99/05140 | 2/1999 |
| WO | 00/34262 | 6/2000 |
| WO | 01/09111 | 2/2001 |
| WO | 02/28850 | 4/2002 |
| WO | 03/004485 | 1/2003 |
| WO | 03/074046 | 9/2003 |
| WO | 03/082878 | 10/2003 |
| WO | 2004/094431 | 11/2004 |
| WO | 2004/113316 | 12/2004 |
| WO | 2005/000829 | 1/2005 |
| WO | 2005/095401 | 10/2005 |
| WO | 2005/103055 | 11/2005 |
| WO | 2006/072430 | 7/2006 |
| WO | 2007/123269 | 11/2007 |
| WO | 2008/125874 | 10/2008 |
| WO | 2008/146064 | 12/2008 |
| WO | 2009/110520 | 9/2009 |

OTHER PUBLICATIONS

Association of the National Pharmaceutical Industry, Costa Rican Opposition to Letters Patent (with English translation), published Dec. 5, 2011, for 2011-0474 which is International Publication No. WO 2010/104194, filed by Takeda Pharmaceutical Co. Ltd. as JP 2009/056719.
B. A. Yankner et al., "Neurotoxicity of a Fragment of the Amyloid Precursor Associated with Alzheimer's Disease", Science, vol. 245, pp. 417-420, Jul. 28, 1989.
C. W. Cotman et al., "β-Amyloid Neurotoxicity: A Discussion of In Vitro Findings", Neurobiology of Aging, vol. 13, pp. 587-590, 1992.
C. Hilbich et al., "Aggregation and Secondary Structure of Synthetic Amyloid βA4 Peptides of Alzheimer's Disease", Journal of Molecular Biology, vol. 218, pp. 149-163, 1991.
S. R. Datta et al., "Akt Phosphorylation of BAD Couples Survival Signals to the Cell-Intrinsic Death Machinery", Cell, vol. 91, pp. 231-241, Oct. 17, 1997.
A. Rukenstein et al., "Multiple Agents Rescue PC12 Cells from Serum-Free Cell Death by Translation- and Transcription-Independent Mechanisms", The Journal of Neuroscience, vol. 11, No. 8, pp. 2552-2563, Aug. 1991.
R. Yao et al., "Requirement for Phosphatidylinositol-3 Kinase in the Prevention of Apoptosis by Nerve Growth Factor", Science, vol. 267, pp. 2003-2006, Mar. 31, 1995.

(Continued)

*Primary Examiner* — Kristin Bianchi
(74) *Attorney, Agent, or Firm* — Wenderoth, Lind & Ponack, L.L.P.

(57) ABSTRACT

The present invention provides a compound represented by the following formula (I):

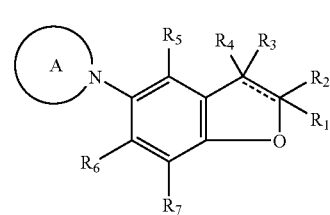

wherein:
Ring A represents an optionally substituted piperazine ring, an optionally substituted morpholine ring, or an optionally substituted homopiperazine ring;
$R_1$ and $R_2$ are the same or different from each other, and represent a hydrogen atom or optionally substituted lower alkyl;
$R_3$ and $R_4$ are the same or different from each other, and represent a hydrogen atom or halogenated or non-halogenated lower alkyl;
$R_5$ to $R_7$ are the same or different from each other, and represent a hydrogen atom, hydroxy, optionally substituted lower alkyl, optionally substituted lower alkenyl, optionally substituted lower alkoxy, optionally substituted cycloalkyl, optionally substituted aryl, an optionally substituted aromatic heterocyclic ring, optionally substituted amino, or acyl; and ===== represents a single bond or double bond, or a salt thereof.

2 Claims, No Drawings

OTHER PUBLICATIONS

M. Parrizas et al., "Insulin-Like Growth Factor 1 Inhibits Apoptosis Using the Phosphatidylinositol 3'-Kinase and Mitogen-Activated Protein Kinase Pathways", The Journal of Biological Chemistry, vol. 272, No. 1, pp. 154-161, Jan. 3, 1997.

T. Okada et al., "Essential Role of Phosphatidylinositol 3-Kinase in Insulin-Induced Glucose Transport and Antilipolysis in Rat Adipocytes", The Journal of Biological Chemistry, vol. 269, No. 5, pp. 3568-3573, Feb. 4, 1994.

H. Werner et al., "Regulation of Rat Brain/HepG2 Glucose Transporter Gene Expression by Insulin and Insulin-Like Growth Factor-I in Primary Cultures of Neuronal and Glial Cells", Endocrinology, vol. 125, No. 1, pp. 314-320, 1989.

G. Stennis et al., "Modulation of Memory by Insulin and Glucose: Neuropsychological Observations in Alzheimer's Disease", European Journal of Pharmacology, vol. 490, pp. 97-113, 2004.

M. Kawada et al., "Spirocyclopropane Compounds. III. Synthesis of Spiro[Benzofuran-2($3H$),1'-Cyclopropan]-3-Ones for Evaluation as Gastric Antisecretory and Antiulcer Agents", Chemical & Pharmaceutical Bulletin, vol. 32, No. 9, pp. 3532-3550, 1984.

STN Search Results for 792177-20-9; 754967-60-7; 324749-97-5 and 324749-61-3, 2001 and 2004.

International Search Report dated Jun. 18, 2010.

BENZOFURAN DERIVATIVES

TECHNICAL FIELD

The present invention relates to the benzofuran derivatives and a pharmaceutical agent containing the same. More specifically, the present invention relates to the compound having excellent pharmacological activities such as a neurotrophic factor activity-enhancing activity, a glucose metabolism improving activity, a neuronal cell death inhibiting activity, a neurogenesis stimulating activity, a neuronal regeneration stimulating activity, a glucose metabolism improving activity, beta (β)-amyloid inhibiting activity, tau and phosphorylated tau inhibiting activity, a cognitive function improving activity and the like, which is effective as prophylactic and therapeutic agents for central nervous system disorders and the like.

BACKGROUND ART

Neurodegenerative disorders are progressive disorders to cause destructive damages such as the nerve cell death. As principal neurodegenerative disorders, there have been known central nervous system disorders such as Alzheimer's disease, Parkinson's disease, amyotrophic lateral sclerosis (ALS), Huntington's disease and the like, and peripheral neuropathies represented by diabetic neuropathy. Many of them relate to aging and, in fact, the onset increases with aging, whereas there are also some cases in which the onset begins even at a middle age and further at a younger age.

As a result of studies on the structure and function of brains, the roles of neurotransmitters and neurotrophic factors and so on have been gradually elucidated, but many parts of the causes of neurodegenerative disease are still unknown. For Parkinson's disease, its relationship with a specific neurotransmitter, namely dopamine, has been clarified, whereby L-DOPA that is the precursor of dopamine has been used as a drug for reducing the nerve symptoms and for recovering the function. However, L-DOPA does not suppress the progress of neurodegeneration, and the effect of L-DOPA is gradually lost with a progress of the disease condition, namely the degeneration and loss of dopaminergic neurons. Also, Alzheimer's disease is a disorder that is caused by the degeneration and loss of a variety of nerve cells such as acetylcholinergic neuronal cells, monoamine type neuronal cells, and the like, and causes deposit of senile plaque or change in neurofibrils. As for the drugs therefor, cholinesterase inhibitors or memantine, which is an antagonist for NMDA, have been marketed. Nevertheless, like L-DOPA for Parkinson's disease, they are still symptomatic therapy to improve the nerve symptoms temporarily. In this regard, drugs that can protect neuronal cells from the toxicity of the factors causing cell death including Alzheimer's disease or Parkinson's disease and can inhibit progress of neurodegenerative disorders have not been reported.

Furthermore, it is considered that the cell death in neurodegenerative disorders is caused by the toxicity of the factors that are intrinsic to the respective diseases and, for example, in Alzheimer's disease, the endogenous β-amyloid is considered to be a factor to cause the cell death. β-Amyloid is a protein constituting the senile plaque, which is a neuropathological characteristic to be seen in brain of a patient suffering from Alzheimer's disease, and is composed of 40 to 43 amino acids. It has been found that the addition of this β-amyloid to a primary culture system of hippocampus nerve cell causes nerve cell death [see, Non-Patent Document No. 1] and, also, it has been shown that the coagulation of β-amyloid is indispensable for the expression of its toxicity and the like [see, Non-Patent Document Nos. 2 and 3]. For toxicity expression mechanism of β-amyloid, it has been believed that 1) β-amyloid forms an ion channel to allow an influx of calcium ions, 2) β-amyloid accelerates generation of free radicals, 3) β-amyloid activates tau protein kinase I (TPK-I)/glycogen synthase kinase 3 beta (GSK-3β) and promotes the phosphorylation of tau, 4) β-amyloid activates the microglia, from which the neurotoxin is secreted, and the like. Recently, it has been elucidated that neurotrophic factors such as IGF-1 (insulin-like growth factor), NGF (nerve growth factor), BDNF (brain derived neurotrophic factor), GDNF (glial cell line derived neurotrophic factor) and the like inhibit the apoptosis of nerve cells caused by β-amyloid and cell death (apoptosis) is caused by dysfunction of nutritional factor signal cascade [see, Non-Patent Document No. 4]. With respect to them, it has been reported that IGF-1 (insulin-like growth factor 1) signal phosphorylates Akt, also referred to as protein kinase B (PKB), via phosphatidylinositol-3'-kinase (PI-3 kinase: PI-3K), and the activated Akt phosphorylates a substrate like Bad or glycogen synthase kinase 3b (GSK-3β) and the like to inhibit neuronal cell death. As a mechanism therefor, it becomes evident that inhibition of GSK-3β based on activation of PI-3 kinase is involved [see, Non-Patent Document Nos. 5 to 7]. When PI-3 kinase is inhibited by β-amyloid and TPK-I/GSK-3β is activated, pyruvate dehydrogenase (PDH) is inhibited, thereby affecting the synthetic reaction system of acetylcholine to lower the content of acetylcholine. This is in agreement with an observation that the content of acetylcholine is lowered in the brain of a patient suffering from Alzheimer's disease. On the contrary, it is expected that the activation of PI-3 kinase can accomplish not only the prevention of nerve cell death but also an increase in the content of acetylcholine in brain, thereby improving the nerve symptoms. In addition, it is expected that inhibition of TPK-I/GSK-3β can increase the intracerebral glucose utilization, which is lowered in Alzheimer's disease [see, Non-Patent Document Nos. 7 and 8]. Further, correlation between glucose metabolism in brain and cognitive function in brain was also reported [see, Non-Patent Document No. 9] and it is expected that improving the glucose metabolism in brain may also improve the cognitive function of the brain.

As a compound useful for the prophylaxis or treatment of central nervous system disorders or brain disorders, benzofuran compounds are publicly known (for example, see Patent Document Nos. 1 to 7). Further, it is also publicly known that some kinds of benzofuran compounds have an activity of promoting growth and differentiation of neuronal progenitor cells (for example, see Patent Document Nos. 2 and 4).

Still further, it is also publicly known that the benzofuran compounds have medical use other than the use for central nervous system disorders (for example, see Patent Document Nos. 8 and 9 and Non-Patent Document No. 10).

Non-Patent Document No. 10 discloses the following compound:

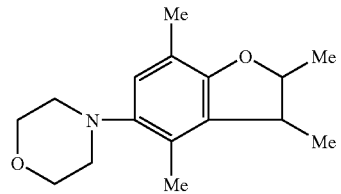

Specifications of respective Patent Documents should be referred for the definitions of the following compounds disclosed in Patent Document Nos. 10-16. Patent Document No. 10 discloses the following compound:

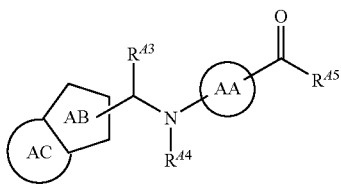

Patent Document No. 11 discloses the following compound:

(I)

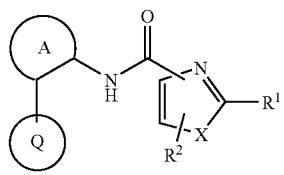

Patent Document No. 12 discloses the following compound:

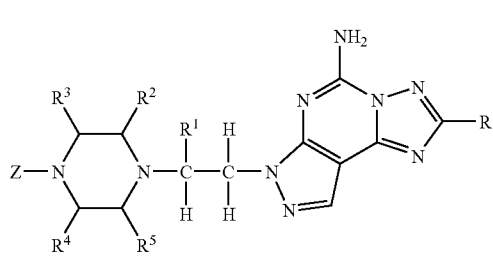

Patent Document No. 13 discloses the following compound:

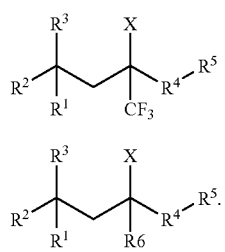

(IA)

(IB)

Patent Document No. 14 discloses the following compound:

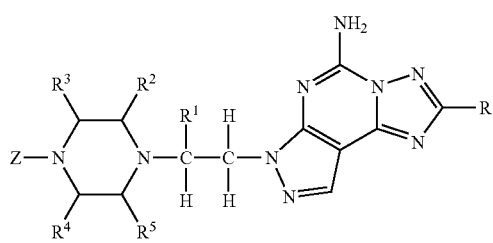

Patent Document No. 15 discloses the following compound:

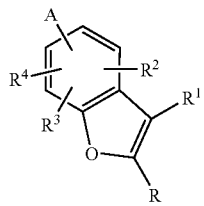

Patent Document No. 16 discloses the following compound:

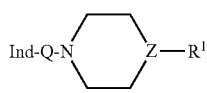

Patent Document No. 17 discloses the following compound:

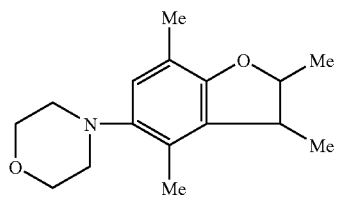

LIST OF DOCUMENTS

Patent Document

[Patent Document 1] WO2000-34262
[Patent Document 2] WO2002-28850
[Patent Document 3] WO03-074046
[Patent Document 4] WO2003-004485
[Patent Document 5] WO2005-000829
[Patent Document 6] WO99-05140
[Patent Document 7] WO2003-082878
[Patent Document 8] U.S. Pat. No. 5,681,954
[Patent Document 9] U.S. Pat. No. 4,558,043 A
[Patent Document 10] WO2009110520
[Patent Document 11] WO2007123269
[Patent Document 12] WO 2005103055
[Patent Document 13] WO 2005095401
[Patent Document 14] WO 2004094431
[Patent Document 15] WO 2001009111
[Patent Document 16] EP 648767A
[Patent Document 17] Japanese Patent Laid-open Publication No. 04-149546

Non-Patent Document

[Non-Patent Document 1] Science, Vol. 245, 417-420 pages, 1989
[Non-Patent Document 2] Neurobiology of Aging, Vol. 13, 587-590 pages, 1992
[Non-Patent Document 3] Journal of Molecular Biology, Vol. 218, 149-163 pages, 1991
[Non-Patent Document 4] Cell, Vol. 91, 231-241 pages, 1997

[Non-Patent Document 5] J. Neurosci., Vol. 11, 2552-2563 pages, 1991

[Non-Patent Document 6] Science, Vol. 267, 2003-2006 pages, 1995

[Non-Patent Document 7] J. Biol. Chem., Vol. 272, 154-161 pages, 1997

[Non-Patent Document 7] J. Biol. Chem., Vol. 269, 3568-3573 pages, 1994

[Non-Patent Document 8] Endocrinology, Vol. 125, 314-320 pages, 1989

[Non-Patent Document 9] European Journal of Pharmacology, Vol. 490, 97-113 pages, 2004

[Non-Patent Document 10] Chemical & Pharmaceutical Bulletin (1984), 32(9), 3532-50

SUMMARY OF THE INVENTION

Problems to be Solved by the Invention

Object of the present invention is to provide the novel benzofuran derivatives having excellent pharmacological activities such as neuron protecting activity, neurogenesis stimulating activity, nerve regeneration stimulating activity, cognitive function improving activity and the like, and also low toxicity and high transition to central nervous system.

Means for Solving the Problems

The present inventors diligently made researches to solve the above-described problems, and found that a benzofuran derivative represented by formula (I) has excellent neuroprotective activity, neurogenesis (nerve regeneration) stimulating activity and cognitive function improving activity and further has low phototoxicity and high transition to the central nervous system. Thus, the present invention was achieved.

That is, the present invention relates to:

[1] A compound represented by the following Formula (I):

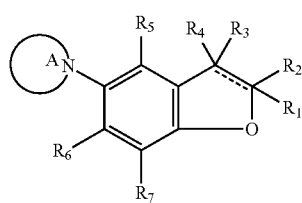

(I)

wherein:

Ring A represents an optionally substituted piperazine ring, an optionally substituted morpholine ring, or an optionally substituted homopiperazine ring;

$R_1$ and $R_2$ are the same or different from each other, and represent a hydrogen atom or optionally substituted lower alkyl;

$R_3$ and $R_4$ are the same or different from each other, and represent a hydrogen atom or halogenated or non-halogenated lower alkyl;

$R_5$ to $R_7$ are the same or different from each other, and represent a hydrogen atom, a halogen atom, hydroxy, optionally substituted lower alkyl, optionally substituted lower alkenyl, optionally substituted lower alkoxy, optionally substituted aliphatic cyclic hydrocarbon group, optionally substituted aryl, an optionally substituted heterocyclic ring, optionally substituted amino, or acyl; and ----- represents a single bond or double bond, wherein:

$R_2$ and $R_3$ do not exist when carbon atoms respectively adjacent to $R_2$ and $R_3$ form a double bond, and there is no case where all of $R_1$ to $R_7$ are hydrogen atoms; and $R_1$ and $R_2$ may form a ring together with an adjacent carbon atom; or a salt thereof, with the proviso that:

(a) the compound where at least one of $R_1$ to $R_7$ is a substituent represented by the formula:

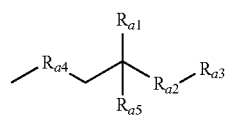

wherein:

$R_{a1}$ represents a hydroxy, or an amino which may be substituted with $C_{1-6}$ alkyl;

$R_{a2}$ represents carbonyl or an optionally substituted methylene, $R_{a3}$ represents an optionally substituted heterocyclic ring;

$R_{a4}$ represents a bond, or a methylene which may be substituted with a substituent selected from $C_{1-5}$ alkyl, $C_{5-15}$ arylalkyl, and $C_{3-5}$ spirocycloalkyl; and $R_{a5}$ represents a hydrogen atom or a substituent;

(b) the compound where at least one of $R_5$ and $R_6$ is a substituent represented by the formula:

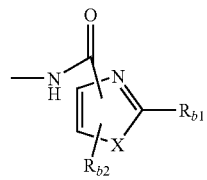

wherein:

X represents a sulfur atom or an oxygen atom;

$R_{b1}$ represents a substituent; and $R_{b2}$ represents a hydrogen atom, a halogen atom, or a nitrogen-containing saturated heterocyclic ring;

(c) the compound where the partial structural formula:

of Formula (I) is the formula:

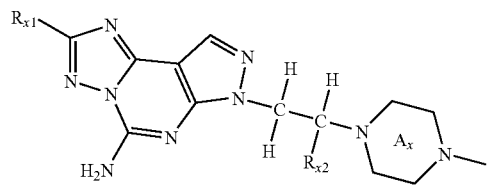

wherein:

$R_{x1}$ and $R_{x2}$ are the same or different from each other, and represent a substituent;

Ring $A_x$ represents a piperazine ring which may be substituted with a substituent selected from alkyl and alkoxyalkyl;

(d) the compound where the ring A represents homopiperazine ring, and

----- represents a double bond;

(e) the compound where the partial structural formula:

of Formula (I) is the formula:

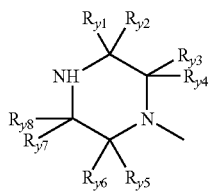

wherein:

$R_{y1}$ to $R_{y8}$ are the same or different from each other, and represent a hydrogen atom or a substituent, and ----- represents a double bond;

(f) the compound where the partial structural formula:

of the Formula (I) is the formula:

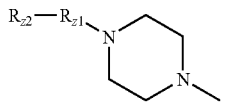

wherein:

$R_{z1}$ represents $C_{2-4}$ alkylene;

$R_{z2}$ represents an optionally substituted indole-3-yl;

(g) the following compounds:

N-{[4-({Cyclohexyl[3-methyl-5-morpholino-1-benzofuran-2-yl]methyl}amino)phenyl]carbonyl}-N-methyl-β-alanine,

[3-Methyl-5-morpholino-1-benzofuran-2-yl]methanol,

Cyclohexyl[3-methyl-5-morpholino-1-benzofuran-2-yl]methanol,

N-{[4-({Cyclohexyl[3-methyl-5-morpholino-1-benzofuran-2-yl]methyl}amino)phenyl]carbonyl}-N-methyl-β-alanine ethyl ester, 2-[4-(6-Amino-2,3-dihydro-1-benzofuran-5-yl)piperazin-1-yl]acetamide, 1-[2-(Methoxymethyl)-2,3-dihydro-1-benzofuran-5-yl]piperazine, 1-[6-Fluoro-2-(methoxymethyl)-2,3-dihydro-1-benzofuran-5-yl]piperazine,

[6-Fluoro-5-(piperazin-1-yl)-2,3-dihydro-1-benzofuran-2-yl]methanol,

[5-(piperazin-1-yl)-2,3-dihydro-1-benzofuran-2-yl]methanol, and (h) 4-(2,3-dihydro-2,3,4,7-tetramethyl-5-benzofuranyl)morpholine are excluded [hereinbelow, sometimes abbreviated as Compound (I)];

[2] The compound according to item [1], wherein:

$R_5$ to $R_7$ are the same or different from each other, and represent a hydrogen atom, a hydroxy, optionally substituted lower alkyl, optionally substituted lower alkenyl, optionally substituted lower alkoxy, optionally substituted cycloalkyl, optionally substituted aryl, an optionally substituted aromatic heterocyclic ring, optionally substituted amino, or acyl;

[3] The compound according to item [1] or [2], wherein the partial structural formula:

of Formula (I) is any one of the following formulae:

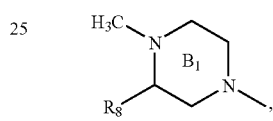 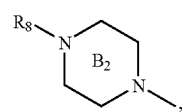

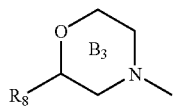 or 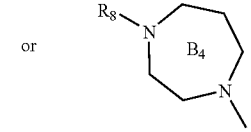

wherein:

$R_8$ is optionally substituted aryl or an optionally substituted aromatic heterocyclic ring;

Ring $B_1$ is a further optionally substituted piperazine ring;

Ring $B_2$ is a further optionally substituted piperazine ring;

Ring $B_3$ is a further optionally substituted morpholine ring; and

Ring $B_4$ is a further optionally substituted homopiperazine ring;

[4] The compound according to item [3], wherein the partial structural formula:

of Formula (I) is any one of the following formulae:

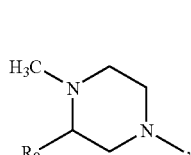 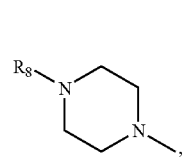

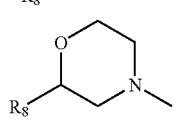 or 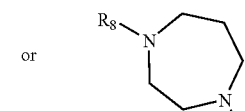

wherein:

$R_8$ is:

(1) $C_{6-14}$ aryl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $C_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) a 5- to 10-membered aromatic heterocyclic ring containing 1 to 4 heteroatoms selected from a nitrogen atom, a sulfur atom, and an oxygen atom, other than a carbon atom, and which may be substituted with 1 to 3 substituents selected from a halogen atom, $C_{1-6}$ alkyl, $C_{1-6}$ alkoxy, and phenyl which may be substituted with $C_{1-6}$ alkoxy;

[4a] The compound according to item [4], wherein $R_8$ is:

(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) pyridyl, pyrimidinyl, thiadiazolyl, thiazolyl, pyrazolyl, isoxazolyl, imidazolyl, or pyrazolopyrimidinyl which may be substituted with 1 to 3 substituents selected from a halogen atom, $C_{1-6}$ alkyl, $C_{1-6}$ alkoxy, and phenyl which may be substituted with $C_{1-6}$ alkoxy;

[4b] The compound according to item [4], wherein the partial structural formula:

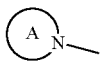

of Formula (I) is the following formula:

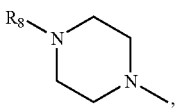

wherein:

$R_8$ is:

(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl;

(2) pyridyl which may be substituted with 1 to 3 $C_{1-6}$ alkoxy groups;

(3) pyrimidinyl which may be substituted with 1 to 3 substituents selected from phenyl which may be substituted with $C_{1-6}$ alkoxy, and a halogen atom;

(4) thiadiazolyl which may be substituted with a phenyl;

(5) thiazolyl;

(6) pyrazolyl which may be substituted with 1 to 2 $C_{1-6}$ alkyl groups;

(7) isoxazolyl;

(8) imidazolyl which may be substituted with 1 to 2 $C_{1-6}$ alkyl groups; or (9) pyrazolopyrimidinyl which may be substituted with 1 to 2 $C_{1-6}$ alkyl groups;

[5] The compound according to item [3], wherein the partial structural formula:

of Formula (I) is the following formula:

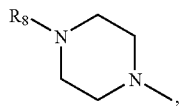

wherein:

$R_8$ is a phenyl which may be substituted with 1 to 3 substituents selected from:

(1) a halogen atom;

(2) $C_{1-6}$ alkoxy which may be substituted with a halogen atom;

(3) $C_{1-6}$ alkyl which may be substituted with a substituent selected from a halogen atom, a hydroxy, amino, and $diC_{1-6}$ alkylamino;

(4) $C_{1-6}$ alkylthio;

(5) $C_{1-6}$ alkylsulfonyl;

(6) cyano;

(7) carbamoyl;

(8) $C_{1-6}$ alkylsulfinyl; and (9) $C_{1-6}$ alkylcarbonyl;

[6] The compound according to item [3], wherein the partial structural formula:

of Formula (I) is the following formula:

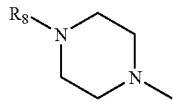

wherein:

$R_8$ is a phenyl which is substituted with 1 to 3 $C_{1-6}$ alkoxy;

[7] The compound according to any one of items [1] to [6], wherein:

$-----$ represents a single bond;

[7a] The compound according to any one of items [1] to [7], wherein $R_1$ represents an optionally substituted $C_{1-6}$ alkyl;

[8] The compound according to any one of items [1] to [7], wherein:

$R_1$ is a hydrogen atom or $C_{1-6}$ alkyl which may be substituted with a hydroxy;

$R_2$ is:

(1) a hydrogen atom, or (2) $C_{1-6}$ alkyl which may be substituted with a substituent selected from a hydroxy, amino, di-$C_{1-6}$ alkylamino, ($C_{1-6}$ alkyl)(benzyl)amino, mono-$C_{1-6}$ alkylamino, di-benzylamino, $C_{1-6}$alkyl-carbonylamino, formyloxy, $C_{1-6}$ alkylsulfonyloxy, cyano, carboxy, mono-$C_{1-6}$ alkyl-carbamoyl, $C_{1-6}$ alkoxy which may be substituted with a substituent selected from $C_{1-6}$ alkoxy and phenyl, $C_{1-6}$ alkylthio, $C_{1-6}$ alkylsulfonyl, morpholino, thiomorpholine 1,1-dioxidothiomorpholine, pyrazolyl, imidazolyl substituted with $C_{1-6}$ alkyl, pyrrolidinyl, piperidyl substituted with oxo or hydroxy, and 1,4-dioxa-8-azaspiro[4,5]deca-8-yl; or $R_1$ and $R_2$ form a cyclopentane ring or a tetrahydropyran ring together with an adjacent carbon atom;

[9] The compound according to any one of items [1] to [8], wherein:
$R_1$ is $C_{1-6}$ alkyl; and
$R_2$ is a hydrogen atom, or $C_{1-6}$ alkyl which may be substituted with a hydroxy;

[10] The compound according to any one of items [1] to [9], wherein:
$R_3$ is a hydrogen atom or $C_{1-6}$ alkyl; and
$R_4$ is a hydrogen atom;

[11] The compound according to any one of items [1] to [10], wherein:
$R_3$ and $R_4$ are a hydrogen atom;

[12] The compound according to any one of items [1] to [11], wherein:
$R_5$ is a hydrogen atom, optionally substituted $C_{1-6}$ alkyl, optionally substituted $C_{2-6}$ alkenyl, optionally substituted $C_{3-6}$ cycloalkyl, optionally substituted $C_{6-14}$ aryl, or a 5- to 6-membered aromatic heterocyclic ring which may be substituted, and contains 1 to 4 heteroatoms selected from a nitrogen atom and an oxygen atom other than a carbon atom;
$R_6$ is a hydrogen atom, optionally substituted $C_{1-6}$ alkyl, optionally substituted $C_{6-14}$ aryl, a 5- to 6-membered aromatic heterocyclic ring which may be substituted, and contains 1 to 4 heteroatoms selected from a nitrogen atom and an oxygen atom other than a carbon atom, or a halogen atom, and
$R_7$ is a hydrogen atom, hydroxy, optionally substituted $C_{1-6}$ alkyl, optionally substituted $C_{1-6}$ alkoxy, or $C_{1-6}$ alkylcarbonyl;

[13] The compound according to any one of items [1] to [12], wherein:
$R_5$ is a hydrogen atom, $C_{1-6}$ alkyl, $C_{2-6}$ alkenyl, $C_{3-6}$ cycloalkyl, phenyl substituted with $diC_{1-6}$ alkylamino, or furyl;
$R_6$ is a hydrogen atom, $C_{1-6}$ alkyl, phenyl substituted with $C_{1-6}$ alkyl, pyridyl, or a halogen atom; and
$R_7$ is a hydrogen atom, hydroxy, $C_{1-6}$ alkyl which may be substituted with a hydroxy, $C_{1-6}$ alkoxy which may be substituted with $C_{1-6}$ alkoxy, or $C_{1-6}$ alkylcarbonyl;

[14] The compound according to any one of items [1] to [13], wherein:
$R_5$ is $C_{1-6}$ alkyl;
$R_6$ is $C_{1-6}$ alkyl; and
$R_7$ is $C_{1-6}$ alkyl or $C_{1-6}$ alkoxy;

[15] The compound according to item [3], wherein the partial structural formula:

of Formula (I) is any one of the following formulae:

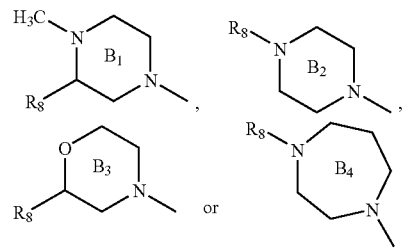

wherein:
$R_8$ is optionally substituted aryl or an optionally substituted aromatic heterocyclic ring;
Ring $B_1$ is a further optionally substituted piperazine ring;
Ring $B_2$ is a further optionally substituted piperazine ring;
Ring $B_3$ is a further optionally substituted morpholine ring;
Ring $B_4$ is a further optionally substituted homopiperazine ring;

===== is a single bond;
$R_5$ is a hydrogen atom, optionally substituted $C_{1-6}$ alkyl, optionally substituted $C_{2-6}$ alkenyl, optionally substituted $C_{3-6}$ cycloalkyl, optionally substituted $C_{6-14}$ aryl, optionally substituted 5- to 6-membered aromatic heterocyclic ring containing 1 to 4 heteroatoms selected from a nitrogen atom and an oxygen atom other than a carbon atom;
$R_6$ is a hydrogen atom, optionally substituted $C_{1-6}$ alkyl, optionally substituted $C_{6-14}$ aryl, optionally substituted aromatic heterocyclic ring, or a halogen atom; and
$R_7$ is a hydrogen atom, hydroxy, optionally substituted $C_{1-6}$ alkyl, optionally substituted $C_{1-6}$ alkoxy, or $C_{1-6}$ alkylcarbonyl;

[16] The compound according to item [3], wherein the partial structural formula:

of Formula (I) is any one of the following formulae:

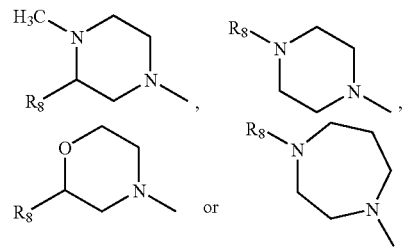

wherein:
$R_8$ is:
(1) $C_{6-14}$ aryl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) a 5- to 10-membered aromatic heterocyclic ring containing 1 to 4 hetero atoms selected from a nitrogen atom, a sulfur atom, and an oxygen atom, other than a carbon atom, and which may be substituted with 1 to 3 substituents selected from a halogen atom, $C_{1-6}$ alkyl, $C_{1-6}$ alkoxy, and phenyl which may be substituted with $C_{1-6}$ alkoxy;

----- is a single bond;

$R_1$ is a hydrogen atom or $C_{1-6}$ alkyl which may be substituted with a hydroxy;

$R_2$ is:
(1) a hydrogen atom; or
(2) $C_{1-6}$ alkyl which may be substituted with a substituent selected from a hydroxy, amino, di-$C_{1-6}$ alkylamino, ($C_{1-6}$ alkyl)(benzyl)amino, mono-$C_{1-6}$ alkylamino, di-benzylamino, $C_{1-6}$ alkyl-carbonylamino, formyloxy, $C_{1-6}$ alkylsulfonyloxy, cyano, carboxy, mono-$C_{1-6}$ alkyl-carbamoyl, $C_{1-6}$ alkoxy which may be substituted with a substituent selected from $C_{1-6}$ alkoxy and phenyl, $C_{1-6}$ alkylthio, $C_{1-6}$ alkylsulfonyl, morpholino, 1,1-dioxidothiomorpholine, pyrazolyl, imidazolyl substituted with $C_{1-6}$ alkyl, pyrrolidinyl, piperidinyl substituted with oxo or hydroxy, and 1,4-dioxa-8-azaspiro[4,5]deca-8-yl; or $R_1$ and $R_2$ form a cyclopentane ring or a tetrahydropyran ring together with an adjacent carbon atom;

$R_3$ is a hydrogen atom or $C_{1-6}$ alkyl; and
$R_4$ is a hydrogen atom;
$R_5$ is a hydrogen atom, $C_{1-6}$ alkyl, $C_{2-6}$ alkenyl, $C_{3-6}$ cycloalkyl, phenyl substituted with di$C_{1-6}$ alkylamino, or furyl;
$R_6$ is a hydrogen atom, $C_{1-6}$ alkyl, phenyl substituted with $C_{1-6}$ alkyl, pyridyl, or a halogen atom, and
$R_7$ is a hydrogen atom, hydroxy, $C_{1-6}$ alkyl which may be substituted with a hydroxy, $C_{1-6}$ alkoxy which may be substituted with $C_{1-6}$ alkoxy, or $C_{1-6}$ alkylcarbonyl;

[16a] The compound according to item [16], wherein $R_8$ is:
(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and di$C_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or
(2) pyrimidinyl, thiadiazolyl, thiazolyl, pyrazolyl, isoxazolyl or imidazolyl which may be substituted with 1 to 3 substituents selected from a halogen atom, $C_{1-6}$ alkyl, $C_{1-6}$ alkoxy, and phenyl which may be substituted with $C_{1-6}$ alkoxy;

[16b] The compound according to item [16], wherein the partial structural formula:

of Formula (I) is the following formula:

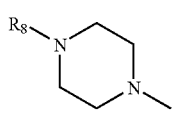

wherein:

$R_8$ is:
(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and di$C_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl;
(2) pyridyl which may be substituted with 1 to 3 $C_{1-6}$ alkoxy groups;
(3) pyrimidinyl which may be substituted with 1 to 3 substituents selected from phenyl which may be substituted with $C_{1-6}$ alkoxy, and a halogen atom;
(4) thiadiazolyl which may be substituted with a phenyl;
(5) thiazolyl;
(6) pyrazolyl which may be substituted with 1 to 2 $C_{1-6}$ alkyl groups;
(7) isoxazolyl; or
(8) imidazolyl which may be substituted with 1 to 2 $C_{1-6}$ alkyl groups;

[17] The compound according to item [16], wherein the partial structural formula:

of Formula (I) is the following formula:

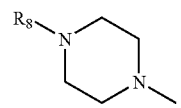

wherein:

$R_8$ is a phenyl which may be substituted with 1 to 3 substituents selected from:
(1) a halogen atom;
(2) $C_{1-6}$ alkoxy which may be substituted with a halogen atom;
(3) $C_{1-6}$ alkyl which may be substituted with a substituent selected from a halogen atom, a hydroxy, amino, and di$C_{1-6}$ alkylamino;
(4) $C_{1-6}$ alkylthio;
(5) $C_{1-6}$ alkylsulfonyl;
(6) cyano;
(7) carbamoyl;
(8) $C_{1-6}$ alkylsulfinyl; and
(9) $C_{1-6}$ alkylcarbonyl;

[18] The compound according to item [3], wherein the partial structural formula:

of Formula (I) is the following formula:

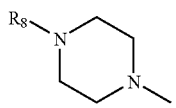

wherein:
R8 is a phenyl which is substituted with 1 to 3 $C_{1-6}$ alkoxy;
----- is a single bond;
R1 is $C_{1-6}$ alkyl;
R2 is a hydrogen atom, or $C_{1-6}$ alkyl which may be substituted with a hydroxy;
R3 and R4 are a hydrogen atom;
R5 is $C_{1-6}$ alkyl;
R6 is $C_{1-6}$ alkyl; and
R7 is $C_{1-6}$ alkyl or $C_{1-6}$ alkoxy;

[19]
1-(4-Methoxyphenyl)-4-(2,2,4,6,7-pentamethyl-2,3-dihydro-1-benzofuran-5-yl)piperazine or a salt thereof;

[20]
1-(4-Methoxyphenyl)-4-[(2R)-2,4,6,7-tetramethyl-2,3-dihydro-1-benzofuran-5-yl]piperazine or a salt thereof;

[21]
1-(4-Methoxyphenyl)-4-[(2S)-2,4,6,7-tetramethyl-2,3-dihydro-1-benzofuran-5-yl]piperazine or a salt thereof;

[22]
1-(4-Methoxyphenyl)-4-(7-methoxy-2,2,4,6-tetramethyl-2,3-dihydro-1-benzofuran-5-yl)piperazine or a salt thereof;

[23]
1-(4-Ethoxyphenyl)-4-(7-methoxy-2,2,4,6-tetramethyl-2,3-dihydro-1-benzofuran-5-yl)piperazine or a salt thereof;

[24] (−)-{5-[4-(4-methoxyphenyl)piperazin-1-yl]-2,4,6,7-tetramethyl-2,3-dihydro-1-benzofuran-2-yl}methanol or a salt thereof;

[25] (+)-{5-[4-(4-methoxyphenyl)piperazin-1-yl]-2,4,6,7-tetramethyl-2,3-dihydro-1-benzofuran-2-yl}methanol or a salt thereof;

[26] A prodrug of the compound according to any one of items [1] to [25]

[27] A pharmaceutical composition comprising the compound according to any one of items [1] to [25] or a prodrug thereof;

[28] The pharmaceutical composition according to item [27], which is an IGF-1 signal modulator or protein kinase B activator;

[29] The pharmaceutical composition according to item [27], which is a prophylactic or therapeutic agent for central nervous system diseases;

[30] The pharmaceutical composition according to item [27], which is a prophylactic or therapeutic agent for Alzheimer's disease;

[30a] The pharmaceutical composition according to item [27], which is a prophylactic or therapeutic agent for Parkinson's disease, amyotrophic lateral sclerosis, Huntington's disease, depression, anxiety disorder, manic-depressive disease, schizophrenia, posttraumatic stress disorder, cerebral infarction, cerebral stroke, diabetes or hypertension;

[30b] The pharmaceutical composition according to item [27] which is a quality-of-life improving agent for heart failure after myocardial infarction, a quality-of-life improving agent for use after cerebral infarction, a blood glucose reducing agent, an insulin resistance improving agent or a blood triglyceride reducing agent;

[31] A method for preventing or treating central nervous system diseases, which comprises administering an effective amount of the pharmaceutical composition according to item [27] to a mammal;

[32] A method for preventing or treating Alzheimer's disease, which comprises administering an effective amount of the pharmaceutical composition according to item [27] to a mammal;

[33] Use of the compound according to any one of items [1] to [25] or a prodrug thereof for producing a prophylactic or therapeutic agent for central nervous system diseases; and

[34] Use of the compound according to any one of items [1] to [25] or a prodrug thereof for producing a prophylactic or therapeutic agent for Alzheimer's disease.

Further, the present invention relates to:

[1'] A compound represented by the following formula (I'):

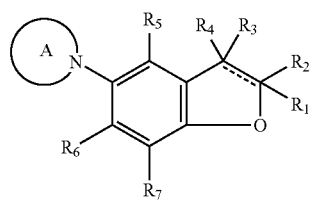

wherein:
Ring A represents an optionally substituted piperazine ring, an optionally substituted morpholine ring, or an optionally substituted homopiperazine ring;
R1 and R2 are the same or different from each other, and represent a hydrogen atom or optionally substituted lower alkyl;
R3 and R4 are the same or different from each other, and represent a hydrogen atom or halogenated or non-halogenated lower alkyl;
R5 to R7 are the same or different from each other, and represent a hydrogen atom, hydroxy, optionally substituted lower alkyl, optionally substituted lower alkenyl, optionally substituted lower alkoxy, optionally substituted cycloalkyl, optionally substituted aryl, an optionally substituted aromatic heterocyclic ring, optionally substituted amino, or acyl; and
----- represents a single bond or double bond,
wherein:
R2 and R3 do not exist when carbon atoms respectively adjacent to R2 and R3 form a double bond, and not all of R1 to R7 are hydrogen atom; and
R1 and R2 may form a ring together with an adjacent carbon atom (excluding 4-(2,3-dihydro-2,3,4,7-tetramethyl-5-benzofuranyl morpholine) and 6-chloro-4-[4-[2,3-dihydro-5-(4-morpholinyl)-7-benzofuranyl]-2-hydroxy-4-methyl-2-(trifluoromethyl)pentyl]thieno[3,2-b]pyridine-7(4H)-one), or a salt thereof;

[2'] The compound according to item [1'], wherein the partial structural formula of formula (I'):

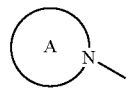

is any one of the following formulae:

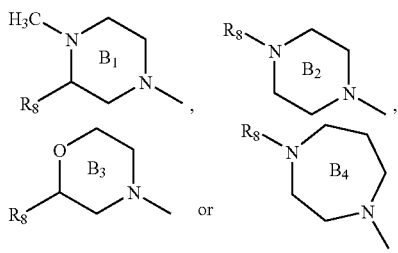

wherein:
R$_8$ is optionally substituted aryl or an optionally substituted aromatic heterocyclic ring;
Ring B$_1$ is a further optionally substituted piperazine ring;
Ring B$_2$ is a further optionally substituted piperazine ring;
Ring B$_3$ is a further optionally substituted morpholine ring; and
Ring B$_4$ is a further optionally substituted homopiperazine ring;

[3'] A prodrug of the compound according to item [1'];

[4'] A pharmaceutical composition comprising the compound according to item [1'] or a prodrug thereof;

[5'] The pharmaceutical composition according to item [4'], which is an IGF-1 signal modulator or protein kinase B activator;

[5a'] The pharmaceutical composition according to item [4'], which is an agent for stimulating growth and differentiation of stem cells, an agent for stimulating growth and differentiation of neural precursor cells, an agent for stimulating neurogenesis, or an agent for stimulating nerve regeneration;

[6'] The pharmaceutical composition according to item [4'], which is a prophylactic or therapeutic agent for central nervous system diseases;

[6a'] The pharmaceutical composition according to item [4'], which is a prophylactic or therapeutic agent for neurodegenerative disease, neuropsychiatric disease, mild cognition disorder, mild memory disorder, cerebral vascular disorder, cerebrovascular dementia, ischemic disease or cerebral ischemic disease;

[7'] The pharmaceutical composition according to item [4'], which is a prophylactic or therapeutic agent for Alzheimer's disease;

[7a'] The pharmaceutical composition according to item [4'], which is a prophylactic or therapeutic agent for Parkinson's disease, amyotrophic lateral sclerosis, Huntington's disease, depression, anxiety disorder, manic-depressive disease, schizophrenia, posttraumatic stress disorder, cerebral infarction, cerebral stroke, diabetes or hypertension;

[7b'] The pharmaceutical composition according to item [4'], which is a quality-of-life improving agent for heart failure after myocardial infarction, a quality-of-life improving agent for use after cerebral infarction, a blood glucose reducing agent, an insulin resistance improving agent or a blood triglyceride reducing agent;

[8'] A method for preventing or treating central nervous system diseases, which comprises administering an effective amount of the pharmaceutical composition according to item [4'] to a mammal;

[9'] A method for preventing or treating Alzheimer's disease, which comprises administering an effective amount of the pharmaceutical composition according to item [4'] to a mammal;

[10'] Use of the compound according to item [1'] or a prodrug thereof for producing a prophylactic or therapeutic agent for central nervous system diseases; and

[11'] Use of the compound according to item [1'] or a prodrug thereof for producing a prophylactic or therapeutic agent for Alzheimer's disease.

Advantageous Effects of the Invention

The compound of the present invention, a salt thereof or a prodrug thereof has excellent neurogenesis promoting activity and nerve cell regeneration promoting activity, and further has low phototoxicity and high ability to transfer to the central nervous system. Therefore, for example, it is useful as an IGF-1 signal modulator, protein kinase B activator, and prophylactic or therapeutic agent for central nervous system diseases (e.g., Alzheimer's disease).

MODE FOR CARRYING OUT THE INVENTION

Hereinbelow, definition of the substituents that are comprised in Compound (I) is explained.

As for the "lower alkyl" in the "lower alkyl which may be substituted" (i.e., "optionally substituted lower alkyl") that is indicated by $R_1$, $R_2$, and $R_5$ to $R_7$, $C_{1-6}$ alkyl (for example: methyl, ethyl, propyl, isopropyl, butyl, isobutyl, sec-butyl, tert-butyl, pentyl, hexyl and the like) and the like are included.

As for the "substituent" in the "lower alkyl which may be substituted", (1) a halogen atom (for example, fluorine, chlorine, bromine, iodine and the like), (2) $C_{1-3}$ alkylenedioxy (for example, methylenedioxy, ethylenedioxy and the like), (3) nitro, (4) cyano, (5) $C_{1-6}$ alkyl which may be halogenated (for example, methyl, ethyl, propyl, isopropyl, butyl, isobutyl, sec-butyl, tert-butyl, pentyl, hexyl and the like which may have 1 to 5 (preferably 1 to 3) fluorine, chlorine, bromine and iodine), (6) $C_{2-6}$ alkenyl which may be halogenated (for example, vinyl, propenyl, isopropenyl, 2-buten-1-yl, 4-penten-1-yl, 5-hexen-1-yl and the like which may have 1 to 5 (preferably 1 to 3) fluorine, chlorine, bromine and iodine), (7) carboxy-$C_{2-6}$ alkenyl (for example, 2-carboxyethenyl, 2-carboxy-2-methylethenyl and the like), (8) $C_{2-6}$ alkynyl which may be halogenated (for example, 2-butyn-1-yl, 4-pentyn-1-yl, 5-hexyn-1-yl and the like which may have 1 to 5 (preferably 1 to 3) fluorine, chlorine, bromine and iodine), (9) $C_{3-8}$ cycloalkyl which may be halogenated (for example, cyclopropyl, cyclobutyl, cyclopentyl, cyclohexyl, cycloheptyl, cyclooctyl and the like which may have 1 to 5 (preferably 1 to 3) fluorine, chlorine, bromine and iodine), (10) $C_{6-14}$ aryl (for example, phenyl, 1-naphthyl, 2-naphthyl, 2-biphenylyl, 3-biphenylyl, 4-biphenylyl, 2-anthryl and the like), (11) $C_{1-8}$ alkoxy which may be halogenated (for example, methoxy, ethoxy, propoxy, isopropoxy, butoxy, isobutoxy, sec-butoxy, tert-butoxy, pentoxy, hexyloxy and the like which may have 1 to 5 (preferably 1 to 3) fluorine, chlorine, bromine and iodine), (12) $C_{1-6}$ alkoxy-carbonyl-$C_{1-6}$ alkoxy (for example, ethoxycarbonylmethyloxy and the like), (13) hydroxy, (14) $C_{6-14}$ aryloxy (for example, phenyloxy, 1-naphthyloxy, 2-naphthyloxy and the like), (15) $C_{7-16}$ aralkyloxy (for example, benzyloxy, phenethyloxy and the like), (16) mercapto, (17) $C_{1-6}$ alkylthio which may be halogenated (for example, methylthio, ethylthio, propylthio, isopropylthio, butylthio, isobutylthio, sec-butylthio, tert-butylthio, pentylthio, hexylthio and the like which may have 1 to 5 (preferably 1 to 3) fluorine, chlorine, bromine and iodine), (18) $C_{6-14}$ arylthio (for example, phenylthio, 1-naphthylthio, 2-naphthylthio and the like), (19) $C_{7-16}$ aralkylthio (for example, benzylthio, phenethylthio and the like), (20) amino which may be substituted with a substituent (for example: methyl, ethyl, benzyl and the like), (21) mono-$C_{1-6}$ alkylamino (for example, methylamino, ethylamino and the like), (22) mono-$C_{6-14}$ arylamino (for example, phenylamino, 1-naphthylamino, 2-naphthylamino and the like), (23) di-$C_{1-6}$ alkylamino (for example, dimethylamino, diethylamino, ethylmethylamino and the like), (24) di-$C_{6-14}$ arylamino (for example, diphenylamino and the like), (25) formyl, (26) carboxy, (27) $C_{1-6}$ alkyl-carbonyl (for example, acetyl, propionyl and the like), (28) $C_{3-8}$ cycloalkyl-carbonyl (for example, cyclopropylcarbonyl, cyclopentylcarbonyl, cyclohexylcarbonyl, cycloheptylcarbonyl, cyclooctylcarbonyl and the like), (29) $C_{1-6}$ alkoxy-carbonyl (for example, methoxycarbonyl, ethoxycarbonyl, propoxycarbonyl, tert-butoxycarbonyl and the like), (30) $C_{6-14}$ aryl-carbonyl (for example, benzoyl, 1-naphthoyl, 2-naphthoyl and the like), (31) $C_{7-16}$ aralkyl-carbonyl (for example, phenylacetyl, 3-phenylpropionyl and the like), (32) $C_{6-14}$ aryloxy-carbonyl (for example, phenoxycarbonyl and the like), (33) $C_{7-16}$ aralkyloxy-carbonyl (for example, benzyloxycarbonyl, phenethyloxycarbonyl and the like), (34) 5- or 6-membered heterocyclic carbonyl (for example, nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like), (35) carbamoyl, (36) mono-$C_{1-6}$ alkyl-carbamoyl (for example, methylcarbamoyl, ethylcarbamoyl and the like), (37) di-$C_{1-6}$ alkyl-carbamoyl (for example, dimethylcarbamoyl, diethylcarbamoyl, ethylmethylcarbamoyl and the like), (38) mono-$C_{6-14}$ aryl-carbamoyl (for example, phenylcarbamoyl, 1-naphthylcarbamoyl, 2-naphthylcarbamoyl and the like), (39) 5- or 6-membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), (40) $C_{1-6}$ alkylsulfonyl (for example, methylsulfonyl, ethylsulfonyl and the like), (41) $C_{6-14}$ arylsulfonyl (for example, phenylsulfonyl, 1-naphthylsulfonyl, 2-naphthylsulfonyl and the like), (42) formylamino, (43) $C_{1-6}$ alkyl-carbonylamino (for example, acetylamino and the like), (44) $C_{6-14}$ aryl-carbonylamino (for example, benzoylamino, naphthoylamino and the like), (45) $C_{1-6}$ alkoxy-carbonylamino (for example, methoxycarbonylamino, ethoxycarbonylamino, propoxycarbonylamino, butoxycarbonylamino and the like), (46) $C_{1-6}$ alkylsulfonylamino (for example, methylsulfonylamino, ethylsulfonylamino and the like), (47) $C_{6-14}$ arylsulfonylamino (for example, phenylsulfonylamino, 2-naphthylsulfonylamino, 1-naphthylsulfonylamino and the like), (48) $C_{1-6}$ alkyl-carbonyloxy (for example, acetoxy, propionyloxy and the like), (49) $C_{6-14}$ aryl-carbonyloxy (for example, benzoyloxy, naphthylcarbonyloxy and the like), (50) $C_{1-6}$ alkoxy-carbonyloxy (for example, methoxycarbonyloxy, ethoxycarbonyloxy, propoxycarbonyloxy, butoxycarbonyloxy and the like), (51) mono-$C_{1-6}$ alkyl-carbamoyloxy (for example, methylcarbamoyloxy, ethylcarbamoyloxy and the like), (52) di-$C_{1-6}$ alkyl-carbamoyloxy (for example, dimethylcarbamoyloxy, diethylcarbamoyloxy and the like), (53) mono $C_{6-14}$ aryl-carbamoyloxy (for example, phenylcarbamoyloxy, naphthylcarbamoyloxy and the like), (54) nicotinoyloxy, (55) 5- to 7-membered saturated cyclic amino (for example: piperidino, pyrrolidinyl and the like which may be substituted with a substituent (for example: methyl, ethyl, benzyl and the like)), (56) 5- to 10-membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), (57) sulfo, (58) morpholino, (59) thiomorpholino which may have an oxygen added thereto, (60) pyrazolyl which may be substituted with a substituent (for example: methyl, ethyl, benzyl and the like), (61) imidazolyl which may be substituted with a substituent (for example: methyl, ethyl, benzyl and the like), (62) monospirobicycle which may be substituted with a substituent (for example: methyl, ethyl, benzyl and the like), and the like are included. There can be 1 to 5, preferably 1 to 3 substituents at a substitutable position, and when there are two or more substituents, each substituent can be the same or different from each other.

Preferably, the above-described substituent is (1) a halogen atom (for example, fluorine, chlorine, bromine, iodine and the like), (2) $C_{1-3}$ alkylenedioxy (for example, methylenedioxy, ethylenedioxy and the like), (3) nitro, (4) cyano, (5) $C_{1-6}$ alkyl which may be halogenated (for example, methyl, ethyl, propyl, isopropyl, butyl, isobutyl, sec-butyl, tert-butyl, pentyl, hexyl and the like which may have 1 to 5 (preferably 1 to 3) fluorine, chlorine, bromine and iodine), (6) $C_{2-6}$ alkenyl which may be halogenated (for example, vinyl, propenyl, isopropenyl, 2-buten-1-yl, 4-penten-1-yl, 5-hexen-1-yl and the like which may have 1 to 5 (preferably 1 to 3) fluorine, chlorine, bromine and iodine), (7) carboxy-$C_{2-6}$ alkenyl (for example, 2-carboxyethenyl, 2-carboxy-2-methylethenyl and the like), or (8) $C_{2-6}$ alkynyl which may be halogenated (for example, 2-butyn-1-yl, 4-pentyn-1-yl, 5-hexen-1-yl and the like which may have 1 to 5 (preferably 1 to 3) fluorine, chlorine, bromine and iodine).

As for the "lower alkyl which may be halogenated" that is indicated by $R_3$ and $R_4$, $C_{1-6}$ alkyl (for example, methyl, ethyl, propyl, isopropyl, butyl, isobutyl, sec-butyl, tert-butyl, pentyl, hexyl and the like) which may be substituted with 1 to 5 (preferably 1 to 3) halogen atoms (for example, fluorine, chlorine, bromine and iodine and the like) are included. As a specific example thereof, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like can be mentioned.

As for the "lower alkenyl" in the "lower alkenyl which may be substituted" that is indicated by $R_5$ to $R_7$, $C_{2-6}$ alkenyl (for example: vinyl, allyl, isopropenyl, butenyl, isobutenyl, sec-butenyl and the like) and the like are included, for example.

As a specific example of the "substituent" in the "lower alkenyl which may be substituted", those that are the same as the "substituent" in the "lower alkyl which may be substituted" described above can be mentioned, and there can be 1 to 5, preferably 1 to 3 substituents at a substitutable position.

As for the "lower alkoxy" in the "lower alkoxy which may be substituted" that is indicated by $R_5$ to $R_7$, $C_{1-6}$ alkoxy are included. Specifically, methoxy, ethoxy, propoxy, isopropoxy, butoxy, isobutoxy, sec-butoxy, pentyloxy, hexyloxy and the like are included.

As a specific example of the "substituent" in the "lower alkoxy which may be substituted", those that are the same as the "substituent" in the "lower alkyl which may be substituted" described above can be mentioned, and there can be 1 to 5, preferably 1 to 3 substituents at a substitutable position.

Examples of the "aliphatic cyclic hydrocarbon group" in the "aliphatic cyclic hydrocarbon group which may be substituted" represented by $R_5$ to $R_7$ include $C_{3-8}$ cycloalkyl (e.g., cyclopropyl, cyclobutyl, cyclopentyl, cyclohexyl, cycloheptyl, and cyclooctyl), $C_{3-8}$ cycloalkenyl (e.g., cyclopropenyl, cyclopentenyl, cyclohexenyl, cycloheptenyl, and 2,4-cycloheptadienyl), and $C_{3-10}$ cycloalkynyl (e.g., cyclopropynyl, cyclobutynyl, cyclopentynyl, cyclohexynyl, cycloheptynyl, and cyclooctynyl).

Examples of the "substituent" of the "aliphatic cyclic hydrocarbon group which may be substituted" include those similar to the "substituent" of the above-described "lower alkyl which may be substituted", and there can be 1 to 5, preferably 1 to 3 substituents at a substitutable position.

As for the "cycloalkyl" in the "cycloalkyl which may be substituted" that is indicated by $R_5$ to $R_7$, $C_{3-8}$ cycloalkyl (for example: cyclopropyl, cyclobutyl, cyclopentyl, cyclohexyl, cycloheptyl, cyclooctyl and the like) and the like can be mentioned.

As a specific example of the "substituent" in the "cycloalkyl which may be substituted", those that are the same as the "substituent" in the "lower alkyl which may be substituted" described above can be mentioned, and there can be 1 to 5, preferably 1 to 3 substituents at a substitutable position.

As for the "aryl" in the "aryl which may be substituted" that is indicated by $R_5$ to $R_7$, $C_{6-20}$ aryl, preferably $C_{6-14}$ aryl can be mentioned, for example. As a specific example thereof, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl, anthryl, anthracenyl and the like can be mentioned. Phenyl is particularly preferred.

As for the "substituent" in the "aryl which may be substituted", those that are the same as the "substituent" in the "lower alkyl which may be substituted" described above can be mentioned, and there can be 1 to 5, preferably 1 to 3 substituents at a substitutable position.

Examples of the "heterocyclic ring" in the "heterocyclic ring which may be substituted" represented by $R_5$ to $R_7$ include an aromatic heterocyclic group and a non-aromatic heterocyclic group. As for the above-described "aromatic heterocyclic group" and the "aromatic heterocyclic" group in the "aromatic heterocycle which may be substituted" that is indicated by $R_5$ to $R_7$, a 5- to 14-membered, preferably 5- to 10-membered aromatic heterocyclic group which comprises, in addition to carbon atom, at least one hetero atom (for example 1 to 4) selected from nitrogen atom, sulfur atom and oxygen atom can be mentioned, for example.

As a specific example thereof, a 5- to 6-membered monocyclic aromatic heterocyclic group such as furyl, thienyl, pyrrolyl, oxazolyl, isooxazolyl, thiazolyl, isothiazolyl, imidazolyl, 1-methyl-1H-imidazolyl, pyrazolyl, 1-methyl-1H-pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and a 8- to 12-membered fused polycyclic aromatic heterocyclic group such as pyrazolopyrimidinyl, benzofuranyl, isobenzofuranyl, benzo[b]thienyl, indolyl, isoindolyl, 1H-indazolyl, benzimidazolyl, benzoxazolyl, 1,2-benzisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like are used. Of these, furyl and pyridyl are particularly preferred.

As for the "substituent" in the "aromatic heterocycle which may be substituted", those that are the same as the "substituent" in the "alkyl which may be substituted" described above can be mentioned, and there can be 1 to 5, preferably 1 to 3 substituents at a substitutable position.

As for the above-described "non-aromatic heterocyclic group", a 5- to 14-membered, preferably 5- to 10-membered non-aromatic heterocyclic group which comprises, in addition to carbon atom, at least one hetero atom (for example 1 to 4) selected from nitrogen atom, sulfur atom and oxygen atom can be mentioned, for example. Examples thereof include a 4- to 7-membered (preferably 5- or 6-membered) monocyclic non-aromatic heterocyclic group containing 1 to 4 hetero atoms selected from an oxygen atom, a sulfur atom (the sulfur atom may be oxidized) and a nitrogen atom as ring-constituting atoms other than a carbon atom, and a condensed non-aromatic heterocyclic group. Examples of the condensed non-aromatic heterocyclic group include a group formed by condensation of the 4- to 7-membered monocyclic non-aromatic heterocyclic group and 1 or 2 rings selected from a 5- or 6-membered aromatic or non-aromatic heterocyclic ring containing 1 or 2 nitrogen atoms (e.g., pyrrole, imidazole, pyrazole, pyrazine, pyridine and pyrimidine), a 5-membered aromatic or non-aromatic heterocyclic ring containing a sulfur atom (e.g., thiophene) and a benzene ring.

Specific examples thereof include: monocyclic non-aromatic heterocyclic group such as pyrrolidinyl (e.g., 1-pyrrolidinyl, 2-pyrrolidinyl, 3-pyrrolidinyl), piperidinyl (e.g., piperidino, 2-piperidinyl, 3-piperidinyl, 4-piperidinyl), homopiperidinyl (e.g., homopiperidino, 2-homopiperidinyl, 3-homopiperidinyl, 4-homopiperidinyl), tetrahydropyridyl (e.g., 1,2,3,6-tetrahydropyrid-1-yl), dihydropyridyl (e.g., 2,3-dihydropyrid-4-yl), morpholinyl (e.g, morpholino, 2-morpholinyl), thiomorpholinyl (e.g., thiomorpholino), 1,1-dioxidethiomorpholinyl (e.g., 1,1-dioxidethiomorpholino), piperazinyl (e.g., 1-piperazinyl, 2-piperazinyl), hexamethyleneiminyl (e.g., 1-hexamethyleneiminyl), oxazolidinyl (e.g., 2-oxazolidinyl), thiazolidinyl (e.g., 3-thiazolidinyl, 2-thiazolidinyl), imidazolidinyl (e.g., 2-imidazolidinyl, 3-imidazolidinyl), oxazolinyl (e.g., 2-oxazolinyl), thiazolinyl (e.g., 2-thiazolinyl), imidazolinyl (e.g., 2-imidazolinyl, 3-imidazolinyl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidetetrahydrothiopyranyl (e.g., 1-oxidetetrahydrothiopyrane-4-yl), 1,1-dioxidetetrahydrothiopyranyl (e.g., 1,1-dioxidetetrahydrothiopyrane-4-yl), tetrahydrofuryl (e.g., tetrahydrofuran-3-yl, tetrahydrofuran-2-yl), pyrazolidinyl (e.g., 1-pyrazolidinyl, 3-pyrazolidinyl), pyrazolinyl (e.g., 1-pyrazolinyl), tetrahydropyrimidinyl (e.g., 1-tetrahydropyrimidinyl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), dihydrooxadiazolyl (e.g., 4,5-dihydro-1,2,4-oxadiazol-3-yl), thiadinyl (e.g., 1,4-thiadine-2-yl), 1,1-dioxidothiazinanyl (e.g., 1,1-dioxide-1,2-thiazinan-2-yl), dihydropyridazinyl (e.g., 1,6-dihydropyridazin-3-yl), tetrahydropyridazinyl (e.g., 1,4,5,6-tetrahydropyridazin-3-yl), dihydrothioxazinyl (e.g., 2,3-dihydro-1,4-thioxazin-3-yl), and dihydrothiazinyl (e.g., 3,4-dihydro-2H-1,4-thiazin-5-yl); and condensed non-aromatic heterocyclic group such as dihydroindolyl (e.g., 2,3-dihydro-1H-indol-1-yl), dihydroisoindolyl (e.g., 2,3-dihydro-1H-isoindol-1-yl, 1,3-dihydro-2H-isoindol-2-yl), dihydrobenzofuranyl (e.g., 2,3-dihydro-1-benzofuran-5-yl), dihydrobenzodioxanyl (e.g., 2,3-dihydro-1,4-benzodioxanyl), dihydrobenzodioxepinyl (e.g., 3,4-dihydro-2H-1,5-benzodioxepin-7-yl) chromenyl (e.g., 4H-chromene-2-yl, 2H-chromene-3-yl, 2H-chromen-7-yl), dihydroquinolinyl (e.g., 1,2-dihydroquinolin-4-yl, 3,4-dihydroquinolin-1(2H)-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl, 1,2,3,4-tetrahydroisoquinolin-2-yl), dihydrophthalazinyl (e.g., 3,4-dihydrophthalazin-1-yl, 1,4-dihydrophthalazin-4-yl), tetrahydrobenzoazepinyl (e.g., 2,3,4,5-tetrahydro-1H-benzo[c]azepin-1-yl), benzodioxolyl (e.g., 1,3-benzodioxol-5-yl), and benzothiazine (e.g., 3,4-dihydro-2H-1,4-benzothiazin-2-yl).

As for the "substituent" in the case where the above-described "non-aromatic heterocyclic ring" has a substituent, those that are the same as the "substituent" in the "alkyl which may be substituted" described above can be mentioned, and there can be 1 to 5, preferably 1 to 3 substituents at a substitutable position.

As for the "amino which may be substituted" that is indicated by $R_5$ to $R_7$, amino, mono-$C_{1-6}$ alkylamino (for example: methylamino, ethylamino and the like), mono-$C_{6-14}$ arylamino (for example: phenylamino, 1-naphthylamino, 2-naphthylamino and the like), di-$C_{1-6}$ alkylamino (for example: dimethylamino, diethylamino and the like), di-$C_{6-14}$ arylamino (for example: diphenylamino and the like), acylamino and the like can be mentioned. As an example of the acylamino, formylamino, $C_{1-6}$ alkyl-carbonylamino (for example, acetylamino and the like), $C_{6-14}$ aryl-carbonylamino (for example, phenylcarbonylamino, naphthylcarbonylamino and the like), $C_{1-6}$ alkoxy-carbonylamino (for example, methoxycarbonylamino, ethoxycarbonylamino, propoxycarbonylamino, butoxycarbonylamino and the like), $C_{1-6}$ alkylsulfonylamino (for example, methylsulfonylamino, ethylsulfonylamino and the like), $C_{6-14}$ arylsulfonylamino (for example, phenylsulfonylamino, 2-naphthylsulfonylamino, 1-naphthylsulfonylamino and the like) and the like can be mentioned.

As for the "substituent" in the "amino which may be substituted", those that are the same as the "substituent" in the "alkyl which may be substituted" described above can be mentioned, and there can be 1 to 2 substituents at a substitutable position.

As for the "acyl" that is indicated by $R_5$ to $R_7$, formyl, carboxy, carbamoyl, $C_{1-6}$ alkyl-carbonyl (for example, acetyl, propionyl and the like), $C_{3-6}$ cycloalkyl-carbonyl (for example, cyclopropylcarbonyl, cyclopentylcarbonyl, cyclohexylcarbonyl and the like), $C_{1-6}$ alkoxy-carbonyl (for example, methoxycarbonyl, ethoxycarbonyl, propoxycarbonyl, tert-butoxycarbonyl and the like), $C_{6-14}$ aryl-carbonyl (for example, benzoyl, 1-naphthoyl, 2-naphthoyl and the like), $C_{7-16}$ aralkyl-carbonyl (for example, phenylacetyl, phenylpropionyl and the like), $C_{6-14}$ aryloxy-carbonyl (for example, phenoxycarbonyl and the like), $C_{7-16}$ aralkyloxycarbonyl (for example, benzyloxycarbonyl, phenethyloxycarbonyl and the like), 5- or 6-membered heterocyclic carbonyl (for example, nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl and the like), mono-$C_{1-6}$ alkyl-carbamoyl (for example, methylcarbamoyl, ethylcarbamoyl and the like), di-$C_{1-6}$ alkyl-carbamoyl (for example, dimethylcarbamoyl, diethylcarbamoyl, ethylmethylcarbamoyl and the like), $C_{6-14}$ arylcarbamoyl (for example, phenylcarbamoyl, 1-naphthylcarbamoyl, 2-naphthylcarbamoyl and the like), thiocarbamoyl, 5- or 6-membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), $C_{1-6}$ alkylsulfonyl (for example, methylsulfonyl, ethylsulfonyl and the like), $C_{6-14}$ arylsulfonyl (for example, phenylsulfonyl, 1-naphthylsulfonyl, 2-naphthylsulfonyl and the like), $C_{1-6}$ alkylsulfinyl (for example, methylsulfinyl, ethylsulfinyl and the like), $C_{6-14}$ arylsulfinyl (for example, phenylsulfinyl, 1-naphthylsulfinyl, 2-naphthylsulfinyl and the like) and the like can be mentioned, for example. Of these, acetyl and propionyl are particularly preferred.

In Formula (I),

----- represents a single bond or a double bond. A single bond is preferable for

----- in Formula (I), where $R_2$ and $R_3$ do not exist when carbon atoms respectively adjacent to $R_2$ and $R_3$ form a double bond, and there is no case where all of $R_1$ to $R_7$ are hydrogen atoms. $R_1$ and $R_2$ may form a ring together with an adjacent carbon atom As for $R_1$, a hydrogen atom, or optionally substituted $C_{1-6}$ alkyl ($C_{1-3}$ alkyl is more preferable) is preferable. Among others, a hydrogen atom; methyl, ethyl, n-propyl, and isopropyl which may be substituted with a substituent (e.g., hydroxy, halogen (e.g., chlorine, fluorine), aryl, aromatic heterocyclic ring, and the like) are preferable.

In another embodiment, $R_1$ is preferably optionally substituted $C_{1-6}$ alkyl, more preferably $C_{1-6}$ alkyl which may be substituted with a hydroxy, and further more preferably $R_1$ is $C_{1-6}$ alkyl.

In still another embodiment, $R_1$ is preferably a hydrogen atom, or $C_{1-6}$ alkyl which may be substituted with a hydroxy, and more preferably $C_{1-6}$ alkyl.

Preferably, $R_2$ is a hydrogen atom, optionally substituted $C_{1-6}$ alkyl (more preferably $C_{1-3}$ alkyl); and among others a hydrogen atom; methyl; methyl, ethyl, and the like which may be substituted with a substituent [e.g., amino which may be substituted with a substituent (e.g., methyl, ethyl, benzyl and the like); morpholino; thiomorpholino (e.g., 1,1-dioxidothiomorpholine); pyrazolyl; 2-methyl-1H-imidazolyl; 1,4-dioxa-8-azaspiro[4,5]decane; pyrrolidinyl; dimethyltetrahydrofuranyl; methylthio; piperidine and the like] are preferable.

In another embodiment, $R_2$ is preferably
(1) a hydrogen atom, or
(2) $C_{1-6}$ alkyl which may be substituted with a substituent selected from a hydroxy, amino, di-$C_{1-6}$ alkylamino, ($C_{1-6}$ alkyl)(benzyl)amino, mono-$C_{1-6}$ alkylamino, di-benzylamino, $C_{1-6}$ alkyl-carbonylamino, formyloxy, $C_{1-6}$ alkylsulfonyloxy, cyano, carboxy, mono-$C_{1-6}$ alkyl-carbamoyl, $C_{1-6}$ alkoxy which may be substituted with a substituent selected from $C_{1-6}$ alkoxy and phenyl, $C_{1-6}$ alkylthio, $C_{1-6}$ alkylsulfonyl, morpholino, 1,1-dioxidothiomorpholine, pyrazolyl, imidazolyl substituted with $C_{1-6}$ alkyl, pyrrolidinyl, piperidyl substituted with an oxo or hydroxy, and 1,4-dioxa-8-azaspiro [4,5]deca-8-yl; and more preferably, a hydrogen atom, or $C_{1-6}$ alkyl which may be substituted with a hydroxy.

Further, $R_1$ and $R_2$ may form an optionally substituted 3- to 8-membered (more preferably 3- to 5-membered) homocyclic or heterocyclic ring together with an adjacent carbon atom. Among others, a homocyclic or heterocyclic ring such as cyclopropyl, cyclobutyl, cyclopentyl, pyranyl, piperidyl, and the like are preferable.

In another embodiment, the "optionally substituted 3- to 8-membered homocyclic or heterocyclic ring" is preferably a cyclopentane ring or a tetrahydropyran ring.

$R_3$ is preferably a hydrogen atom, $C_{1-6}$ alkyl (more preferably $C_{1-4}$ alkyl) which may be halogenated. Among others, a hydrogen atom, methyl, ethyl, n-propyl, isopropyl, tert-butyl, and the like are preferable.

In another embodiment, $R_3$ is preferably a hydrogen atom, or $C_{1-6}$ alkyl; and more preferably a hydrogen atom. $R_4$ is preferably a hydrogen atom, $C_{1-6}$ alkyl (more preferably $C_{1-4}$ alkyl) which may be halogenated. Among others, a hydrogen atom, methyl, ethyl, and the like are preferable.

In another embodiment, $R_4$ is preferably a hydrogen atom.

$R_5$ is preferably a hydrogen atom, optionally substituted $C_{1-6}$ alkyl (more preferably $C_{1-3}$ alkyl), optionally substituted $C_{2-6}$ alkenyl (more preferably $C_{2-4}$ alkenyl), optionally substituted cycloalkyl, optionally substituted aryl, optionally substituted aromatic heterocyclic ring, optionally substituted amino, acyl, and the like. Among others, a hydrogen atom, methyl, ethyl, n-propyl, isopropyl, isopropenyl, vinyl, cyclopropyl, phenyl which may be substituted with a substituent (e.g., amino), furyl, pyridyl, and the like are preferable.

In another embodiment, $R_5$ is preferably a hydrogen atom, optionally substituted $C_{1-6}$ alkyl, optionally substituted $C_{2-6}$ alkenyl, optionally substituted $C_{3-6}$ cycloalkyl, optionally substituted $C_{6-14}$ aryl, or a 5- to 6-membered aromatic heterocyclic ring which may be substituted, and contains 1 to 4 heteroatoms selected from a nitrogen atom and an oxygen atom other than a carbon atom.

As for the "$C_{6-14}$ aryl", a phenyl is preferable. As for the "a 5- to 6-membered aromatic heterocyclic ring which contains 1 to 4 heteroatoms selected from a nitrogen atom and an oxygen atom other than a carbon atom", a furyl is preferable.

$R_5$ is more preferably a hydrogen atom, $C_{1-6}$ alkyl, $C_{1-6}$ alkenyl, $C_{3-6}$ cycloalkyl, phenyl which is substituted with $diC_{1-6}$ alkylamino, or furyl. $C_{1-6}$ alkyl is particularly preferable.

$R_6$ is preferably a hydrogen atom, optionally substituted $C_{1-6}$ alkyl (preferably $C_{1-3}$ alkyl), optionally substituted $C_{1-6}$ alkenyl (more preferably $C_{2-4}$ alkenyl), optionally substituted cycloalkyl, optionally substituted aryl, optionally substituted aromatic heterocyclic ring, optionally substituted amino, acyl, and the like. Among others, a hydrogen atom, methyl, ethyl, phenyl which may be substituted with a substituent (e.g., methyl), 4-tolyl, 4-methoxyphenyl, pyridyl, and the like are preferable.

In another embodiment, $R_6$ is preferably a hydrogen atom, optionally substituted $C_{1-6}$ alkyl, optionally substituted $C_{6-14}$ aryl, optionally substituted 5- to 6-membered aromatic heterocyclic ring containing 1 to 4 heteroatoms selected from a nitrogen atom and an oxygen atom other than a carbon atom, or a halogen atom.

As for the "$C_{6-14}$ aryl", phenyl is preferable. As for the "5- to 6-membered aromatic heterocyclic ring containing 1 to 4 heteroatoms selected from a nitrogen atom and an oxygen atom other than a carbon atom", pyridyl is preferable.

$R_6$ is more preferably a hydrogen atom, $C_{1-6}$ alkyl, phenyl substituted with $C_{1-6}$ alkyl, pyridyl, or a halogen atom. $C_{1-6}$ alkyl is particularly preferable.

$R_7$ is preferably a hydrogen atom, hydroxy, optionally substituted $C_{1-6}$ alkyl (more preferably $C_{1-3}$ alkyl), optionally substituted $C_{1-6}$ alkoxy (more preferably $C_{1-3}$ alkoxy), or optionally substituted acyl. Among others, a hydrogen atom, a hydroxy, methyl, ethyl, n-propyl, isopropyl, 1-hydroxyethyl, methoxy, ethoxy, isopropyloxy, acetyl, propionyl, and the like are preferable.

In another embodiment, $R_7$ is preferably a hydrogen atom, hydroxy, $C_{1-6}$ alkyl which may be substituted, $C_{1-6}$ alkoxy which may be substituted, or $C_{1-6}$ alkylcarbonyl.

More preferably, $R_7$ is a hydrogen atom, a hydroxy, $C_{1-6}$ alkyl which may be substituted with a hydroxy, $C_{1-6}$ alkoxy which may be substituted with $C_{1-6}$ alkoxy, or $C_{1-6}$ alkylcarbonyl.

$C_{1-6}$ alkyl and $C_{1-6}$ alkoxy are particularly preferable.

Ring A represents an optionally substituted piperazine ring, an optionally substituted morpholine ring, or an optionally substituted homopiperazine ring.

As for the substituent in the "optionally substituted piperazine ring", "optionally substituted morpholine ring", and "optionally substituted homopiperazine ring" indicated by ring A, those that are the same as the "substituent" in the "lower alkyl which may be substituted" described above are included, and there can be 1 to 5 (preferably 1 to 3) substituents at a substitutable position.

As for ring A, the "optionally substituted piperazine ring" is preferably:

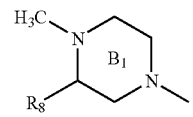

[in the formula, $R_8$ is aryl which may be substituted or aromatic heterocycle which may be substituted;

ring $B_1$ is a piperazine ring which may be further substituted] or

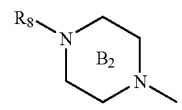

[in the formula, $R_8$ is aryl which may be substituted or aromatic heterocycle which may be substituted;

ring $B_2$ is a piperazine ring which may be further substituted].

In addition, as for ring A, the "optionally substituted morpholine ring" is preferably:

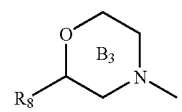

[in the formula, $R_8$ is aryl which may be substituted or aromatic heterocycle which may be substituted;

ring $B_3$ is a morpholine ring which may be further substituted].

In addition, as for ring A, the "optionally substituted homopiperazine ring" is preferably:

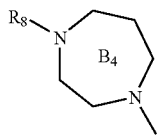

[in the formula, $R_8$ is aryl which may be substituted or aromatic heterocycle which may be substituted;

ring $B_4$ is a homopiperazine ring which may be further substituted].

The "aryl which may be substituted (or optionally substituted aryl)" indicated by $R_8$, those that are the same as the "optionally substituted aryl" in $R_5$ to $R_7$ are included.

The "optionally substituted aromatic heterocyclic ring" indicated by $R_g$, those that are the same as the "optionally substituted aromatic heterocyclic ring" in $R_5$ to $R_7$.

$R_8$ is preferably optionally substituted phenyl, an optionally substituted nitrogen-containing aromatic heterocyclic ring, an optionally substituted sulfur-containing aromatic heterocyclic ring, and the like. Among others, phenyl which has $C_{1-6}$ alkoxy (more preferably $C_{1-3}$ alkoxy), $C_{1-6}$ alkylsulfanyl, $C_{1-6}$ alkylsulfinyl, $C_{1-6}$ alkylsulfonyl, alkylamide and/or a halogen as a substituent, phenyl or 4-tolyl which has $C_{1-6}$ alkyl (more preferably $C_{1-3}$ alkyl) as a substituent, a 5- to 10-membered (more preferably 5- to 7-membered) nitrogen-containing aromatic heterocyclic group which may be substituted, a 5- to 10-membered (more preferably 5- to 7-membered) sulfur-containing aromatic heterocyclic group which may be substituted and the like are preferable. In particular, phenyl which may be substituted with a substituent (for example, methyl which may be substituted with a substituent (for example, fluorine), ethyl which may be substituted with a substituent (for example, hydroxy), isopropyl, cyano, dimethylamino, methoxy which may be substituted with a substituent (for example, fluorine, chlorine), ethoxy, fluorine, chlorine, bromine, methylsulfanyl, methylsulfinyl, methylsulfonyl, dimethylaminomethyl, aminomethyl, acetyl and the like), pyridyl which may be substituted with a substituent (for example, methoxy), benzamide, 2,3-dihydro-1,4-benzo-dioxin, 4-phenyltriazolyl, thiazolyl, thiazole, thiadiazole which may be substituted with a substituent (for example, phenyl), pyrimidyl which may be substituted with a substituent (for example, chlorine, phenyl which may be substituted with a substituent (for example, methoxy)), pyrazol-4-yl which may be substituted with a substituent (for example, methyl) and the like are preferable.

As for the "substituent" in the "5- to 10-membered (more preferably 5- to 7-membered) nitrogen-containing aromatic heterocyclic group which may be substituted" or "5- to 10-membered (more preferably 5- to 7-membered) sulfur-containing aromatic heterocyclic group which may be substituted", those that are the same as the "substituent" in the "alkyl which may be substituted" described above are included, and there can be 1 to 5, preferably 1 to 3 substituents at a substitutable position.

In another embodiment, the aryl or the two substituents on the aromatic heterocyclic ring in $R_8$ may bind to each other and form a condensed ring which may be substituted, together with the aryl or the aromatic heterocyclic ring. As for the "condensed ring which may be substituted", 2,3-dihydro-1, 4-benzodioxin ring, 2,3-dihydrobenzofuran ring which may be substituted with a substituent (e.g., $C_{1-6}$ alkyl such as a methyl), 1,3-benzodioxol ring which may be substituted with a substituent (e.g., a halogen atom such as fluorine) and the like are included.

As for the "substituent" in ring $B_1$, ring $B_2$, ring $B_3$, and ring $B_4$, those that are the same as the "substituent" in the "lower alkyl which may be substituted" described above are included, and there can be 1 to 5, preferably 1 to 3 substituents at a substitutable position.

In another embodiment, the partial structural formula:

of Formula (I) is preferably any one of the following formulae:

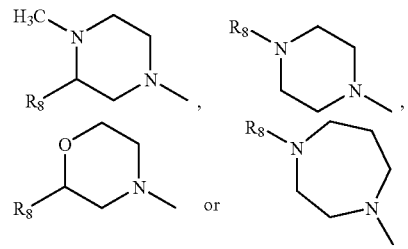

wherein:

$R_8$ is:

(1) $C_{6-14}$ aryl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $C_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) a 5- to 10-membered aromatic heterocyclic ring containing 1 to 4 heteroatoms selected from a nitrogen atom, a sulfur atom, and an oxygen atom, other than a carbon atom, and which may be substituted with 1 to 3 substituents selected from a halogen atom, $C_{1-6}$ alkyl, $C_{1-6}$ alkoxy, and phenyl which may be substituted with $C_{1-6}$ alkoxy.

As for "$C_{6-14}$ aryl" in $R_8$ above, phenyl is preferable. As for the "5- to 10-membered aromatic heterocyclic ring containing 1 to 4 heteroatoms selected from a nitrogen atom, a sulfur atom, and an oxygen atom, other than a carbon atom" in $R_8$ above, pyridyl, pyrimidinyl, thiadiazolyl, thiazolyl, pyrazolyl, isoxazolyl, imidazolyl, or pyrazolopyrimidinyl are preferable.

The partial structural formula:

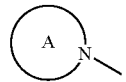

of Formula (I) is more preferably the following formula:

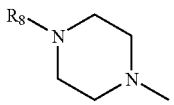

wherein:

$R_8$ is:

(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and di$C_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl;

(2) pyridyl which may be substituted with 1 to 3 $C_{1-6}$ alkoxy groups;

(3) pyrimidinyl which may be substituted with 1 to 3 substituents selected from phenyl which may be substituted with $C_{1-6}$ alkoxy, and a halogen atom;

(4) thiadiazolyl which may be substituted with a phenyl;

(5) thiazolyl;

(6) pyrazolyl which may be substituted with 1 to 2 $C_{1-6}$ alkyl groups;

(7) isoxazolyl;

(8) imidazolyl which may be substituted with 1 to 2 $C_{1-6}$ alkyl groups; or (9) pyrazolopyrimidinyl which may be substituted with 1 to 2 $C_{1-6}$ alkyl groups; and further more preferably, the following formula:

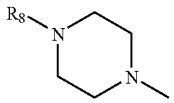

wherein:

$R_8$ is a phenyl which may be substituted with 1 to 3 substituents selected from:

(1) a halogen atom;

(2) $C_{1-6}$ alkoxy which may be substituted with a halogen atom;

(3) $C_{1-6}$ alkyl which may be substituted with a substituent selected from a halogen atom, a hydroxy, amino, and di$C_{1-6}$ alkylamino;

(4) $C_{1-6}$ alkylthio;

(5) $C_{1-6}$ alkylsulfonyl;

(6) cyano;

(7) carbamoyl;

(8) $C_{1-6}$ alkylsulfinyl; and (9) $C_{1-6}$ alkylcarbonyl.

Particularly preferably, the partial structural formula:

of Formula (I) is the following formula:

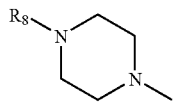

wherein:

$R_8$ is a phenyl which is substituted with 1 to 3 $C_{1-6}$ alkoxy.

As for Compound (I), ring A is preferably any one of the following formulae:

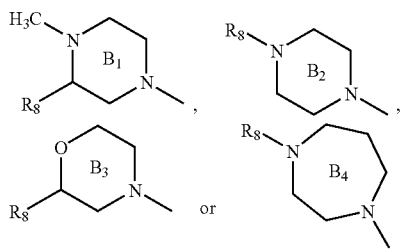

wherein:

$R_8$ is phenyl having $C_{1-6}$ alkoxy and/or a halogen as a substituent, phenyl having $C_{1-6}$ alkyl as a substituent, 5- to 10-membered nitrogen-containing aromatic heterocyclic group which may be substituted, 5- to 10-membered sulfur-containing aromatic heterocyclic group which may be substituted and the like;

ring $B_1$ is a piperazine ring which may be further substituted;

ring $B_2$ is a piperazine ring which may be further substituted;

ring $B_3$ is a morpholine ring which may be further substituted;

ring $B_4$ is a homopiperazine ring which may be further substituted, $R_1$ is a hydrogen atom, or $C_{1-6}$ alkyl which may be substituted, $R_2$ is a hydrogen atom, or $C_{1-6}$ alkyl which may be substituted, or, $R_1$ and $R_2$ together with adjacent carbon atom may form 3- to 8-membered homocycle or heterocycle which may be substituted, $R_3$ is a hydrogen atom, or $C_{1-6}$ alkyl which may be halogenated, $R_4$ is a hydrogen atom, or $C_{1-6}$ alkyl which may be halogenated, $R_5$ is a hydrogen atom, $C_{1-6}$ alkyl which may be substituted, $C_{2-6}$ alkenyl which may be substituted, cycloalkyl which may be substituted, aryl which may be substituted, aromatic heterocycle which may be substituted, amino which may be substituted, or acyl, $R_6$ is a hydrogen atom, $C_{1-6}$ alkyl which may be substituted, $C_{2-6}$ alkenyl which may be substituted, cycloalkyl which may be substituted, aryl which may be substituted, aromatic heterocycle which may be substituted, amino which may be substituted, or acyl, $R_7$ is a hydrogen atom, hydroxy, $C_{1-6}$ alkyl which may be substituted, $C_{1-6}$ alkoxy which may be substituted, or acyl which may be substituted.

Among them, those in which ring A is

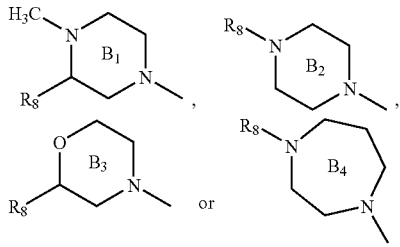

[in the formula,

R₈ is phenyl having $C_{1-3}$ alkoxy and/or a halogen as a substituent, phenyl having $C_{1-3}$ alkyl as a substituent, 5- to 7-membered nitrogen-containing aromatic heterocyclic group which may be substituted, 5- to 7-membered sulfur-containing aromatic heterocyclic group which may be substituted and the like;

ring $B_1$ is a piperazine ring which may be further substituted;

ring $B_2$ is a piperazine ring which may be further substituted;

ring $B_3$ is a morpholine ring which may be further substituted;

ring $B_4$ is a homopiperazine ring which may be further substituted], $R_1$ is a hydrogen atom, or $C_{1-3}$ alkyl which may be substituted, $R_2$ is a hydrogen atom, or $C_{1-3}$ alkyl which may be substituted, or, $R_1$ and $R_2$ together with adjacent carbon atom may form 3- to 5-membered homocycle or heterocycle which may be substituted, $R_3$ is a hydrogen atom, or $C_{1-4}$ alkyl which may be halogenated, $R_4$ is a hydrogen atom, or $C_{1-4}$ alkyl which may be halogenated, $R_5$ is a hydrogen atom, $C_{1-3}$ alkyl which may be substituted, $C_{2-4}$ alkenyl which may be substituted, cycloalkyl which may be substituted, aryl which may be substituted, aromatic heterocycle which may be substituted, amino which may be substituted, or acyl, $R_6$ is a hydrogen atom, $C_{1-3}$ alkyl which may be substituted, $C_{2-4}$ alkenyl which may be substituted, cycloalkyl which may be substituted, aryl which may be substituted, aromatic heterocycle which may be substituted, amino which may be substituted, or acyl, $R_7$ is a hydrogen atom, hydroxy, $C_{1-3}$ alkyl which may be substituted, $C_{1-3}$ alkoxy which may be substituted, or acyl which may be substituted, are preferable.

Among them, those in which ring A is

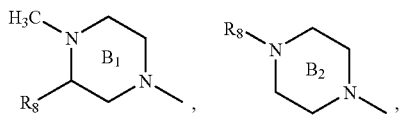

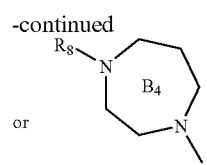

[in the formula,

R₈ is phenyl which may be substituted with a substituent (for example, methyl which may be substituted with a substituent (for example, fluorine), ethyl which may be substituted with a substituent (for example, hydroxy), isopropyl, cyano, dimethylamino, methoxy which may be substituted with a substituent (for example, fluorine, chlorine), ethoxy, fluorine, chlorine, bromine, methylsulfanyl, methylsulfinyl, methylsulfonyl, dimethylaminomethyl, aminomethyl, acetnyl and the like), benzamide, 2,3-dihydro-1,4-benzodioxin, 4-phenyltriazolyl, thiazolyl which may be substituted with a substituent (for example, phenyl), thiazole, pyrimidyl which may be substituted with a substituent (for example, chlorine, phenyl which may be substituted with a substituent (for example, methoxy)), pyrazol-4-yl which may be substituted with a substituent (for example, methyl) and the like;

ring $B_1$ is a piperazine ring which may be further substituted;

ring $B_2$ is a piperazine ring which may be further substituted;

ring $B_3$ is a morpholine ring which may be further substituted;

ring $B_4$ is a homopiperazine ring which may be further substituted], $R_1$ is a hydrogen atom, or methyl which may be substituted with a substituent (for example, hydroxy), ethyl, $R_2$ is a hydrogen atom, methyl, or methyl which may be substituted with a substituent (for example, methoxy, amino which may be substituted with a substituent (for example: methyl, benzyl and the like), methylsulfanyl, methylsulfonyl, morpholino, thiomorpholino (for example: 1,1-dioxido thiomorpholine), pyrazolyl, 2-methyl-1H-imidazolyl, 1,4-dioxa-8-azaspiro[4,5]decane, pyrrolidinyl, dimethyltetrahydrofuranyl, methylthio, piperidino and the like), ethyl, or $R_1$ and $R_2$ together with adjacent carbon atom form cyclopropyl, cyclobutyl, cyclopentyl, pyranyl or piperidinyl, $R_3$ is a hydrogen atom, methyl, ethyl, n-propyl, isopropyl, or tert-butyl, $R_4$ is a hydrogen atom, methyl, ethyl, $R_5$ is a hydrogen atom, methyl, ethyl, n-propyl, isopropyl, isopropenyl, vinyl, cyclopropyl, phenyl which may be substituted with a substituent (for example, amino), furyl, or pyridyl, $R_6$ is a hydrogen atom, methyl, phenyl which may be substituted with a substituent (for example, methyl), 4-tolyl, 4-methoxyphenyl, or pyridyl, $R_7$ is a hydrogen atom, hydroxy, methyl, ethyl, n-propyl, isopropyl, 1-hydroxyethyl, methoxy, ethoxy, isopropyloxy, acetyl, or propionyl, are preferable.

Among them, in particular, those in which
ring A is

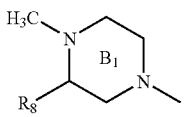

[in the formula,
R$_8$ is phenyl which is substituted with 1 to 2 methoxy groups],
R$_1$ and R$_2$ are methyl,
R$_3$ and R$_4$ are a hydrogen atom,
R$_5$ to R$_7$ are methyl,
are preferable.
Or, those in which
ring A is

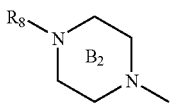

[in the formula,
R$_8$ is phenyl which may be substituted with a substituent (methyl which may be substituted with fluorine, ethyl which may be substituted with hydroxy, isopropyl, cyano, dimethylamino, methoxy which may be substituted with fluorine or chlorine, ethoxy, fluorine, chlorine, bromine, methylsulfanyl, methylsulfinyl, methylsulfonyl, dimethylaminomethyl, aminomethyl, acetnyl), pyridyl which may be substituted with methoxy, benzamide, 2,3-dihydro-1,4-benzodioxine, triazolyl which may be substituted with phenyl (for example, 4-phenyltriazolyl), thiazolyl, thiazole, thiadiazole which may be substituted with phenyl, pyrimidyl which may be substituted with a substituent (for example, chlorine, phenyl which may be substituted with a substituent (for example, methoxy)), or pyrazol-4-yl which may be substituted with methyl],
R$_1$ is a hydrogen atom, methyl which may be substituted with hydroxy, or ethyl,
R$_2$ is a hydrogen atom, or methyl which may be substituted with a substituent (methoxy, amino, amino which is substituted with methyl or ethyl, amino which is substituted with benzyl, methylsulfanyl, methylsulfonyl, morpholino, thiomorpholino, pyrazolyl, 2-methyl-1H-imidazolyl, 1,4-dioxa-8-azaspiro[4,5]decane, pyrrolidinyl, dimethyltetrahydrofuranyl, piperidino, or methylthio),
or, R$_1$ and R$_2$ together with adjacent carbon atom form cyclopentyl or pyranyl,
R$_3$ is a hydrogen atom, methyl or tert-butyl,
R$_4$ is a hydrogen atom,
R$_5$ is a hydrogen atom, methyl, ethyl, isopropyl, isopropenyl, vinyl, cyclopropyl, phenyl, dimethylaminophenyl or furyl,
R$_6$ is a hydrogen atom, methyl, 4-tolyl or pyridyl,
R$_7$ is a hydrogen atom, hydroxy, methyl, 1-hydroxyethyl, methoxy, ethoxy, isopropyloxy, or acetyl,
are preferable.

Or, those in which
ring A is

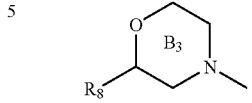

[in the formula,
R$_8$ is phenyl which may be substituted with methoxy, or benzyl],
R$_1$ and R$_2$ are methyl,
R$_3$ and R$_4$ are a hydrogen atom,
R$_5$ and R$_6$ are a hydrogen atom or methyl,
R$_7$ is methyl
are preferred.
Or, those in which
ring A is

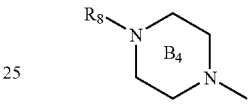

[in the formula,
R$_8$ is phenyl which may be substituted with methoxy],
R$_1$ and R$_2$ are methyl and the like,
R$_3$ and R$_4$ are a hydrogen atom,
R$_5$ to R$_7$ are methyl and the like
are preferred.
In another embodiment, Compound (I) is preferably the following compound: Compound (I-1), Compound (I-2), Compound (I-3), Compound (I-4), Compound (I-5), or Compound (I-6).
[Compound I-1]
Compound (I), wherein
R$_1$ is a hydrogen atom or C$_{1-6}$ alkyl which may be substituted with a hydroxy;
R$_2$ is:
(1) a hydrogen atom, or
(2) C$_{1-6}$ alkyl which may be substituted with a substituent selected from a hydroxy, amino, di-C$_{1-6}$ alkylamino, (C$_{1-6}$ alkyl)(benzyl)amino, mono-C$_{1-6}$ alkylamino, di-benzylamino, C$_{1-6}$alkyl-carbonylamino, formyloxy, C$_{1-6}$ alkylsulfonyloxy, cyano, carboxy, mono-C$_{1-6}$ alkyl-carbamoyl, C$_{1-6}$ alkoxy which may be substituted with a substituent selected from C$_{1-6}$ alkoxy and phenyl, C$_{1-6}$ alkylthio, C$_{1-6}$ alkylsulfonyl, morpholino, 1,1-dioxidothiomorpholine, pyrazolyl, imidazolyl substituted with C$_{1-6}$ alkyl, pyrrolidinyl, piperidyl substituted with an oxo or hydroxy, and 1,4-dioxa-8-azaspiro [4,5]deca-8-yl; or
R$_1$ and R$_2$ form a cyclopentane ring or a tetrahydropyran ring together with an adjacent carbon atom.
As for Compound (I-1), those in which
R$_1$ is C$_{1-6}$ alkyl; and
R$_2$ is a hydrogen atom, or C$_{1-6}$ alkyl which may be substituted with a hydroxy are particularly preferable. Among others, R$_1$ and R$_2$ are preferably C$_{1-6}$ alkyl, and particularly methyl.
[Compound (I-2)]
Compound (I), wherein
R$_3$ is a hydrogen atom or C$_{1-6}$ alkyl; and
R$_4$ is a hydrogen atom.

As for Compound (I-2), those in which R₃ and R₄ are a hydrogen atom are preferable.

[Compound (I-3)]

Compound (I), wherein

R₅ is a hydrogen atom, optionally substituted $C_{1-6}$ alkyl, optionally substituted $C_{2-6}$ alkenyl, optionally substituted $C_{3-6}$ cycloalkyl, optionally substituted $C_{6-14}$ aryl, or a 5- to 6-membered aromatic heterocyclic ring which may be substituted, and contains 1 to 4 heteroatoms selected from a nitrogen atom and an oxygen atom other than a carbon atom;

R₆ is a hydrogen atom, optionally substituted $C_{1-6}$ alkyl, optionally substituted $C_{6-14}$ aryl, a 5- to 6-membered aromatic heterocyclic ring which may be substituted, and contains 1 to 4 heteroatoms selected from a nitrogen atom and an oxygen atom other than a carbon atom, or a halogen atom, and R₇ is a hydrogen atom, hydroxy, optionally substituted $C_{1-6}$ alkyl, optionally substituted $C_{1-6}$ alkoxy, or $C_{1-6}$ alkylcarbonyl.

As for the "$C_{6-14}$ aryl", phenyl is preferable. As for the "5- to 6-membered aromatic heterocyclic ring which contains 1 to 4 heteroatoms selected from a nitrogen atom and an oxygen atom other than a carbon atom", furyl and pyridyl are preferable. A furyl is preferable for the aromatic heterocyclic ring in R₅, and a pyridyl is preferable for the aromatic heterocyclic ring in R₆.

As for Compound (I-3), those in which

R₅ is a hydrogen atom, $C_{1-6}$ alkyl, $C_{2-6}$ alkenyl, $C_{3-6}$ cycloalkyl, phenyl substituted with $diC_{1-6}$ alkylamino, or furyl;

R₆ is a hydrogen atom, $C_{1-6}$ alkyl, phenyl substituted with $C_{1-6}$ alkyl, pyridyl, or a halogen atom; and R₇ is a hydrogen atom, hydroxy, $C_{1-6}$ alkyl which may be substituted with a hydroxy, $C_{1-6}$ alkoxy which may be substituted with $C_{1-6}$ alkoxy, or $C_{1-6}$ alkylcarbonyl are more preferable; and those in which R₅ is $C_{1-6}$ alkyl;
R₆ is $C_{1-6}$ alkyl; and
R₇ is $C_{1-6}$ alkyl or $C_{1-6}$ alkoxy are further more preferable.

[Compound (I-4)]

Compound (I), wherein the partial structural formula:

of Formula (I) is any one of the following formulae:

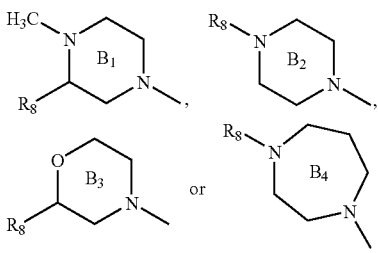

wherein:

R₈ is optionally substituted aryl or an optionally substituted aromatic heterocyclic ring;

Ring B₁ is a further optionally substituted piperazine ring;
Ring B₂ is a further optionally substituted piperazine ring;
Ring B₃ is a further optionally substituted morpholine ring;
Ring B₄ is a further optionally substituted homopiperazine ring;

- - - - -
is a single bond;

R₅ is a hydrogen atom, optionally substituted $C_{1-6}$ alkyl, optionally substituted $C_{2-6}$ alkenyl, optionally substituted $C_{3-6}$ cycloalkyl, optionally substituted $C_{6-14}$ aryl, optionally substituted 5- to 6-membered aromatic heterocyclic ring containing 1 to 4 heteroatoms selected from a nitrogen atom and an oxygen atom other than a carbon atom;

R₆ is a hydrogen atom, optionally substituted $C_{1-6}$ alkyl, optionally substituted $C_{6-14}$ aryl, optionally substituted 5- or 6-membered aromatic heterocyclic ring containing 1 to 4 heteroatoms selected from a nitrogen atom and an oxygen atom other than a carbon atom, or a halogen atom; and R₇ is a hydrogen atom, hydroxy, optionally substituted $C_{1-6}$ alkyl, optionally substituted $C_{1-6}$ alkoxy, or $C_{1-6}$ alkylcarbonyl.

[Compound (I-5)]

Compound (I), wherein the partial structural formula:

of Formula (I) is any one of the following formulae:

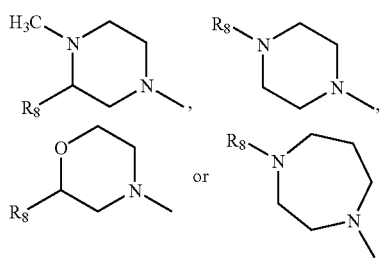

wherein:

R₈ is:

(1) $C_{6-14}$ aryl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) a 5- to 10-membered aromatic heterocyclic ring containing 1 to 4 hetero atoms selected from a nitrogen atom, a sulfur atom, and an oxygen atom, other than a carbon atom, and which may be substituted with 1 to 3 substituents selected from a halogen atom, $C_{1-6}$ alkyl, $C_{1-6}$ alkoxy, and phenyl which may be substituted with $C_{1-6}$ alkoxy;

- - - - -
is a single bond;

R₁ is a hydrogen atom or $C_{1-6}$ alkyl which may be substituted with a hydroxy;

R₂ is:

(1) a hydrogen atom; or (2) $C_{1-6}$ alkyl which may be substituted with a substituent selected from a hydroxy, amino, di-$C_{1-6}$ alkylamino, ($C_{1-6}$ alkyl)(benzyl)amino, mono-$C_{1-6}$ alkylamino, di-benzylamino, $C_{1-6}$ alkyl-carbonylamino, formyloxy, $C_{1-6}$ alkylsulfonyloxy, cyano, carboxy, mono-$C_{1-6}$ alkyl-carbamoyl, $C_{1-6}$ alkoxy which may be substituted with a substituent selected from $C_{1-6}$ alkoxy and phenyl, $C_{1-6}$ alkylthio, $C_{1-6}$ alkylsulfonyl, morpholino, 1,1-dioxidothiomorpholine, pyrazolyl, imidazolyl substituted with $C_{1-6}$ alkyl, pyrrolidinyl, piperidinyl substituted with an oxo or hydroxy, and 1,4-dioxa-8-azaspiro[4,5]deca-8-yl; or $R_1$ and $R_2$ form a cyclopentane ring or a tetrahydropyran ring together with an adjacent carbon atom;

$R_3$ is a hydrogen atom or $C_{1-6}$ alkyl; and $R_4$ is a hydrogen atom;

$R_5$ is a hydrogen atom, $C_{1-6}$ alkyl, $C_{2-6}$ alkenyl, $C_{3-6}$ cycloalkyl, phenyl substituted with $diC_{1-6}$ alkylamino, or furyl;

$R_6$ is a hydrogen atom, $C_{1-6}$ alkyl, phenyl substituted with $C_{1-6}$ alkyl, pyridyl, or a halogen atom, and $R_7$ is a hydrogen atom, hydroxy, $C_{1-6}$ alkyl which may be substituted with a hydroxy, $C_{1-6}$ alkoxy which may be substituted with $C_{1-6}$ alkoxy, or $C_{1-6}$ alkylcarbonyl.

$R_8$ is preferably:

(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl; or (2) pyrimidinyl, thiadiazolyl, thiazolyl, pyrazolyl, isoxazolyl, imidazolyl, or pyrazolopyrimidinyl which may be substituted with 1 to 3 substituents selected from a halogen atom, $C_{1-6}$ alkyl, $C_{1-6}$ alkoxy, and phenyl which may be substituted with $C_{1-6}$ alkoxy.

As for Compound (I-5), the partial structural formula:

of Formula (I) is preferably the following formula:

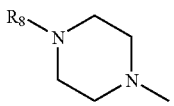

wherein:

$R_8$ is:

(1) phenyl which may be substituted with 1 to 3 substituents selected from (i) a halogen atom; (ii) $C_{1-6}$ alkoxy which may be substituted with a halogen atom; (iii) $C_{1-6}$ alkyl which may be substituted with a substituent selected from a halogen atom, a hydroxy, amino, and $diC_{1-6}$ alkylamino; (iv) $C_{1-6}$ alkylthio; (v) $C_{1-6}$ alkylsulfonyl; (vi) cyano; (vii) carbamoyl; (viii) $C_{1-6}$ alkylsulfinyl; and (ix) $C_{1-6}$ alkylcarbonyl;

(2) pyridyl which may be substituted with 1 to 3 $C_{1-6}$ alkoxy groups;

(3) pyrimidinyl which may be substituted with 1 to 3 substituents selected from phenyl which may be substituted with $C_{1-6}$ alkoxy, and a halogen atom;

(4) thiadiazolyl which may be substituted with a phenyl;

(5) thiazolyl;

(6) pyrazolyl which may be substituted with 1 to 2 $C_{1-6}$ alkyl groups;

(7) isoxazolyl;

(8) imidazolyl which may be substituted with 1 to 2 $C_{1-6}$ alkyl groups; or (9) pyrazolopyrimidinyl which may be substituted with 1 to 2 $C_{1-6}$ alkyl groups.

The partial structural formula:

of Formula (I) is more preferably the following formula:

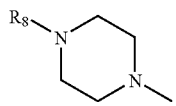

wherein:

$R_8$ is a phenyl which may be substituted with 1 to 3 substituents selected from:

(1) a halogen atom;

(2) $C_{1-6}$ alkoxy which may be substituted with a halogen atom;

(3) $C_{1-6}$ alkyl which may be substituted with a substituent selected from a halogen atom, a hydroxy, amino, and $diC_{1-6}$ alkylamino;

(4) $C_{1-6}$ alkylthio;

(5) $C_{1-6}$ alkylsulfonyl;

(6) cyano;

(7) carbamoyl;

(8) $C_{1-6}$ alkylsulfinyl; and (9) $C_{1-6}$ alkylcarbonyl.

[Compound (I-6)]

Compound (I), wherein the partial structural formula:

of Formula (I) is the following formula:

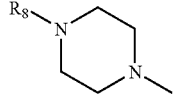

wherein:

$R_8$ is a phenyl which is substituted with 1 to 3 $C_{1-6}$ alkoxy;

is a single bond;

$R_1$ is $C_{1-6}$ alkyl;

$R_2$ is a hydrogen atom, or $C_{1-6}$ alkyl which may be substituted with a hydroxy;

$R_3$ and $R_4$ are a hydrogen atom;

$R_5$ is $C_{1-6}$ alkyl;

$R_6$ is $C_{1-6}$ alkyl; and $R_7$ is $C_{1-6}$ alkyl or $C_{1-6}$ alkoxy.

As for Compound (I-6), $R_1$ and $R_2$ are preferably $C_{1-6}$ alkyl, particularly methyl.

As a more specific example of Compound (I), the compounds described in the following Example 1 to Example 144 or salts thereof are preferable. Particularly preferable are the following compounds:

1-(4-Methoxyphenyl)-4-(2,2,4,6,7-pentamethyl-2,3-dihydro-1-benzofuran-5-yl)piperazine or a salt thereof;

1-(4-Methoxyphenyl)-4-[(2R)-2,4,6,7-tetramethyl-2,3-dihydro-1-benzofuran-5-yl]piperazine or a salt thereof;

1-(4-Methoxyphenyl)-4-[(2S)-2,4,6,7-tetramethyl-2,3-dihydro-1-benzofuran-5-yl]piperazine or a salt thereof;

1-(4-Methoxyphenyl)-4-(7-methoxy-2,2,4,6-tetramethyl-2,3-dihydro-1-benzofuran-5-yl)piperazine or a salt thereof;

1-(4-Ethoxyphenyl)-4-(7-methoxy-2,2,4,6-tetramethyl-2,3-dihydro-1-benzofuran-5-yl)piperazine or a salt thereof;

(−)-{5-[4-(4-methoxyphenyl)piperazin-1-yl]-2,4,6,7-tetramethyl-2,3-dihydro-1-benzofuran-2-yl}methanol or a salt thereof; and (+)-{5-[4-(4-methoxyphenyl)piperazin-1-yl]-2,4,6,7-tetramethyl-2,3-dihydro-1-benzofuran-2-yl}methanol or a salt thereof.

Hereinbelow, the method of producing Compound (I) will be described. Further, all of the Compounds (Ia), (Ib), (Ic), (Id), (Ie), (7) and (7a) described below are included in Compound (I). Compound (I) can be produced by using a general organic synthesis method or in view of other well known synthesis method (for example: pamphlet of WO2004/016576). Each symbol for the compounds that are described in brief drawings of reaction scheme has the same meaning as defined in the above. The compounds described in the reaction scheme include salt form of the compounds, and as an example of the salt, those that are the same as the salt of Compound (I) can be also mentioned.

Reaction scheme 1:

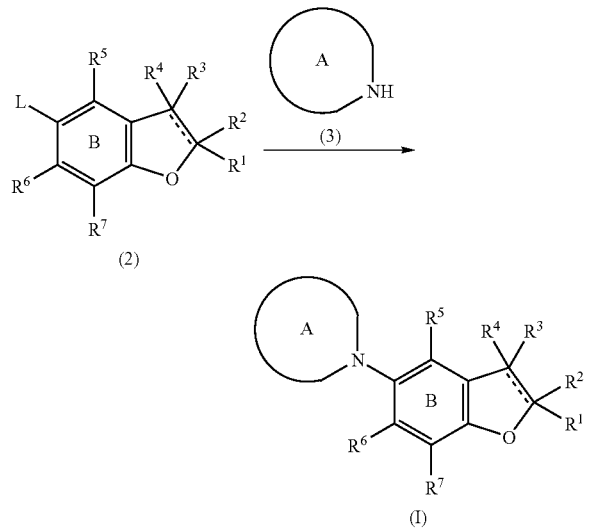

In Reaction scheme 1, L is a leaving group, and other symbols are as defined in the above.

According to Reaction scheme 1, compound (2) is reacted with the 4- to 8-membered cyclic amino compound (3) represented by the following formula:

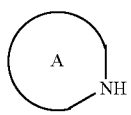

(in the formula, ring A is as defined in the above), in the presence of a base, if desired, to produce Compound (I). If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

As for the "substituent which may be included (in ring B) in addition to L" of Compound (2), those that are the same as the "substituent which may be further included" in ring B of Compound (I) are used in the same number.

Compound (3) can be easily obtained as a commercial product, and also can be produced according to a method known per se.

The amount of compound (3) to be used is about 0.5 to about 10 moles, preferably about 1.0 to about 3.0 moles compared to 1 mole of the compound (2).

As an example of the "leaving group" that is indicated by L, a halogen atom (for example, fluorine, chlorine, bromine, iodine and the like), $C_{1-6}$ alkylsulfonyloxy which may be halogenated (for example, methanesulfonyloxy, trifluoromethanesulfonyloxy, trichloromethanesulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like are included, for example.

The amount of the base to be used is about 0.8 to about 10 moles, preferably about 1.0 to about 5.0 moles compared to 1 mole of the compound (2).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (2).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis(dibenzylideneacetone) palladium and the like can be used.

The amount of the phosphine to be used is about 0.001 to about 10 moles, preferably about 0.01 to about 1.0 mole compared to 1 mole of the compound (2). The amount of the palladium catalyst to be used is about 0.0001 to about 5.0 moles, preferably about 0.01 to about 0.5 moles compared to 1 mole of the compound (2):

Reaction time is generally about 30 minutes to about 72 hours, preferably about 1 hour to about 48 hours. Reaction temperature is generally about −20 to about 200° C., preferably about 0 to about 150° C.

Reaction scheme 2

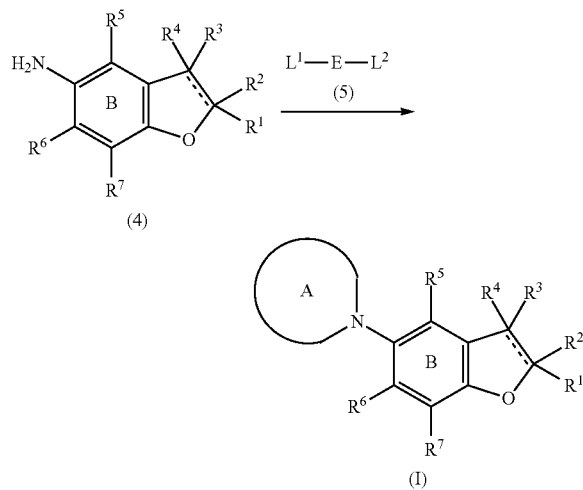

In Reaction scheme 2, $L^1$ and $L^2$ represent the same or different leaving group, E represents an atomic group which constitutes ring A except the nitrogen atom bonded to ring B of Compound (I), and other symbols are as defined in the above.

According to Reaction scheme 2, compound (4) is reacted with compound (5) represented by the following formula:

$$L^1\text{-}E\text{-}L^2$$

in the presence of a base, if desired, to produce Compound (I).

As for the "substituent which may be further included" in ring B for compound (4), those that are the same as the "substituent which may be further included" in ring B of Compound (I) are used in the same number.

Compound (5) can be easily obtained as a commercial product, and also can be produced according to a method known per se.

As an example of the "leaving group" that is indicated by $L^1$ and $L^2$, hydroxy, a halogen atom (for example, fluorine, chlorine, bromine, iodine and the like), $C_{1-5}$ alkylsulfonyloxy (for example, methanesulfonyloxy, ethanesulfonyloxy, trichloromethanesulfonyloxy and the like) which may be halogenated, $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro, and the like can be mentioned. Specifically, benzenesulfonyloxy, m-nitrobenzenesulfonyloxy, p-toluenesulfonyloxy and the like can be mentioned.

The amount of compound (5) to be used is about 0.8 to about 5.0 moles, preferably about 1.0 to about 2.0 moles compared to 1 mole of the compound (4).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like are included, for example.

The amount of the base to be used is about 0.5 to about 10 moles, preferably about 1.0 to about 3.0 moles compared to 1 mole of the compound (4). Further, if desired, the reaction can be carried out in the co-presence of quaternary ammonium salts or metal iodides with the base.

As an example of the "quaternary ammonium salts", tetrabutyl ammonium iodide and the like can be mentioned, for example.

As an example of the "metal iodide", sodium iodide, potassium iodide and the like can be mentioned, for example.

The amount of the quaternary ammonium salts to be used is about 0.1 to about 3.0 moles, preferably about 0.5 to about 1.0 mole compared to 1 mole of the compound (4).

The amount of the metal iodide to be used is about 0.1 to about 3.0 moles, preferably about 0.5 to about 1.0 mole compared to 1 mole of the compound (4).

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

Reaction scheme 3

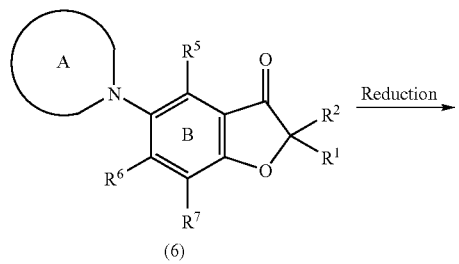

(6)

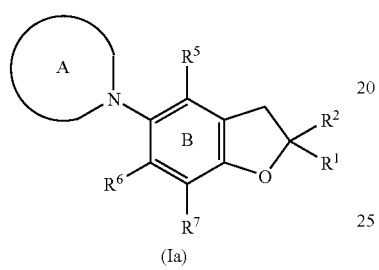

(Ia)

Reaction scheme 4

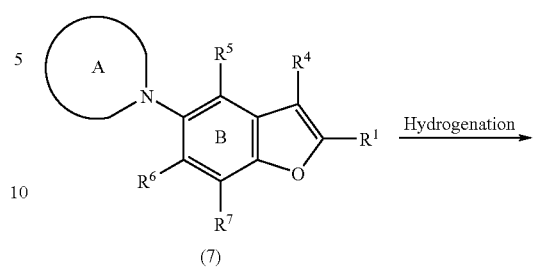

(7)

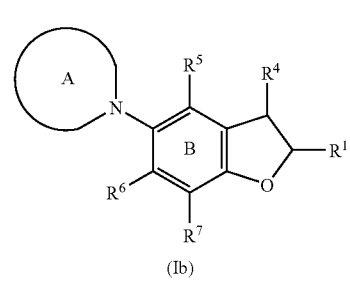

(Ib)

In Reaction scheme 3, the symbols are as defined in the above.

Compound (Ia) is produced by reducing compound (6) with a reducing agent according to Reaction scheme 3.

As for the "substituent which may be further included" in ring B for compound (6), those that are the same as the "substituent which may be further included" in ring B of Compound (Ia) are used in the same number.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (6).

The amount of the Lewis acids to be used is about 0.8 to about 10.0 moles, preferably about 1.0 to about 5.0 moles compared to 1 mole of the compound (6).

It is advantageous to carry out the reaction by using a solvent inert to the reaction. Such a solvent, though being not particularly limited as far as the reaction proceeds, is preferably exemplified by alcohols such as methanol, ethanol, propanol, and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

In Reaction scheme 4, the symbols are as defined in the above.

Compound (Ib) is produced according to contact hydrogenation reaction of compound (7) in the presence of various catalysts under hydrogen atmosphere according to Reaction scheme 4.

As for the "substituent which may be further included" in ring B for compound (7), those that are the same as the "substituent which may be further included" in ring B of Compound (Ib) are used in the same number.

As for the catalyst to be used, platinum oxide, activated carbon that is added with platinum, activated carbon that is added with palladium, nickel, copper-chrome oxide, rhodium, cobalt, ruthenium and the like are used. The amount of the catalyst to be used is about 5 to about 1000% by weight compared to compound (7).

It is advantageous to carry out the reaction by using a solvent inert to the reaction. Such a solvent, though being not particularly limited as far as the reaction proceeds, is preferably exemplified by alcohols such as methanol, ethanol, propanol, and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, water, or a mixed solvent thereof, and the like.

Reaction time is generally about 30 minutes to about 48 hours, preferably about 30 minutes to about 24 hours. Reaction temperature is generally about 0 to about 120° C., preferably about 20 to about 80° C.

Reaction scheme 5

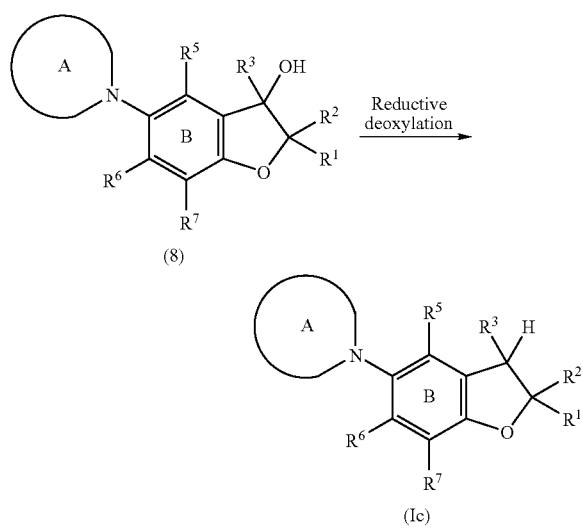

In Reaction scheme 5, the symbols are as defined in the above.

Compound (Ic) is produced according to reductive deoxylation of compound (8) by using a reducing agent according to Reaction scheme 5.

As for the "substituent which may be further included" in ring B for compound (8), those that are the same as the "substituent which may be further included" in ring B of Compound (Ic) are used in the same number.

As for the reductive deoxylation, a hydrogenation method known per se, a method using organosilicon reagent (alkylsilane reagent and the like) and the like are included.

Compound (Ic) can be produced by reacting compound (8) with a metal catalyst under hydrogen atmosphere according to the hydrogenation method. If desired, an appropriate acid catalyst can be added.

As for the "metal catalyst", Raney nickel, platinum oxide, metal palladium, activated carbon that is added with palladium, and the like are used. The amount of each "metal catalyst" to be used is about 1 to about 1000% by weight, preferably about 5 to about 20% by weight compared to compound (8).

As for the "acid catalyst", organic acids such as formic acid, acetic acid, trifluoroacetic acid, p-toluene sulfonic acid and the like, mineral acids such as sulfuric acid, hydrochloric acid, hydrobromic acid and the like are used. The amount of the each "acid catalyst" to be used is about 0.1 to excess moles compared to 1 mole of the compound (8).

It is advantageous to carry out the reaction by using a solvent inert to the reaction. Such a solvent, though being not particularly limited as far as the reaction proceeds, is preferably exemplified by alcohols such as methanol, ethanol, propanol, and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, organic acids such as acetic acid and the like, water, or a mixed solvent thereof, and the like. Hydrogen pressure is generally about 1 to about 100 atm, preferably about 1 to about 5 atm. Reaction time is generally about 30 minutes to about 48 hours, preferably about 1 to 24 hours. Reaction temperature is generally about 0 to about 120° C., preferably about 20 to about 80° C.

Regarding the method of using an organosilylating reagent (alkylsilane reagent), Compound (Ic) can be produced by reacting compound (8) with the alkylsilane reagent and acid.

Examples of the alkylsilane reagent include triethylsilane, phenyldimethyl silane and the like. The amount of the "alkylsilane reagent" to be used is about 0.8 to about 20 moles, preferably about 1 to about 10 moles compared to 1 mole of the compound (8).

As for the acid, organic acids such as trifluoroacetic acid and the like are used. The amount of the acids to be used is about 0.1 to excess moles compared to 1 mole of the compound (8).

It is advantageous to carry out the reaction by not using any solvent or by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane and the like, hydrocarbons such as benzene, toluene, cyclohexane, hexane and the like, organic acids such as acetic acid, trifluoroacetic acid and the like, or a mixed solvent thereof, and the like.

Reaction scheme 6

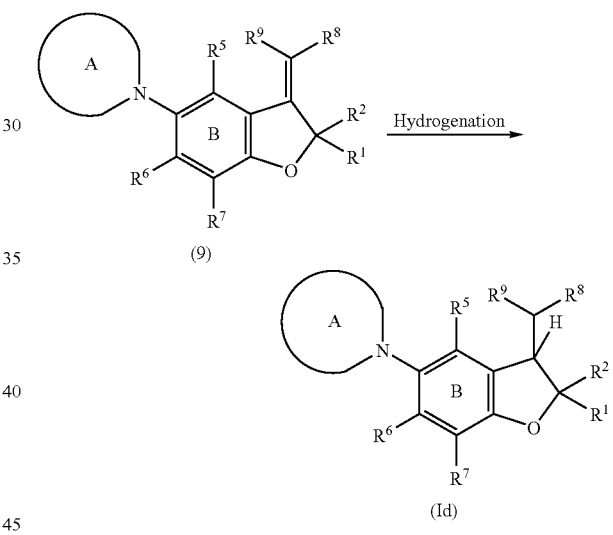

In Reaction scheme 6, $R^8$ and $R^9$ are a hydrogen, or lower alkyl group which may be substituted, and other symbols are as defined in the above.

Compound (Id) is produced according to contact hydrogenation reaction of compound (9) in the presence of various catalysts under hydrogen atmosphere according to Reaction scheme 6.

As for the "substituent which may be further included" in ring B for compound (9), those that are the same as the "substituent which may be further included" in ring B of Compound (Id) are used in the same number.

As for the catalyst to be used, platinum oxide, activated carbon that is added with platinum, activated carbon that is added with palladium, nickel, copper-chrome oxide, rhodium, cobalt, ruthenium and the like are used. The amount of the catalyst to be used is about 5 to about 1000% by weight compared to compound (9).

It is advantageous to carry out the reaction by using a solvent inert to the reaction. Such a solvent, though being not particularly limited as far as the reaction proceeds, is preferably exemplified by alcohols such as methanol, ethanol, propanol, and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, water and the like or a mixed solvent thereof, and the like.

Reaction time is generally about 30 minutes to about 48 hours, preferably about 30 minutes to about 24 hours. Reaction temperature is generally about 0 to about 120° C., preferably about 20 to about 80° C.

Reaction scheme 7

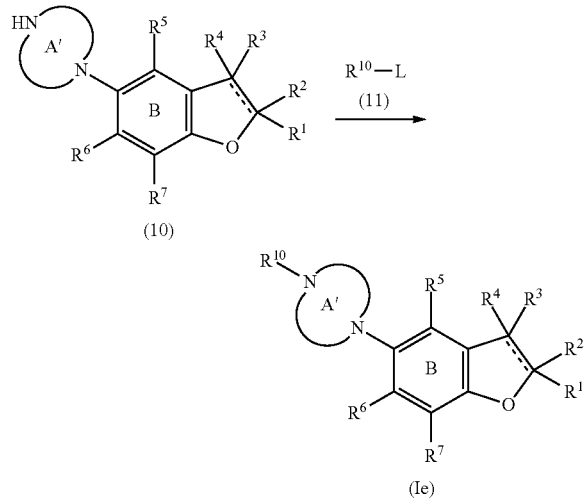

In Reaction scheme 7, L is a leaving group, $R^{10}$ is a benzene ring or a heteroaryl ring which may be substituted, and other symbols are as defined in the above.

According to Reaction scheme 7, compound (10) is reacted with benzene and the heterocyclic derivative (11) that is represented by the following formula:

$$R^{10}\text{-L}$$

in the presence of a base, if desired, to give Compound (Ie). If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

As for the "substituent which may be further included" in ring B of compound (10), those that are the same as the "substituent which may be further included" in ring B of Compound (Ie) are used in the same number.

Compound (11) can be easily obtained as a commercial product, and also can be produced according to a method known per se.

The amount of compound (11) to be used is about 0.5 to about 10 moles, preferably about 1.0 to about 3.0 moles compared to 1 mole of the compound (10).

As an example of the "leaving group" that is indicated by L, a halogen atom (for example, fluorine, chlorine, bromine, iodine and the like), $C_{1-5}$ alkylsulfonyloxy which may be halogenated (for example, methanesulfonyloxy, trifluoromethanesulfonyloxy, trichloromethanesulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like are included, for example.

The amount of the base to be used is about 0.8 to about 10.0 moles, preferably about 1.0 to about 5.0 moles compared to 1 mole of the compound (10).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (10).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis (dibenzylideneacetone) palladium and the like can be used.

The amount of the phosphine to be used is about 0.001 to about 10.0 moles, preferably about 0.01 to about 1.0 mole compared to 1 mole of the compound (10). The amount of the palladium catalyst to be used is about 0.0001 to about 5.0 moles, preferably about 0.01 to about 0.5 moles compared to 1 mole of the compound (10).

Reaction time is generally about 30 minutes to about 72 hours, preferably about 1 hour to about 48 hours. Reaction temperature is generally about −20 to about 200° C., preferably about 0 to about 150° C.

Reaction scheme 8

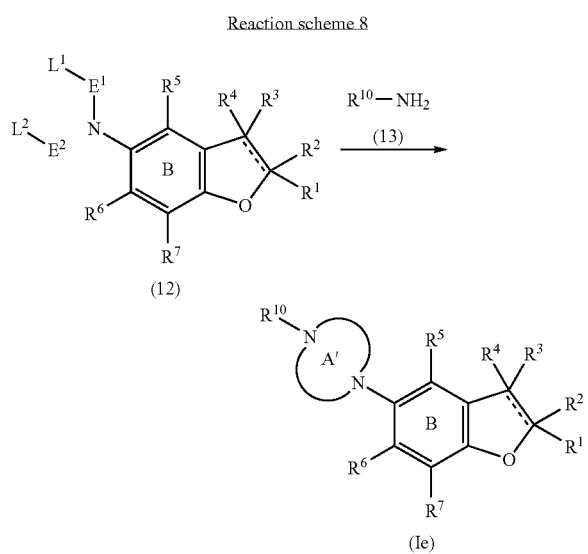

In Reaction scheme 8, $L^1$ and $L^2$, which are the same or different from each other, are a leaving group, $R^{10}$ is a benzene ring or a heteroaryl ring which may be substituted, $E^1$ and $E^2$ are an atomic group constituting ring A' except the two nitrogen atoms in Compound (Ie), and other symbols are as defined in the above.

According to Reaction scheme 8, compound (12) is reacted with compound (13) that is represented by the following formula in the presence of a base, if desired, to give Compound (Ie).

$R^{10}$—$NH_2$

As for the "substituent which may be further included" in ring B of compound (12), those that are the same as the "substituent which may be further included" in ring B of Compound (Ie) are used in the same number.

Compound (13) can be easily obtained as a commercial product, and also can be produced according to a method known per se.

As an example of the "leaving group" that is indicated by $L^1$ and $L^2$, hydroxy, a halogen atom (for example, fluorine, chlorine, bromine, iodine and the like), $C_{1-5}$ alkylsulfonyloxy which may be halogenated (for example, methanesulfonyloxy, ethanesulfonyloxy, trichloromethanesulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

The amount of compound (13) to be used is about 0.8 to about 5.0 moles, preferably about 1.0 to about 2.0 moles compared to 1 mole of the compound (12).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like are included, for example.

The amount of the base to be used is about 0.5 to about 10.0 moles, preferably about 1.0 to about 3.0 moles compared to 1 mole of the compound (12). Further, if desired, the reaction can be carried out in the co-presence of quaternary ammonium salts or metal iodides with the base.

As an example of the "quaternary ammonium salts", tetrabutyl ammonium iodide and the like can be mentioned, for example.

As an example of the "metal iodide", sodium iodide, potassium iodide and the like can be mentioned, for example.

The amount of the quaternary ammonium salts to be used is about 0.1 to about 3.0 moles, preferably about 0.5 to about 1.0 mole compared to 1 mole of the compound (12).

The amount of the metal iodide to be used is about 0.1 to about 3.0 moles, preferably about 0.5 to about 1.0 mole compared to 1 mole of the compound (12).

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

Further, the substituents of $R^1$, $R^2$, $R^3$, $R^4$, $R^5$, $R^6$, $R^7$ of Compound (I) of the present invention that is represented by the following formula and the substituent which binds to the atoms constituting ring A except the nitrogen atom bonded to ring B:

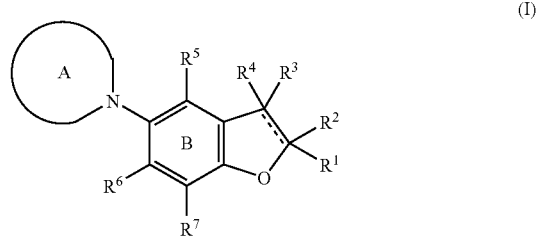

can be converted to others based on a general organic reaction, for example, a reduction reaction, an oxidation reaction, a substitution reaction, an alkylation reaction, a hydrolysis reaction, an addition reaction using an alkyl lithium reagent or Grignard reagent, an aldol reaction, a coupling reaction using palladium catalyst, like a Suzuki coupling reaction and Buchwald amination reaction, a dehydrating condensation reaction like esterification, amidation and the like, a reductive alkylation reaction and the like.

The product can be isolated from the reaction mixture according to a method generally known in the art, and can be easily purified by common means for separation (for example, recrystallization, distillation, chromatography and the like).

Compound (2) is produced according to the methods known per se, for example the method described in JP-A No. 5-140142, or other methods that are similar to them.

Further, compound (2a), which is included in compound (2), is also produced according to the method described in the following Reaction scheme.

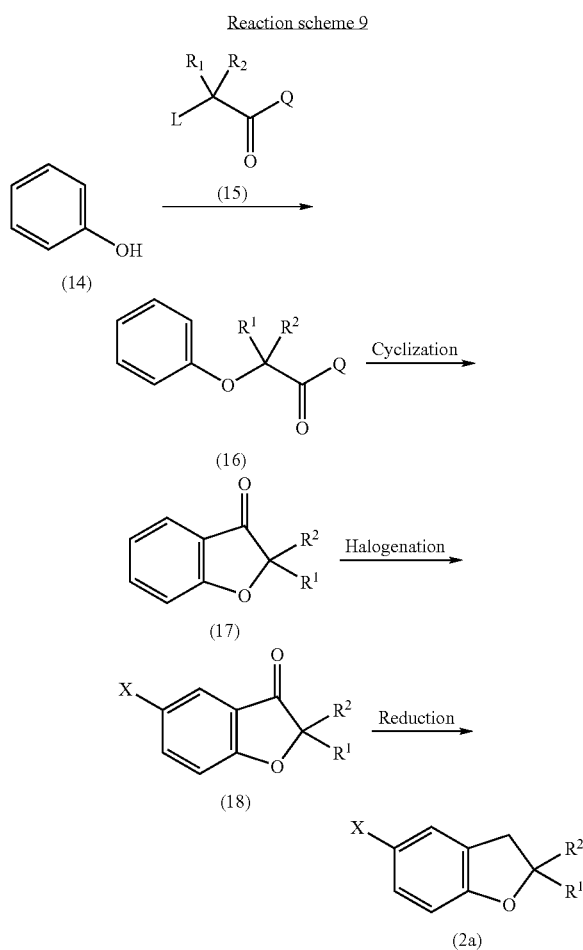

In Reaction scheme 9, the group indicated by —CO—Q is carboxylic acid or reactive derivatives thereof, L is a leaving group, X is a halogen atom, and other symbols are as defined in the above.

Compound (16) is produced by reacting compound (14) and compound (15) in the presence of a base, if desired.

Compound (14) and Compound (15) can be easily obtained as a commercial product, and also can be produced according to a method known per se.

As an example of the "leaving group" that is indicated by L, hydroxy, a halogen atom (for example, fluorine, chlorine, bromine, iodine and the like), $C_{1-6}$ alkylsulfonyloxy (for example, methanesulfonyloxy, ethanesulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), halogen (for example, chloro, bromo, iodo and the like) and nitro and the like can be mentioned. As a specific example, benzenesulfonyloxy, p-toluenesulfonyloxy, p-bromobenzenesulfonyloxy, m-nitrobenzenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of compound (15) to be used is about 0.8 to about 5.0 moles, preferably about 1.0 to about 3.0 moles compared to 1 mole of the compound (14).

The amount of the base to be used is about 0.8 to about 5.0 moles, preferably about 1.0 to about 3.0 moles compared to 1 mole of the compound (14). Further, if desired, the reaction can be carried out in the co-presence of quaternary ammonium salts with the base.

As an example of the "quaternary ammonium salts", tetrabutyl ammonium iodide and the like can be mentioned, for example.

The amount of the quaternary ammonium salts to be used is about 0.1 to about 2.0 moles, preferably about 0.5 to about 1.0 mole compared to 1 mole of the compound (14).

It is advantageous to carry out the reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, ketones such as acetone, methylethyl ketone and the like, and a mixed solvent thereof, and the like.

Reaction time is generally about 30 minutes to about 96 hours, preferably about 1 hour to about 72 hours. Reaction temperature is generally about 0 to about 120° C., preferably about 0 to about 60° C.

Instead of the reaction above, Mitsunobu reaction can also be employed [Synthesis, 1981, 1 to 27 pages].

For the reaction, compound (14) and compound (15) in which L is OH are reacted in the presence of azodicarboxylates (for example, diethylazodicarboxylate and the like) and phosphines (for example, triphenyl phosphine, tributyl phosphine and the like).

The amount of compound (15) to be used is about 0.8 to about 5.0 moles, preferably about 1.0 to about 3.0 moles compared to 1 mole of the compound (14).

The amount of the "azodicarboxylates" and the "phosphines" to be used is about 0.8 to about 5.0 moles, preferably about 1.0 to about 3.0 moles, respectively, compared to 1 mole of the compound (14).

It is advantageous to carry out the reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

Reaction time is generally about 5 minutes to about 48 hours, preferably about 30 minutes to about 24 hours. Reaction temperature is generally about −20 to about 200° C., preferably about 0 to about 100° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (17) is produced by subjecting compound (16) to a cyclization reaction which is known in the art per se.

As for the cyclization reaction, it is carried out by using acid.

For the reaction, Q is preferably hydroxy, halogen and the like. According to the reaction, compound (16) is reacted with acid to obtain compound (17), as desired.

As for the "acid", Lewis acids such as aluminum chloride, iron chloride, tin chloride (IV), titanium tetrachloride, boron trifluoride diethyl ether and the like, mineral acids such as polyphosphoric acid, sulfuric acid and the like, and organic acids such as trifluoroacetic acid, methanesulfonic acid, p-toluenesulfonic acid, trifluoromethanesulfonic acid and the like are used.

The amount of the "acid" to be used is a catalytic amount to excess amount, preferably about 0.8 to about 10 moles compared to 1 mole of the compound (16).

It is advantageous to carry out the reaction by not using a solvent or by using a solvent inert to the reaction. Such a solvent, though being not particularly limited as far as the reaction proceeds, is preferably exemplified by carbon disulfide, nitroalkanes such as nitromethane and the like, nitroaryls such as nitrobenzene and the like, halogenated carbons such as dichloromethane, 1,2-dichloroethane, 1,2-dichlorobenzene and the like, organic acids such as acetic acid, trifluoroacetic acid and the like, acid anhydrides such as acetic anhydride, trifluoroacetic anhydride and the like or a mixed solvent thereof, and the like.

Reaction time is generally about 10 minutes to about 96 hours, preferably about 10 minutes to about 12 hours. Reaction temperature is generally about −70 to about 200° C., preferably about −40 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (18) is produced by reacting compound (17) with a halogenating reagent.

As for the "halogenating reagent", chlorine, bromine iodine, imides such as N-chlorosuccinic imide, N-bromosuccinic imide and the like, halogen adducts such as benzyltrimethylammonium tribromide and the like are used. The amount of the halogenating reagent to be used is about 0.8 to about 5.0 moles, preferably about 1.0 to about 2.0 moles compared to 1 mole of the compound (17).

It is advantageous to carry out the reaction by using a solvent inert to the reaction. Such a solvent, though being not particularly limited as far as the reaction proceeds, is preferably exemplified by ethers such as diethyl ether, diisopropyl ether, tetrahydrofuran, dioxane, 1,2-dimethoxyethane and the like, alcohols such as methanol, ethanol, propanol and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, organic acids such as acetic acid, propionic acid and the like, nitroalkanes such as nitromethane and the like, aromatic amines such as pyridine, lutidine, quinoline and the like, or a mixed solvent thereof, and the like.

The reaction is carried out in the presence of base, Lewis acid or iron, if desired.

As for the "base", basic salts such as sodium carbonate, calcium carbonate, cesium carbonate, sodium hydrogen carbonate, sodium acetate, potassium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, can be mentioned, for example. The amount of the base to be used is about 0.8 to about 10 moles compared to 1 mole of the compound (17).

As for the "Lewis acid", iron chloride, aluminum chloride, boron trifluoride and the like can be mentioned. The amount of the Lewis acid to be used is about 0.01 to about 5 moles compared to 1 mole of the compound (17).

The amount of the "iron" to be used is about 0.01 to about 5 moles compared to 1 mole of the compound (17).

Reaction temperature is generally about −50 to about 150° C., preferably about −20 to about 100° C. Reaction time is generally about 5 minutes to about 24 hours, preferably about 10 minutes to about 12 hours.

Compound (2a) is produced by reducing compound (18) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (18).

The amount of the Lewis acids to be used is about 0.8 to about 10.0 moles, preferably about 1.0 to about 5.0 moles compared to 1 mole of the compound (18).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N- dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, and a mixed solvent thereof, and the like.

Reaction time is generally about 10 minutes to about 72 hours, preferably about 30 minutes to about 24 hours. Reaction temperature is generally about −20 to about 200° C., preferably about 20 to about 120° C.

Further, when a halogen atom is substituted at the para-position of the hydroxy group of compound (14), compound (2a) can be produced without performing the halogenation.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Further, compound (2b), which is included in compound (2), is also produced according to the method described in the following Reaction scheme.

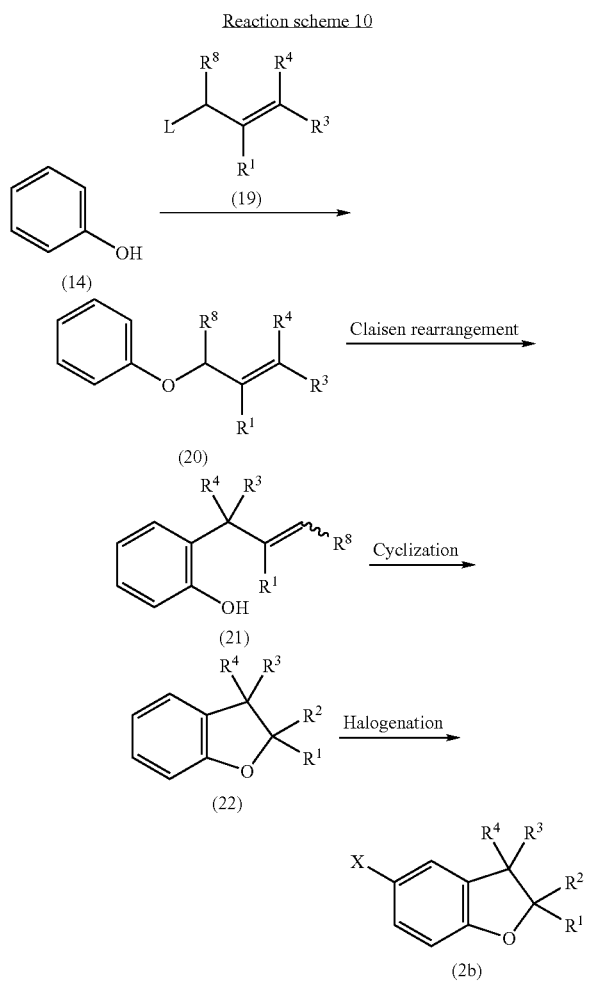

In Reaction scheme 10, L is a leaving group, X is a halogen atom, $R^{11}$ is a hydrogen atom or a group that is obtained by removing one methylene from $R^2$, and other symbols are as defined in the above.

Compound (20) is produced by reacting compound (14) and compound (19) in the presence of a base, if desired.

Compound (14) can be easily obtained as a commercial product, and also can be produced according to a method known per se.

Compound (19) can be easily obtained as a commercial product, and also can be produced according to a method known per se.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

The amount of compound (19) to be used is about 0.8 to about 5.0 moles, preferably about 1.0 to about 2.0 moles compared to 1 mole of the compound (14).

As for the "base", inorganic bases including alkali metal hydroxides such as sodium hydroxide, potassium hydroxide and the like, alkali metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, basic salts such as potassium hydrogen carbonate, sodium carbonate, potassium carbonate, sodium acetate and the like can be mentioned, for example.

The amount of the base to be used is about 0.5 to about 5.0 moles, preferably about 1.0 to about 3.0 moles compared to 1 mole of the compound (14).

It is advantageous to carry out the reaction by using a solvent inert to the reaction. Such a solvent is preferably exemplified by alcohols such as methanol, ethanol, propanol and the like, hydrocarbons such as cyclohexane, hexane, benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, water or a mixed solvent thereof, and the like.

Reaction time is generally about 10 minutes to about 8 hours, preferably about 30 minutes to about 3 hours. Reaction temperature is generally about 0 to about 120° C., preferably about 25 to about 100° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (21) is produced by Claisen rearrangement of compound (20).

It is advantageous to carry out the reaction by not using any solvent or by using a solvent inert to the reaction. Such a solvent, though being not particularly limited as far as the reaction proceeds, is preferably exemplified by alcohols such as methanol, ethanol, propanol and the like, hydrocarbons such as cyclohexane, hexane, benzene, toluene, xylene, mesitylene and the like, organic acids such as formic acid, acetic acid and the like, ethers such as tetrahydrofuran, dioxane, 1,2-dimethoxyethane, diethyl ether, diisopropyl ether and the like, anilines such as N,N-dimethylaniline, N,N-diethylaniline and the like, halogenated hydrocarbons such as dichloromethane, chloroform, carbon tetrachloride, 1,2-dichloroethane and the like or a mixed solvent thereof, and the like.

Further, if desired, the reaction can be carried out by using an acid catalyst.

As for the acid catalyst, Lewis acids such as aluminum chloride, boron trifluoride and the like are used.

The amount of the acid catalyst to be used is, in case of Lewis acid, generally about 0.1 to about 20 moles, preferably about 0.1 to about 5.0 moles compared to 1 mole of the compound (20).

Reaction time is generally about 30 minutes to about 24 hours, preferably about 1 to about 6 hours. Reaction temperature is generally about −70 to about 300° C., preferably about 150 to about 250° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (22) is produced by the ring closure of compound (21) using an acid catalyst. As for the acid catalyst, mineral acids such as hydrochloric acid, hydrobromic acid sulfuric acid and the like, sulfonic acids such as p-toluenesulfonic acid, camphor sulfonic acid and the like, Lewis acids such as aluminum chloride, boron trifluoride and the like are used.

The amount of the acid catalyst to be used is generally about 0.8 to about 100 moles, preferably about 10 to about 50 moles compared to 1 mole of the compound (21) for the mineral acids. The amount of the acid catalyst to be used is generally about 0.01 to about 20 moles, preferably about 0.05 to about 5 moles compared to 1 mole of the compound (21) for the sulfonic acids, for example.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

Reaction time is generally about 30 minutes to about 24 hours, preferably about 30 minutes to about 6 hours. Reaction temperature is generally about −78 to about 200° C., preferably about −20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (2b) is produced by reacting compound (22) with a halogenating reagent.

As for the "halogenating reagent", chlorine, bromine, iodine, imides such as N-chlorosuccinic imide, N-bromosuccinic imide and the like, halogen adducts such as benzyltrimethylammonium tribromide and the like are used. The amount of the halogenating reagent to be used is about 0.8 to about 5.0 moles, preferably about 1.0 to about 2.0 moles compared to 1 mole of the compound (22).

It is advantageous to carry out the reaction by using a solvent inert to the reaction. Such a solvent, though being not particularly limited as far as the reaction proceeds, is preferably exemplified by ethers such as diethyl ether, diisopropyl ether, tetrahydrofuran, dioxane, 1,2-dimethoxyethane and the like, alcohols such as methanol, ethanol, propanol and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, organic acids such as acetic acid, propionic acid and the like, nitroalkanes such as nitromethane and the like, aromatic amines such as pyridine, lutidine, quinoline and the like, or a mixed solvent thereof, and the like.

The reaction is carried out in the presence of a base, Lewis acid or iron, if desired.

As for the "base", basic salts such as sodium carbonate, calcium carbonate, cesium carbonate, sodium hydrogen carbonate, sodium acetate, potassium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like can be mentioned, for example. The amount of the base to be used is about 0.8 to about 10 moles compared to 1 mole of the compound (22).

As for the "Lewis acid", iron chloride, aluminum chloride, boron trifluoride and the like can be mentioned. The amount of the Lewis acid to be used is about 0.01 to about 5 moles compared to 1 mole of the compound (22).

The amount of the "iron" to be used is about 0.01 to about 5 moles compared to 1 mole of the compound (22).

Reaction temperature is generally about −50 to about 150° C., preferably about −20 to about 100° C. Reaction time is generally about 5 minutes to about 24 hours, preferably about 10 minutes to about 12 hours.

Further, when a halogen atom is substituted at the para-position of the hydroxy group of compound (14), compound (2b) can be produced without performing the halogenation.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Further, compound (2c), which is included in compound (2), is also produced according to the method described in the following Reaction scheme.

Reaction scheme 11

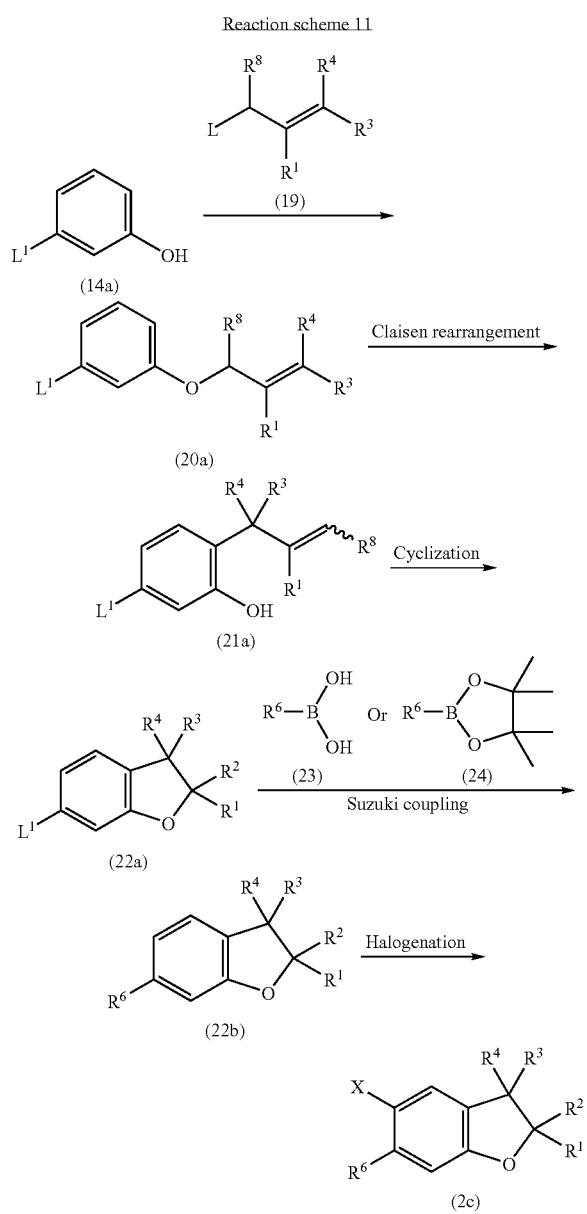

In Reaction scheme 11, L and $L^1$ are a leaving group, X is a halogen atom, $R^{11}$ is a hydrogen atom or a group that is obtained by removing one methylene from $R^2$, and other symbols are as defined in the above.

Compound (20a) is produced by reacting compound (14a) and compound (19) in the presence of a base, if desired.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As an example of the "leaving group" that is indicated by $L^1$, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

Compound (14a) can be easily obtained as a commercial product, and also can be produced according to a method known per se.

Compound (19) can be easily obtained as a commercial product, and also can be produced according to a method known per se.

The amount of compound (19) to be used is about 0.8 to about 5.0 moles, preferably about 1.0 to about 2.0 moles compared to 1 mole of the compound (14a).

As for the "base", inorganic bases including alkali metal hydroxides such as sodium hydroxide, potassium hydroxide and the like, alkali metal alcoholates such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, basic salts such as potassium hydrogen carbonate, sodium carbonate, potassium carbonate, sodium acetate and the like can be mentioned.

The amount of the base to be used is about 0.5 to about 5.0 moles, preferably about 1.0 to about 3.0 moles compared to 1 mole of the compound (14a).

It is advantageous to carry out the reaction by using a solvent inert to the reaction. Such a solvent is preferably exemplified by alcohols such as methanol, ethanol, propanol and the like, hydrocarbons such as cyclohexane, hexane, benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, water, or a mixed solvent thereof, and the like.

Reaction time is generally about 10 minutes to about 8 hours, preferably about 30 minutes to about 3 hours. Reaction temperature is generally about 0 to about 120° C., preferably about 25 to about 100° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (21a) is produced by Claisen rearrangement of compound (20a).

It is advantageous to carry out the reaction by not using any solvent or by using a solvent inert to the reaction. Such a solvent, though being not particularly limited as far as the reaction proceeds, is preferably exemplified by alcohols such as methanol, ethanol, propanol and the like, hydrocarbons such as cyclohexane, hexane, benzene, toluene, xylene, mesitylene and the like, organic acids such as formic acid, acetic acid and the like, ethers such as tetrahydrofuran, dioxane, 1,2-dimethoxyethane, diethyl ether, diisopropyl ether and the like, anilines such as N,N-dimethylaniline, N,N-diethylaniline and the like, halogenated hydrocarbons such as dichloromethane, chloroform, carbon tetrachloride, 1,2-dichloroethane and the like or a mixed solvent thereof, and the like.

Further, if desired, the reaction can be carried out by using an acid catalyst.

As for the acid catalyst, Lewis acids such as aluminum chloride, boron trifluoride and the like can be mentioned.

The amount of the acid catalyst to be used is generally about 0.1 to about 20 moles, preferably about 0.1 to about 5.0 moles compared to 1 mole of the compound (20a), in case of Lewis acid, for example.

Reaction time is generally about 30 minutes to about 24 hours, preferably about 1 to about 6 hours. Reaction temperature is generally about −70 to about 300° C., preferably about 150 to about 250° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (22a) is produced by the ring closure of compound (21a) using an acid catalyst. As for the acid catalyst, mineral acids such as hydrochloric acid, hydrobromic acid, sulfuric acid and the like, sulfonic acids such as p-toluenesulfonic acid, camphor sulfonic acid and the like, and Lewis acids such as aluminum chloride, boron trifluoride and the like are used.

The amount of the acid catalyst to be used is generally about 0.8 to about 100 moles, preferably about 10 to about 50 moles compared to 1 mole of the compound (21a) for the mineral acid, for example. The amount of the acid catalyst to be used is generally about 0.01 to about 20 moles, preferably about 0.05 to about 5 moles compared to 1 mole of the compound (21a) for the sulfonic acids, for example.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

Reaction time is generally about 30 minutes to about 24 hours, preferably about 30 minutes to about 6 hours. Reaction temperature is generally about −78 to about 200° C., preferably about −20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (22b) can be produced by reacting compound (22a) with compound (23) or compound (24) in a solvent under basic condition, in the presence of a transition metal catalyst.

Compound (23) and compound (24) can be easily obtained as a commercial product, and also can be produced according to a method known per se.

The amount of compound (23) or compound (24) to be used is about 0.5 to about 10 moles, preferably about 0.9 to about 3 moles compared to 1 mole of the compound (22a).

As for the "base", carbonate salts of alkali metal or alkaline earth metal (for example, sodium carbonate, potassium carbonate and the like), hydrogen carbonate salts of alkali metal or alkaline earth metal (for example, sodium hydrogen carbonate, potassium hydrogen carbonate and the like), hydroxides of alkali metal or alkaline earth metal (for example, sodium hydroxide, potassium hydroxide and the like), triethylamine, 4-dimethylaminopyridine, N-ethyldiisopropylamine, triethylenediamine, 4-methylmorpholine and the like are used, for example.

As for the "transition metal catalyst", palladium catalyst [for example, tetrakis(triphenyl phosphine) palladium, 1,1-bis(diphenylphosphino) ferrocene dichloropalladium, dichlorobis(triphenylphosphine)palladium and the like] and the like can be mentioned. The amount of transition metal catalyst to be used is about 0.001 to about 3 moles, preferably about 0.02 to about 0.2 moles compared to 1 mole of the compound (22a).

As a Solvent, by ethers such as diethyl ether, diisopropyl ether, tetrahydrofuran, dioxane, 1,2-dimethoxyethane and the like, alcohols such as methanol, ethanol, propanol and the like, hydrocarbons such as benzene, toluene, carbon disulfide, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, water or a mixed solvent thereof, and the like are used.

Reaction temperature is generally 0 to 250° C., preferably 50 to 150° C. Reaction time is generally about 5 minutes to about 48 hours, preferably about 30 minutes to about 24 hours.

The reaction time of this reaction can be shortened by using a microwave reaction apparatus, etc.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (2c) is produced by reacting compound (22b) and a halogenating reagent.

As for the "halogenating reagent", chlorine, bromine, iodine, imides such as N-chlorosuccinic imide, N-bromosuccinic imide and the like, halogen adducts such as benzyltrimethylammonium tribromide and the like are used. The amount of the halogenating reagent to be used is about 0.8 to about 5.0 moles, preferably about 1.0 to about 2.0 moles compared to 1 mole of the compound (22b).

It is advantageous to carry out the reaction by using a solvent inert to the reaction. Such a solvent, though being not particularly limited as far as the reaction proceeds, is preferably exemplified by ethers such as diethyl ether, diisopropyl ether, tetrahydrofuran, dioxane, 1,2-dimethoxyethane and the like, alcohols such as methanol, ethanol, propanol and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, organic acids such as acetic acid, propionic acid and the like, nitroalkanes such as nitromethane and the like, aromatic amines such as pyridine, lutidine, quinoline and the like, or a mixed solvent thereof, and the like.

The reaction is carried out in the presence of base, Lewis acid or iron, if desired.

As for the "base", basic salts such as sodium carbonate, calcium carbonate, cesium carbonate, sodium hydrogen carbonate, sodium acetate, potassium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, can be mentioned, for example. The amount of the base to be used is about 0.8 to about 10 moles compared to 1 mole of the compound (22b).

As for the "Lewis acid", iron chloride, aluminum chloride, boron trifluoride and the like can be mentioned. The amount of the Lewis acid to be used is about 0.01 to about 5 moles compared to 1 mole of the compound (22b).

The amount of the "iron" to be used is about 0.01 to about 5 moles compared to 1 mole of the compound (22b).

Reaction temperature is generally about −50 to about 150° C., preferably about −20 to about 100° C. Reaction time is generally about 5 minutes to about 24 hours, preferably about 10 minutes to about 12 hours.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4) is produced according to methods known per se, or a method similar to them.

Compound (4a), that is included in compound (4), can be also produced according to the method described in the following Reaction scheme.

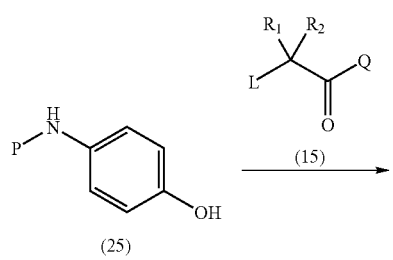

Reaction scheme 12

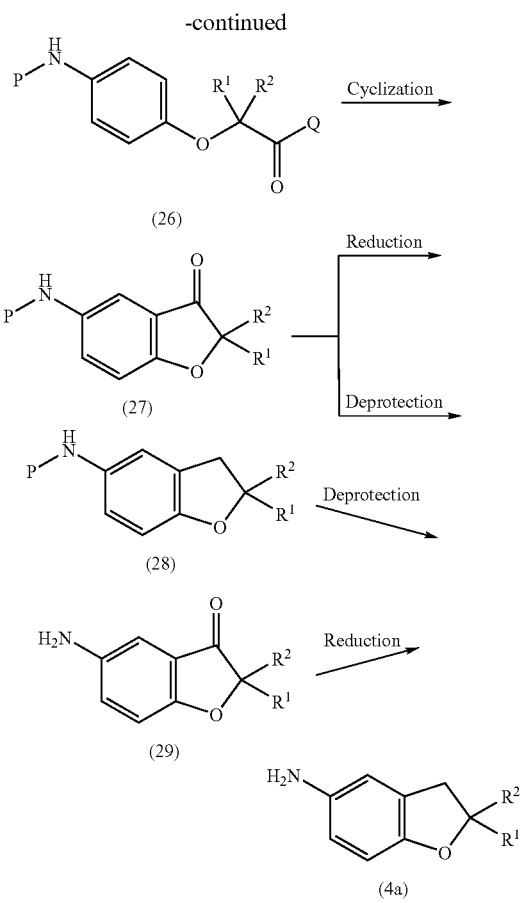

In Reaction scheme 12, the group indicated by —CO-Q is carboxylic acid or reactive derivatives thereof, P is a protecting group of an amino group, L is a leaving group, and other symbols are as defined in the above.

Compound (26) is produced by reacting compound (25) and compound (15) in the presence of a base, if desired.

Compound (25) can be easily obtained as a commercial product, and also can be produced according to the methods known per se and the methods similar to them.

Compound (15) can be easily obtained as a commercial product, and also can be produced according to a method known per se.

As an example of the "leaving group" that is indicated by L, hydroxy, a halogen atom (for example, fluorine, chlorine, bromine, iodine and the like), $C_{1-6}$ alkylsulfonyloxy (for example, methanesulfonyloxy, ethanesulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), halogen (for example, chloro, bromo, iodine and the like) and nitro and the like can be mentioned. As a specific example, benzenesulfonyloxy, p-toluenesulfonyloxy, p-bromobenzenesulfonyloxy, m-nitrobenzenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of compound (15) to be used is about 0.8 to about 5.0 moles, preferably about 1.0 to about 3.0 moles compared to 1 mole of the compound (25).

The amount of the base to be used is about 0.8 to about 5.0 moles, preferably about 1.0 to about 3.0 moles compared to 1 mole of the compound (25). Further, if desired, the reaction can be carried out in the co-presence of quaternary ammonium salts with the base.

As an example of the "quaternary ammonium salts", tetrabutyl ammonium iodide and the like can be mentioned, for example.

The amount of the quaternary ammonium salts to be used is about 0.1 to about 2.0 moles, preferably about 0.5 to about 1.0 mole compared to 1 mole of the compound (25).

It is advantageous to carry out the reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, ketones such as acetone, methyl ethyl ketone and the like, or a mixed solvent thereof, and the like.

Reaction time is generally about 30 minutes to about 96 hours, preferably about 1 hour to about 72 hours. Reaction temperature is generally about 0 to about 120° C., preferably about 0 to about 60° C.

Instead of the reaction above, Mitsunobu reaction [Synthesis, 1981, 1 to 27 pages] can be employed.

For the reaction, compound (25) and compound (15) in which L is OH are reacted in the presence of azodicarboxylates (for example, diethylazodicarboxylate and the like) and phosphines (for example, triphenyl phosphine, tributyl phosphine and the like).

The amount of compound (15) to be used is about 0.8 to about 5.0 moles, preferably about 1.0 to about 3.0 moles compared to 1 mole of the compound (25).

The amount of the "azodicarboxylates" and the "phosphines" to be used is about 0.8 to about 5.0 moles, preferably about 1.0 to about 3.0 moles, respectively, compared to 1 mole of the compound (25).

It is advantageous to carry out the reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 5 minutes to about 48 hours, preferably about 30 minutes to about 24 hours. Reaction temperature is generally about −20 to about 200° C., preferably about 0 to about 100° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (27) is produced by subjecting compound (26) to a cyclization reaction which is known per se in the art.

As for the cyclization reaction, it is carried out by using acid.

For the reaction, Q is preferably hydroxy, halogen and the like. According to the reaction, compound (26) is reacted with acid to obtain compound (27) as desired.

As for the "acid", Lewis acids such as aluminum chloride, iron chloride, tin chloride (IV), titanium tetrachloride, boron trifluoride diethyl ether and the like, mineral acids such as polyphosphoric acid, sulfuric acid and the like, and organic acids such as trifluoroacetic acid, methanesulfonic acid, p-toluenesulfonic acid, trifluoromethanesulfonic acid and the like are used.

The amount of the "acid" to be used is a catalytic amount to excess amount, preferably about 0.8 to about 5 moles compared to 1 mole of the compound (26).

It is advantageous to carry out the reaction by not using any solvent or by using a solvent inert to the reaction. Such a solvent, though being not particularly limited as far as the reaction proceeds, is preferably exemplified by carbon disulfide, nitroalkanes such as nitromethane and the like, nitroaryls such as nitrobenzene and the like, halogenated hydrocarbons such as dichloromethane, 1,2-dichloroethane, 1,2-dichlorobenzene and the like, organic acids such as acetic acid, trifluoroacetic acid and the like, acid anhydrides such as acetic anhydride, trifluoroacetic anhydride and the like or a mixed solvent thereof, and the like.

Reaction time is generally about 10 minutes to about 96 hours, preferably about 10 minutes to about 12 hours. Reaction temperature is generally about −70 to about 200° C., preferably about −40 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (28) is produced by reducing compound (27) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (27).

The amount of the Lewis acids to be used is about 0.8 to about 10.0 moles, preferably about 1.0 to about 5.0 moles compared to 1 mole of the compound (27).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4a) is produced by removing the protecting group of compound (28).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (29) is produced by removing the protecting group of compound (27).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4a) is also produced by reducing compound (29) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (29).

The amount of the Lewis acids to be used is about 0.8 to about 10.0 moles, preferably about 1.0 to about 5.0 moles compared to 1 mole of the compound (29).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4b), that is included in compound (4), can be also produced according to the method described in the following Reaction scheme.

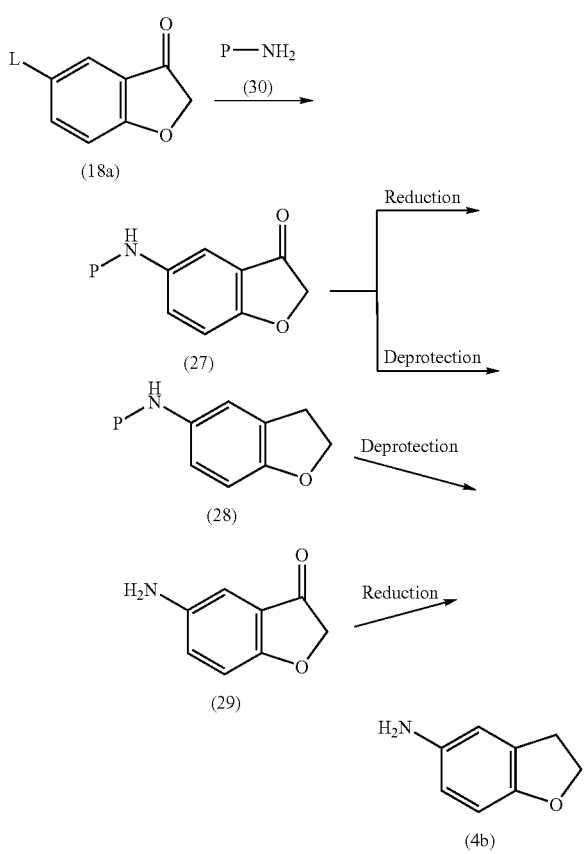

Reaction scheme 13

In Reaction scheme 13, L is a leaving group, P is a protecting group of an amino group, and other symbols are as defined in the above.

Compound (27) is produced by reacting compound (18a) and compound (30) in the presence of a base, if desired. If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

Compound (30) can be easily obtained as a commercial product, and also can be produced according to the methods known per se.

The amount of compound (30) to be used is about 0.5 to about 10 moles, preferably about 1.0 to about 3.0 moles compared to 1 mole of the compound (18a).

As an example of the "leaving group" that is indicated by L, a halogen atom (for example, fluorine, chlorine, bromine, iodine and the like), $C_{1-6}$ alkylsulfonyloxy which may be halogenated (for example, methanesulfonyloxy, trifluoromethanesulfonyloxy, trichloromethanesulfonyloxy and the like), $C_{5-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned, for example.

The amount of the base to be used is about 0.8 to about 10 moles, preferably about 1.0 to about 5.0 moles compared to 1 mole of the compound (18a).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (18a).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis(dibenzylideneacetone) palladium and the like can be used.

The amount of the phosphine to be used is about 0.001 to about 10 moles, preferably about 0.01 to about 1.0 mole compared to 1 mole of the compound (18a).

The amount of the palladium catalyst to be used is about 0.0001 to about 5.0 moles, preferably about 0.01 to about 0.5 moles compared to 1 mole of the compound (18a).

Reaction time is generally about 30 minutes to about 72 hours, preferably about 1 hour to about 48 hours. Reaction temperature is generally about −20 to about 200° C., preferably about 0 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (28) is produced by reducing compound (27) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (27).

The amount of the Lewis acids to be used is about 0.8 to about 10.0 moles, preferably about 1.0 to about 5.0 moles compared to 1 mole of the compound (27).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

The product can be used for the next reaction as a reaction solution as it is or as a crude product. However, it can be separated from the reaction mixture according to a method generally known in the art, and can be easily purified by common means for separation (for example, recrystallization, distillation, chromatography and the like).

Compound (4b) is produced by removing the protecting group of compound (28).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (29) is produced by removing the protecting group of compound (27).

As for the method of removing the protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4b) is produced by reducing compound (29) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (29).

The amount of the Lewis acids to be used is about 0.8 to about 10.0 moles, preferably about 1.0 to about 5.0 moles compared to 1 mole of the compound (29).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4b), that is included in compound (4), can be also produced according to the method described in the following Reaction scheme.

Reaction scheme 14

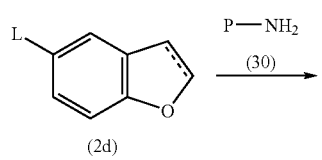
(2d)

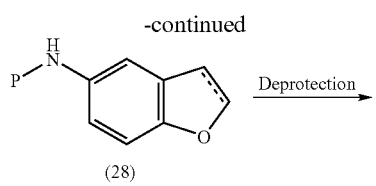
(28)

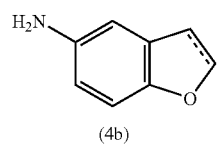
(4b)

In Reaction scheme 14, L is a leaving group, P is a protecting group of an amino group, and other symbols are as defined in the above.

Compound (28) is produced by reacting compound (2d) and compound (30) in the presence of a base, if desired. If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

Compound (30) can be easily obtained as a commercial product, and also can be produced according to the methods known per se.

The amount of compound (30) to be used is about 0.5 to about 10 moles, preferably about 1.0 to about 3.0 moles compared to 1 mole of the compound (2d).

As an example of the "leaving group" that is indicated by L, a halogen atom (for example, fluorine, chlorine, bromine, iodine and the like), $C_{1-6}$ alkylsulfonyloxy which may be halogenated (for example, methanesulfonyloxy, trifluoromethanesulfonyloxy, trichloromethanesulfonyloxy and the like), $C_{5-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned, for example.

The amount of the base to be used is about 0.8 to about 10 moles, preferably about 1.0 to about 5.0 moles compared to 1 mole of the compound (2d).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (2d).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis(dibenzylideneacetone) palladium and the like can be used.

The amount of the phosphine to be used is about 0.001 to about 10 moles, preferably about 0.01 to about 1.0 mole compared to 1 mole of the compound (2d). The amount of the palladium catalyst to be used is about 0.0001 to about 5.0 moles, preferably about 0.01 to about 0.5 moles compared to 1 mole of the compound (2d).

Reaction time is generally about 30 minutes to about 72 hours, preferably about 1 hour to about 48 hours. Reaction temperature is generally about −20 to about 200° C., preferably about 0 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4b) is produced by removing the protecting group of compound (28).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Further, compound (4c), which is included in compound (4), is also produced according to the method described in the following Reaction scheme.

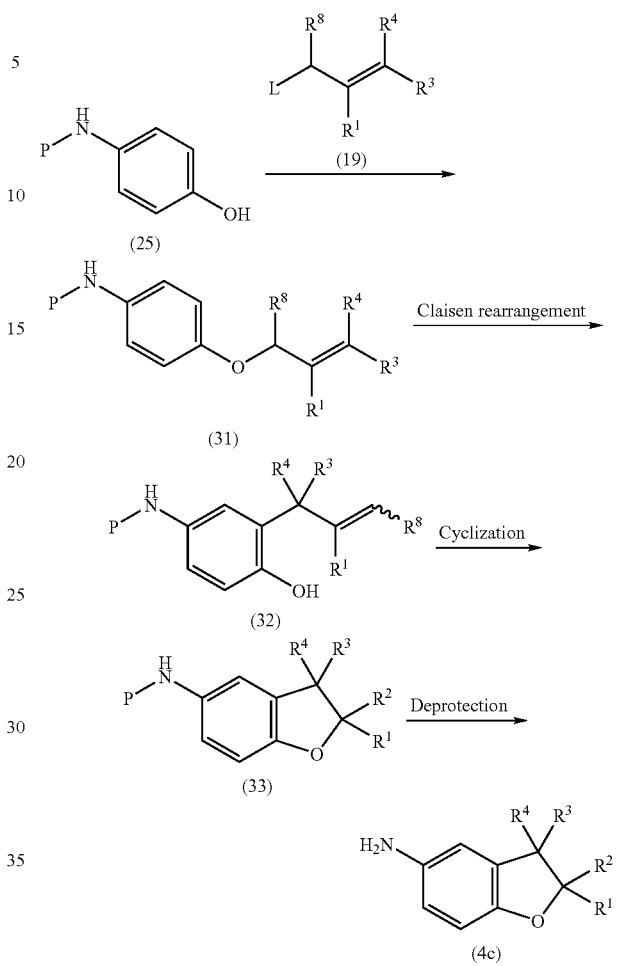

In Reaction scheme 15, L is a leaving group, P is a protecting group of an amino group, $R^{11}$ is a hydrogen atom or a group that is obtained by removing one methylene from $R^2$, and other symbols are as defined in the above.

Compound (31) is produced by reacting compound (25) and compound (19) in the presence of a base, if desired.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

Compound (25) can be easily obtained as a commercial product, and also can be produced according to methods known per se and the methods similar to them.

Compound (19) can be easily obtained as a commercial product, and also can be produced according to methods known per se.

The amount of compound (19) to be used is about 0.8 to about 5.0 moles, preferably about 1.0 to about 2.0 moles compared to 1 mole of the compound (25).

As for the "base", inorganic bases including alkali metal hydroxides such as sodium hydroxide, potassium hydroxide and the like, alkali metal alcoholates such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, basic salts such as potassium hydrogen carbonate, sodium carbonate, potassium carbonate, sodium acetate and the like can be mentioned.

The amount of the base to be used is about 0.5 to about 5.0 moles, preferably about 1.0 to about 3.0 moles compared to 1 mole of the compound (25).

It is advantageous to carry out the reaction by using a solvent inert to the reaction. Such a solvent is preferably exemplified by alcohols such as methanol, ethanol, propanol and the like, hydrocarbons such as cyclohexane, hexane, benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, water, or a mixed solvent thereof, and the like.

Reaction time is generally about 10 minutes to about 8 hours, preferably about 30 minutes to about 3 hours. Reaction temperature is generally about 0 to about 120° C., preferably about 25 to about 100° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (32) is produced by Claisen rearrangement of compound (31).

It is advantageous to carry out the reaction by not using any solvent or by using a solvent inert to the reaction. Such a solvent, though being not particularly limited as far as the reaction proceeds, is preferably exemplified by alcohols such as methanol, ethanol, propanol and the like, hydrocarbons such as cyclohexane, hexane, benzene, toluene, xylene, mesitylene and the like, organic acids such as formic acid, acetic acid and the like, ethers such as tetrahydrofuran, dioxane, 1,2-dimethoxyethane, diethyl ether, diisopropyl ether and the like, anilines such as N,N-dimethylaniline, N,N-diethylaniline and the like, halogenated hydrocarbons such as dichloromethane, chloroform, carbon tetrachloride, 1,2-dichloroethane and the like or a mixed solvent thereof.

Further, if desired, the reaction can be carried out by using an acid catalyst.

As for the acid catalyst, Lewis acids such as aluminum chloride, boron trifluoride and the like can be used.

The amount of the acid catalyst to be used is generally about 0.1 to about 20 moles, preferably about 0.1 to about 5.0 moles compared to 1 mole of the compound (20), when Lewis acid is used, for example.

Reaction time is generally about 30 minutes to about 24 hours, preferably about 1 to about 6 hours. Reaction temperature is generally about −70 to about 300° C., preferably about 150 to about 250° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (33) is produced by the ring closure of compound (32) using an acid catalyst. As for the acid catalyst, mineral acids such as hydrochloric acid, hydrobromic acid, sulfuric acid and the like, sulfonic acids such as p-toluenesulfonic acid, camphor sulfonic acid and the like, and Lewis acids such as aluminum chloride, boron trifluoride and the like are used.

The amount of the acid catalyst to be used is generally about 0.8 to about 100 moles, preferably about 10 to about 50 moles compared to 1 mole of the compound (32) for the mineral acid. The amount of the acid catalyst to be used is generally about 0.01 to about 20 moles, preferably about 0.05 to about 5 moles compared to 1 mole of the compound (32) for the sulfonic acid, for example.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

Reaction time is generally about 30 minutes to about 24 hours, preferably about 30 minutes to about 6 hours. Reaction temperature is generally about −78 to about 200° C., preferably about −20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4c) is produced by removing the protecting group of compound (33).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (6) is produced according to the methods known per se in the art, or methods that are similar to them.

Compound (6a), that is included in compound (6), can be also produced according to the method described in the following Reaction scheme.

Reaction scheme 16

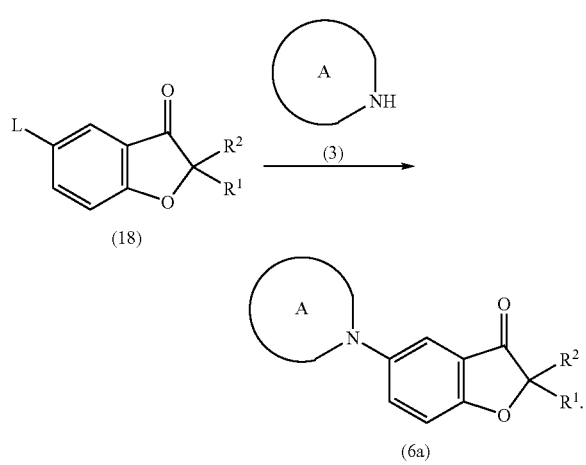

In Reaction scheme 16, L is a leaving group, and other symbols are as defined in the above.

Compound (3) can be easily obtained as a commercial product, and also can be produced according to a method known per se.

Compound (6a) is produced by reacting compound (18) and compound (3) in the presence of a base, if desired. If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

The amount of compound (3) to be used is about 0.5 to about 10 moles, preferably about 1.0 to about 3.0 moles compared to 1 mole of the compound (18).

As an example of the "leaving group" that is indicated by L, a halogen atom (for example, fluorine, chlorine, bromine, iodine and the like), $C_{1-6}$ alkylsulfonyloxy which may be halogenated (for example, methanesulfonyloxy, trifluoromethanesulfonyloxy, trichloromethanesulfonyloxy and the like), $C_{5-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned, for example.

The amount of the base to be used is about 0.8 to about 10 moles, preferably about 1.0 to about 5.0 moles compared to 1 mole of the compound (18).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (18).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis (dibenzylideneacetone) palladium and the like can be used.

The amount of the phosphine to be used is about 0.001 to about 10 moles, preferably about 0.01 to about 1.0 mole compared to 1 mole of the compound (18).

The amount of the palladium catalyst to be used is about 0.0001 to about 5.0 moles, preferably about 0.01 to about 0.5 moles compared to 1 mole of the compound (18).

Reaction time is generally about 30 minutes to about 72 hours, preferably about 1 hour to about 48 hours. Reaction temperature is generally about -20 to about 200° C., preferably about 0 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (6b), that is included in compound (6), can be also produced according to the method described in the following Reaction scheme.

Reaction scheme 17

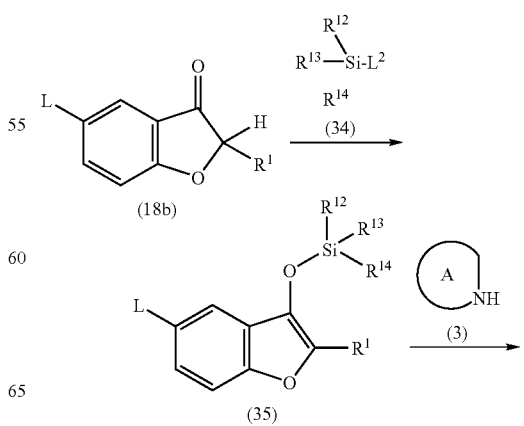

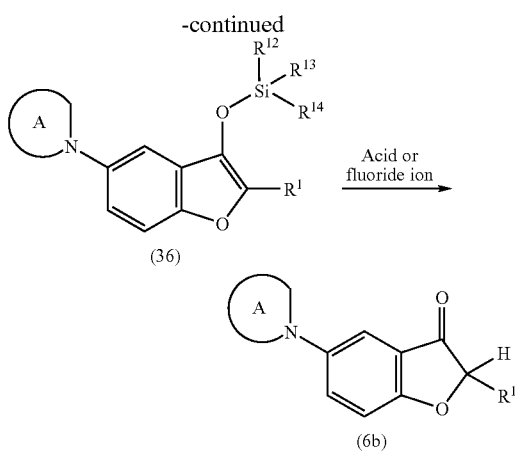

In Reaction scheme 17, L and $L^2$ are the same or different leaving group, $R^{12}$, $R^{13}$ and $R^{14}$ are a lower alkyl group or a phenyl group, and other symbols are as defined in the above.

Compound (35) is produced by reacting compound (18b) and compound (34) in the presence of a base, if desired.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As an example of the "leaving group" that is indicated by $L^1$, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

Compound (34) can be easily obtained as a commercial product, and also can be produced according to a method known per se.

As for the "base", basic salts such as sodium carbonate, potassium carbonate, cesium carbonate, sodium hydrogen carbonate and the like, aromatic amines such as pyridine, lutidine and the like, tertiary amines such as triethylamine, ethylisopropylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of compound (34) to be used is about 0.8 to about 5.0 moles, preferably about 1.0 to about 3.0 moles compared to 1 mole of the compound (18b).

The amount of the base to be used is about 0.8 to about 5.0 moles, preferably about 1.0 to about 3.0 moles compared to 1 mole of the compound (18b).

It is advantageous to carry out the reaction by using a solvent inert to the reaction. Such a solvent is preferably exemplified by alcohols such as methanol, ethanol, propanol and the like, hydrocarbons such as cyclohexane, hexane, benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, water, or a mixed solvent thereof, and the like.

Reaction time is generally about 10 minutes to about 8 hours, preferably about 30 minutes to about 3 hours. Reaction temperature is generally about −70 to about 100° C., preferably about −20 to about 50° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (36) is produced by reacting compound (35) and compound (3) that is represented by the following formula:

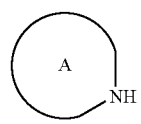

in the presence of a base, if desired. If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

Compound (3) can be easily obtained as a commercial product, and also can be produced according to the methods known per se.

The amount of compound (3) to be used is about 0.5 to about 10 moles, preferably about 1.0 to about 3.0 moles compared to 1 mole of the compound (35).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned, for example.

The amount of the base to be used is about 0.8 to about 10 moles, preferably about 1.0 to about 5.0 moles compared to 1 mole of the compound (35).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (35).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis(dibenzylideneacetone) palladium and the like can be used.

The amount of the phosphine to be used is about 0.001 to about 10 moles, preferably about 0.01 to about 1.0 mole compared to 1 mole of the compound (35). The amount of the palladium catalyst to be used is about 0.0001 to about 5.0 moles, preferably about 0.01 to about 0.5 moles compared to 1 mole of the compound (35).

Reaction time is generally about 30 minutes to about 72 hours, preferably about 1 hour to about 48 hours. Reaction temperature is generally about −20 to about 200° C., preferably about 0 to about 150° C.

The product can be used for the next reaction as a reaction solution as it is or as a crude product. However, it can be separated from the reaction mixture according to a method generally known in the art, and can be easily purified by common means for separation (for example, recrystallization, distillation, chromatography and the like).

Compound (6b) is produced by reacting compound (36) with acid or a fluoride ion.

As for the "acid", organic acids such as formic acid, acetic acid, trifluoroacetic acid, methanesulfonic acid, p-toluene sulfonic acid, camphor sulfonic acid, trifluoromethanesulfonic acid and the like, mineral acids such as hydrochloric acid, sulfuric acid, hydrobromic acid and the like, and Lewis acids such as zinc chloride, aluminum chloride, and the like can be mentioned.

The amount of the acid to be used is generally about 0.8 to about 100 moles, preferably about 10 to about 50 moles compared to 1 mole of the compound (36) for the mineral acids. The amount of the acid to be used is generally about 0.01 to about 20 moles, preferably about 0.05 to about 5 moles compared to 1 mole of the compound (36) for the sulfonic acids, for example. The amount of the acid to be used is generally about 0.1 to about 20 moles, preferably about 0.1 to about 5.0 moles compared to 1 mole of the compound (36) for the Lewis acids, for example.

Reaction time is generally about 5 minutes to about 24 hours, preferably about 30 minutes to about 6 hours. Reaction temperature is generally about −70 to about 200° C., preferably about 0 to about 50° C.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

As for the source of the "fluoride ion", ammonium fluorides such as tributylammonium fluoride and the like, silicate fluorides such as tris(dimethylamino) sulfonium difluorotrimethyl silicate and the like, metal fluorides such as sodium fluoride, potassium fluoride and the like can be mentioned.

The amount of the fluoride ion source to be used is generally about 0.8 to about 20 moles, preferably about 1 to about 5 moles compared to 1 mole of the compound (36) for the ammonium fluorides. The amount of the fluoride ion source to be used is generally about 0.8 to about 20 moles, preferably about 1 to about 10 moles compared to 1 mole of the compound (36) for the silicate fluorides, and about 1 to about 30 moles, preferably about 1 to about 10 moles compared to 1 mole of the compound (36) for the metal fluorides, for example.

Reaction time is generally about 5 minutes to about 24 hours, preferably about 30 minutes to about 6 hours. Reaction temperature is generally about −70 to about 200° C., preferably about 0 to about 80° C.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (7) is produced according to the methods known per se in the art, or methods that are similar to them.

Compound (7a), that is included in compound (7), can be also produced according to the method described in the following Reaction scheme.

Reaction scheme 18

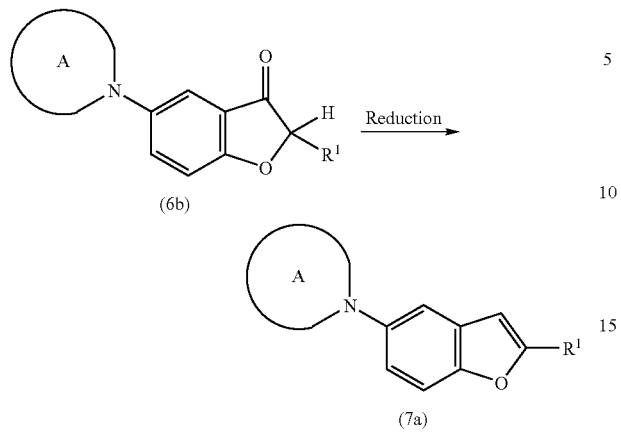

(6b)

(7a)

In Reaction scheme 18, the symbols are as defined in the above.

Compound (7a) is produced by reducing compound (6b) with a reducing agent.

As for the "reducing agent", metal hydrides such as sodium borohydride, lithium aluminum hydride, sodium bis(2-methoxyethoxy)aluminum hydride, borane tetrahydrofuran complex, aluminum diisobutyl hydride and the like are used. If desired, Lewis acids such as titanium tetrachloride or aluminum chloride and the like can be added.

The amount of the reducing agent to be used is about 0.8 to about 10.0 moles, preferably about 1.0 to about 5.0 moles compared to 1 mole of the compound (6b).

The amount of the Lewis acids to be used is about 0.8 to about 10.0 moles, preferably about 1.0 to about 5.0 moles compared to 1 mole of the compound (6b).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 1 hour to about 48 hours. Reaction temperature is generally about −20 to about 200° C., preferably about 0 to about 120° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (8) is produced according to the methods known per se in the art, or methods that are similar to them.

Compound (8a), that is included in compound (8), can be also produced according to the method described in the following Reaction scheme.

Reaction scheme 19

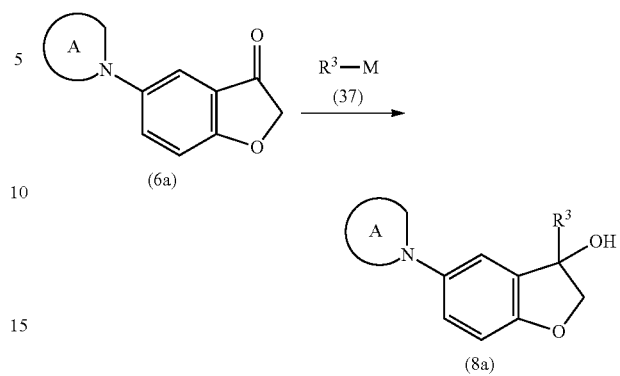

(6a)

(8a)

In Reaction scheme 19, M is a metal, and other symbols are as defined in the above.

Organometallic compound (37), which is represented by the following formula, can be easily obtained as a commercial product, and also can be produced according to the methods known per se, for example the method described in Lectures on Experimental Science, edited by The Chemical Society of Japan, 4$^{th}$ ed. Vol. 25, published by Maruzen Company, Ltd.

$R^3$-M

According to Reaction scheme 19, compound (8a) can be obtained by reacting compound (6a) with organometallic compound (37).

As for organometallic compound (37), a Grignard reagent or organo lithium reagent is preferred.

The amount of compound (37) to be used is about 0.8 to about 30 moles, preferably about 1.0 to about 20 moles compared to 1 mole of the compound (6a).

It is advantageous to carry out the reaction by not using any solvent or by using a solvent inert to the reaction. Such a solvent, though being not particularly limited as far as the reaction proceeds, is preferably exemplified by alcohols such as methanol, ethanol, propanol and the like, hydrocarbons such as hexane, cyclohexane, benzene, toluene, xylene and the like, ethers such as diethyl ether, diisopropyl ether, tetrahydrofuran, dioxane, 1,2-dimethoxyethane and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like or a mixed solvent thereof, and the like.

Reaction time is generally about 10 minutes to about 24 hours, preferably about 30 minutes to about 12 hours. Reaction temperature is generally about −100 to about 120° C., preferably about −80 to about 60° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (9) is produced according to the methods known per se in the art, or methods that are similar to them.

Compound (9a), that is included in compound (9), can be also produced according to the method described in the following Reaction scheme.

Reaction scheme 20

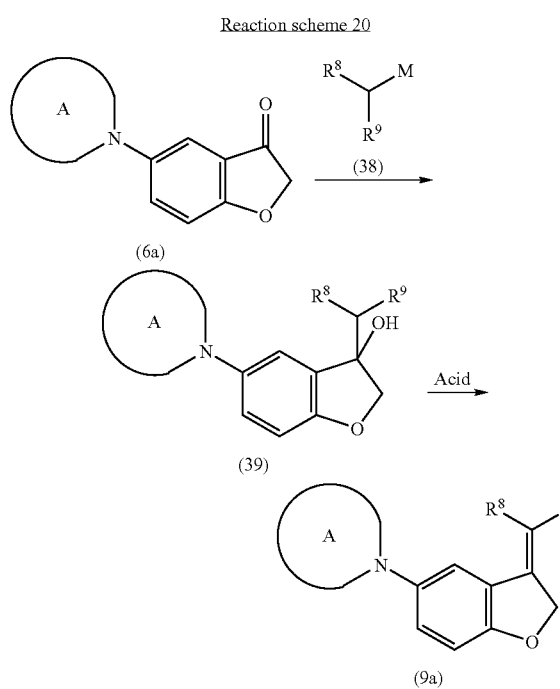

In Reaction scheme 20, $R^8$ and $R^9$ are a hydrogen or a lower alkyl group which may be substituted, M is metal, and other symbols are as defined in the above.

Organometallic compound (38), which is represented by the following formula, can be easily obtained as a commercial product, and also can be produced according to the methods known per se, for example the method described in Lectures on Experimental Science, edited by The Chemical Society of Japan, 4$^{th}$ ed. Vol. 25, published by Maruzen Company, Ltd.

According to Reaction scheme 20, compound (39) can be obtained by reacting compound (6a) with organometallic compound (38).

As for organometallic compound (38), a Grignard reagent or organo lithium reagent is preferred.

The amount of compound (38) to be used is about 0.8 to about 30 moles, preferably about 1.0 to about 20 moles compared to 1 mole of the compound (6a).

It is advantageous to carry out the reaction by not using any solvent or by using a solvent inert to the reaction. Such a solvent, though being not particularly limited as far as the reaction proceeds, is preferably exemplified by alcohols such as methanol, ethanol, propanol and the like, hydrocarbons such as hexane, cyclohexane, benzene, toluene, xylene and the like, ethers such as diethyl ether, diisopropyl ether, tetrahydrofuran, dioxane, 1,2-dimethoxyethane, and the like, amides such as N,N-dimethylformamide, N,N-dimethylacetamide, hexamethylphosphoric triamide and the like, sulfoxides such as dimethyl sulfoxide and the like, halogenated carbons such as dichloromethane, chloroform, carbon tetrachloride, 1,2-dichloroethane and the like or a mixed solvent thereof.

Reaction time is generally about 10 minutes to about 24 hours, preferably about 30 minutes to about 12 hours. Reaction temperature is generally about −100 to about 120° C., preferably about −80 to about 60° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (9a) is produced by dehydration of compound (39) by using acid.

As for the "acid", organic acids such as formic acid, acetic acid, trifluoroacetic acid, methanesulfonic acid, p-toluenesulfonic acid, camphor sulfonic acid, trifluoromethanesulfonic acid and the like, mineral acids such as hydrochloric acid, sulfuric acid, hydrobromic acid and the like, and Lewis acids such as zinc chloride, aluminum chloride and the like can be mentioned.

The amount of the acid to be used is generally about 0.8 to about 100 moles, preferably about 10 to about 50 moles compared to 1 mole of the compound (39) for the mineral acids. The amount of the acid to be used is generally about 0.01 to about 20 moles, preferably about 0.05 to about 5 moles compared to 1 mole of the compound (39) for the sulfonic acids, for example. The amount of the acids to be used is generally about 0.1 to about 20 moles, preferably about 0.1 to about 5.0 moles compared to 1 mole of the compound (39) for the Lewis acids, for example.

Reaction time is generally about 30 minutes to about 24 hours, preferably about 1 to about 6 hours. Reaction temperature is generally about −70 to about 300° C., preferably about 20 to about 200° C.

It is advantageous to carry out the reaction by not using any solvent or by using a solvent inert to the reaction. Such a solvent is not particularly limited as far as the reaction proceeds. However, when mineral acids are used, it is preferably a mixture solvent of water and an organic solvent including alcohols such as methanol, ethanol, propanol and the like, saturated hydrocarbons such as cyclohexane, hexane and the like, aromatic hydrocarbons such as benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, or water.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (10) is produced according to the methods known per se in the art, or methods that are similar to them.

Compound (10a), that is included in compound (10), can be also produced according to the method described in the following Reaction scheme.

Reaction scheme 21

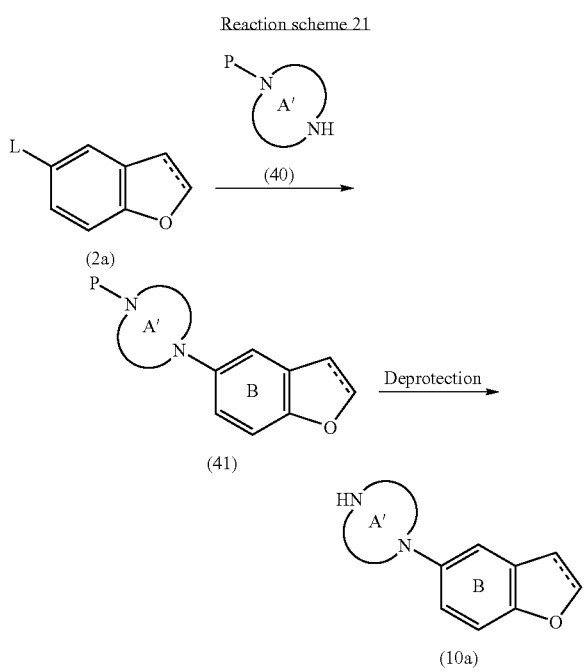

In Reaction scheme 21, L is a leaving group, P is a protecting group, and other symbols are as defined in the above.

Compound (41) is produced by reacting compound (2a) and compound (40), that is expressed as the above formula according to Reaction scheme 21, in the presence of a base, if desired. If necessary, a catalyst such as copper, copper salt and the like can be used. In addition, in view of the method described in Chemistry Letters 1983, 927-928 pages, a catalyst such as palladium or nickel and the like and a ligand (for example, phosphine, pyridines and the like) can be used.

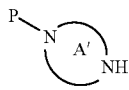

Compound (40) can be easily obtained as a commercial product, and also can be produced according to the methods known per se.

The amount of compound (40) to be used is about 0.5 to about 10 moles, preferably about 1.0 to about 3.0 moles compared to 1 mole of the compound (2a).

As an example of the "leaving group" that is indicated by L, a halogen atom (for example, fluorine, chlorine, bromine, iodine and the like), $C_{1-6}$ alkylsulfonyloxy which may be halogenated (for example, methanesulfonyloxy, trifluoromethanesulfonyloxy, trichloromethanesulfonyloxy and the like), $C_{5-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned, for example.

The amount of the base to be used is about 0.8 to about 10 moles, preferably about 1.0 to about 5.0 moles compared to 1 mole of the compound (2a).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

As for the copper catalyst, copper, halogenated copper (CuI, CuBr, CuCl and the like), copper oxide (CuO) and the like are used.

The amount of copper catalyst to be used is about 0.1 to about 10 moles, preferably about 0.5 to about 2.0 moles compared to 1 mole of the compound (18).

As for the ligand, phosphines are preferable. Trialkyl phosphine, triaryl phosphine, trialkoxy phosphine and the like are used. As for the palladium catalyst, palladium acetate, palladium chloride, tetrakis(triphenyl phosphine) palladium, bis(dibenzylideneacetone) palladium and the like can be used.

The amount of the phosphine to be used is about 0.001 to about 10 moles, preferably about 0.01 to about 1.0 mole compared to 1 mole of the compound (2a). The amount of the palladium catalyst to be used is about 0.0001 to about 5.0 moles, preferably about 0.01 to about 0.5 moles compared to 1 mole of the compound (2a).

Reaction time is generally about 30 minutes to about 72 hours, preferably about 1 hour to about 48 hours. Reaction temperature is generally about −20 to about 200° C., preferably about 0 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (10a) is produced by removing the protecting group of compound (41).

As for the method of removing protecting group, methods known per se in the art or the methods similar to them are used. For example, a method of treating with acid, base, UV light, hydrazine, phenyl hydrazine, sodium N-methyldithiocarbamate, tetrabutyl ammonium fluoride, palladium acetate and the like or a reduction reaction is used.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (12) is produced according to the methods known per se in the art, or methods that are similar to them.

Further, compound (12a), which is included in compound (12), is also produced according to the method described in the following Reaction scheme.

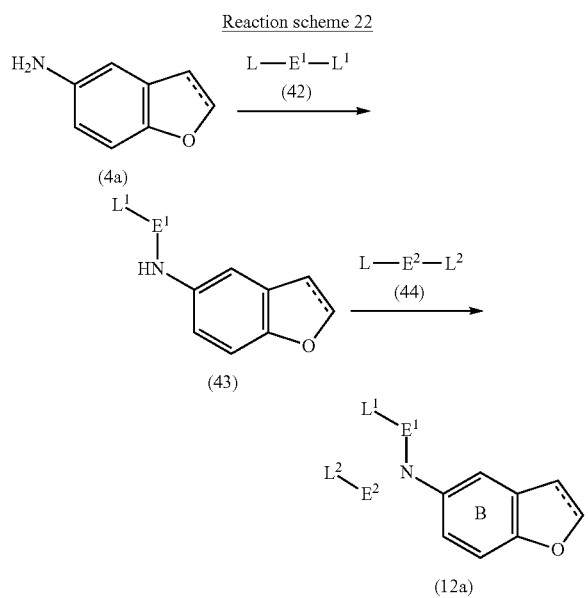

In Reaction scheme 22, L, L¹ and L², which are the same or different from each other, are a leaving group, E¹ and E² are an atomic group constituting ring A' except the two nitrogen atoms in Compound (Ie), that is included in the compounds of the present invention, and other symbols are as defined in the above.

According to Reaction scheme 22, compound (4a) is reacted with compound (42) that is represented by the following formula in the presence of a base, if desired, to give Compound (43).

L-E¹-L¹

Compound (42) can be easily obtained as a commercial product, and also can be produced according to the methods known per se.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As an example of the "leaving group" that is indicated by L¹, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

L and L¹ can be the same or different from each other. However, they are preferably different from each other.

The amount of compound (42) to be used is about 0.8 to about 5.0 moles, preferably about 1.0 to about 2.0 moles compared to 1 mole of the compound (4a).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of the base to be used is about 0.5 to about 10.0 moles, preferably about 1.0 to about 3.0 moles compared to 1 mole of the compound (4a). Further, if desired, the reaction can be carried out in the co-presence of quaternary ammonium salts or metal iodides with the base.

As an example of the "quaternary ammonium salts", tetrabutyl ammonium iodide and the like can be mentioned, for example.

As an example of the "metal iodide", sodium iodide, potassium iodide and the like can be mentioned, for example.

The amount of the quaternary ammonium salts to be used is about 0.1 to about 3.0 moles, preferably about 0.5 to about 1.0 mole compared to 1 mole of the compound (4a).

The amount of the metal iodide to be used is about 0.1 to about 3.0 moles, preferably about 0.5 to about 1.0 mole compared to 1 mole of the compound (4a).

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (43) is reacted with compound (44) that is represented by the following formula in the presence of a base, if desired, to give Compound (12a).

L-E$^2$-L$^2$

Compound (44) can be easily obtained as a commercial product, and also can be produced according to the methods known per se.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As an example of the "leaving group" that is indicated by L$^2$, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

L and L$^2$ can be the same or different from each other. However, they are preferably different from each other.

The amount of compound (44) to be used is about 0.8 to about 5.0 moles, preferably about 1.0 to about 2.0 moles compared to 1 mole of the compound (43).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of the base to be used is about 0.5 to about 10.0 moles, preferably about 1.0 to about 3.0 moles compared to 1 mole of the compound (43). Further, if desired, the reaction can be carried out in the co-presence of quaternary ammonium salts or metal iodides with the base.

As an example of the "quaternary ammonium salts", tetrabutyl ammonium iodide and the like can be mentioned, for example.

As an example of the "metal iodide", sodium iodide, potassium iodide and the like can be mentioned, for example.

The amount of the quaternary ammonium salts to be used is about 0.1 to about 3.0 moles, preferably about 0.5 to about 1.0 mole compared to 1 mole of the compound (43).

The amount of the metal iodide to be used is about 0.1 to about 3.0 moles, preferably about 0.5 to about 1.0 mole compared to 1 mole of the compound (43).

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

When, L$^1$ is identical to L$^2$, and E$^1$ is identical to E$^2$, compound (4a) is reacted with compound (42) (=compound (44)) that is represented by the following formula in the presence of a base, if desired, to give Compound (12a).

L-E$^1$-L$^1$(L-E$^2$-L$^2$)

Compound (42) (=compound (44)) can be easily obtained as a commercial product, and also can be produced according to the methods known per se.

As an example of the "leaving group" that is indicated by L, hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluenesulfonyloxy and the like can be mentioned.

As an example of the "leaving group" that is indicated by L$^1$ (=L$^2$), hydroxy, a halogen atom (for example, fluorine, chlorine, bromine, iodine and the like), $C_{1-6}$ alkylsulfonyloxy (for example, methylsulfonyloxy, ethylsulfonyloxy and the like), $C_{6-10}$ arylsulfonyloxy which may have a substituent and the like can be mentioned.

As an example of the "$C_{6-10}$ arylsulfonyloxy which may have a substituent", $C_{6-10}$ arylsulfonyloxy which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro and the like can be mentioned. As a specific example, benzenesulfonyloxy, m-nitrobenzenesulfonyloxy, p-toluene-sulfonyloxy and the like can be mentioned.

L and $L^1$ (=$L^2$) can be the same or different from each other. However, they are preferably different from each other.

The amount of compound (42) (=compound (44)) to be used is about 1.5 to about 10.0 moles, preferably about 2.0 to about 4.0 moles compared to 1 mole of the compound (4a).

As for the "base", basic salts such as sodium carbonate, potassium carbonate, cesium carbonate, sodium hydrogen carbonate and the like, aromatic amines such as pyridine, lutidine and the like, tertiary amines such as triethylamine, tripropylamine, N-ethyldiisopropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned, for example.

The amount of the base to be used is about 1 to about 20.0 moles, preferably about 2.0 to about 6.0 moles compared to 1 mole of the compound (4a). Further, if desired, the reaction can be carried out in the co-presence of quaternary ammonium salts or metal iodides with the base.

As an example of the "quaternary ammonium salts", tetrabutyl ammonium iodide and the like can be mentioned, for example.

As an example of the "metal iodides", sodium iodide, potassium iodide and the like can be mentioned, for example.

The amount of the quaternary ammonium salts to be used is about 0.1 to about 3.0 moles, preferably about 0.5 to about 1.0 mole compared to 1 mole of the compound (4a).

The amount of the metal iodide to be used is about 0.1 to about 3.0 moles, preferably about 0.5 to about 1.0 mole compared to 1 mole of the compound (4a).

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (4a), which is included in compound (4), is also produced according to the method described in the following Reaction scheme.

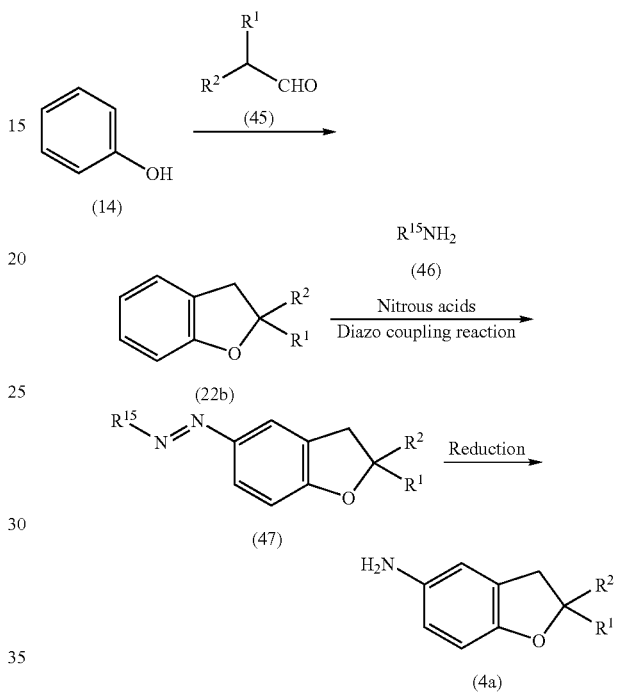

In Reaction scheme 23, $R^{15}$ is a $C_{6-10}$ aryl group which may have 1 to 3 substituents that are selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), halogen and nitro, and other symbols are as defined in the above.

According to Reaction scheme 23, compound (14) is reacted with compound (45) that is represented by the following formula in the presence of an acid, if desired, to give Compound (22b).

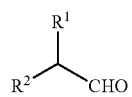

Compound (14) can be easily obtained as a commercial product, and also can be produced according to the methods known per se.

Compound (45) can be easily obtained as a commercial product, and also can be produced according to the methods known per se.

The amount of compound (45) to be used is about 0.8 to about 5.0 moles, preferably about 1.0 to about 2.0 moles compared to 1 mole of the compound (14).

As for the "acid", organic acids such as formic acid, acetic acid, trifluoroacetic acid, methanesulfonic acid, p-toluene sulfonic acid, camphor sulfonic acid, trifluoromethanesulfonic acid and the like, mineral acids such as hydrochloric acid, sulfuric acid, hydrobromic acid and the like, and Lewis acids such as zinc chloride, aluminum chloride, titanium tetrachloride and the like can be mentioned.

The amount of the acid to be used is generally about 0.1 to about 100 moles, preferably about 0.2 to about 50 moles compared to 1 mole of the compound (14) for the mineral acids. The amount of the acid to be used is generally about 0.01 to about 20 moles, preferably about 0.05 to about 5 moles compared to 1 mole of the compound (14) for the organic acids, for example. The amount of the acids to be used is generally about 0.1 to about 20 moles, preferably about 0.1 to about 5.0 moles compared to 1 mole of the compound (39) for the Lewis acids, for example.

It is advantageous to carry out the reaction by using a solvent inert to the reaction. Such a solvent, though being not particularly limited as far as the reaction proceeds, is preferably exemplified by alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane, heptane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 10 minutes to about 72 hours, preferably about 1 hour to about 24 hours. Reaction temperature is generally about −20 to about 200° C., preferably about 20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Diazonium salt, which is prepared from Compound (46) represented by the following formula and nitrous acids in an acid solution, is reacted with Compound (22b) to give Compound (47).

Compound (46) can be easily obtained as a commercial product, and also can be produced according to the methods known per se.

The amount of compound (46) to be used is about 0.8 to about 10.0 moles, preferably about 1.0 to about 5.0 moles compared to 1 mole of the compound (22b).

As the "nitrous acids", nitrous acid, sodium nitrite, potassium nitrite, ethyl nitrite, amyl nitrite, isoamyl nitrite, etc. can be used.

The amount of the nitrous acids to be used is about 0.8 to about 10.0 moles, preferably about 1.0 to about 5.0 moles compared to 1 mole of the compound (22b).

Examples of the "acid" include hydrochloric acid and hydrobromic acid. The amount of the acid to be used is about 1 to about 1000 moles compared to 1 mole of the compound (22b).

It is advantageous to carry out the reaction by using a solvent inert to the reaction. Such a solvent, though being not particularly limited as far as the reaction proceeds, is preferably exemplified by water, alcohols such as methanol, ethanol, propanol, butanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, organic acids such as acetic acid, trifluoroacetic acid and the like, or a mixed solvent thereof, and the like.

Reaction time is generally about 30 minutes to about 72 hours, preferably about 3 hours to about 24 hours. Reaction temperature is generally about −20 to about 200° C., preferably about 20 to about 150° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (47) is subjected to catalytic reduction under hydrogen atmosphere using a metal catalyst to give Compound (4a). If desired, a suitable acid may be added thereto.

As the "metal catalyst", Raney nickel, platinum oxide, metal palladium, palladium-carrying activated carbon, etc. can be used.

The amount of the "metal catalyst" to be used is generally about 1 to about 1000 wt %, preferably about 5 to about 20 wt % with respect to the compound (47).

As the "acid", organic acids such as formic acid, acetic acid, trifluoroacetic acid and p-toluenesulfonic acid, mineral acids such as sulfuric acid, hydrochloric acid and hydrobromic acid, etc. can be used. The amount of the "acid catalyst" to be used is about 0.1 to an excess amount compared to 1 mole of the compound (47).

It is advantageous to carry out the reaction by using a solvent inert to the reaction. Such a solvent, though being not particularly limited as far as the reaction proceeds, is preferably exemplified by alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, organic acids such as acetic acid and the like, water, or a mixed solvent thereof, and the like. Hydrogen pressure is generally about 1 to about 100 atm, preferably about 1 to about 5 atm.

Reaction time is generally about 30 minutes to about 48 hours, preferably about 1 hour to about 24 hours. Reaction temperature is generally about 0 to about 120° C., preferably about 20 to about 80° C.

Compound (4a) can also be produced by reducing Compound (47) with a reducing agent.

As for the "reducing agent", sodium hydrosulfite, or metal hydrides such as sodium borohydride, lithium aluminum hydride, sodium bis(2-methoxyethoxy)aluminum hydride, borane tetrahydrofuran complex, aluminum diisobutyl hydride and the like, or metals such as iron, zinc, tin dichloride and the like, etc. are used.

The amount of the "sodium hydrosulfite" to be used is about 0.8 to about 10.0 moles, preferably about 1.0 to about 5.0 moles compared to 1 mole of the compound (47).

The amount of the "metal hydrides" to be used is about 0.8 to about 10.0 moles, preferably about 1.0 to about 5.0 moles compared to 1 mole of the compound (47).

The amount of the "metals" to be used is generally about 0.8 to about 20 moles, preferably about 1.0 to about 10 moles compared to 1 mole of the compound (47). If desired, an acid may be added thereto.

Examples of the "acid" include organic acids such as formic acid and acetic acid, mineral acids such as hydrochloric acid and hydrobromic acid, etc. The amount of the acid to be used is generally about 1 to about 1000 moles compared to 1 mole of the compound (47).

It is advantageous to carry out the reaction by using a solvent inert to the reaction. Such a solvent, though being not particularly limited as far as the reaction proceeds, is preferably exemplified by water, alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, or a mixed solvent thereof, and the like.

Reaction time is generally about 10 minutes to about 72 hours, preferably about 30 minutes to about 24 hours. Reaction temperature is generally about −20 to about 200° C., preferably about 20 to about 120° C.

The product can be used for the next reaction as a reaction solution as it is or as a crude product. However, it can be isolated from the reaction mixture according to a method generally known in the art, and can be easily purified by common means for separation (for example, recrystallization, distillation, chromatography and the like).

Compound (I) produced by such method can be isolated and purified by a typical separation means such as recrystallization, distillation, chromatography, etc.

When Compound (I) contains an optical isomer, a stereoisomer, a regioisomer or a rotation isomer, these are also encompassed in compound (I) and can be obtained as a single product according to synthesis and separation methods known per se (for example, concentration, solvent extraction, column chromatography, recrystallization, etc.). For example, when Compound (I) has an optical isomer, the optical isomer resolved from this compound is also encompassed in compound (I).

The optical isomer can be produced by a method known per se. To be specific, an optically active synthetic intermediate is used, or the final racemate is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is added to a chiral column such as ENANTIO-OVM (manufactured by Tosoh Corporation), CHIRAL series (manufactured by Daicel Chemical Industries, Ltd.) and the like, and developed with water, various buffers (for example, phosphate buffer, etc.) and organic solvents (for example, ethanol, methanol, isopropanol, acetonitrile, trifluoroacetic acid, diethylamine, etc.) solely or in mixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is formed into a single substance by a typical separation means (for example, a fractional recrystallization, a chromatography method, etc.) and the like, and is subjected to a chemical treatment such as hydrolysis reaction and the like to separate an optically active reagent moiety, whereby an optical isomer is obtained. For example, when Compound (I) contains hydroxy, or primary or secondary amino in the molecule, the compound and an optically active organic acid (for example, MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When Compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by applying it to acid hydrolysis or basic hydrolysis.

Compound (I) may be in the form of a crystal.

The crystal of Compound (I) can be produced by crystallization of Compound (I) according to a crystallization method known per se.

Herein, examples of the crystallization method include a method of crystallization from a solution, a method of crystallization from vapor, a method of crystallization from the melts and the like.

The "crystallization method from a solution" may be typically a method of shifting a non-saturated state to supersaturated state by varying factors involved in solubility of compounds (solvent composition, pH, temperature, ionic strength, redox state, etc.) or the amount of solvent. To be specific, for example, a concentration method, a slow cooling method, a reaction method (a diffusion method, an electrolysis method), a hydrothermal growth method, a flux method and the like can be mentioned. Examples of the solvent to be used include aromatic hydrocarbons (for example, benzene, toluene, xylene, etc.), halogenated hydrocarbons (for example, dichloromethane, chloroform, etc.), saturated hydrocarbons (for example, hexane, heptane, cyclohexane, etc.), ethers (for example, diethyl ether, diisopropyl ether, tetrahydrofuran, dioxane, etc.), nitriles (for example, acetonitrile, etc.), ketones (for example, acetone, etc.), sulfoxides (for example, dimethyl sulfoxide, etc.), acid amides (for example, N,N-dimethylformamide, etc.), esters (for example, ethyl acetate, etc.), alcohols (for example, methanol, ethanol, isopropyl alcohol, etc.), water and the like. These solvents are used alone or in a combination of two or more at a suitable ratio (e.g., 1:1 to 1:100 (a volume ratio)). Depending on necessity, seed crystals can be also used.

The "crystallization method from vapor" may be, for example, a vaporization method (a sealed tube method, a gas stream method), a gas phase reaction method, a chemical transportation method and the like.

The "crystallization method from the melts" may, be, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving Compound (I) in a suitable solvent (e.g., alcohols such as methanol, ethanol, etc., etc.) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

As a method for the interpretation of obtained crystals, crystal interpretation based on powder X-ray diffraction is a method that is generally used. In addition, as a method for determining the bearing of crystals, a mechanical method or an optical method and the like can be also mentioned.

Crystals of the Compound (I) that are obtained from the preparation method described above (hereinbelow, abbreviated as the "crystals of the present invention") have high purity, high quality, low hygroscopic property and very excellent stability and do not deteriorate even when they are stored for a long period of time under general condition. In addition, also having excellent biological properties (for example, pharmacokinetics in a living body (absorption, distribution, metabolism, excretion), drug efficacy expression, etc.), they are extremely useful as a medicament.

The crystal of Compound (I) can be a pharmaceutically acceptable co-crystal or a co-crystal salt. The term "co-crystal" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

In the present specification, the specific rotation ($[\alpha]_D$) means, for example, a specific rotation measured using a polarimeter (JASCO, P-1030 polarimeter (No. AP-2)) and the like.

In the present specification, the melting point means that measured using, for example, melting-point apparatus (Stanford Research Systems, Inc., OptiMelt), a micro melting point apparatus (Yanako, MP-500VD) or a DSC (differential scanning calorimetry) device (SEIKO, EXSTAR6000) and the like.

[Prodrug]

The prodrug of Compound (I) indicates a compound which can convert into Compound (I) under the physiological condition in the living body, i.e., by a reaction with an enzyme, a gastric acid, or the like, specifically, a compound which can convert into Compound (I) by enzymatic oxidation, reduction, hydrolysis, etc., and a compound which can convert into Compound (I) by hydrolysis with gastric acid, etc. The prodrug of Compound (I) includes a compound wherein an amino group of Compound (I) is modified with acyl, alkyl or phosphoric acid (e.g., a compound wherein an amino group of Compound (I) is modified with eicosanoyl, alanyl, pentylaminocarbonyl, (5-methyl-2-oxo-1,3-dioxolen-4-yl)methoxycarbonyl, tetrahydrofuryl, pyrrolidylmethyl, pivaloyloxymethyl or tert-butyl, etc.); a compound wherein a hydroxy group of Compound (I) is modified with acyl, alkyl, phosphoric acid or boric acid (e.g., a compound wherein a hydroxy group of Compound (I) is modified with acetyl, palmitoyl, propanoyl, pivaloyl, succinyl, fumaryl, alanyl or dimethylaminomethylcarbonyl, etc.); a compound wherein a carboxy group of Compound (I) is modified to ester or amide (e.g., a compound wherein a carboxyl group of Compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from Compound (I) by a method known per se.

In addition, the prodrug of Compound (I) may be a compound, which is converted into Compound (I) under the physiological conditions, as described in "Pharmaceutical Research and Development", Vol. 7 (Molecular Design), pp. 163-198 (1990), published by Hirokawa Publishing Co.

[Salt]

Compound (I) and prodrug thereof may form a salt. As for the salt of the compound, it is not specifically limited unless it inhibits the reaction. A salt of the compound includes, for example, a salt with inorganic base, an ammonium salt, a salt with an organic base, a salt with an inorganic acid, a salt with an organic acid, a salt with an amino acid, etc. Suitable examples of the salt with inorganic base include an alkali metal salt such as a sodium salt, a potassium salt, etc., an alkaline earth metal salt such as a calcium salt, a magnesium salt, and an aluminum salt and an ammonium salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc.

Suitable examples of the salts with a basic amino acid include salts with arginine, lysine, ornithine, etc. Suitable examples of the salts with an acidic amino acid include salts with aspartic acid and glutamic acid, etc.

Among these, pharmaceutically acceptable salts are preferred. For example, if the compound has an acidic functional group therein, preferred are inorganic salts such as an alkali metal salt (e.g., sodium salt, potassium salt, etc.), an alkaline earth metal salt (e.g., calcium salt, magnesium salt, barium salt, etc.), an ammonium salt, etc. If the compound has a basic functional group, preferred are salts with an inorganic acid such as hydrobromic acid, nitric acid, sulfuric acid, phosphoric acid, etc., or salts with an organic acid such as acetic acid, phthalic acid, fumaric acid, oxalic acid, tartaric acid, maleic acid, citric acid, succinic acid, methanesulfonic acid, p-toluenesulfonic acid, etc.

Compound (I) may be either a hydrate or a non-hydrate. Examples of the hydrates include 0.5 hydrate, 1 hydrate, 1.5 hydrate and 2 hydrate, etc.

Compound (I) may be either a solvate or as a non-solvate.

Further, when $R^2$ in Compound (I) is a branched alkyl which may be substituted or a cycloalkyl which may be substituted, the compound may have a resonance structure.

When Compound (I) is obtained as a mixture of optically active substances (i.e., racemate), it can be resolved into the desired (R) form or (S) form according to the means for optical resolution that is known in the pertinent art.

Compound (I) may be labeled with an isotope (e.g., $^3H$, $^{14}C$, $^{35}S$, etc.). Compound (I) may also be a deuterated compound.

[Therapeutic Use]

Compound (I) of the present invention, salt thereof or prodrug thereof (hereinbelow, abbreviated as "Compound (I')") has an excellent neuron protecting activity, a neurogenesis stimulating activity, a neuronal regeneration stimulating activity, a cognitive function improving activity and the like. Further, Compound (I') is safe as having low toxicity, in particular low light toxicity, and is useful as a medicament because it has high transition to central nervous system. Accordingly, as a pharmaceutical agent, Compound (I') can be administered to mammals (e.g., mouse, rat, hamster, rabbit, cat, dog, cow, sheep, monkey, human etc.) as it is or as pharmaceutical composition wherein Compound (I') is mixed with pharmaceutically acceptable carriers, etc.

Compound (I') is useful as an agent for controlling IGF-1 signal, an agent for stimulating growth and differentiation of stem cells, an agent for stimulating growth and differentiation of neural precursor cells, an agent for activating protein kinase B, an agent for stimulating neurogenesis or an agent for stimulating neuron regeneration. The compound of the present invention is particularly useful as agent for controlling IGF-1 signal.

Further, Compound (I') is useful for the prophylaxis or treatment of the disorders described below, for example.

Central Nervous System Disorders (1) Neuropsychiatric disorders (e.g., depression, anxiety, manic depression, schizophrenia, anxiety neurosis, obsessive-compulsive neurosis, hyperactivity, etc.), (2) Neurodegenerative disorders (e.g., Alzheimer's disease, Parkinson's disease, amyotrophic lateral sclerosis, Huntington's disease, spinocerebral degeneration, multiple sclerosis (MS), Pick disease), (3) Memory disorders (e.g., senile dementia, mild cognitive disorder, mild memory disorder)

(4) Cerebrovascular disorders (e.g., cerebral infarction, stroke, cerebrovascular dementia)

(5) Head trauma, spinal cord injury (6) Ischemic disorders (e.g., angina pectoris, myocardial infarction, etc.)

(7) Cerebral ischemic disorders (e.g., cerebral infarction, etc.)

(8) Metabolic disorders (e.g., diabetes, hypertension, etc.)

(9) Peripheral neuronal disorders (e.g., diabetic neuronal disorder, urinary tract and bladder dysfunction disorder)

(10) Circulatory system disorders (e.g., arteriosclerosis)

Compound (I') is particularly useful as an agent for the prophylaxis or treatment of neurodegenerative disorders, more specifically, Alzheimer's disease.

Further, Compound (I') can be used, as it is or as a mixture with a pharmaceutically acceptable carrier, etc., as an agent for improving quality of life in heart failure after myocardial infarction, an agent for improving quality of life after cerebral infarction, an agent for lowering blood sugar, an agent for improving insulin resistance, or as an agent for lowering triglyceride in blood.

Still further, as an agent for stimulating growth and differentiation of stem cells, iPS cell, and/or neural precursor cells, the compound of the present invention is effective, for example, for neuronal degenerative disorders (e.g., Alzheimer's disease, Parkinson's disease, amyotrophic lateral sclerosis (ALS), Huntington's disease, spinocerebral degeneration, etc.), neuropsychiatric disorders (e.g., schizophrenia, etc.), head trauma, spinal cord injury, cerebrovascular disorders, cerebrovascular dementia, etc., and it is used as an agent for the prophylaxis and treatment of these central nervous system disorders.

[Preparation]

When Compound (I') is used as a pharmaceutical agent for the above described disorders, it can be administered, as it is or as a mixture with a pharmaceutically acceptable carrier, orally or parenterally (e.g., intravenous, intramuscular, subcutaneous, intraorgan, intranasal, intradermal, instillation, intracerebral, intrarectal, intravaginal, intraperitoneal, directly to lesion) in the form of tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection), drop, percutaneous absorbent, ointment, lotion, patch, suppositories (e.g., rectal suppository, vaginal suppository), pellets, transnasal preparations, pulmonary preparations (inhalant), eye drops and the like.

For the production of such pharmaceutical preparations, for example, each of the items in General Rules for Preparations in the Japanese Pharmacopoeia, can be made reference to.

In addition, the pharmaceutical preparations of the present invention may be formulated into a sustained release preparation containing active ingredients and biodegradable polymer compounds. The sustained release preparation can be produced according to the method described in JP-A No. 9-263545.

In the pharmaceutical preparations of the present invention, the content of Compound (I') varies depending on the administration method, the carrier, the forms of the preparations, etc., but is generally in the order of 0.01 to 100% by weight, preferably 0.1 to 50% by weight, more preferably 0.5 to 20% by weight, in the amount of Compound (I) relative to the total weight of the preparation.

As a pharmaceutically acceptable carrier, various organic or inorganic carrier substances conventionally used as preparation materials can be used. For example, an excipient, a lubricant, a binder and a disintegrant for solid preparations; a solvent, a solubilizing agent, a suspending agent, an tonicity agent, a buffer agent and a soothing agent for liquid preparations and the like are used. If necessary, preparation additives such as a preservative, an antioxidant, a colorant, a sweetening agent and the like can be used.

Preferable examples of the excipient include lactose, sucrose, D-mannitol, starch, crystalline cellulose, light anhydrous silicic acid and the like.

Preferable examples of the lubricant include magnesium stearate, calcium stearate, talc, colloidal silica and the like.

Preferable examples of the binder include crystalline cellulose, sucrose, D-mannitol, dextrin, hydroxypropylcellulose, hydroxypropylmethylcellulose, polyvinylpyrrolidone and the like.

Preferable examples of the disintegrant include starch, carboxymethylcellulose, calcium carboxymethylcellulose, croscarmellose sodium, sodium carboxymethyl starch and the like.

Preferable examples of the solvent include injection solvent, alcohol, propylene glycol, macrogol, sesame oil, corn oil and the like.

Preferable examples of the solubilizing agent include polyethylene glycol, propylene glycol, D-mannitol, benzyl benzoate, ethanol, trisaminomethane, a hydrophilic surface active agent such as Tween (registered trademark) 80, cyclodextrin (for example, α-, β- or γ-cyclodextrin or 2-hydroxypropyl-β-cyclodextrin or methyl-β-cyclodextrin and the like), cholesterol, triethanolamine, sodium carbonate, sodium citrate and the like. Preferable examples of the suspending agent include surface active agents such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; and the like.

Preferable examples of the tonicity agent include sodium chloride, glycerin, D-mannitol and the like.

Preferable examples of the buffer agent include buffers such as phosphate, acetate, carbonate, citrate and the like.

Preferable examples of the soothing agent include benzyl alcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite salt, ascorbic acid and the like.

A pharmaceutical composition can be produced according to a conventional method by adding the compound of the present invention generally in a proportion of 0.1 to 95% (w/w) relative to the total amount of the preparation, though subject to change depending on the preparation form, administration method, carrier and the like.

[Concomitant Drugs]

Compound (I') can be used as a pharmaceutical agent with other pharmaceutical preparations.

As for the drugs that can be concomitantly used with Compound (I') (hereinbelow, abbreviated as "concomitant drugs"), the followings can be exemplified.

(1) Agent for the Prophylaxis or Treatment of Central Nervous System Disorders

Therapeutic agent for depression, therapeutic agent for anxiety (e.g., benzodiazepine such as chlordiazepoxide, diazepam, potassium clorazepate, lorazepam, clonazepam, alprazolam, etc.), mood stabilizer (e.g., lithium carbonate, etc.), 5-HT2 antagonists (e.g., nefazodone, etc.), 5-HT1A agonists (e.g., tandospirone, buspirone, gepiron, etc.), CRF antagonist (e.g., Pexacerfont, etc.), β3 agonists (e.g., Amibegron, etc.), melatonine agonists (e.g., ramelteon, aglomelatine, etc.), α2 antagonists (e.g., mirtazapine, setiptiline, etc.), NK2 antagonists (e.g., Saredutant, etc.), GR antagonists (e.g., Mifepristone, etc.), NK-1 antagonists (e.g., Casopitant, Orvepitant, etc.), therapeutic agent for schizophrenia (e.g., chlorpromazine, haloperidol, sulpiride, clozapine, aripiprazole, quetiapine, olanzapine, risperidone, etc.), acetylcholine esterase inhibitor (e.g., donepezil, rivastigmine, galantamine, zanapezil, etc.), NMDA antagonists (e.g., memantine, etc.), inhibitor for production, secretion, accumulation, coagulation and/or deposit of β amyloid protein [β secretase inhibitor, γ secretase inhibitor (e.g., LY-450139, E-2012, E-2212), β amyloid protein coagulation inhibitor (e.g., PTI-00703, ALZHEMED (NC-531), PPI-368 (JP-B No. 11-514333), PPI-558 (JP-B No. 2001-500852), SKF-74652 (Biochem. J. (1999), 340(1), 283-289)), β amyloid vaccine, β amyloid antibody (e.g., AAB-001), β amyloid degrading enzyme, etc.], an agent for restoring brain function (e.g., aniracetam, nicergoline, etc.), therapeutic agent for Parkinson's disease [e.g., dopamine receptor agonists (e.g., L-DOPA, bromocriptine, pergolide, talipexole, pramipexole, cabergoline, amantadine, etc.), COMT inhibitor (e.g., entacapone, etc.)], therapeutic agent for attention deficit hyperactivity disorder (e.g., modafinil, etc.), therapeutic agent for amyotrophic lateral sclerosis (e.g., riluzole, neurotrophic factor, etc.), therapeutic agent for insomnia (e.g., etizolam, zopiclone, triazolam, zolpidem, indiplon, etc.), therapeutic agent for hypersomnia (e.g., modafinil, etc.), therapeutic agent for cerebrovascular disorders (edaravone, tPA, etc.), anti-cytokine agent (TNF inhibiting agent, MAP kinase inhibiting agent, etc.), steroid drugs (e.g., dexamethasone, hexestrol, cortisone acetate, etc.), and the like.

(2) Agent for the Prophylaxis or Treatment of Urinary Incontinence

Adrenaline α1 receptor agonist (e.g., ephedrine hydrochloride, midodrine hydrochloride etc.), adrenaline β2 receptor agonist (e.g., Clenbuterol, etc.), norepinephrine uptake inhibitory substance, norepinephrine and serotonin uptake inhibitory substance (e.g., duloxetine etc.), tricyclic antidepressant (e.g., imipramine hydrochloride etc.), anticholinergic drug or smooth muscle stimulant (e.g., oxybutynin hydrochloride, propiverine hydrochloride, celimeverine hydrochloride etc.), female sex hormone drug (e.g., binding-type estrogen (premarin), estriol etc.) and the like.

(3) Agent for Treating Diabetes

Insulin preparations [e.g., animal insulin preparations extracted from the bovine or swine pancreas; human insulin preparations synthesized by a genetic engineering technique using $Escherichia\ coli$ or a yeast; insulin zinc; protamine zinc insulin; a fragment or a derivative of insulin (e.g., INS-1, etc.)], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), glucokinase activating agent, SGLT (sodium-glucose cotransporter) inhibitors (e.g., T-1095, etc.) and the like.

(4) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(5) Antihyperlipidemic Agent

Statin compounds which inhibit cholesterol synthesis (e.g., pravastatin, simvastatin, lovastatin, atorvastatin, fluvastatin, cerivastatin or salt thereof (e.g., sodium salt, etc.), etc.), squalene synthethase inhibitors or fibrate compounds having triglyceride lowering action (e.g., bezafibrate, clofibrate, simfibrate, clinofibrate, etc.) and the like.

(6) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(7) Antiobesity Agent

Antiobesity drugs acting on the central nervous system (e.g., dexfenfluramine, fenfluramine, phentermine, sibutramine, anfepramone, dexamphetamine, mazindol, phenylpropanolamine, clobenzorex, etc.), pancreatic lipase inhibitors (e.g., orlistat, etc.), β3 agonists (e.g., CL-316243, SR-58611-A, UL-TG-307, AJ-9677, AZ40140, etc.), anorectic peptides (e.g., leptin, CNTF (Ciliary Neurotrophic Factor), etc.), cholecystokinin agonists (e.g., lintitript, FPL-15849, etc.), and the like.

(8) Diuretic Agent

Xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, benzylhydrochlorothiazide, penflutizide, polythiazide, methylclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(9) Chemotherapeutic Agent

Alkylating agents (e.g., cyclophosphamide, ifosfamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon or Neo-Furtulon, and the like.

(10) Immunotherapeutic Agent

Microorganism- or bacterium-derived components (e.g., muramyl dipeptide derivatives, Picibanil, etc.), polysaccharides having immunopotentiating activity (e.g., lentinan, schizophyllan, krestin, etc.), cytokines which can be obtained by a genetic engineering method (e.g., interferons, interleukins (IL), etc.), colony stimulating factors (e.g., granulocyte colony stimulating factor, erythropoietin, etc.) and the like. Among these, IL-1, IL-2, IL-12, and the like.

(11) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), lipid metabolism improving agents (e.g., eicosapentanoic acid) [British Journal of Cancer, vol. 68, pp. 314-318, 1993], growth hormones, IGF-1, and antibodies against the cachexia-inducing factors such as TNF-α, LIF, IL-6 and oncostatin M, and the like.

(12) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(13) Others

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), antiepilepticum (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), γ-aminobutyric acid (GABA) receptor agonists (e.g., gabapentin), GABA uptake inhibitors (e.g., tiagabine), α2 receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, Zolpidem), anticholinergic agents, α1 receptor blocking agents (e.g., tamsulosin, silodosin, naftopidil), muscle relaxants (e.g., baclofen, etc.), potassium channel openers (e.g., nicorandil), calcium channel blocking agents (e.g., nifedipine), agents for preventing or treating Alzheimer's disease (e.g., donepezil, rivastigmine, galanthamine), agents for treating Parkinson's disease (e.g., L-DOPA), agents for preventing or treating multiple sclerosis (e.g., interferon β-1a), histamine H1 receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents for treating HIV infection (saquinavir, zidovudine, lamivudine, nevirapine), agents for treating chronic obstructive pulmonary diseases (salmeterol, thiotropium bromide, cilomilast), and the like.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.). Among these, oxybutynin, propiverine, darifenacin, tolterodine, temiverine, trospium chloride or a salt thereof (e.g., oxybutynin hydrochloride, tolterodine tartrate, etc.) are preferable. In addition, acetylcholinesterase inhibitors (e.g., distigmine, etc.) and the like can be also used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

For concomitant use of the agent of the present invention, the administration time of Compound (I') and the concomitant drug is not restricted, and Compound (I') or pharmaceutical composition thereof and the concomitant drug or pharmaceutical composition thereof can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined administration are not specifically limited if Compound (I') and the concomitant drug are combined at the time of administration. Examples of the administration mode include the following:

(1) administration of a single preparation obtained by simultaneously formulating Compound (I') or pharmaceutical composition thereof and the concomitant drug, (2) simultaneous administration of two kinds of preparations, i.e., Compound (I') or pharmaceutical preparation thereof and the concomitant drug or pharmaceutical preparation thereof, which have been separately formulated, by the same administration route, (3) administration of two kinds of preparations, i.e., Compound (I') or pharmaceutical preparation thereof and the concomitant drug or pharmaceutical preparation thereof, which have been separately formulated, by the same administration route at a time interval, (4) simultaneous administration of two kinds of preparations, i.e., Compound (I') or pharmaceutical preparation thereof and the concomitant drug or pharmaceutical preparation thereof, which have been separately formulated, by different administration routes, (5) administration of two kinds of preparations, i.e., Compound (I') or pharmaceutical preparation thereof and the concomitant drug or pharmaceutical preparation thereof, which have been separately formulated, by different administration routes at a time interval (e.g., administration in the order of Compound (I') or pharmaceutical preparation thereof; the concomitant drug or pharmaceutical preparation thereof, or vice versa) and the like.

In the combination agent of the present invention, the mixing ratio between Compound (I') and the concomitant drug can be appropriately selected depending on the administration subject, administration route, disease, and the like.

For example, content of Compound (I') in the combination agent of the present invention varies depending on the form of preparation. However, it is generally about 0.01 to 100% by weight, preferably about 0.1 to 50% by weight, and more preferably about 0.5 to 20% by weight relative to the total preparation.

Content of the concomitant drugs in the combination agent of the present invention varies depending on the form of preparation. However, it is generally about 0.01 to 100% by weight, preferably about 0.1 to 50% by weight, and more preferably about 0.5 to 20% by weight relative to the total preparation.

Content of the additives including carriers and the like in the combination agent of the present invention varies depending on the form of preparation. However, it is generally about 1 to 99.99% by weight, and preferably about 10 to 90% by weight relative to the total preparation.

Further, for a case in which Compound (I') and the concomitant drugs are formulated separately, they can be used in the same amount as described in the above.

[Administration Method]

For the administration of Compound (I') as a pharmaceutical agent to mammals like a human, etc., the administration method generally include oral administration by using a tablet, a capsule (including soft capsule, micro capsule), powder, a granule and the like or parenteral administration including an injection product, a suppository, a pellet and the like. "Parenteral" administration includes administration to proximal region such as intravenous, intramuscular, subcutaneous, into the organ, intranasal, intradermal, by ocular instillation, intracerebral, intrarectal, intraluminal and intraperitoneal administration and the like, or administration directly to the lesion.

The dosage of Compound (I') varies depending on the administration route, symptoms, age of a patient, etc. For example, when it is administered orally as a therapeutic agent for Alzheimer's disease to a patient suffering from Alzheimer's disease (body weight of 40 to 80 kg), it can be administered at a dose of 0.1 to 200 mg/kg body weight per day, preferably 1 to 100 mg/kg body weight per day, more preferably 1 to 50 mg/kg body weight per day. This dosage can be administered once a day or in two or three divided portions a day.

When the pharmaceutical agent comprising Compound (I') is a sustained release preparation, the dosage of Compound (I') is set so as to achieve release of 1 to 100 mg of Compound (I') from the administered preparation for a week when it is applied via parenteral administration, for example.

The dosage of the concomitant drug can be set at any value unless side effects are problematical. The daily dosage of the concomitant drug varies depending on the severity of the symptom, age, sex, body weight, sensitivity difference of the subject, administration time, interval, and nature, preparation type, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg (body weight) of a mammal and this is usually administered in one to four divided portions a day.

When the concomitant drugs are administered, it may be permissible that Compound (I') and the concomitant drugs are administered simultaneously. However, it is also possible that Compound (I') is administered after the administration of the concomitant drugs. Alternatively, the concomitant drugs can be administered after Compound (I') is administered. When administered at a time interval, the interval varies depending on the effective ingredient to be administered, preparation form and administration method, and for example, when the concomitant drugs are administered first, a method in which Compound (I') is administered within time range of from 1 minute to 3 days, preferably from 10 minutes to 1 day, more preferably from 15 minutes to 1 hour after administration of the concomitant drug is exemplified. When Compound (I') is administered first, a method in which the concomitant drugs are administered within time range of from 1 minute to 1 day, preferably from 10 minutes to 6 hours, more preferably from 15 minutes to 1 hour after administration of Compound (I') is exemplified.

EXAMPLES

Reference Example 1

1,2,5-trimethyl-3-[(2-methylprop-2-en-1-yl)oxy]benzene 3-bromo-2-methylpropene (29.8 g, 221 mmol) was added to a mixture of DMF (130 mL) containing 2,3,5-trimethylphenol (25.0 g, 184 mmol) and potassium carbonate (50.9 g, 368 mmol), and the resulting mixture was stirred at 80° C. for 15 hours. After cooled to room temperature, the reaction solution was distributed using ethyl acetate and water. The organic layer was washed with saturated saline, and then dried using anhydrous magnesium sulfate. The solvent was removed under reduced pressure, and the obtained residue was purified by silica gel column chromatography (hexane-ethyl acetate 50:1 to 9:1) to give 33.6 g of the title compound (yield: 96%) as an oily product.

$^1$H-NMR (CDCl$_3$): δ1.84 (3H, s), 2.14 (3H, s), 2.23 (3H, s), 2.27 (3H, s), 4.39 (2H, s), 4.94-4.99 (1H, m), 5.09-5.14 (1H, m), 6.52 (1H, s), 6.61 (1H, s).

Reference Example 2

2,3,5-trimethyl-6-(2-methylprop-2-en-1-yl)phenol

A mixture of 1,2,5-trimethyl-3-[(2-methylprop-2-en-1-yl)oxy]benzene (33.6 g, 177 mmol) synthesized in Reference Example 1 and N,N-diethylaniline (100 mL) was stirred under argon atmosphere at 220 to 230° C. for 11 hours. After cooled to room temperature, the reaction solution was distributed using ethyl acetate and 1N hydrochloric acid. The organic layer was washed with 1N hydrochloric acid and saturated saline, and then dried using anhydrous magnesium sulfate. The solvent was removed under reduced pressure, and the obtained residue was purified by silica gel column chromatography (hexane-ethyl acetate 40:1 to 9:1) to give 28.6 g of the title compound (yield: 85%) as an oily product.

$^1$H-NMR (CDCl$_3$): δ1.77 (3H, s), 2.13 (3H, s), 2.22 (6H, s), 3.35 (2H, s), 4.70-4.75 (1H, s), 4.84-4.89 (1H, m), 5.07 (1H, s), 6.61 (1H, s).

Reference Example 3

2,2,4,6,7-pentamethyl-2,3-dihydro-1-benzofuran

A mixture of 2,3,5-trimethyl-6-(2-methylprop-2-en-1-yl)phenol (13.0 g, 68.3 mmol) synthesized in Reference Example 2, p-toluenesulfonic acid monohydrate (1.30 g, 6.83 mmol) and toluene (130 mL) was stirred under heated reflux for 1.5 hours. After cooled to room temperature, the reaction solution was distributed by addition of 1N sodium hydroxide aqueous solution. The organic layer was washed with 1N sodium hydroxide aqueous solution and saturated saline, and then dried using anhydrous magnesium sulfate. The solvent was removed under reduced pressure, and the obtained residue was purified by basic silica gel chromatography (hexane-ethyl acetate 49:1 to 24:1) to give 11.1 g of the title compound (yield: 85%).

$^1$H-NMR (CDCl$_3$): δ1.46 (6H, s), 2.07 (3H, s), 2.14 (3H, s), 2.19 (3H, s), 2.90 (2H, s), 6.48 (1H, s).

Reference Example 4

5-bromo-2,2,4,6,7-pentamethyl-2,3-dihydro-1-benzofuran

N-bromosuccinimide (12.5 g, 70.0 mmol) was added to a solution of acetonitrile (165 mL) containing 2,2,4,6,7-pentamethyl-2,3-dihydro-1-benzofuran (11.1 g, 58.3 mmol) synthesized in Reference Example 3 under ice-cooling condition, and the mixture was warmed to room temperature. After stirring for 5 hours, water was added to the reaction solution. The generated precipitate was collected by filtration and washed with a mixture of acetonitrile/water (1/2). The solid was dried to give 13.5 g of the title compound (yield: 86%).

$^1$H-NMR (CDCl$_3$): δ1.46 (6H, s), 2.15 (3H, s), 2.25 (3H, s), 2.34 (3H, s), 2.97 (2H, s), 6.48 (1H, s).

Reference Example 5

1-bromo-3-[(2-methylprop-2-en-1-yl)oxy]benzene

The title compound as an oily product was obtained in the same manner as described for Reference Example 1 using 3-bromophenol (19.8 g, 114 mmol) and 3-bromo-2-methylpropene (18.5 g, 137 mmol). The yield was 100%.

$^1$H-NMR (CDCl$_3$): δ1.82 (3H, s), 4.41 (2H, s), 4.97-5.02 (1H, m), 5.06-5.11 (1H, m), 6.82-6.88 (1H, m), 7.04-7.20 (3H, m).

Reference Example 6

5-bromo-2-(2-methylprop-2-en-1-yl)phenol 5.46 g of the title compound was synthesized in the same manner as described for Reference Example 2 using 1-bromo-3-[(2-methylprop-2-en-1-yl)oxy]benzene (26.0 g, 114 mmol) synthesized in Reference Example 5 (yield: 21%).

$^1$H-NMR (CDCl$_3$): δ1.73 (3H, s), 3.33 (2H, s), 4.84-4.87 (1H, m), 4.92-4.96 (1H, m), 5.28 (1H, s), 6.92-6.97 (1H, m), 6.98-7.04 (2H, m).

Reference Example 7

6-bromo-2,2-dimethyl-2,3-dihydro-1-benzofuran 5.18 g of the title compound was synthesized in the same manner as described for Reference Example 3 using 1-bromo-3-[(2-methylprop-2-en-1-yl)oxy]benzene (5.46 g, 24.0 mmol) synthesized in Reference Example 6 (yield: 95%).

$^1$H-NMR (CDCl$_3$): δ1.46 (6H, s), 2.94 (2H, s), 6.87 (d, 1H, J=1.5 Hz), 6.90-7.00 (2H, m).

Reference Example 8

2,2-dimethyl-6-(4-methylphenyl)-2,3-dihydro-1-benzofuran 4-methylphenylboric acid (1.35 g, 9.91 mmol), tetrakis(triphenylphosphine)palladium (382 mg, 0.331 mmol), an aqueous solution of 2N sodium carbonate (4.5 mL) and ethanol (83 mL) were sequentially added to a solution of dimethoxyethane (9 mL) containing 6-bromo-2,2-dimethyl-2,3-dihydro-1-benzofuran (1.50 g, 6.61 mmol) synthesized in Reference Example 7, and the mixture was stirred under microwave irradiation at 150° C. for 10 minutes. After cooled to room temperature, water was added to the reaction solution, and extraction was performed using ethyl acetate. The extract was washed with saturated sodium hydrogencarbonate and saturated saline, and then dried using anhydrous magnesium sulfate. The solvent was removed under reduced pressure, and the obtained residue was purified by silica gel column chromatography (hexane-ethyl acetate 99:1 to 93/7) to give 880 mg of the title compound (yield: 56%).

$^1$H-NMR (CDCl$_3$): δ1.50 (6H, s), 2.38 (3H, s), 3.04 (2H, s), 6.94 (1H, d, J=1.5 Hz), 7.03 (1H, dd, J=1.5, 7.5 Hz), 7.14-7.25 (3H, m), 7.42-7.48 (2H, m).

Reference Example 9

5-bromo-2,2-dimethyl-6-(4-methylphenyl)-2,3-dihydro-1-benzofuran 510 mg of the title compound was synthesized in the same manner as described for Reference Example 4 using 2,2-dimethyl-6-(4-methylphenyl)-2,3-dihydro-1-benzofuran (400 mg, 1.68 mmol) synthesized in Reference Example 8 (yield: 96%).

$^1$H-NMR (CDCl$_3$): δ1.50 (6H, s), 2.40 (3H, s), 3.03 (2H, s), 6.69 (1H, s), 7.17-7.41 (5H, m).

Reference Example 10

3-(2,2-dimethyl-2,3-dihydro-1-benzofuran-6-yl)pyridine 490 mg of the title compound as an oily product was obtained in the same manner as described for Reference Example 8 using 6-bromo-2,2-dimethyl-2,3-dihydro-1-benzofuran (680 mg, 2.99 mmol) synthesized in Reference Example 7 and 3-pyridineboronic acid (551 mg, 4.49 mmol) (yield: 73%).

$^1$H-NMR (CDCl$_3$): δ1.52 (6H, s), 3.06 (2H, s), 6.94 (1H, d, J=1.5 Hz), 7.03 (1H, dd, J=1.5, 7.8 Hz), 7.20-7.25 (1H, m), 7.30-7.37 (1H, m), 7.80-7.86 (1H, m), 8.56 (1H, dd, J=4.8 Hz), 8.81 (1H, dd, J=0.9, 2.4 Hz).

Reference Example 11

3-(5-bromo-2,2-dimethyl-2,3-dihydro-1-benzofuran-6-yl)pyridine 160 mg of the title compound was synthesized in the same manner as described for Reference Example 4 using 3-(2,2-dimethyl-2,3-dihydro-1-benzofuran-6-yl)pyridine (489 mg, 2.17 mmol) synthesized in Reference Example 10 (yield: 24%).

$^1$H-NMR (CDCl$_3$): δ1.51 (6H, s), 3.06 (2H, s), 6.94 (1H, d, J=1.5 Hz), 7.03 (1H, dd, J=1.5, 7.8 Hz), 7.20-7.25 (1H, m), 7.30-7.37 (1H, m), 7.80-7.86 (1H, m), 8.56 (1H, dd, J=4.8 Hz), 8.81 (1H, dd, J=0.9, 2.4 Hz).

Reference Example 12

1,2-dimethyl-3-[(2-methylprop-2-en-1-yl)oxy]benzene 49.5 g of the title compound as an oily product was obtained in the same manner as described for Reference Example 1 using 2,3-dimethylphenol (36.0 g, 295 mmol) and 3-bromo-2-methylpropene (47.7 g, 354 mmol) (yield: 95%).

$^1$H-NMR (CDCl$_3$): δ1.82-1.87 (3H, m), 2.19 (3H, s), 2.27 (3H, s), 4.41 (2H, brs), 4.95-5.00 (1H, m), 5.09-5.14 (1H, m), 6.69 (1H, d, J=8.1 Hz), 6.77 (1H, d, J=7.5 Hz), 7.03 (1H, dd, J=7.5, 8.1 Hz, 1H).

Reference Example 13

2,3-dimethyl-6-(2-methylprop-2-en-1-yl)phenol 52.0 g of the title compound (containing solvent) as an oily product was obtained in the same manner as described for Reference Example 2 using 1,2-dimethyl-3-[(2-methylprop-2-en-1-yl)oxy]benzene (49.5 g, 281 mmol) synthesized in Reference Example 12.

$^1$H-NMR (CDCl$_3$): δ1.73 (3H, s), 2.15 (3H, s), 2.25 (3H, s), 3.35 (2H, brs), 4.87-4.96 (2H, m), 5.23 (1H, s), 6.69 (1H, d, J=7.8 Hz), 6.82 (1H, d, J=7.8 Hz).

Reference Example 14

2,2,6,7-tetramethyl-2,3-dihydro-1-benzofuran 24.0 g of the title compound was synthesized in the same manner as described for Reference Example 3 using 2,3-dimethyl-6-(2-methylprop-2-en-1-yl)phenol (containing solvent, 52 g) synthesized in Reference Example 13 (2-step yield: 48%).

$^1$H-NMR (CDCl$_3$): δ1.46 (6H, s), 2.11 (3H, s), 2.22 (3H, s), 2.98 (2H, s), 6.58-6.66 (1H, m), 6.81-6.89 (1H, m).

Reference Example 15

5-bromo-2,2,6,7-tetramethyl-2,3-dihydro-1-benzofuran 2.34 g of the title compound was obtained in the same manner as described for Reference Example 4 using 2,2,6,7-tetramethyl-2,3-dihydro-1-benzofuran (1.91 g, 10.8 mmol) synthesized in Reference Example 14 (yield: 85%).

Melting point: 66-69° C. (methanol)

$^1$H-NMR (CDCl$_3$): δ1.45 (6H, s), 2.16 (3H, s), 2.30 (3H, s), 2.97 (2H, s), 7.16 (1H, m).

Reference Example 16

2-(2,3-dimethylphenoxy)-2-methylpropanoic acid

Sodium hydroxide (82.0 g, 2.05 mol) was added to a solution of methyl ethyl ketone (400 mL) containing 2,3-dimethylphenol (50.0 g, 410 mmol), and the mixture was stirred at 50° C. for 1 hour. After that, a solution of methyl ethyl ketone (200 mL) containing 2-bromo-2-methylpropionic acid (103 g, 615 mmol) was added thereto, and the mixture was stirred at 50° C. for 4 hours. After cooled to room temperature, the reaction solution was distributed by adding water and diethyl ether. 6N hydrochloric acid was added to the aqueous layer to be acidic, and then extraction was performed using ethyl acetate. The extract was washed with saturated saline, and then dried using anhydrous magnesium sulfate. The solvent was removed under reduced pressure, and the obtained residue was purified by silica gel chromatography (hexane-ethyl acetate 95:5 to 50/50) to give 38.3 g of the title compound (yield: 45%).

$^1$H-NMR (CDCl$_3$): δ1.60 (6H, s), 2.17 (3H, s), 2.27 (3H, s), 6.71 (1H, d, J=7.8 Hz), 6.86 (1H, d, J=7.8 Hz), 6.99 (1H, t, J=7.8 Hz).

Reference Example 17

2,2,6,7-tetramethyl-1-benzofuran-3(2H)-one

Oxalyl dichloride (21 mL, 221 mmol) and DMF (3 drops) were sequentially added to a solution of THF (300 mL) containing 2-(2,3-dimethylphenoxy)-2-methylpropanoic acid (38.3 g, 184 mmol) synthesized in Reference Example 16 under ice-cooling condition, and the mixture was warmed to room temperature and stirred for 1 hour. The reaction solution was concentrated under reduced pressure, and then the residue was dissolved in methylene chloride (250 mL). To this solution, aluminium chloride (36.2 g, 276 mmol) was added at −78° C., and the mixture was warmed to room temperature and stirred for 15 hours. The reaction solution was concentrated under reduced pressure, and then water was added to the residue and extraction was performed using ethyl acetate. The extract was washed with saturated saline, and then dried using anhydrous magnesium sulfate. The solvent was removed under reduced pressure, and the obtained residue was purified by silica gel chromatography (hexane-ethyl acetate 95:5 to 5/1) to give 26.4 g of the title compound (yield: 75%).

$^1$H-NMR (CDCl$_3$): δ1.46 (6H, s), 2.21 (3H, s), 2.35 (3H, s), 6.87 (1H, d, J=7.8 Hz), 7.40 (1H, d, J=7.8 Hz).

Reference Example 18

5-bromo-2,2,6,7-tetramethyl-1-benzofuran-3(2H)-one

Bromine (10.0 mL, 195 mmol) was added to a solution of acetic acid (150 mL) containing 2,2,6,7-tetramethyl-1-benzofuran-3(2H)-one (26.4 g, 139 mmol) synthesized in Reference Example 17, and the mixture was stirred at room temperature for 3 hours. After that, the reaction solution was poured into 5% aqueous solution of sodium sulfite. The generated crystals were collected by filtration, and recrystallized from methanol to give 32.8 g of the title compound (yield: 88%).
$^1$H-NMR (CDCl$_3$): δ1.45 (6H, s), 2.29 (3H, s), 2.44 (3H, s), 7.71 (1H, s).

Reference Example 19

5-(benzylamino)-2,2,6,7-tetramethyl-1-benzofuran-3(2H)-one

Sodium t-butoxide (13.9 g, 145 mmol) was added to a mixture of toluene (100 mL) containing 5-bromo-2,2,6,7-tetramethyl-1-benzofuran-3(2H)-one (12.8 g, 48.2 mmol) synthesized in Reference Example 18, benzylamine (15.5 g, 145 mmol), palladium acetate (541 mg, 2.41 mmol) and BINAP (4.50 g, 7.23 mmol), and the mixture was stirred under heated reflux for 20 hours. After cooled to room temperature, water was added to the reaction solution, and extraction was performed using ethyl acetate. The organic layer was washed with saturated saline, and then dried using anhydrous magnesium sulfate. The solvent was removed under reduced pressure, and the obtained residue was purified by silica gel chromatography (hexane-ethyl acetate 100:0 to 50:50) to give 9.48 g of the title compound (yield: 67%).
$^1$H-NMR (CDCl$_3$): δ1.43 (6H, s), 2.19 (3H, s), 2.26 (3H, s), 3.67 (1H, s), 4.32 (2H, s), 6.69 (1H, s), 7.24-7.42 (5H, m).

Reference Example 20

5-amino-2,2,6,7-tetramethyl-1-benzofuran-3(2H)-one

5% palladium carbon (50% water content, 9.50 g) was added to a mixed solution of tetrahydrofuran (100 mL) and methanol (100 mL) containing 5-(benzylamino)-2,2,6,7-tetramethyl-1-benzofuran-3(2H)-one (9.48 g, 32.1 mmol) synthesized in Reference Example 19, and the mixture was stirred under hydrogen atmosphere at room temperature for 22 hours. Palladium carbon was removed by filtration, and then the solvent was removed under reduced pressure to give 6.59 g of the title compound (yield: 100%).
$^1$H-NMR (CDCl$_3$): δ1.43 (6H, s), 2.19 (3H, s), 2.24 (3H, s), 3.49 (2H, br s), 6.79 (1H, s).

Reference Example 21

5-amino-4-bromo-2,2,6,7-tetramethyl-1-benzofuran-3(2H)-one

Tetrabutylammonium tribromide (31.0 g, 64.2 mmol) was added to a tetrahydrofuran solution (200 mL) containing 5-amino-2,2,6,7-tetramethyl-1-benzofuran-3(2H)-one (6.59 g, 32.1 mmol) synthesized in Reference Example 20 at 0° C., and the mixture was stirred at 0° C. for 2 hours. To the mixture, a saturated sodium sulfite aqueous solution was added, and extraction was performed using ethyl acetate. The extract was dried using anhydrous magnesium sulfate. After that, the solvent was removed under reduced pressure, and the obtained residue was purified by silica gel column chromatography (hexane-ethyl acetate 98:2 to 85:15) to give 6.60 g of the title compound (yield: 72%).
$^1$H-NMR (CDCl$_3$): δ1.44 (6H, s), 2.21 (3H, s), 2.25 (3H, s), 3.97 (2H, br s).

Reference Example 22

5-amino-4-ethenyl-2,2,6,7-tetramethyl-1-benzofuran-3(2H)-one 2-ethenyl-4,4,5,5-tetramethyl-1,3,2-dioxaborolan (3.79 g, 24.6 mmol), tetrakistriphenyl phosphine palladium (605 mg, 0.523 mmol), sodium carbonate (1.36 g, 12.8 mmol), water (8 mL) and ethanol (5 mL) were added to a solution of DME (14 mL) containing 5-amino-4-bromo-2,2,6,7-tetramethyl-1-benzofuran-3(2H)-one (2.00 g, 7.04 mmol) synthesized in Reference Example 21, and the mixture was stirred under argon atmosphere at 100° C. for 45 hours. After cooled to room temperature, water was added to the mixture, and extraction was performed using ethyl acetate. It was dried using anhydrous magnesium sulfate. After that, the solvent was removed under reduced pressure, and the obtained residue was purified by silica gel column chromatography (hexane-ethyl acetate: 98:2 to 85:15) to give 1.47 g of the title compound (yield: 91%).
$^1$H-NMR (CDCl$_3$): δ1.42 (6H, s), 2.21 (3H, s), 2.24 (3H, s), 3.88 (2H, br s), 5.65-5.77 (2H, m), 7.27-7.40 (1H, m).

Reference Example 23

4-ethenyl-5-[4-(4-methoxyphenyl)piperazin-1-yl]-2,2,6,7-tetramethyl-1-benzofuran-3(2H)-one N,N-bis(2-bromoethyl)-4-methoxyaniline (2.45 g, 7.63 mmol) and sodium hydrogencarbonate (1.25 g, 1.40 mmol) were added to a solution of DMF (36 mL) containing 5-amino-4-ethenyl-2,2,6,7-tetramethyl-1-benzofuran-3(2H)-one (1.47 g, 6.36 mmol) synthesized in Reference Example 22, and the mixture was stirred at 120° C. for 16 hours. After cooled to room temperature, water was added to the mixture, and extraction was performed using ethyl acetate. It was dried using anhydrous magnesium sulfate. After that, the solvent was removed under reduced pressure, and the obtained residue was purified by silica gel column chromatography (hexane-ethyl acetate: 100:0 to 90:10) to give 217 mg of the title compound (yield: 8%).
Melting point: 147-148° C. (methanol-hexane)
$^1$H-NMR (CDCl$_3$): δ1.42 (6H, s), 2.22 (3H, s), 2.37 (3H, s), 2.98-3.41 (8H, m), 3.78 (3H, s), 5.64 (1H, dd, J=11.7, 1.8 Hz), 5.78 (1H, dd, J=17.7, 1.8 Hz), 6.86 (2H, d, J=9.3 Hz), 6.96 (2H, d, J=9.3 Hz), 7.06 (1H, dd, J=17.7, 11.7 Hz).

Reference Example 24

4-ethyl-5-[4-(4-methoxyphenyl)piperazin-1-yl]-2,2,6,7-tetramethyl-1-benzofuran-3(2H)-one 5% palladium carbon (50% water content, 100 mg) was added to a solution of ethanol (5 mL) containing 4-ethenyl-5-[4-(4-methoxyphenyl)piperazin-1-yl]-2,2,6,7-tetramethyl-1-benzofuran-3(2H)-one (100 mg, 0.246 mmol) synthesized in Reference Example 23, and the mixture was stirred under hydrogen atmosphere at room temperature for 20 hours. Palladium carbon was removed by filtration, and then the solvent was removed under reduced pressure. The obtained residue was purified by silica gel column chromatography (hexane-ethyl acetate 100:0 to 95:5) to give 36.7 mg of the title compound (yield: 36%).

Melting point: 133-134° C. (hexane)

$^1$H-NMR (CDCl$_3$): δ1.18 (3H, t, J=7.5 Hz), 1.43 (6H, s), 2.18 (3H, s), 2.35 (3H, s), 3.04-3.38 (10H, m), 3.79 (3H, s), 6.87 (2H, d, J=9.0 Hz), 6.97 (2H, d, J=9.0 Hz).

Reference Example 25

5-amino-4-cyclopropyl-2,2,6,7-tetramethyl-1-benzofuran-3(2H)-one 809 mg of the title compound was synthesized in the same manner as described for Reference Example 22 using 5-amino-4-bromo-2,2,6,7-tetramethyl-1-benzofuran-3(2H)-one (1.50 mg, 5.28 mmol) synthesized in Reference Example 21 and cyclopropylboronic acid (2.28 g, 26.5 mmol) (yield: 62%).

$^1$H-NMR (CDCl$_3$): δ0.45-0.65 (2H, m), 1.00-1.20 (m, 2H), 1.60-1.75 (1H, m), 1.41 (6H, s), 2.19 (3H, s), 2.22 (3H, s), 3.89 (2H, br s).

Reference Example 26

4-cyclopropyl-5-[4-(4-methoxyphenyl)piperazin-1-yl]-2,2,6,7-tetramethyl-1-benzofuran-3(2H)-one 124 mg of the title compound was synthesized in the same manner as described for Reference Example 23 using 5-amino-4-cyclopropyl-2,2,6,7-tetramethyl-1-benzofuran-3(2H)-one (810 mg, 3.30 mmol) synthesized in Reference Example 25 (yield: 9%).

Melting point: 143-144° C. (hexane)

$^1$H-NMR (CDCl$_3$): δ0.67-0.76 (2H, m), 1.03-1.13 (2H, m), 1.42 (6H, s), 1.95-2.06 (1H, m), 2.18 (3H, s), 2.35 (3H, s), 2.95-3.23 (4H, m), 3.25-3.40 (2H, m), 3.50-3.66 (2H, m), 3.79 (3H, s), 6.87 (2H, d, J=9.0 Hz), 6.97 (2H, d, J=9.0 Hz).

Reference Example 27

5-amino-2,2,6,7-tetramethyl-4-(1-methylethenyl)-1-benzofuran-3(2H)-one 1.37 g of the title compound was synthesized in the same manner as described for Reference Example 22 using 5-amino-4-bromo-2,2,6,7-tetramethyl-1-benzofuran-3(2H)-one (1.50 g, 5.28 mmol) synthesized in Reference Example 21 and 4,4,5,5-tetramethyl-2-(1-methylethenyl)-1,3,2-dioxaborolan (5.00 g, 29.8 mmol) (yield: 100%).

$^1$H-NMR (CDCl$_3$): δ1.41 (6H, s), 2.07 (3H, s), 2.21 (3H, s), 2.24 (3H, s), 3.67 (2H, br s), 4.98-5.03 (1H, m), 5.43-5.48 (1H, m).

Reference Example 28

4-cyclopropyl-5-[4-(4-methoxyphenyl)piperazin-1-yl]-2,2,6,7-tetramethyl-1-benzofuran-3(2H)-one 267 mg of the title compound was synthesized in the same manner as described for Reference Example 23 using 5-amino-2,2,6,7-tetramethyl-4-(1-methylethenyl)-1-benzofuran-3(2H)-one (1.47 g, 5.30 mmol) synthesized in Reference Example 27 (yield: 12%).

Melting point: 176-178° C. (methanol-hexane)

$^1$H-NMR (CDCl$_3$): δ1.42 (6H, s), 2.16 (3H, s), 2.22 (3H, s), 2.37 (3H, s), 2.85-3.65 (8H, m), 3.78 (3H, s), 4.85 (1H, s), 5.30 (1H, s), 6.86 (2H, d, J=9.0 Hz), 6.94 (2H, d, J=9.0 Hz).

Reference Example 29

5-[4-(4-methoxyphenyl)piperazin-1-yl]-2,2,6,7-tetramethyl-4-(1-methylethyl)-1-benzofuran-3(2H)-one Toluene (5 mL) and chlorotris(triphenyl phosphine) rhodium (1) (60 mol %) were added to a solution of methanol (5 mL) containing 5-[4-(4-methoxyphenyl)piperazin-1-yl]-2,2,6,7-tetramethyl-4-(1-methylethyl)-1-benzofuran-3(2H)-one (130 mg, 0.309 mmol) synthesized in Reference Example 28, and the mixture was stirred under hydrogen atmosphere at room temperature for 40 hours. Water was added to the mixture, and extraction was performed using ethyl acetate. It was dried using anhydrous magnesium sulfate. After that, the solvent was removed under reduced pressure, and the obtained residue was purified by silica gel column chromatography (hexane-ethyl acetate 100:0 to 90:10) to give 97.0 mg of the title compound (yield: 74%).

Melting point: 152-153° C. (hexane)

$^1$H-NMR (CDCl$_3$): δ1.38 (6H, d, J=7.2 Hz), 1.42 (6H, s), 2.18 (3H, s), 2.37 (3H, s), 2.95-3.40 (8H, m), 3.70-3.85 (4H, m), 6.87 (2H, d, J=9.3 Hz), 6.98 (2H, d, J=9.3 Hz).

Reference Example 30

5-amino-4-[4-(dimethylamino)phenyl]-2,2,6,7-tetramethyl-1-benzofuran-3(2H)-one 5.39 g of the title compound was obtained in the same manner as described for Reference Example 22 using 5-amino-4-bromo-2,2,6,7-tetramethyl-1-benzofuran-3(2H)-one (6.19 g, 21.8 mmol) synthesized in Reference Example 21 and 4-(dimethylamino)phenylboric acid (5.40 g, 32.7 mmol) (yield: 76%).

$^1$H-NMR (CDCl$_3$): δ1.39 (6H, s), 2.23 (3H, s), 2.28 (3H, s), 3.00 (6H, s), 3.53 (2H, brs), 6.79-6.86 (2H, m), 7.19-7.26 (2H, m).

Reference Example 31

4-[4-(dimethylamino)phenyl]-5-[4-(4-methoxyphenyl)piperazin-1-yl]-2,2,6,7-tetramethyl-1-benzofuran-3(2H)-one 1.50 g of the title compound was obtained in the same manner as described for Reference Example 23 using 5-amino-4-[4-(dimethylamino)phenyl]-2,2,6,7-tetramethyl-1-benzofuran-3(2H)-one (5.39 g, 16.6 mmol) synthesized in Reference Example 30 (yield: 23%).

$^1$H-NMR (CDCl$_3$): δ1.39 (6H, s), 2.26 (3H, s), 2.41 (3H, s), 2.71-3.17 (14H, m), 3.75 (3H, s), 6.71-6.89 (6H, m), 7.05-7.16 (2H, m).

Reference Example 32

5-amino-4-furan-3-yl-2,2,6,7-tetramethyl-1-benzofuran-3(2H)-one 1.16 g of the title compound was synthesized in the same manner as described for Reference Example 22 using 5-amino-4-bromo-2,2,6,7-tetramethyl-1-benzofuran-3(2H)-one (1.72 g, 6.05 mmol) synthesized in Reference Example 21 and furan-3-boric acid (1.02 g, 9.08 mmol) (yield: 71%).

¹H-NMR (CDCl₃): δ1.40 (6H, s), 2.23 (3H, s), 2.27 (3H, s), 3.67 (2H, brs), 6.56 (1H, dd, J=0.6, 2.1 Hz), 7.57 (1H, dd, J=1.5, 2.1 Hz), 7.62 (1H, dd, J=1.5, 2.1 Hz).

Reference Example 33

4-furan-3-yl-5-[4-(4-methoxyphenyl)piperazin-1-yl]-2,2,6,7-tetramethyl-1-benzofuran-3(2H)-one 530 mg of the title compound was synthesized in the same manner as described for Reference Example 23 using 5-amino-4-furan-3-yl-2,2,6,7-tetramethyl-1-benzofuran-3(2H)-one (1.08 g, 3.98 mmol) synthesized in Reference Example 32 (yield: 30%).

¹H-NMR (CDCl₃): δ1.41 (6H, s), 2.26 (3H, s), 2.40 (3H, s), 2.83-3.05 (6H, m), 3.09-3.21 (2H, m), 3.77 (3H, s), 6.46 (1H, dd, J=0.9, 1.8 Hz), 6.78-6.92 (4H, m), 7.44 (1H, dd, J=0.9, 1.5 Hz), 7.52 (1H, dd, J=1.5, 1.8 Hz).

Reference Example 34

2-methyl-2-(2,3,5-trimethylphenoxy)propanoic acid 145 g of the title compound was synthesized in the same manner as described for Reference Example 16 using 2,3,5-trimethylphenol (138 g, 1.01 mol) (yield: 64%).

¹H-NMR (CDCl₃): δ1.59 (6H, s), 2.12 (3H, s), 2.23 (3H, s), 2.24 (3H, s), 6.54 (1H, s), 6.72 (1H, s).

Reference Example 35

2,2,4,6,7-pentamethyl-1-benzofuran-3(2H)-one

Polyphosphoric acid (1.5 kg) was added to 2-methyl-2-(2,3,5-trimethylphenoxy)propanoic acid (226 g, 1.02 mol) synthesized in Reference Example 34, and the mixture was stirred at 70° C. After reaction for 2 hours, the resulting mixture was poured into iced water and extracted using ethyl acetate. The extract was washed with 0.5 N sodium hydroxide aqueous solution and saturated saline, and dried using anhydrous magnesium sulfate. The solvent was removed under reduced pressure. Methanol was added to the residue, and the generated crystals were collected by filtration to give 164 g of the title compound (yield: 79%).

¹H-NMR (CDCl₃): δ1.44 (6H, s), 2.16 (3H, s), 2.30 (3H, s), 2.51 (3H, s), 6.63 (1H, s).

Reference Example 36

5-bromo-2,2,4,6,7-pentamethyl-1-benzofuran-3(2H)-one

Bromine (12.3 mL, 241 mmol) was added dropwise to a solution of acetic acid (400 mL) containing 2,2,4,6,7-pentamethyl-1-benzofuran-3(2H)-one (40.9 g, 200 mmol) synthesized in Reference Example 35, and then it was stirred at room temperature. After stirring for 1 hour, the reaction solution was poured into 5% aqueous solution of sodium sulfite. The generated crystals were collected by filtration, and recrystalized from methanol to give 47.4 g of the title compound (yield: 84%).

¹H-NMR (CDCl₃): δ1.44 (6H, s), 2.26 (3H, s), 2.47 (3H, s), 2.66 (3H, s).

Reference Example 37

2,2,4,6,7-pentamethyl-5-[4-(4-methylphenyl)piperazin-1-yl]-1-benzofuran-3(2H)-one 970 mg of the title compound was synthesized in the same manner as described for Reference Example 19 using 5-bromo-2,2,4,6,7-pentamethyl-1-benzofuran-3(2H)-one (2.00 g, 7.06 mmol) synthesized in Reference Example 36 and 1-(4-methylphenyl)piperazine (2.49 g, 14.1 mmol) (yield: 36%).

¹H-NMR (CDCl₃): δ1.43 (6H, s), 2.18 (3H, s), 2.29 (3H, s), 2.35 (3H, s), 2.60 (3H, s), 3.07-3.21 (4H, m), 3.25-3.42 (4H, m), 6.87-6.95 (2H, m), 7.06-7.14 (2H, m).

Reference Example 38

5-[3-(4-methoxyphenyl)-4-methylpiperazin-1-yl]-2,2,4,6,7-pentamethyl-1-benzofuran-3(2H)-one 2.41 g of the title compound was synthesized as a diastereomer mixture (3:2) in the same manner as described for Reference Example 19 using 5-bromo-2,2,4,6,7-pentamethyl-1-benzofuran-3(2H)-one (2.27 g, 8.02 mmol) synthesized in Reference Example 36 and 2-(4-methoxyphenyl)-1-methylpiperazine (3.31 g, 16.0, mmol) (yield: 74%).

¹H-NMR (CDCl₃): δ1.30-1.49 (6H, m), 2.07-2.14 (4.2H, m), 2.18 (1.8H, s), 2.26 (1.2H, s), 2.41 (1.8H, s), 2.44-2.60 (2.8H, m), 2.63 (1.2H, s), 2.67-2.89 (2H, m), 2.91-3.01 (1H, m), 3.03-3.17 (1H, m), 3.21-3.43 (1H, m), 3.52-3.73 (1H, m), 3.80 (3H, s), 6.81-6.91 (2H, m), 7.22-7.34 (2H, m).

Reference Example 39

5-[3-(3,4-dimethoxyphenyl)-4-methylpiperazin-1-yl]-2,2,4,6,7-pentamethyl-1-benzofuran-3(2H)-one 794 mg of the title compound was obtained as a diastereomer mixture (3:2) in the same manner as described for Reference Example 19 using 5-bromo-2,2,4,6,7-pentamethyl-1-benzofuran-3(2H)-one (991 mg, 3.50 mmol) synthesized in Reference Example 36 and 2-(3,4-dimethoxyphenyl)-1-methylpiperazine (1.65 g, 7.00 mmol) (yield: 52%).

¹H-NMR (CDCl₃): δ1.35-1.48 (6H, m), 2.13 (4.2H, m), 2.18 (1.8H, s), 2.27 (1.2H, s), 2.42 (1.8H, s), 2.46-2.61 (4.2H, m), 2.70-2.89 (2H, m), 2.93-3.02 (1H, m), 3.04-3.16 (1H, m), 3.24-3.44 (1H, m), 3.53-3.73 (1H, m), 3.87 (3H, s), 3.91 (3H, s), 6.77-6.84 (1H, m), 6.85-6.97 (2H, m).

Reference Example 40

5-[2-(4-methoxyphenyl)morpholine-4-yl]-2,2,4,6,7-pentamethyl-1-benzofuran-3(2H)-one 621 mg of the title compound was obtained as a diastereomer mixture (3:2) in the same manner as described for Reference Example 19 using 5-bromo-2,2,4,6,7-pentamethyl-1-benzofuran-3(2H)-one (708 mg, 2.50 mmol) synthesized in Reference Example 36 and 2-(4-methoxyphenyl)morpholine (966 mg, 5.00 mmol) (yield: 63%).

¹H-NMR (CDCl₃): δ1.34-1.48 (6H, m), 2.14 (1.2H, s), 2.20 (1.8H, s), 2.26 (1.2H, s), 2.45 (1.8H, s), 2.56 (1.8H, s), 2.63-2.76 (2.2H, m) 2.79-2.96 (1H, m), 3.25-3.45 (1H, m), 3.45-3.67 (1H, m), 3.80 (3H, s), 3.89-4.13 (2H, m), 4.57-4.68 (1H, m), 6.81-6.93 (2H, m), 7.27-7.35 (2H, m).

Reference Example 41

5-(2-benzylmorpholine-4-yl)-2,2,4,6,7-pentamethyl-1-benzofuran-3(2H)-one 748 mg of the title compound was obtained as a diastereomer mixture (3:2) in the same manner as described for Reference Example 19 using 5-bromo-2,2,4,6,7-pentamethyl-1-benzofuran-3(2H)-one (708 mg, 2.50 mmol) synthesized in Reference Example 36 and 2-benzylmorpholine (1.22 g, 5.01 mmol) (yield: 79%).
$^1$H-NMR (CDCl$_3$): δ1.35-1.48 (6H, m), 2.08-2.19 (3H, m), 2.24-2.33 (3H, m), 2.51 (1.2H, s), 2.57 (1.8H, s), 2.60-2.73 (3H, m), 2.89-3.01 (1H, m), 3.06-3.26 (1H, m), 3.36-3.56 (1H, m), 3.71-3.99 (3H, m), 7.14-7.33 (5H, m).

Reference Example 42

5-[4-(4-methoxyphenyl)piperazin-1-yl]-2,2,4,6,7-pentamethyl-1-benzofuran-3(2H)-one 16.1 g of the title compound was synthesized in the same manner as described for Reference Example 19 using 5-bromo-2,2,4,6,7-pentamethyl-1-benzofuran-3(2H)-one (19.0 g, 67.1 mmol) synthesized in Reference Example 36 and 1-(4-methoxyphenyl)piperazine (38.7 g, 201 mmol) (yield: 61%).
$^1$H-NMR (CDCl$_3$): δ1.43 (6H, s), 2.18 (3H, s), 2.35 (3H, s), 2.61 (3H, s), 3.04-3.29 (6H, m), 3.31-3.42 (2H, m), 3.79 (3H, s), 6.83-6.91 (2H, m), 6.93-7.01 (2H, m).

Reference Example 43

(2,3,5-trimethylphenoxy)acetic acid 28.7 g of the title compound was obtained in the same manner as described for Reference Example 16 using 2,3,5-trimethylphenol (25.0 g, 184 mmol) (yield: 84%).
$^1$H-NMR (CDCl$_3$): δ2.16 (3H, s), 2.24 (3H, s), 2.27 (3H, s), 4.66 (2H, s), 6.45 (1H, s), 6.69 (1H, s).

Reference Example 44

4,6,7-trimethyl-1-benzofuran-3(2H)-one 20.7 g of the title compound was obtained in the same manner as described for Reference Example 17 using (2,3,5-trimethylphenoxy)acetic acid (28.7 g, 148 mmol) synthesized in Reference Example 43 (yield: 79%).
$^1$H-NMR (CDCl$_3$): δ2.17 (3H, s), 2.30 (3H, s), 2.52 (3H, s), 4.58 (2H, s), 6.64 (1H, s).

Reference Example 45

5-bromo-4,6,7-trimethyl-1-benzofuran-3(2H)-one

N-bromosuccinimide (27.1 g, 152 mmol) was added to a solution of methylene chloride (200 mL) containing 4,6,7-trimethyl-1-benzofuran-3(2H)-one (20.7 g, 117 mmol) synthesized in Reference Example 44, and the mixture was stirred at room temperature for 24 hours. After that, the solvent was removed under reduced pressure, and water was added to the residue. The generated crystals were collected by filtration, and recrystallized from ethyl acetate to give 24.0 g of the title compound (yield: 80%).
$^1$H-NMR (CDCl$_3$): δ2.27 (3H, s), 2.47 (3H, s), 2.67 (3H, s), 4.61 (2H, s).

Reference Example 46

5-bromo-4,6,7-trimethyl-2',3',5',6'-tetrahydro-3H-spiro[1-benzofuran-2,4'-pyran]-3-one Potassium tert-butoxide (2.63 g, 23.5 mmol) was added to a solution of THF (60 mL) containing 5-bromo-4,6,7-trimethyl-1-benzofuran-3(2H)-one (2.00 g, 7.83 mmol) synthesized in Reference Example 45 and bis(2-bromoethyl)ether (2.72 g, 11.7 mmol), and the mixture was stirred at room temperature. After stirring for 15 hours, the reaction solution was poured into a saturated ammonium chloride aqueous solution and extracted using ethyl acetate. The extract was washed with saturated saline, and dried using anhydrous magnesium sulfate. The solvent was removed under reduced pressure, and the obtained residue was purified by silica gel column chromatography (hexane-ethyl acetate 98:2 to 92:8) to give 200 mg of the title compound (yield: 8%).
$^1$H-NMR (CDCl$_3$): δ1.44-1.55 (2H, m), 2.02-2.18 (2H, m), 2.30 (3H, s), 2.48 (3H, s), 2.66 (3H, s), 3.80-3.94 (2H, m), 3.99-4.10 (2H, m).

Reference Example 47

5-[4-(4-methoxyphenyl)piperazin-1-yl]-4,6,7-trimethyl-2',3',5',6'-tetrahydro-3H-spiro[1-benzofuran-2,4'-pyran]-3-one 100 mg of the title compound was synthesized in the same manner as described for Reference Example 19 using 5-bromo-4,6,7-trimethyl-2',3',5',6'-tetrahydro-3H-spiro[1-benzofuran-2,4'-pyran]-3-one (240 mg, 0.738 mmol) synthesized in Reference Example 46 and 1-(4-methoxyphenyl)piperazine (426 mg, 2.21 mmol) (yield: 31%).
$^1$H-NMR (CDCl$_3$): δ1.43-1.53 (2H, m), 2.02-2.18 (2H, m), 2.22 (3H, s), 2.37 (3H, s), 2.61 (3H, s), 3.04-3.42 (8H, m), 3.79 (3H, s), 3.82-3.94 (2H, m), 3.99-4.09 (2H, m), 6.83-6.91 (2H, m), 6.93-7.01 (2H, m).

Reference Example 48

5-bromo-4,6,7-trimethyl-3H-spiro[1-benzofuran-2,1'-cyclopentane]-3-one 430 mg of the title compound was synthesized in the same manner as described for Reference Example 45 using 5-bromo-4,6,7-trimethyl-1-benzofuran-3(2H)-one (1.00 g, 3.92 mmol) synthesized in Reference Example 45 and 1,4-dibromobutane (1.27 g, 5.88 mmol) (yield: 35%):
$^1$H-NMR (CDCl$_3$): δ1.81-2.14 (8H, m), 2.25 (3H, s), 2.46 (3H, s), 2.67 (3H, s).

Reference Example 49

5-[4-(4-methoxyphenyl)piperazin-1-yl]-4,6,7-trimethyl-3H-spiro[1-benzofuran-2,1'-cyclopentane]-3-one 180 mg of the title compound was obtained in the same manner as described for Reference Example 19 using 5-bromo-4,6,7-trimethyl-3H-spiro[1-benzofuran-2,1'-cyclopentane]-3-one (400 mg, 1.29 mmol) synthesized in Reference Example 48 and 1-(4-methoxyphenyl)piperazine (652 mg, 3.39 mmol) (yield: 33%).

$^1$H-NMR (CDCl$_3$): δ1.81-2.11 (8H, m), 2.17 (3H, s), 2.35 (3H, s), 2.62 (3H, s), 3.04-3.42 (8H, m), 3.79 (3H, s), 6.83-6.91 (2H, m), 6.93-7.01 (2H, m).

Reference Example 50

1,2,5-trimethyl-3-(prop-2-en-1-yloxy)benzene 61.7 g of the title compound was obtained as an oily product in the same manner as described for Reference Example 1 using 2,3,5-trimethylphenol (50.0 g, 368 mmol) and allyl bromide (38.1 mL) (yield: 95%).

$^1$H-NMR (CDCl$_3$): δ2.13 (3H, s), 2.23 (3H, s), 2.27 (3H, s), 4.48-4.52 (2H, m), 5.21-5.30 (1H, m), 5.38-5.47 (1H, m), 6.00-6.15 (1H, m), 6.53 (1H, s), 6.61 (1H, s).

Reference Example 51

2,3,5-trimethyl-6-prop-2-en-1-ylphenol 52.0 g of the title compound was obtained as an oily product in the same manner as described for Reference Example 2 using 1,2,5-trimethyl-3-(prop-2-en-1-yloxy)benzene (61.7 g, 351 mmol) synthesized in Reference Example 50 (yield: 84%).

$^1$H-NMR (CDCl$_3$): δ2.14 (3H, s), 2.23 (3H, s), 2.24 (3H, s), 3.41 (2H, dt, J=5.8, 1.6 Hz), 4.86 (1H, s), 5.03-5.14 (2H, m), 5.89-6.05 (1H, m), 6.63 (1H, s).

Reference Example 52

2,4,6,7-tetramethyl-2,3-dihydro-1-benzofuran

Concentrated hydrochloric acid (130 mL) was added to a solution of ethanol (520 mL) containing 2,3,5-trimethyl-6-prop-2-en-1-ylphenol (52.0 g, 295 mmol) synthesized in Reference Example 51, and the mixture was heated to reflux for 16 hours. The reaction solution was neutralized with a sodium hydrogencarbonate aqueous solution, and then the mixture was extracted using ethyl acetate. The organic layer was washed with saturated saline, and then dried using anhydrous magnesium sulfate. The solvent was removed under reduced pressure, and the obtained residue was purified by silica gel column chromatography (hexane-ethyl acetate 95:5) to give 35.7 g of the title compound as an oily product (yield: 69%).

$^1$H-NMR (CDCl$_3$): δ1.49 (3H, d, J=6.3 Hz), 2.11 (3H, s), 2.18 (3H, s), 2.22 (3H, s), 2.71 (1H, dd, J=15.1, 7.7 Hz), 3.22 (1H, dd, J=15.1, 8.8 Hz), 4.85-5.00 (1H, m), 6.50 (1H, s).

Reference Example 53

5-bromo-2,4,6,7-tetramethyl-2,3-dihydro-1-benzofuran 43.4 g of the title compound was obtained in the same manner as described for Reference Example 4 using 2,4,6,7-tetramethyl-2,3-dihydro-1-benzofuran (35.7 g, 203 mmol) synthesized in Reference Example 52 (yield: 84%).

$^1$H-NMR (CDCl$_3$): δ1.47 (3H, d, J=6.3 Hz), 2.17 (3H, s), 2.28 (3H, s), 2.35 (3H, s), 2.77 (1H, dd, J=15.1, 7.7 Hz), 3.28 (1H, dd, J=15.1, 8.8 Hz), 4.84-4.97 (1H, m).

Reference Example 54

(2R)-5-bromo-2,4,6,7-tetramethyl-2,3-dihydro-1-benzofuran and (2S)-5-bromo-2,4,6,7-tetramethyl-2,3-dihydro-1-benzofuran 5-bromo-2,4,6,7-tetramethyl-2,3-dihydro-1-benzofuran (13.5 g) obtained in Reference Example 53 was fractionated using high-performance liquid chromatography (column: CHIRALCEL OD manufactured by Daicel Chemical Industries, Ltd., mobile phase: hexane). The fraction solution comprising an optically-active substance having a shorter retention time was concentrated to give 5.76 g of (R)-form as a solid (>99.9% ee, Specific optical rotation $[\alpha]_D^{20}$=+14.6° (c=0.52, chloroform)). Further, the fraction solution comprising an optically-active substance having a longer retention time was concentrated to give 6.55 g of (S)-form as a solid (>99.9% ee, Specific optical rotation $[\alpha]_D^{20}$=−16.5° (c=0.52, chloroform)).

Reference Example 55 tert-butyl 4-(2,4,6,7-tetramethyl-2,3-dihydro-1-benzofuran-5-yl)piperazine-1-carboxylate 16.1 g of the title compound was obtained as an oily product in the same manner as described for Reference Example 19 using 5-bromo-2,4,6,7-tetramethyl-2,3-dihydro-1-benzofuran (20.0 g, 78.4 mmol) synthesized in Reference Example 53 and tert-butyl piperazine-1-carboxylate (43.7 g, 235 mmol) (yield: 57%).

$^1$H-NMR (CDCl$_3$): δ1.46 (3H, d, J=6.4 Hz), 1.49 (9H, s), 2.08 (3H, s), 2.16 (3H, s), 2.19 (3H, s), 2.69 (1H, dd, J=15.1, 7.9 Hz), 2.94-3.09 (4H, m), 3.20 (1H, dd, J=15.1, 8.7 Hz), 3.40-3.61 (4H, m), 4.81-4.94 (1H, m).

Reference Example 56

1-(2,4,6,7-tetramethyl-2,3-dihydro-1-benzofuran-5-yl)piperazine tert-butyl 4-(2,4,6,7-tetramethyl-2,3-dihydro-1-benzofuran-5-yl)piperazine-1-carboxylate (16.1 g, 44.7 mmol) synthesized in Reference Example 55 was added to an ethyl acetate solution containing 2N hydrogen chloride, and the mixture was stirred at 50° C. for 3 hours. The reaction solution was poured into an aqueous solution of 2N sodium hydroxide, and the mixture was extracted using ethyl acetate. The extract was washed with saturated saline, and dried using anhydrous sodium sulfate. After that, the solvent was removed under reduced pressure, and the obtained residue was purified by basic silica gel column chromatography (ethyl acetate-methanol 90:10) to give 11.3 g of the title compound as an oily product (yield: 97%).

$^1$H-NMR (CDCl$_3$): δ1.46 (3H, d, J=6.4 Hz), 2.08 (3H, s), 2.19 (3H, s), 2.22 (3H, s), 2.69 (1H, dd, J=15.1, 8.0 Hz), 2.91-3.12 (8H, m), 3.20 (1H, dd, J=15.1, 8.7 Hz), 4.80-4.94 (1H, m).

Reference Example 57 tert-butyl 4-(2,2,4,6,7-pentamethyl-3-oxo-2,3-dihydro-1-benzofuran-5-yl)piperazine-1-carboxylate Sodium t-butoxide (13.45 g, 140 mmol) was added to a mixture of toluene (300 mL) containing 4-(2,2,4,6,7-pentamethyl-3-oxo-2,3-dihydro-1-benzofuran-5-yl)piperazine (28.32 g, 100 mmol) synthesized in Reference Example 36, N-Boc-piperazine (22.35 g, 120 mmol), palladium acetate (448 mg, 2 mmol) and BINAP (3.74 g, 6 mmol) at room temperature, and the mixture was heated to reflux under argon atmosphere. After a reaction for 16 hours, it was cooled to room temperature and diluted with ethyl acetate. The organic layer was washed with saturated saline, and then dried using anhydrous sodium sulfate. The solvent was removed under reduced pressure. The residue was purified by silica gel chromatography (hexane-ethyl acetate 9:1 to 4:1), and recrystallized from hexane to give 20.5 g of the title compound (yield: 53%).

$^1$H-NMR (CDCl$_3$): δ1.42 (6H, s), 1.49 (9H, s), 2.17 (3H, s), 2.31 (3H, s), 2.55 (3H, s), 2.91-2.99 (2H, m), 3.07-3.16 (2H, m), 3.33-3.42 (2H, m), 3.62-3.71 (2H, m).

Reference Example 58

2,2,4,6-pentamethyl-5-piperazin-1-yl-1-benzofuran-3(2H)-one 10.32 g of the title compound was synthesized in the same manner as described for Reference Example 56 using tert-butyl 4-(2,2,4,6,7-pentamethyl-3-oxo-2,3-dihydro-1-benzofuran-5-yl)piperazine-1-carboxylate (19.43 g, 50 mmol) synthesized in Reference Example 57 (yield: 72%).

$^1$H-NMR (CDCl$_3$): δ1.42 (6H, s), 2.17 (3H, s), 2.34 (3H, s), 2.58 (3H, s), 2.89-3.02 (6H, m), 3.08-3.21 (2H, m).

Reference Example 59

5-[4-(4-methoxy-3-methylphenyl)piperazin-1-yl]-2,2,4,6,7-pentamethyl-1-benzofuran-3(2H)-one Sodium t-butoxide (999 mg, 10.4 mmol) was added to a mixture of toluene (18 mL) containing 2,2,4,6,7-pentamethyl-5-piperazin-1-yl-1-benzofuran-3(2H)-one (1.00 g, 3.47 mmol) synthesized in Reference Example 58, 4-bromo-2-methylanisole (2.09 g, 10.4 mmol), palladium acetate (39 mg, 0.174 mmol) and BINAP (325 mg, 0.522 mmol), and the mixture was stirred under heated reflux for 15 hours. After cooled to room temperature, the reaction solution was diluted with water and extracted using ethyl acetate. The organic layer was washed with saturated saline, and then dried using anhydrous magnesium sulfate. The solvent was removed under reduced pressure, and the obtained residue was purified by silica gel chromatography (hexane-ethyl acetate 95:5 to 85:15). Crystallization was performed using ethyl acetate-hexane to give 320 mg of the title compound (yield: 23%).

Melting point: 129-131° C.

$^1$H-NMR (CDCl$_3$): δ1.43 (6H, s), 2.18 (3H, s), 2.22 (3H, s), 2.35 (3H, s), 2.61 (3H, s), 3.02-3.42 (8H, m), 3.80 (3H, s), 6.74-6.84 (2H, m), 6.85-6.89 (1H, m).

Reference Example 60 tert-butyl 4-(2,2,4,6,7-pentamethyl-2,3-dihydro-1-benzofuran-5-yl)piperazine-1-carboxylate 4.88 g of the title compound was obtained as an oily product in the same manner as described for Reference Example 57 using 5-bromo-2,2,4,6,7-pentamethyl-2,3-dihydro-1-benzofuran (9.42 g, 35 mmol) synthesized in Reference Example 4 and tert-butyl piperazine-1-carboxylate (7.82 g, 42 mmol) (yield: 37%).

$^1$H-NMR (CDCl$_3$): δ1.46 (6H, s), 1.48-1.52 (9H, m), 2.07 (3H, s), 2.14 (3H, s), 2.20 (3H, s), 2.90 (2H, s), 2.93-3.12 (4H, m), 3.39-3.50 (2H, m), 3.50-3.62 (2H, m).

Reference Example 61

1-(2,2,4,6,7-pentamethyl-2,3-dihydro-1-benzofuran-5-yl)piperazine 0.85 g of the title compound was obtained in the same manner as described for Reference Example 56 using tert-butyl 4-(2,2,4,6,7-pentamethyl-2,3-dihydro-1-benzofuran-5-yl)piperazine-1-carboxylate (4.87 g, 13.0 mmol) synthesized in Reference Example 60 (yield: 24%).

$^1$H-NMR (DMSO-d6): δ1.36 (6H, s), 1.94 (3H, s), 2.09 (3H, s), 2.11 (3H, s), 2.85 (2H, s), 2.89-3.12 (8H, m), 6.25-7.61 (1H, m).

Reference Example 62 tert-butyl 4-(2,2,4,6,7-pentamethyl-3-oxo-2,3-dihydro-1-benzofuran-5-yl)-1,4-diazepane-1-carboxylate tert-butyl 1,4-diazepane-1-carboxylate (2.50 g, 12.5 mmol), palladium acetate (70.0 mg, 0.312 mmol), BINAP (579 mg, 0.901 mmol) and sodium tert-butoxide (1.79 g, 18.6 mmol) were added to a solution of toluene (20 mL) containing 5-bromo-2,2,4,6,7-pentamethyl-1-benzofuran-3(2H)-one (1.77 g, 6.25 mmol) synthesized in Reference Example 36, and the mixture was heated to reflux under argon atmosphere for 29 hours. After cooled to room temperature, the mixture was diluted with water and extracted using ethyl acetate. It was dried using anhydrous magnesium sulfate. After that, the solvent was removed under reduced pressure, and the obtained residue was purified by silica gel column chromatography (hexane-ethyl acetate: 100:0 to 95:5) to give 340 mg of the title compound (yield: 14%).

$^1$H-NMR (CDCl$_3$): δ1.42 (6H, s), 1.49 (9H, d, J=4.2 Hz), 1.70-1.90 (2H, m), 2.16 (3H, s), 2.29 (3H, s), 2.52 (3H, s), 3.05-3.25 (4H, m), 3.40-3.75 (4H, m).

Reference Example 63

5-(1,4-diazepan-1-yl)-2,2,4,6,7-pentamethyl-1-benzofuran-3(2H)-one 456 mg of the title compound was synthesized in the same manner as described for Reference Example 56 using tert-butyl 4-(2,2,4,6,7-pentamethyl-3-oxo-2,3-dihydro-1-benzofuran-5-yl)-1,4-diazepane-1-carboxylate (600 mg, 1.54 mmol) synthesized in Reference Example 62 (yield: 100%).

$^1$H-NMR (CDCl$_3$): δ1.42 (6H, s), 1.80-1.92 (2H, m), 2.17 (3H, s), 2.55 (3H, s), 2.95-3.30 (8H, m), 3.78 (3H, s).

Reference Example 64

5-[4-(4-methoxyphenyl)-1,4-diazepan-1-yl]-2,2,4,6,7-pentamethyl-1-benzofuran-3(2H)-one Bis(tri-tert-butylphosphine)palladium (20.0 mg, 0.0387 mmol) and sodium tert-butoxide (500 mg, 5.16 mmol) were added to a solution of o-xylene (20 mL) containing 5-(1,4-diazepan-1-yl)-2,2,4,6,7-pentamethyl-1-benzofuran-3(2H)-one synthesized in Reference Example 63, and the mixture was stirred under argon atmosphere at 120° C. for 12 hours. After cooled to room temperature, the mixture was diluted with water and extracted using ethyl acetate. It was dried using anhydrous magnesium sulfate. After that, the solvent was removed under reduced pressure, and the obtained residue was purified by silica gel column chromatography (hexane-ethyl acetate 100:0 to 90:10) to give 240 mg of the title compound (yield: 45%).

$^1$H-NMR (CDCl$_3$): δ1.41 (6H, s), 1.85-2.01 (2H, m), 2.13 (3H, s), 2.17 (3H, s), 2.45 (3H, s), 3.00-3.30 (4H, m), 3.56-3.75 (4H, m), 3.77 (3H, s), 6.72 (2H, d, J=9.3 Hz), 6.84 (2H, d, J=9.3 Hz).

Reference Example 65

2-bromo-3,5-dimethylphenol

N-bromosuccinimide (178 g, 1.00 mmol) was slowly added to a solution of toluene (1.0 L) containing 3,5-dimethylphenol (122 g, 1.00 mol) under ice-cooling condition, and then the mixture was warmed to room temperature and stirred for 2 hours. The mixture was concentrated under reduced pressure, and then the residue was suspended in hexane (400 mL) to remove insolubles by filtration. The filtrate was concentrated, and the obtained residue was purified by silica gel column chromatography (hexane-ethyl acetate 9:1) to give 61.6 g of the title compound (yield: 31%).

$^1$H-NMR (CDCl$_3$): δ2.23 (3H, s), 2.34 (3H, s), 5.51 (1H, s), 6.60-6.64 (1H, m), 6.66-6.69 (1H, m).

Reference Example 66

2-(2-bromo-3,5-dimethylphenoxy)-2-methylpropanoic acid 8.10 g of the title compound was synthesized in the same manner as described for Reference Example 16 using 2-bromo-3,5-dimethylphenol (7.61 g, 37.8 mmol) synthesized in Reference Example 65 (yield: 75%).

$^1$H-NMR (CDCl$_3$): δ1.64 (6H, s), 2.27 (3H, s), 2.39 (3H, s), 6.73 (1H, s), 6.85 (1H, s).

Reference Example 67

7-bromo-2,2,4,6-tetramethyl-1-benzofuran-3(2H)-one 2.57 g of the title compound was synthesized in the same manner as described for Reference Example 17 using 2-(2-bromo-3,5-dimethylphenoxy)-2-methylpropanoic acid (4.00 g, 13.9 mmol) synthesized in Reference Example 66 (yield: 69%).

$^1$H-NMR (CDCl$_3$): δ1.49 (6H, s), 2.45 (3H, s), 2.51 (3H, s), 6.74 (1H, s).

Reference Example 68

7-methoxy-2,2,4,6-tetramethyl-1-benzofuran-3(2H)-one

A mixture of 7-bromo-2,2,4,6-tetramethyl-1-benzofuran-3(2H)-one (2.90 g, 10.8 mmol) synthesized in Reference Example 67, copper bromide (1.86 g, 13.0 mmol) and 28% sodium methoxide/methanol solution (60 mL) was stirred under heated reflux for 15 hours. After cooled to room temperature, the reaction solution was poured into water and extracted using ethyl acetate. The extract was washed with saturated saline, and dried using anhydrous magnesium sulfate. After that, the solvent was removed under reduced pressure. The residue was purified by silica gel column chromatography (hexane-ethyl acetate 99:1 to 94:6) to give 1.18 g of the title compound (yield: 50%).

$^1$H-NMR (CDCl$_3$): δ1.47 (6H, s), 2.30 (3H, s), 2.49 (3H, s), 3.92 (3H, s), 6.60 (1H, s).

Reference Example 69

7-hydroxy-2,2,4,6-tetramethyl-1-benzofuran-3(2H)-one

A mixture of 7-methoxy-2,2,4,6-tetramethyl-1-benzofuran-3(2H)-one (1.10 g, 4.99 mmol) synthesized in Reference Example 68, 48% hydrobromic acid (20 mL) and acetic acid (4 mL) was stirred at 100° C. for 15 hours. The reaction solution was poured into cold saturated sodium bicarbonate water in ice bath and extracted using ethyl acetate. The extract was washed with saturated saline, and dried using anhydrous magnesium sulfate, followed by concentration under reduced pressure. The obtained residue was purified by silica gel column chromatography (hexane-ethyl acetate 95:5 to 80/20) to give 980 mg of the title compound (yield: 95%).

$^1$H-NMR (CDCl$_3$): δ1.46 (6H, s), 2.30 (3H, s), 2.47 (3H, s), 4.88 (1H, s), 6.58 (1H, s).

Reference Example 70

7-(methoxymethoxy)-2,2,4,6-tetramethyl-1-benzofuran-3(2H)-one

Potassium carbonate (1.23 g, 8.92 mmol) and chloromethylmethylether (539 mg, 6.69 mmol) were sequentially added to a suspension of DMF (20 mL) containing 7-hydroxy-2,2,4,6-tetramethyl-1-benzofuran-3(2H)-one (920 mg, 4.46 mmol) synthesized in Reference Example 69 at 0° C. The reaction solution was warmed to room temperature and stirred for 15 hours. The resulting mixture was poured into saturated sodium bicarbonate water, and extraction was performed using ethyl acetate. The extract was washed with saturated saline, and dried using anhydrous magnesium sulfate, followed by concentration under reduced pressure. The residue was purified by silica gel chromatography (hexane-ethyl acetate 95:5 to 85/15) to give 920 mg of the title compound (yield: 82%).

$^1$H-NMR (CDCl$_3$): δ1.45 (6H, s), 2.34 (3H, s), 2.49 (3H, s), 3.58 (3H, s), 5.21 (2H, s), 6.62 (1H, brs).

Reference Example 71

5-bromo-7-(methoxymethoxy)-2,2,4,6-tetramethyl-1-benzofuran-3(2H)-one 990 mg of the title compound was synthesized in the same manner as described for Reference Example 4 using 7-(methoxymethoxy)-2,2,4,6-tetramethyl-1-benzofuran-3(2H)-one (920 mg, 3.68 mmol) synthesized in Reference Example 70 (yield: 82%).

$^1$H-NMR (CDCl$_3$): δ1.46 (6H, s), 2.49 (3H, s), 2.64 (3H, s), 3.58 (3H, s), 5.22 (2H, s).

Reference Example 72

7-(methoxymethoxy)-5-[4-(4-methoxyphenyl)piperazin-1-yl]-2,2,4,6-tetramethyl-1-benzofuran-3(2H)-one 800 mg of the title compound was obtained in the same manner as described for Reference Example 19 using 5-bromo-7-(methoxymethoxy)-2,2,4,6-tetramethyl-1-benzofuran-3(2H)-one (990 mg, 3.01 mmol) synthesized in Reference Example 71 and 1-(4-methoxyphenyl)piperazine (1.73 g, 9.02 mmol) (yield: 60%).

$^1$H-NMR (CDCl$_3$): δ1.45 (6H, s), 2.39 (3H, s), 2.58 (3H, s), 3.03-3.28 (6H, m), 3.29-3.42 (2H, m), 3.60 (3H, s), 3.79 (3H, s), 5.20 (2H, s), 6.82-6.91 (2H, m), 6.92-7.01 (2H, m).

Reference Example 73

7-hydroxy-5-[4-(4-methoxyphenyl)piperazin-1-yl]-2,2,4,6-tetramethyl-1-benzofuran-3(2H)-one Concentrated hydrochloric acid (0.1 mL) was added to a solution of ethanol (16 mL) containing 7-(methoxymethoxy)-5-[4-(4-methoxyphenyl)piperazin-1-yl]-2,2,4,6-tetramethyl-1-benzofuran-3(2H)-one (800 mg, 1.82 mmol) synthesized in Reference Example 72 and the mixture was stirred under heated reflux for 24 hours. After that, concentrated hydrochloric acid (0.1 mL) was further added thereto, and the mixture was stirred under heated reflux for 24 hours. The reaction solution was cooled to room temperature and poured into saturated sodium bicarbonate water, and extraction was performed using ethyl acetate. The extract was washed with saturated saline, and dried using anhydrous magnesium sulfate, followed by concentration under reduced pressure. The residue was crystallized using ethyl acetate and hexane to give 630 mg of the title compound (yield: 87%).

$^1$H-NMR (CDCl$_3$): δ1.45 (6H, s), 2.35 (3H, s), 2.55 (3H, s), 3.02-3.42 (8H, m), 3.79 (3H, s), 4.97 (1H, s), 6.82-6.90 (2H, m), 6.92-7.01 (2H, m).

Reference Example 74

7-ethoxy-5-[4-(4-methoxyphenyl)piperazin-1-yl]-2,2,4,6-tetramethyl-1-benzofuran-3(2H)-one Ethyl iodide (88 mg, 0.567 mmol) was added to a suspension of DMF (4 mL) containing 7-hydroxy-5-[4-(4-methoxyphenyl)piperazin-1-yl]-2,2,4,6-tetramethyl-1-benzofuran-3(2H)-one (150 mg, 0.378 mmol) synthesized in Reference Example 73 and potassium carbonate (104 mg, 0.756 mmol) at 0° C. The reaction solution was warmed to room temperature and stirred for 15 hours. The resulting mixture was poured into water and extraction was performed using ethyl acetate. The extract was washed with saturated saline, and dried using anhydrous magnesium sulfate, followed by concentration under reduced pressure. The residue was purified by silica gel chromatography (hexane-ethyl acetate 95:5 to 80/20), and recrystallized from ethyl acetate and hexane to give 70 mg of the title compound (yield: 44%).

Melting point: 109-112° C.

$^1$H-NMR (CDCl$_3$): δ1.39 (3H, t, J=7.2 Hz), 1.45 (6H, s), 2.35 (3H, s), 2.58 (3H, s), 3.03-3.39 (8H, m), 3.79 (3H, s), 4.13 (2H, q, J=7.2 Hz), 6.80-6.90 (2H, m), 6.91-7.01 (2H, m).

Reference Example 75

5-bromo-7-methoxy-2,2,4,6-tetramethyl-1-benzofuran-3(2H)-one 190 mg of the title compound was synthesized in the same manner as described for Reference Example 4 using 7-methoxy-2,2,4,6-tetramethyl-1-benzofuran-3(2H)-one (200 mg, 0.908 mmol) synthesized in Reference Example 68 (yield: 70%).

$^1$H-NMR (CDCl$_3$): δ1.47 (6H, s), 2.44 (3H, s), 2.63 (3H, s), 3.92 (3H, s).

Reference Example 76

7-methoxy-5-[4-(4-methoxyphenyl)piperazin-1-yl]-2,2,4,6-tetramethyl-1-benzofuran-3(2H)-one 90 mg of the title compound was synthesized in the same manner as described for Reference Example 19 using 5-bromo-7-methoxy-2,2,4,6-tetramethyl-1-benzofuran-3(2H)-one (190 mg, 0.635 mmol) synthesized in Reference Example 75 and 1-(4-methoxyphenyl)piperazine (366 mg, 1.91 mmol) (yield: 35%).

Melting point: 125-127° C. (ethyl acetate-hexane)

$^1$H-NMR (CDCl$_3$): δ1.46 (6H, s), 2.35 (3H, s), 2.58 (3H, s), 3.03-3.41 (8H, m), 3.79 (3H, s), 3.91 (3H, s), 6.81-6.90 (2H, m), 6.91-7.00 (2H, m).

Reference Example 77

2-bromo-1,5-dimethyl-3-(prop-2-en-1-yloxy)benzene 40.4 g of the title compound was obtained in the same manner as described for Reference Example 1 using 2-bromo-3,5-dimethylphenol (35.0 g, 174 mmol) synthesized in Reference Example 65 and allyl bromide (18.1 mL, 209 mmol) (yield: 96%).

$^1$H-NMR (CDCl$_3$): δ2.27 (3H, s), 2.37 (3H, s), 4.57 (2H, dt, J=4.9, 1.7 Hz), 5.26-5.33 (1H, m), 5.45-5.54 (1H, m), 6.00-6.14 (1H, m), 6.53-6.57 (1H, m), 6.67-6.71 (1H, m).

Reference Example 78

2-bromo-3,5-dimethyl-6-prop-2-en-1-ylphenol 24.4 g of the title compound was obtained as an oily product in the same manner as described for Reference Example 2 using 2-bromo-1,5-dimethyl-3-(prop-2-en-1-yloxy)benzene (40.4 g, 168 mmol) synthesized in Reference Example 77 (yield: 60%).

$^1$H-NMR (CDCl$_3$): δ2.23 (3H, s), 2.34 (3H, s), 3.45 (2H, dt, J=6.0, 1.6 Hz), 4.92-5.04 (2H, m), 5.64 (1H, s), 5.86-6.00 (1H, m), 6.67 (1H, s).

Reference Example 79

7-bromo-2,4,6-trimethyl-2,3-dihydro-1-benzofuran 22.8 g of the title compound was obtained as an oily product in the same manner as described for Reference Example 52 using 2-bromo-3,5-dimethyl-6-prop-2-en-1-ylphenol (24.1 g, 100 mmol) synthesized in Reference Example 78 (yield: 95%).

$^1$H-NMR (CDCl$_3$): δ1.52 (3H, d, J=6.3 Hz), 2.16 (3H, s), 2.33 (3H, s), 2.79 (1H, dd, J=15.3, 7.6 Hz), 3.31 (1H, dd, J=15.3, 8.8 Hz), 4.96-5.10 (1H, m), 6.56 (1H, s).

Reference Example 80

7-methoxy-2,4,6-trimethyl-2,3-dihydro-1-benzofuran

A mixture of 7-bromo-2,4,6-trimethyl-2,3-dihydro-1-benzofuran (10.0 g, 41.5 mmol) synthesized in Reference Example 79, copper iodide (I) (7.88 g, 41.5 mmol), 28% sodium methoxide/methanol solution (41.5 mL) and DMF (20.7 mL) was stirred at 120° C. for 2 hours. After cooled, 3N hydrochloric acid was added to the reaction solution to be neutralized, and it was diluted with ethyl acetate. Insolubles were removed by Celite filtration, and the obtained filtrate was washed with water and saturated saline. The organic layer was dried using magnesium sulfate, and then the solvent was removed under reduced pressure. The obtained residue was purified by silica gel column chromatography (hexane-ethyl acetate 94:6) to give 5.5 g of the title compound as an oily product (yield: 69%).

$^1$H-NMR (CDCl$_3$): δ1.48 (3H, d, J=6.0 Hz), 2.14 (3H, s), 2.20 (3H, s), 2.68 (1H, dd, J=15.2, 7.5 Hz), 3.20 (1H, dd, J=15.2, 9.0 Hz), 3.83 (3H, s), 4.91-5.03 (1H, m), 6.45 (1H, s).

Reference Example 81

7-ethoxy-2,4,6-trimethyl-2,3-dihydro-1-benzofuran 4.74 g of the title compound was obtained as an oily product in the same manner as described for Reference Example 80 using 7-bromo-2,4,6-trimethyl-2,3-dihydro-1-benzofuran (7.23 g, 30.0 mmol) synthesized in Reference Example 79 and 28% sodium ethoxide/ethanol solution (30 mL) (yield: 77%).

$^1$H-NMR (CDCl$_3$): δ1.33 (3H, t, J=7.2 Hz), 1.46 (3H, d, J=6.0 Hz), 2.14 (3H, s), 2.20 (3H, s), 2.67 (1H, dd, J=15.3, 7.3 Hz), 3.19 (1H, dd, J=15.3, 8.7 Hz), 4.07 (2H, q, J=7.2 Hz), 4.88-5.03 (1H, m), 6.45 (1H, s).

Reference Example 82

2,4,6-trimethyl-7-(1-methylethoxy)-2,3-dihydro-1-benzofuran 1.38 g of the title compound was obtained as an oily product in the same manner as described for Reference Example 80 using 7-bromo-2,4,6-trimethyl-2,3-dihydro-1-benzofuran (2.41 g, 10.0 mmol) synthesized in Reference Example 79 and 1.67M sodium isopropoxide/isopropanol solution (30 mL) (yield: 63%).

$^1$H-NMR (CDCl$_3$): δ1.28 (3H, d, J=6.2 Hz), 1.29 (3H, d, J=6.2 Hz), 1.47 (3H, d, J=6.3 Hz), 2.15 (3H, s), 2.20 (3H, s), 2.68 (1H, dd, J=15.0, 7.1 Hz), 3.20 (1H, dd, J=15.0, 8.8 Hz), 4.50 (1H, spt, J=6.2 Hz), 4.87-5.02 (1H, m), 6.45 (1H, s).

Reference Example 83

5-bromo-7-methoxy-2,4,6-trimethyl-2,3-dihydro-1-benzofuran 6.2 g of the title compound was obtained as an oily product in the same manner as described for Reference Example 4 using 7-methoxy-2,4,6-trimethyl-2,3-dihydro-1-benzofuran (5.50 g, 28.6 mmol) synthesized in Reference Example 80 (yield: 80%).

$^1$H-NMR (CDCl$_3$): δ1.48 (3H, d, J=6.4 Hz), 2.24 (3H, s), 2.32 (3H, s), 2.76 (1H, dd, J=15.3, 7.4 Hz), 3.28 (1H, dd, J=15.3, 8.9 Hz), 3.82 (3H, s), 4.91-5.04 (1H, m).

Reference Example 84

5-bromo-7-ethoxy-2,4,6-trimethyl-2,3-dihydro-1-benzofuran 6.1 g of the title compound was obtained as an oily product in the same manner as described for Reference Example 4 using 7-ethoxy-2,4,6-trimethyl-2,3-dihydro-1-benzofuran (4.70 g, 22.8 mmol) synthesized in Reference Example 81 (yield: 94%).

$^1$H-NMR (CDCl$_3$): δ1.34 (3H, t, J=7.1 Hz), 1.46 (3H, d, J=6.4 Hz), 2.24 (3H, s), 2.32 (3H, s), 2.75 (1H, dd, J=15.3, 7.3 Hz), 3.27 (1H, dd, J=15.3, 8.9 Hz), 4.05 (2H, q, J=7.1 Hz), 4.88-5.03 (1H, m).

Reference Example 85

5-bromo-2,4,6-trimethyl-7-(1-methylethoxy)-2,3-dihydro-1-benzofuran 1.52 g of the title compound was obtained as an oily product in the same manner as described for Reference Example 4 using 2,4,6-trimethyl-7-(1-methylethoxy)-2,3-dihydro-1-benzofuran (1.20 g, 5.45 mmol) synthesized in Reference Example 82 (yield: 93%).

$^1$H-NMR (CDCl$_3$): δ1.26 (3H, d, J=6.3 Hz), 1.27 (3H, d, J=6.3 Hz), 1.45 (3H, d, J=6.4 Hz), 2.24 (3H, s), 2.31 (3H, s), 2.75 (1H, dd, J=15.3, 7.3 Hz), 3.26 (1H, dd, J=15.3, 8.9 Hz), 4.48 (1H, spt, J=6.3 Hz), 4.87-5.00 (1H, m).

Reference Example 86 tert-butyl 4-(7-methoxy-2,4,6-trimethyl-2,3-dihydro-1-benzofuran-5-yl)piperazine-1-carboxylate 3.26 g of the title compound was obtained as an oily product in the same manner as described for Reference Example 19 using 5-bromo-7-methoxy-2,4,6-trimethyl-2,3-dihydro-1-benzofuran (3.0 g, 11.1 mmol) synthesized in Reference Example 83 and tert-butyl piperazine-1-carboxylate (4.11 g, 22.1 mmol) (yield: 78%).

$^1$H-NMR (CDCl$_3$): δ1.45-1.50 (12H, m), 2.14 (3H, s), 2.20 (3H, s), 2.69 (1H, dd, J=15.3, 7.7 Hz), 2.98-3.05 (4H, m), 3.20 (1H, dd, J=15.3, 8.9 Hz), 3.42-3.57 (4H, m), 3.81 (3H, s), 4.88-5.01 (1H, m).

Reference Example 87 tert-butyl 4-(7-ethoxy-2,4,6-trimethyl-2,3-dihydro-1-benzofuran-5-yl)piperazine-1-carboxylate 3.86 g of the title compound was obtained as an oily product in the same manner as described for Reference Example 19 using 5-bromo-7-ethoxy-2,4,6-trimethyl-2,3-dihydro-1-benzofuran (4.0 g, 14.0 mmol) synthesized in Reference Example 84 and tert-butyl piperazine-1-carboxylate (5.21 g, 28.0 mmol) (yield: 71%).

$^1$H-NMR (CDCl$_3$): δ1.33 (3H, t, J=7.0 Hz), 1.46 (3H, d, J=6.0 Hz), 1.49 (9H, s), 2.14 (3H, s), 2.19 (3H, s), 2.68 (1H, dd, J=15.2, 7.5 Hz), 2.96-3.07 (4H, m), 3.19 (1H, dd, J=15.2, 8.9 Hz), 3.42-3.58 (4H, m), 4.04 (2H, q, J=7.0 Hz), 4.85-4.99 (1H, m).

Reference Example 88

1-(7-methoxy-2,4,6-trimethyl-2,3-dihydro-1-benzofuran-5-yl)piperazine 2.35 g of the title compound was obtained as an oily product in the same manner as described for Reference Example 56 using tert-butyl 4-(7-methoxy-2,4,6-trimethyl-2,3-dihydro-1-benzofuran-5-yl)piperazine-1-carboxylate (3.26 g, 8.67 mmol) synthesized in Reference Example 86 (yield: 98%).

Reference Example 89

1-(7-ethoxy-2,4,6-trimethyl-2,3-dihydro-1-benzofuran-5-yl)piperazine 2.8 g of the title compound was obtained as an oily product in the same manner as described for Reference Example 56 using tert-butyl 4-(7-ethoxy-2,4,6-trimethyl-2,3-dihydro-1-benzofuran-5-yl)piperazine-1-carboxylate (3.80 g, 9.74 mmol) synthesized in Reference Example 87 (yield: 100%).
$^1$H-NMR (CDCl$_3$): δ1.34 (3H, t, J=6.9 Hz), 1.46 (3H, d, J=6.4 Hz), 2.17 (3H, s), 2.22 (3H, s), 2.68 (1H, dd, J=15.1, 7.5 Hz), 2.91-3.08 (8H, m), 3.19 (1H, dd, J=15.1, 8.7 Hz), 4.04 (2H, q, J=6.9 Hz), 4.85-4.99 (1H, m).

Reference Example 90

2-bromo-1,5-dimethyl-3-[(2-methylprop-2-en-1-yl)oxy]benzene 43.4 g of the title compound was synthesized in the same manner as described for Reference Example 1 using 2-bromo-3,5-dimethylphenol (35.6 g, 176 mmol) synthesized in Reference Example 65 (yield: 97%).
$^1$H-NMR (CDCl$_3$): δ1.86 (3H, s), 2.27 (3H, s), 2.37 (3H, s), 4.46 (2H, s), 4.98-5.02 (1H, m), 5.15-5.20 (1H, m), 6.50-6.57 (1H, m), 6.65-6.72 (1H, m).

Reference Example 91

2-bromo-3,5-dimethyl-6-(2-methylprop-2-en-1-yl)phenol 38.1 g of the title compound was synthesized in the same manner as described for Reference Example 2 using 2-bromo-1,5-dimethyl-3-[(2-methylprop-2-en-1-yl)oxy]benzene (43.4 g, 170 mmol) synthesized in Reference Example 90 (yield: 88%).
$^1$H-NMR (CDCl$_3$): δ1.96 (3H, s), 2.12 (3H, s), 2.32 (3H, s), 2.99 (2H, s), 5.56-5.67 (1H, m), 5.90-6.01 (1H, m), 6.55 (1H, s).

Reference Example 92

7-bromo-2,2,4,6-tetramethyl-2,3-dihydro-1-benzofuran 26.0 g of the title compound was synthesized in the same manner as described for Reference Example 52 using 2-bromo-3,5-dimethyl-6-(2-methylprop-2-en-1-yl)phenol (38.1 g, 149 mmol) synthesized in Reference Example 91 (yield: 68%).
$^1$H-NMR (CDCl$_3$): δ1.52 (6H, s), 2.13 (3H, s), 2.31 (3H, s), 2.98 (2H, s), 6.55 (1H, s).

Reference Example 93

7-methoxy-2,2,4,6-tetramethyl-2,3-dihydro-1-benzofuran 10.3 g of the title compound was synthesized in the same manner as described for Reference Example 80 using 7-bromo-2,2,4,6-tetramethyl-2,3-dihydro-1-benzofuran (15.0 g, 58.8 mmol) synthesized in Reference Example 92 (yield: 85%).
Further, by using 2-methoxy-3,5-dimethylphenol (7.60 g, 41.7 mmol), synthesis was also performed according to the following method. That is, to a solution of n-heptane (76 mL) containing 2-methoxy-3,5-dimethylphenol (7.60 g, 41.7 mmol) and isobutyl aldehyde (5.71 mL, 62.6 mmol), trifluoromethanesulfonic acid (1.85 mL, 20.9 mmol) was added dropwise, and the mixture was stirred at 55° C. for 2.5 hours. After cooled to room temperature, the reaction solution was washed with water and dried using anhydrous magnesium sulfate, and then the solvent was removed under reduced pressure. The obtained residue was purified by basic silica gel chromatography (hexane-ethyl acetate 100:0) and silica gel chromatography (hexane-ethyl acetate 100:0-95:5) to give 8.70 g of the title compound (yield 100%).
$^1$H-NMR (CDCl$_3$): δ1.49 (6H, s), 2.12 (3H, s), 2.20 (3H, s), 2.89 (2H, s), 3.82 (3H, s), 6.44 (1H, s).

Reference Example 94

5-bromo-7-methoxy-2,2,4,6-tetramethyl-2,3-dihydro-1-benzofuran 13.8 g of the title compound was synthesized in the same manner as described for Reference Example 4 using 7-methoxy-2,2,4,6-tetramethyl-2,3-dihydro-1-benzofuran (10.3 g, 50.0 mmol) synthesized in Reference Example 93 (yield: 97%).
$^1$H-NMR (CDCl$_3$): δ1.50 (6H, s), 2.23 (3H, s), 2.32 (3H, s), 2.76 (2H, s), 3.80 (3H, s).

Reference Example 95 tert-butyl 4-(7-methoxy-2,2,4,6-tetramethyl-2,3-dihydro-1-benzofuran-5-yl)piperazine-1-carboxylate 3.97 g of the title compound was synthesized in the same manner as described for Reference Example 19 using 5-bromo-7-methoxy-2,2,4,6-tetramethyl-2,3-dihydro-1-benzofuran (3.74 g, 13.1 mmol) synthesized in Reference Example 94 and tert-butyl piperazine-1-carboxylate (4.88 g, 26.2 mmol) (yield: 78%).
$^1$H-NMR (CDCl$_3$): δ1.49 (15H, s), 2.12 (3H, s), 2.20 (3H, s), 2.89 (2H, s), 2.95-3.07 (4H, m), 3.40-3.57 (4H, m), 3.80 (3H, s).

Reference Example 96

1-(7-methoxy-2,2,4,6-tetramethyl-2,3-dihydro-1-benzofuran-5-yl)piperazine 2.48 g of the title compound was synthesized in the same manner as described for Reference Example 56 using tert-butyl 4-(7-methoxy-2,2,4,6-tetramethyl-2,3-dihydro-1-benzofuran-5-yl)piperazine-1-carboxylate (3.97 g, 10.2 mmol) synthesized in Reference Example 95 (yield: 84%).
$^1$H-NMR (CDCl$_3$): δ1.49 (6H, s), 2.15 (3H, s), 2.22 (3H, s), 2.89 (2H, s), 2.90-2.97 (4H, m), 3.00-3.10 (4H, m), 3.80 (3H, s).

Reference Example 97

7-ethoxy-2,2,4,6-tetramethyl-2,3-dihydro-1-benzofuran 4.05 g of the title compound was synthesized in the same manner as described for Reference Example 80 using (Top of column 131)
$^1$H-NMR (CDCl$_3$): δ1.48 (3H, d, J=6.0 Hz), 2.17 (3H, s), 2.23 (3H, s), 2.69 (1H, dd, J=15.2, 7.7 Hz), 2.88-3.10 (8H, m), 3.20 (1H, dd, J=15.2, 9.0 Hz), 3.81 (3H, s), 4.88-5.00 (1H, m).

7-bromo-2,2,4,6-tetramethyl-2,3-dihydro-1-benzofuran (5.00 g, 19.6 mmol) synthesized in Reference Example 92 and 20% sodium ethoxide/ethanol solution (yield: 94%).

$^1$H-NMR (CDCl$_3$): δ1.32 (3H, t, J=7.2 Hz), 1.48 (6H, s), 2.12 (3H, s), 2.19 (3H, s), 2.89 (2H, s), 4.07 (2H, q, J=7.2 Hz), 6.44 (1H, s).

Reference Example 98

5-bromo-7-ethoxy-2,2,4,6-tetramethyl-2,3-dihydro-1-benzofuran 5.38 g of the title compound was synthesized in the same manner as described for Reference Example 4 using 7-ethoxy-2,2,4,6-tetramethyl-2,3-dihydro-1-benzofuran (4.05 g, 18.4 mmol) synthesized in Reference Example 97 (yield: 98%).

$^1$H-NMR (CDCl$_3$): δ1.32 (3H, t, J=6.9 Hz), 1.48 (6H, s), 2.23 (3H, s), 2.32 (3H, s), 2.95 (2H, s), 4.05 (2H, q, J=6.9 Hz).

Reference Example 99

5-[2-(4-methoxyphenyl)morpholine-4-yl]-2,2,6,7-tetramethyl-1-benzofuran-3(2H)-one By using 5-bromo-2,2,6,7-tetramethyl-1-benzofuran-3(2H)-one (488 mg, 1.72 mmol) synthesized in Reference Example 18 and 2-(4-methoxyphenyl)morpholine (500 mg, 2.59 mmol), the reaction was carried out in the same manner as Reference Example 59 to synthesize 224 mg of the title compound (yield 34%).

$^1$H-NMR (CDCl$_3$): δ1.44 (3H, s), 1.45 (3H, s), 2.23 (3H, s), 2.39 (3H, s), 2.77 (1H, dd, J=11.7, 10.2 Hz), 2.83-2.94 (2H, m), 2.95-3.16 (1H, m), 3.80 (3H, s), 3.93-4.06 (1H, m), 4.07-4.18 (1H, m), 4.66 (1H, dd, J=10.2, 2.4 Hz), 6.88 (2H, d, J=8.7 Hz), 7.19 (1H, s), 7.32 (2H, d, J=8.7 Hz).

Reference Example 100

1,4-dimethyl-2-[(2-methylprop-2-en-1-yl)oxy]benzene 35.3 g of the title compound was synthesized in the same manner as described for Reference Example 1 using 2,5-dimethylphenol (25.0 g, 205 mmol) (yield: 100%).

$^1$H-NMR (CDCl$_3$): δ1.85 (3H, s), 2.21 (3H, s), 2.31 (3H, s), 4.41 (2H, s), 4.98 (1H, s), 5.12 (1H, s), 6.63 (1H, s), 6.67 (1H, d, J=7.5 Hz), 7.02 (1H, d, J=7.5 Hz).

Reference Example 101

3,6-dimethyl-2-(2-methylprop-2-en-1-yl)phenol 35.3 g of the title compound was synthesized in the same manner as described for Reference Example 2 using 1,4-dimethyl-2-[(2-methylprop-2-en-1-yl)oxy]benzene (35.3 g, 205 mmol) synthesized in Reference Example 100 (yield: 100%).

$^1$H-NMR (CDCl$_3$): δ1.79 (3H, s), 2.01 (3H, s), 2.25 (3H, s), 3.38 (2H, s), 4.65-4.70 (1H, m), 4.84-4.88 (1H, s), 5.02 (1H, s), 5.12 (1H, s), 6.68 (1H, d, J=8.4 Hz), 6.91 (1H, d, J=8.2 Hz).

Reference Example 102

2,2,4,7-tetramethyl-2,3-dihydro-1-benzofuran 24.3 g of the title compound was synthesized in the same manner as described for Reference Example 52 using 3,6-dimethyl-2-(2-methylprop-2-en-1-yl)phenol (35.3 g, 205 mmol) synthesized in Reference Example 101 (yield: 69%).

$^1$H-NMR (CDCl$_3$): δ1.47 (6H, s), 2.15 (3H, s), 2.17 (3H, s), 2.92 (2H, s), 6.55 (1H, d, J=7.5 Hz), 6.84 (1H, d, J=7.5 Hz).

Reference Example 103

5-bromo-2,2,4,7-tetramethyl-2,3-dihydro-1-benzofuran 2.56 g of the title compound was synthesized in the same manner as described for Reference Example 4 using 2,2,4,7-tetramethyl-2,3-dihydro-1-benzofuran (2.00 g, 11.3 mmol) synthesized in Reference Example 102 (yield: 89%).

$^1$H-NMR (CDCl$_3$): δ1.47 (6H, s), 2.12 (3H, s), 2.21 (3H, s), 2.95 (2H, s), 7.11 (1H, s).

Reference Example 104

3-tert-butyl-5-[4-(4-methoxyphenyl)piperazin-1-yl]-2,2,4,6,7-pentamethyl-2,3-dihydro-1-benzofuran-3-ol A pentane solution (2.00 mL, 3.08 mmol) containing 1.54 M t-butyllithium was added dropwise to a solution of THF (4 mL) containing 5-[4-(4-methoxyphenyl)piperazin-1-yl]-2,2,4,6,7-pentamethyl-1-benzofuran-3(2H)-one (800 mg, 2.03 mmol) synthesized in Reference Example 42 under argon atmosphere at −70° C. or lower, and then the mixture was warmed to 0° C. The reaction solution was stirred under ice-cooling condition for 30 minutes, and then water was added thereto and extraction was performed using ethyl acetate. The organic layer was washed with water and saturated saline, and then dried using anhydrous sodium sulfate. It was concentrated under reduced pressure. The obtained residue was purified by basic silica gel column chromatography (hexane-ethyl acetate 100:0 to 8:1) and silica gel column chromatography (hexane-ethyl acetate 100:0 to 8:1), and after that, crystallization was performed using hexane to give 300 mg of the title compound (yield: 33%).

Melting point: 113 to 115° C.

$^1$H-NMR (CDCl$_3$) δ: 1.03 (9H, s), 1.25 (3H, s), 1.69 (3H, s), 1.79 (1H, s), 2.03 (3H, s), 2.23 (3H, s), 2.36 (3H, s), 3.00-3.42 (8H, m), 3.78 (3H, s), 6.86 (2H, d, J=9.2 Hz), 6.97 (2H, d, J=9.2 Hz).

Reference Example 105

5-[4-(4-methoxyphenyl)piperazin-1-yl]-2,2,3,4,6,7-hexamethyl-2,3-dihydro-1-benzofuran-3-ol A diethylether solution (5.60 mL, 6.38 mmol) containing 1.14 M methyl lithium was added dropwise to a solution of tetrahydrofuran (20 mL) containing 5-[4-(4-methoxyphenyl)piperazin-1-yl]-2,2,4,6,7-pentamethyl-1-benzofuran-3(2H)-one (2.00 g, 5.06 mmol) synthesized in Reference Example 42 under ice-cooling condition, and the mixture was stirred for 10 minutes. Water was added to the reaction solution, and extraction was performed using ethyl acetate. The organic layer was washed with water and saturated saline, and then dried using anhydrous sodium sulfate. The solvent was removed under reduced pressure, and the obtained residue was crystallized using hexane to give 2.00 g of the title compound (yield: 96%).

Melting point: 139 to 141° C.

$^1$H-NMR (CDCl$_3$) δ: 1.31 (3H, s), 1.41 (3H, s), 1.56 (3H, s), 1.70 (1H, s), 2.08 (3H, s), 2.24 (3H, s), 2.43 (3H, s), 3.00-3.40 (8H, m), 3.78 (3H, s), 6.86 (2H, d, J=9.2 Hz), 6.97 (2H, d, J=9.2 Hz).

Reference Example 106

1-(4-methoxyphenyl)-4-(2,2,4,6,7-pentamethyl-3-methylidene-2,3-dihydro-1-benzofuran-5-yl)piperazine 10% hydrochloric acid (5 mL) was added to a suspension of acetonitrile (15 mL) containing 5-[4-(4-methoxyphenyl)piperazin-1-yl]-2,2,3,4,6,7-hexamethyl-2,3-dihydro-1-benzofuran-3-ol (1.70 g, 4.14 mmol) obtained in Reference Example 105, and the mixture was stirred at room temperature for 6 hours. The reaction solution was concentrated under reduced pressure, and after that, 10% potassium carbonate aqueous solution was added to the residue so that the aqueous layer became alkaline. Then, extraction was performed using ethyl acetate. The organic layer was washed with water and saturated saline, and then dried using anhydrous sodium sulfate. The solvent was removed under reduced pressure, and the obtained residue was crystallized using ethanol to give 1.50 g of the title compound (yield: 92%)

Melting point: 134 to 136° C.

$^1$H-NMR (CDCl$_3$) δ: 1.46 (6H, s), 2.12 (3H, s), 2.29 (3H, s), 2.45 (3H, s), 3.04-3.42 (8H, m), 3.79 (3H, s), 4.82 (1H, s), 5.32 (1H, s), 6.86 (2H, d, J=9.5 Hz), 6.98 (2H, d, J=9.5 Hz).

Reference Example 107

[(5-bromo-4,6,7-trimethyl-1-benzofuran-3-yl)oxy](tert-butyl)dimethylsilane

Triethylamine (2.15 g, 21.2 mmol) and tert-butyldimethylsilyl trifluoromethanesulfonate (4.68 g, 17.7 mmol) were sequentially added to a solution of toluene (100 mL) containing 5-bromo-4,6,7-trimethyl-1-benzofuran-3(2H)-one (3.00 g, 11.8 mmol) synthesized in Reference Example 45, and the mixture was stirred at room temperature for 1 hour. The resulting mixture was poured into saturated sodium bicarbonate water, and extraction was performed using ethyl acetate. The extract was washed with saturated saline, and dried using anhydrous magnesium sulfate, followed by concentration under reduced pressure. The residue was purified by silica gel chromatography (hexane-ethyl acetate 99:1 to 94/6) to give 4.14 g of the title compound (yield: 95%).

$^1$H-NMR (CDCl$_3$): δ0.25 (6H, s), 1.03 (9H, s), 2.42 (3H, s), 2.47 (3H, s), 2.70 (3H, s), 7.20 (1H, s).

Reference Example 108

1-(3-{[tert-butyl(dimethyl)silyl]oxy}-4,6,7-trimethyl-1-benzofuran-5-yl)-4-(4-methoxyphenyl)piperazine 600 mg of the title compound was synthesized in the same manner as described for Reference Example 19 using [(5-bromo-4,6,7-trimethyl-1-benzofuran-3-yl)oxy](tert-butyl)dimethylsilane (980 mg, 2.65 mmol) synthesized in Reference Example 107 (yield: 47%).

$^1$H-NMR (CDCl$_3$): δ0.24 (6H, s), 1.02 (9H, s), 2.33 (3H, s), 2.35 (3H, s), 2.64 (3H, s), 3.06-3.44 (8H, m), 3.79 (3H, s), 6.81-6.91 (2H, m), 6.92-7.02 (2H, m), 7.16 (1H, s).

Reference Example 109

5-[4-(4-methoxyphenyl)piperazin-1-yl]-4,6,7-trimethyl-1-benzofuran-3(2H)-one 1N hydrochloric acid (5 mL) was added to a solution of THF (25 mL) containing 1-(3-{[tert-butyl(dimethyl)silyl]oxy}-4,6,7-trimethyl-1-benzofuran-5-yl)-4-(4-methoxyphenyl)piperazine (560 mg, 1.16 mmol) synthesized in Reference Example 108, and the mixture was stirred at room temperature for 1 hour. The resulting mixture was diluted with saturated sodium bicarbonate water. THF in the reaction mixture was removed under reduced pressure, and the residue was extracted using ethyl acetate. The extract was washed with saturated saline, and dried using anhydrous magnesium sulfate, followed by concentration under reduced pressure. The residue was purified by silica gel chromatography (hexane-ethyl acetate 95:5 to 85/15) to give 310 mg of the title compound (yield: 73%).

$^1$H-NMR (CDCl$_3$): δ2.19 (3H, s), 2.36 (3H, s), 2.62 (3H, s), 3.03-3.42 (8H, m), 3.79 (3H, s), 4.56 (2H, s), 6.81-6.91 (2H, m), 6.92-7.02 (2H, m).

Reference Example 110

2-(2,3,5-trimethylphenoxy)propanoic acid 49.6 g of the title compound was obtained in the same manner as described for Reference Example 16 using 2,3,5-trimethylphenol (36.2 g, 266 mmol) (yield: 90%).

$^1$H-NMR (CDCl$_3$): δ1.64 (3H, t, J=6.6 Hz), 2.15 (3H, s), 2.23 (3H, s), 2.25 (3H, s), 4.75 (1H, q, J=6.6 Hz), 6.44 (1H, s), 6.67 (1H, s).

Reference Example 111

2,4,6,7-tetramethyl-1-benzofuran-3(2H)-one 30.5 g of the title compound was obtained in the same manner as described for Reference Example 17 using 2-(2,3,5-trimethylphenoxy)propanoic acid (49.5 g, 238 mmol) synthesized in Reference Example 110 (yield: 68%).

$^1$H-NMR (CDCl$_3$): δ1.50 (3H, d, J=7.2 Hz), 2.17 (3H, s), 2.30 (3H, s), 2.51 (3H, s), 4.57 (1H, q, J=7.2 Hz), 6.63 (1H, s).

Reference Example 112

5-bromo-2,4,6,7-tetramethyl-1-benzofuran-3(2H)-one 32.3 g of the title compound was obtained in the same manner as described for Reference Example 45 using 2,4,6,7-tetramethyl-1-benzofuran-3(2H)-one (28.4 g, 149 mmol) synthesized in Reference Example 111 (yield: 81%).

$^1$H-NMR (CDCl$_3$): δ1.51 (3H, d, J=6.9 Hz), 2.27 (3H, s), 2.47 (3H, s), 2.66 (3H, s), 4.66 (1H, q, J=6.9 Hz).

Reference Example 113

[(5-bromo-2,4,6,7-tetramethyl-1-benzofuran-3-yl)oxy](triethyl)silane 12.0 g of the title compound was obtained in the same manner as described for Reference Example 107 using 5-bromo-2,4,6,7-tetramethyl-1-benzofuran-3(2H)-one (10.0 g, 37.2 mmol) synthesized in Reference Example 112 and triethylsilyl trifluoromethanesulfonate (14.8 g, 55.8 mmol) (yield: 84%).

$^1$H-NMR (CDCl$_3$): δ0.73-0.82 (6H, m), 0.93-1.03 (9H, m), 2.34 (3H, s), 2.39 (3H, s), 2.44 (3H, s), 2.64 (3H, s).

Reference Example 114

1-(4-methoxyphenyl)-4-{2,4,6,7-tetramethyl-3-[(triethylsilyl)oxy]-1-benzofuran-5-yl}piperazine 810 mg of the title compound was obtained in the same manner as described for Reference Example 19 using [(5-bromo-2,4,6,7-tetramethyl-1-benzofuran-3-yl)oxy](triethyl) silane (2.00 g, 5.22 mmol) synthesized in Reference Example 113 (yield: 31%).

$^1$H-NMR (CDCl$_3$): δ0.71-0.84 (6H, m), 0.93-1.05 (9H, m), 2.32 (3H, s), 2.33 (3H, s), 2.34 (3H, s), 2.58 (3H, s), 3.09-3.40 (8H, m), 3.79 (3H, s), 6.82-6.91 (2H, m), 6.94-7.03 (2H, m).

Reference Example 115

5-[4-(4-methoxyphenyl)piperazin-1-yl]-2,4,6,7-tetramethyl-1-benzofuran-3(2H)-one 910 mg of the title compound was synthesized in the same manner as described for Reference Example 109 using 1-(4-methoxyphenyl)-4-{2,4,6,7-tetramethyl-3-[(triethylsilyl) oxy]-1-benzofuran-5-yl}piperazine (1.38 g, 2.79 mmol) synthesized in Reference Example 114 (yield: 86%).

$^1$H-NMR (CDCl$_3$): δ1.50 (3H, d, J=7.2 Hz), 2.19 (3H, s), 2.36 (3H, s), 2.61 (3H, s), 3.05-3.41 (8H, m), 3.79 (3H, s), 4.55 (2H, q, J=7.2 Hz), 6.81-6.90 (2H, m), 6.92-7.01 (2H, m).

Reference Example 116

2-ethyl-5-[4-(4-methoxyphenyl)piperazin-1-yl]-2,4,6,7-tetramethyl-1-benzofuran-3(2H)-one Potassium tert-butoxide (74 mg, 0.473 mmol) was added to a mixture of THF (2 mL) containing 2-ethyl-5-[4-(4-methoxyphenyl)piperazin-1-yl]-2,4,6,7-tetramethyl-1-benzofuran-3 (2H)-one (150 mg, 0.394 mmol) synthesized in Reference Example 115 and iodoethane (74 mg, 0.473 mmol), and the mixture was stirred at room temperature for 1 hour. After that, the reaction solution was poured into a saturated ammonium chloride aqueous solution, and extraction was performed using ethyl acetate. The extract was washed with saturated saline, and dried using anhydrous magnesium sulfate, followed by concentration under reduced pressure. The residue was purified by silica gel chromatography (hexane-ethyl acetate 96/4 to 87/13) to give 60 mg of the title compound (yield: 37%).

$^1$H-NMR (CDCl$_3$): δ0.83 (3H, t, J=7.2 Hz), 1.38 (3H, s), 1.75-1.91 (2H, m), 2.19 (3H, s), 2.35 (3H, s), 2.60 (3H, s), 3.03-3.43 (8H, m), 3.79 (3H, s), 6.82-6.91 (2H, m), 6.93-7.01 (2H, m).

Reference Example 117

2-(3,5-dimethylphenoxy)-2-methylpropanoic acid

A crudely purified product of the title compound (25.5 g) was obtained in the same manner as described for Reference Example 16 using 3,5-dimethylphenol (12.3 g, 100 mmol).

$^1$H-NMR (CDCl$_3$): δ1.59 (6H, s), 2.27 (6H, s), 6.56 (2H, s), 6.72 (1H, s).

Reference Example 118

2,2,4,6-tetramethyl-1-benzofuran-3(2H)-one 11.8 g of the title compound was obtained in the same manner as described for Reference Example 35 using the crudely purified product of 2-(3,5-dimethylphenoxy)-2-methylpropanoic acid (25.5 g) synthesized in Reference Example 117 (2-step yield: 62%).

$^1$H-NMR (CDCl$_3$): δ1.43 (6H, s), 2.37 (3H, s), 2.55 (3H, s), 6.63 (1H, s), 6.67 (1H, s).

Reference Example 119

5-bromo-2,2,4,6-tetramethyl-1-benzofuran-3(2H)-one

Bromine (8.7 mL, 169 mmol) was added to a mixture of acetonitrile (200 mL) containing 2,2,4,6-tetramethyl-1-benzofuran-3(2H)-one (30.7 g, 161 mmol) synthesized in Reference Example 118 and sodium acetate (14.5 g, 177 mmol), and the mixture was stirred at room temperature for 2 hours. After that, the reaction solution was poured into 5% sodium sulfite aqueous solution, and extraction was performed using ethyl acetate. The extract was washed with water and saturated saline, and dried using anhydrous magnesium sulfate. After that, the solvent was removed under reduced pressure. The residue was purified by silica gel chromatography (hexane-ethyl acetate 50:1-9/1), and crystallization was performed using methanol to give 26.2 g of the title compound (yield: 61%).

$^1$H-NMR (CDCl$_3$): δ1.44 (6H, s), 2.48 (3H, s), 2.68 (3H, s), 6.84 (1H, s).

Reference Example 120

5-bromo-2,2,4,6-tetramethyl-2,3-dihydro-1-benzofuran

Lithium aluminium hydride (2.33 mg, 61.5 mmol) was added to a suspension of THF (70 mL) containing aluminium chloride (8.20 g, 6.15 mmol) under ice-cooling condition, and the mixture was stirred for 15 minutes. After that, a solution of THF (30 mL) containing 5-bromo-2,2,4,6-tetramethyl-1-benzofuran-3(2H)-one (6.63 g, 24.6 mmol) synthesized in Reference Example 119 was added thereto, and the mixture was stirred under heated reflux for 2.5 hours. The reaction solution was iced, and after that, water was added dropwise thereto. 0.5N sodium hydroxide aqueous solution was further added thereto, and the mixture was stirred at room temperature for 10 minutes. Insolubles were removed by filtration. The filtrate was subjected to extraction using a mixed solvent of ethyl acetate-diethyl ether (1:1). The extract was washed with saturated saline, and then dried using anhydrous magnesium sulfate. The solvent was removed under reduced pressure, and the obtained residue was purified by silica gel chromatography (hexane-ethyl acetate 9:1). Crystallization was performed using methanol-ethyl acetate to give 5.29 g of the title compound (yield: 84%).

$^1$H-NMR (CDCl$_3$): δ1.46 (6H, s), 2.27 (3H, s), 2.35 (3H, s), 2.95 (2H, s), 6.51 (1H, s).

Reference Example 121

1-(5-bromo-2,2,4,6-tetramethyl-2,3-dihydro-1-benzofuran-7-yl)ethanone

Aluminium chloride (3.56 g, 26.7 mmol) was added to a mixture of chlorobenzene (40 mL) containing 5-bromo-2,2,4,6-tetramethyl-2,3-dihydro-1-benzofuran (4.55 g, 17.8 mmol) synthesized in Reference Example 120 and acetyl chloride (4.20 g, 53.4 mmol) at −40° C., and the mixture was stirred at the same temperature. After stirring for 1 hour, the reaction solution was poured into water, and extraction was performed using ethyl acetate. The extract was washed with saturated sodium bicarbonate water and saturated saline, and dried using anhydrous magnesium sulfate. After that, the solvent was removed under reduced pressure. The residue was purified by silica gel chromatography (hexane-ethyl acetate 99:1-95/5) to give 440 mg of the title compound (yield: 8%).
$^1$H-NMR (CDCl$_3$): δ1.48 (6H, s), 2.29 (3H, s), 2.38 (3H, s), 2.53 (3H, s), 2.97 (2H, s).

Reference Example 122

(2,4,6,7-tetramethyl-2,3-dihydro-1-benzofuran-2-yl)methanol

70% m-chloroperbenzoic acid (1.95 g, 7.89 mmol) was added to a solution of toluene (18 mL) containing 2,3,5-trimethyl-6-(2-methylprop-2-en-1-yl)phenol (1.00 g, 5.26 mmol) synthesized in Reference Example 2, and the mixture was stirred at room temperature for 15 hours. The resulting mixture was poured into water, and extraction was performed using ethyl acetate. The extract was washed with 5% sodium sulfite aqueous solution, saturated sodium bicarbonate water and saturated saline, and dried using anhydrous magnesium sulfate. After that, concentration was performed under reduced pressure, and the residue was dissolved in toluene (10 mL). To this solution, trifluoroacetic acid (0.2 mL) was added, and the mixture was stirred at room temperature for 1 hour. After that, the reaction solution was poured into saturated sodium bicarbonate water, and extraction was performed using ethyl acetate. The extract was washed with saturated saline, and dried using anhydrous magnesium sulfate, followed by concentration under reduced pressure. The residue was purified by silica gel chromatography (hexane-ethyl acetate 95:5-85/15) to give 420 mg of the title compound (yield: 39%).
$^1$H-NMR (CDCl$_3$): δ1.44 (3H, s), 1.88 (1H, dd, J=6.6, 7.2 Hz), 2.08 (3H, s), 2.15 (3H, s), 2.20 (3H, s), 2.80 (1H, d, J=15.3 Hz), 3.13 (1H, d, J=15.3 Hz), 3.61 (1H, dd, J=7.2, 11.7 Hz), 3.67 (1H, dd, J=6.6, 11.7 Hz), 6.51 (1H, s).

Reference Example 123

(5-bromo-2,4,6,7-tetramethyl-2,3-dihydro-1-benzofuran-2-yl)methanol 720 mg of the title compound was synthesized in the same manner as described for Reference Example 4 using (2,4,6,7-tetramethyl-2,3-dihydro-1-benzofuran-2-yl)methanol (860 mg, 0.908 mmol) synthesized in Reference Example 122 (yield: 61%).
$^1$H-NMR (CDCl$_3$): δ1.43 (3H, s), 1.84 (1H, dd, J=6.0, 7.2 Hz), 2.16 (3H, s), 2.27 (3H, s), 2.34 (3H, s), 2.86 (1H, d, J=15.6 Hz), 3.22 (1H, d, J=15.6 Hz), 3.60 (1H, dd, J=7.2, 11.7 Hz), 3.68 (1H, dd, J=6.0, 11.7 Hz).

Reference Example 124

2-(methoxymethyl)-2,4,6,7-tetramethyl-2,3-dihydro-1-benzofuran

60% sodium hydride (60 mg, 1.46 mmol) was added to a solution of THF (3 mL) containing (2,4,6,7-tetramethyl-2,3-dihydro-1-benzofuran-2-yl)methanol (200 mg, 0.970 mmol) synthesized in Reference Example 122 under ice-cooling condition, and the mixture was stirred at 0° C. for 20 minutes. After that, methyl iodide (413 mg, 2.19 mmol) was added thereto, and the mixture was warmed to room temperature, followed by stirring for 15 hours. The reaction solution was poured into a saturated ammonium chloride aqueous solution, and extraction was performed using ethyl acetate. The extract was washed with saturated saline, and dried using anhydrous magnesium sulfate, followed by concentration under reduced pressure. The residue was purified by silica gel chromatography (hexane-ethyl acetate 98:2-92:8) to give 140 mg of the title compound (yield: 66%).
$^1$H-NMR (CDCl$_3$): δ1.40 (3H, s), 2.18 (3H, s), 2.22 (3H, s), 2.34 (3H, s), 2.92 (1H, d, J=15.3 Hz), 3.20 (1H, d, J=15.3 Hz), 4.34 (2H, s), 6.20-6.24 (1H, m), 7.45-7.49 (2H, m).

Reference Example 125

5-bromo-2-(methoxymethyl)-2,4,6,7-tetramethyl-2,3-dihydro-1-benzofuran 120 mg of the title compound was obtained in the same manner as described for Reference Example 4 using 2-(methoxymethyl)-2,4,6,7-tetramethyl-2,3-dihydro-1-benzofuran (140 mg, 0.635 mmol) synthesized in Reference Example 124 (yield: 63%).
$^1$H-NMR (CDCl$_3$): δ1.45 (3H, s), 2.15 (3H, s), 2.26 (3H, s), 2.33 (3H, s), 2.84 (1H, d, J=15.6 Hz), 3.19 (1H, d, J=15.6 Hz), 3.41 (3H, s), 3.44 (2H, s).

Reference Example 126

2-(iodomethyl)-2,4,6,7-tetramethyl-2,3-dihydro-1-benzofuran

Calcium carbonate (1.37 g, 13.7 mmol) and benzyltrimethylammonium dichloroiodate (4.04 g, 11.6 mmol) were sequentially added to a solution of toluene (20 mL)/methanol (10 mL) containing 2,3,5-trimethyl-6-(2-methylprop-2-en-1-yl)phenol (1.00 g, 5.26 mmol) synthesized in Reference Example 2 under ice-cooling condition, and the mixture was stirred at 0° C. for 30 minutes. After that, the reaction solution was concentrated under reduced pressure, and water and ethyl acetate were added to the residue to separate an organic layer. The organic layer was washed with 10% sodium sulfite aqueous solution and saturated saline, and dried using anhydrous magnesium sulfate, followed by concentration under reduced pressure. The residue was purified by silica gel chromatography (hexane-ethyl acetate 100:0-95:5) to give 3.05 g of the title compound (yield: 92%).
$^1$H-NMR (CDCl$_3$): δ1.66 (3H, s), 2.07 (3H, s), 2.16 (3H, s), 2.20 (3H, s), 2.95 (1H, d, J=15.6 Hz), 3.20 (1H, d, J=15.6 Hz), 3.40 (1H, d, J=10.2 Hz), 3.43 (1H, d, J=10.2 Hz), 6.51 (1H, s).

Reference Example 127

2-[(2,4,6,7-tetramethyl-2,3-dihydro-1-benzofuran-2-yl)methyl]-1H-isoindole-1,3(2H)-dione Potassium phthalimide (702 mg, 3.79 mmol) was added to a solution of DMF (10 mL) containing 2-(iodomethyl)-2,4,6,7-tetramethyl-2,3-dihydro-1-benzofuran (1.00 g, 3.16 mmol) synthesized in Reference Example 126, and the mixture was stirred at 140° C. for 15 hours. After that, the reaction solution was cooled to room temperature, and water and ethyl acetate were added thereto to separate an organic layer. The organic layer was washed with water and saturated saline, and dried using anhydrous magnesium sulfate, followed by concentration under reduced pressure. The residue was purified by silica gel chromatography (hexane-ethyl acetate 95:5-75:25) to give 730 mg of the title compound (yield: 69%)

$^1$H-NMR (CDCl$_3$): δ1.54 (3H, s), 2.03 (3H, s), 2.10 (3H, s), 2.11 (3H, s), 2.89 (1H, d, J=15.6 Hz), 3.24 (1H, d, J=15.6 Hz), 3.89 (1H, d, J=14.1 Hz), 3.95 (1H, d, J=14.1 Hz), 6.36 (1H, s), 7.64-7.73 (2H, m), 7.76-7.87 (2H, m).

Reference Example 128

2-[(5-bromo-2,4,6,7-tetramethyl-2,3-dihydro-1-benzofuran-2-yl)methyl]-1H-isoindole-1,3(2H)-dione 530 mg of the title compound was obtained in the same manner as described for Reference Example 4 using 2-[(2,4,6,7-tetramethyl-2,3-dihydro-1-benzofuran-2-yl)methyl]-1H-isoindole-1,3(2H)-dione (730 mg, 2.18 mmol) synthesized in Reference Example 127 (yield: 59%).

$^1$H-NMR (CDCl$_3$): δ1.55 (3H, s), 2.10 (3H, s), 2.22 (3H, s), 2.23 (3H, s), 2.97 (1H, d, J=15.6 Hz), 3.31 (1H, d, J=15.6 Hz), 3.88 (1H, d, J=13.8 Hz), 3.93 (1H, d, J=13.8 Hz), 7.65-7.74 (2H, m), 7.75-7.85 (2H, m).

Reference Example 129

1-(5-bromo-2,4,6,7-tetramethyl-2,3-dihydro-1-benzofuran-2-yl)methanamine

Hydrazine monohydrate (87 mg, 1.73 mmol) was added to a solution of ethanol (13 mL) containing 2-[(5-bromo-2,4,6,7-tetramethyl-2,3-dihydro-1-benzofuran-2-yl)methyl]-1H-isoindole-1,3(2H)-dione (530 mg, 1.28 mmol) synthesized in Reference Example 129, and the mixture was stirred under heated reflux for 3 hours. The reaction solution was cooled to room temperature, and 6N hydrochloric acid (10 mL) was added thereto, followed by stirring under heated reflux for 1 hour. The reaction solution was cooled to room temperature, and then 1N sodium hydroxide aqueous solution was added thereto to become weakly basic, followed by extraction using diisopropyl ether. The organic layer was washed with saturated saline, and dried using anhydrous magnesium sulfate, followed by concentration under reduced pressure. The residue was purified by basic silica gel chromatography (hexane-ethyl acetate 80:20-0:100) to give 250 mg of the title compound (yield: 69%).

$^1$H-NMR (CDCl$_3$): δ1.31 (2H, brs), 1.42 (3H, s), 2.16 (3H, s), 2.27 (3H, s), 2.34 (3H, s), 2.81 (1H, d, J=13.5 Hz), 2.877 (1H, d, J=15.6 Hz), 2.881 (1H, d, J=13.5 Hz), 3.13 (1H, d, J=15.6 Hz).

Reference Example 130

1-(5-bromo-2,4,6,7-tetramethyl-2,3-dihydro-1-benzofuran-2-yl)-N,N-dimethylmethanamine 37% formalin aqueous solution (0.5 mL) was added to a solution of methanol (6 mL) containing 1-(5-bromo-2,4,6,7-tetramethyl-2,3-dihydro-1-benzofuran-2-yl)methanamine (250 mg, 0.880 mmol) synthesized in Reference Example 129, acetic acid (140 mg, 2.33 mmol) and sodium cyanoborohydride (98 mg, 1.56 mol) under ice-cooling condition. The mixture was warmed to room temperature and stirred for 15 hours. Ethyl acetate and saturated sodium bicarbonate water were added to the reaction solution to separate an organic layer. The organic layer was washed with saturated saline, and dried using anhydrous magnesium sulfate, followed by concentration under reduced pressure. The residue was purified by basic silica gel chromatography (hexane-ethyl acetate 97:3-88:12) to give 220 mg of the title compound (yield: 80%).

$^1$H-NMR (CDCl$_3$): δ1.42 (3H, s), 2.13 (3H, s), 2.26 (3H, s), 2.32 (6H, s), 2.33 (3H, s), 2.50 (2H, s), 2.84 (1H, d, J=15.6 Hz), 3.19 (1H, d, J=15.6 Hz).

Reference Example 131

N-methyl-1-phenyl-N-[(2,4,6,7-tetramethyl-2,3-dihydro-1-benzofuran-2-yl)methyl]methanamine N-methylbenzylamine (766 mg, 3.16 mmol) and potassium carbonate (1.09 g, 7.90 mmol) were added to a solution of DMA (5 mL) containing 2-(iodomethyl)-2,4,6,7-tetramethyl-2,3-dihydro-1-benzofuran (1.00 g, 3.16 mmol) synthesized in Reference Example 126, and the mixture was stirred under heated reflux for 4 hours. The reaction solution was cooled to room temperature, and water and ethyl acetate were added thereto to separate an organic layer. The organic layer was washed with water and saturated saline, and dried using anhydrous magnesium sulfate, followed by concentration under reduced pressure. The residue was purified by silica gel chromatography (hexane-ethyl acetate 99:1-93:7) to give 730 mg of the title compound (yield: 75%).

$^1$H-NMR (CDCl$_3$): δ1.44 (3H, s), 2.04 (3H, s), 2.14 (3H, s), 2.18 (3H, s), 2.32 (3H, s), 2.59 (1H, d, J=13.8 Hz), 2.63 (1H, d, J=13.8 Hz), 2.75 (1H, d, J=15.3 Hz), 3.07 (1H, d, J=15.3 Hz), 3.54 (1H, d, J=13.5 Hz), 3.68 (1H, d, J=13.5 Hz), 6.47 (1H, s), 7.17-7.33 (5H, m).

Reference Example 132

N-benzyl-1-(5-bromo-2,4,6,7-tetramethyl-2,3-dihydro-1-benzofuran-2-yl)-N-methylmethanamine 380 mg of the title compound was obtained in the same manner as described for Reference Example 4 using N-methyl-1-phenyl-N-[(2,4,6,7-tetramethyl-2,3-dihydro-1-benzofuran-2-yl)methyl]methanamine (730 mg, 2.36 mmol) synthesized in Reference Example 131 (yield: 41%).

$^1$H-NMR (CDCl$_3$): δ1.42 (3H, s), 2.11 (3H, s), 2.26 (3H, s), 2.30 (3H, s), 2.32 (3H, s), 2.58 (1H, d, J=13.8 Hz), 2.63 (1H, d, J=13.8 Hz), 2.80 (1H, d, J=15.3 Hz), 3.17 (1H, d, J=15.3 Hz), 3.56 (1H, d, J=13.5 Hz), 3.63 (1H, d, J=13.5 Hz), 7.17-7.33 (5H, m).

Reference Example 133

5-bromo-2-(iodomethyl)-2,4,6,7-tetramethyl-2,3-dihydro-1-benzofuran 2.01 g of the title compound was obtained in the same manner as described for Reference Example 4 using 2-(iodomethyl)-2,4,6,7-tetramethyl-2,3-dihydro-1-benzofuran (2.00 g, 6.33 mmol) synthesized in Reference Example 126 (yield: 80%).
$^1$H-NMR (CDCl$_3$): δ1.66 (3H, s), 2.15 (3H, s), 2.27 (3H, s), 2.35 (3H, s), 3.02 (1H, d, J=15.6 Hz), 3.27 (1H, d, J=15.6 Hz), 3.42 (2H, s).

Reference Example 134

5-bromo-2,4,6,7-tetramethyl-2-[(methylsulfanyl)methyl]-2,3-dihydro-1-benzofuran

Sodium thiomethoxide (213 mg, 3.03 mmol) was added to a solution of DMA (3 mL) containing 5-bromo-2-(iodomethyl)-2,4,6,7-tetramethyl-2,3-dihydro-1-benzofuran (270 mg, 0.683 mmol) synthesized in Reference Example 133, and the mixture was stirred at 140° C. for 4 hours. The reaction solution was cooled to room temperature, and water and ethyl acetate were added thereto to separate an organic layer. The organic layer was washed with saturated saline, and dried using anhydrous magnesium sulfate, followed by concentration under reduced pressure. The residue was purified by silica gel chromatography (hexane-ethyl acetate 100:0-90:10) to give 130 mg of the title compound (yield: 68%).
$^1$H-NMR (CDCl$_3$): δ1.53 (3H, s), 2.14 (3H, s), 2.19 (3H, s), 2.27 (3H, s), 2.34 (3H, s), 2.79 (1H, d, J=13.8 Hz), 2.83 (1H, d, J=13.8 Hz), 2.94 (1H, d, J=15.6 Hz), 3.26 (1H, d, J=15.6 Hz).

Reference Example 135

N,N-dibenzyl-1-(5-bromo-2,4,6,7-tetramethyl-2,3-dihydro-1-benzofuran-2-yl)methanamine 330 mg of the title compound was obtained in the same manner as described for Reference Example 131 using 5-bromo-2-(iodomethyl)-2,4,6,7-tetramethyl-2,3-dihydro-1-benzofuran (2.00 g, 6.33 mmol) synthesized in Reference Example 133 and dibenzylamine (750 mg, 3.81 mmol) (yield: 56%).
$^1$H-NMR (CDCl$_3$): δ1.66 (3H, s), 2.15 (3H, s), 2.27 (3H, s), 2.35 (3H, s), 3.02 (1H, d, J=15.6 Hz), 3.27 (1H, d; J=15.6 Hz), 3.42 (2H, s).

Reference Example 136

4-[(5-bromo-2,4,6,7-tetramethyl-2,3-dihydro-1-benzofuran-2-yl)methyl]morpholine 220 mg of the title compound was obtained in the same manner as described for Reference Example 131 using 5-bromo-2-(iodomethyl)-2,4,6,7-tetramethyl-2,3-dihydro-1-benzofuran (270 mg, 0.683 mmol) synthesized in Reference Example 133 and morpholine (298 mg, 3.42 mmol) (yield: 91%).
$^1$H-NMR (CDCl$_3$): δ1.42 (3H, s), 2.11 (3H, s), 2.27 (3H, s), 2.34 (3H, s), 2.46-2.69 (6H, m), 2.84 (1H, d, J=15.3 Hz), 3.19 (1H, d, J=15.3 Hz), 3.59-3.72 (4H, m).

Reference Example 137

1-[(5-bromo-2,4,6,7-tetramethyl-2,3-dihydro-1-benzofuran-2-yl)methyl]piperidine

Piperidine (323 mg, 3.80 mmol) and potassium carbonate (525 mg, 3.80 mmol) were added to a solution of DMA (3 mL) containing 5-bromo-2-(iodomethyl)-2,4,6,7-tetramethyl-2,3-dihydro-1-benzofuran (300 mg, 0.759 mmol) synthesized in Reference Example 133, and the mixture was stirred under microwave irradiation at 150° C. for 10 minutes. The reaction solution was cooled to room temperature, and water and ethyl acetate were added thereto to separate an organic layer. The organic layer was washed with water and saturated saline, and dried using anhydrous magnesium sulfate, followed by concentration under reduced pressure. The residue was purified by silica gel chromatography (hexane-ethyl acetate 95:5-85:15) to give 170 mg of the title compound (yield: 64%).
$^1$H-NMR (CDCl$_3$): δ1.31-1.44 (5H, m), 1.45-1.56 (4H, m), 2.12 (3H, s), 2.26 (3H, s), 2.34 (3H, s), 2.39-2.61 (6H, m), 2.82 (1H, d, J=15.0 Hz), 3.17 (1H, d, J=15.0 Hz).

Reference Example 138

4-[(5-bromo-2,4,6,7-tetramethyl-2,3-dihydro-1-benzofuran-2-yl)methyl]thiomorpholine 1,1-dioxide 180 mg of the title compound was obtained in the same manner as described for Reference Example 131 using 5-bromo-2-(iodomethyl)-2,4,6,7-tetramethyl-2,3-dihydro-1-benzofuran (500 mg, 1.27 mmol) synthesized in Reference Example 133 and thiomorpholine 1,1-dioxide (516 mg, 3.82 mmol) (yield: 35%).
$^1$H-NMR (CDCl$_3$): δ1.43 (3H, s), 2.11 (3H, s), 2.27 (3H, s), 2.34 (3H, s), 2.69 (1H, d, J=14.4 Hz), 2.74 (1H, d, J=14.4 Hz), 2.82-3.30 (10H, m).

Reference Example 139

1-[(5-bromo-2,4,6,7-tetramethyl-2,3-dihydro-1-benzofuran-2-yl)methyl]-1H-pyrazole 60% sodium hydride (91 mg, 2.27 mmol) was added to a solution of DMF (2 mL) containing pyrazole (155 mg, 2.27 mmol) under ice-cooling condition, and the mixture was stirred at 0° C. for 20 minutes. After that, a solution of DMF (1.5 mL) containing 5-bromo-2-(iodomethyl)-2,4,6,7-tetramethyl-2,3-dihydro-1-benzofuran (300 mg, 0.759 mmol) synthesized in Reference Example 133 was added thereto, and the mixture was stirred at 100° C. for 4 hours and at 120° C. for 2 hours. After cooled to room temperature, the reaction solution was distributed using a saturated ammonium chloride aqueous solution and ethyl acetate. The organic layer was washed with saturated saline, and dried using anhydrous magnesium sulfate, followed by concentration under reduced pressure. The residue was purified by silica gel chromatography (hexane-ethyl acetate 95:5-85:15) to give 185 mg of the title compound (yield: 71%).
$^1$H-NMR (CDCl$_3$): δ1.40 (3H, s), 2.18 (3H, s), 2.22 (3H, s), 2.34 (3H, s), 2.92 (1H, d, J=15.3 Hz), 3.20 (1H, d, J=15.3 Hz), 4.34 (2H, s), 6.20-6.24 (1H, m), 7.45-7.49 (2H, m).

Reference Example 140

1-[(5-bromo-2,4,6,7-tetramethyl-2,3-dihydro-1-benzofuran-2-yl)methyl]-2-methyl-1H-imidazole 120 mg of the title compound was obtained in the same manner as described for Reference Example 139 using 5-bromo-2-(iodomethyl)-2,4,6,7-tetramethyl-2,3-dihydro-1-benzofuran (300 mg, 0.759 mmol) synthesized in Reference Example 133 and 2-methylimidazole (186 mg, 2.27 mmol) (yield: 45%).
$^1$H-NMR (CDCl$_3$): δ1.40 (3H, s), 2.17 (3H, s), 2.25 (3H, s), 2.35 (3H, s), 2.40 (3H, s), 2.98 (1H, d, J=16.2 Hz), 3.04 (1H, d, J=16.2 Hz), 3.96 (1H, d, J=14.7 Hz), 4.07 (1H, d, J=14.7 Hz), 6.89-6.95 (2H, s).

Reference Example 141

8-[(5-bromo-2,4,6,7-tetramethyl-2,3-dihydro-1-benzofuran-2-yl)methyl]-1,4-dioxa-8-azaspiro[4.5]decane 1,4-dioxa-8-azaspiro[4.5]decane (725 mg, 5.06 mmol) and potassium carbonate (699 mg, 5.06 mmol) were added to a solution of DMA (3 mL) containing 5-bromo-2-(iodomethyl)-2,4,6,7-tetramethyl-2,3-dihydro-1-benzofuran (400 mg, 1.01 mmol) synthesized in Reference Example 133, and the mixture was stirred under microwave irradiation at 200° C. for 10 minutes. The reaction solution was cooled to room temperature, and water and ethyl acetate were added thereto to separate an organic layer. The organic layer was washed with water and saturated saline, and dried using anhydrous magnesium sulfate, followed by concentration under reduced pressure. The residue was purified by silica gel chromatography (hexane-ethyl acetate 95:5-80:20) to give 310 mg of the title compound (yield: 75%).
$^1$H-NMR (CDCl$_3$): δ1.42 (3H, s), 1.63-1.73 (4H, m), 2.12 (3H, s), 2.26 (3H, s), 2.33 (3H, s), 2.53-2.77 (6H, m), 2.83 (1H, d, J=15.3 Hz), 3.17 (1H, d, J=15.3 Hz), 3.93 (4H, s).

Reference Example 142

1-[(5-bromo-2,4,6,7-tetramethyl-2,3-dihydro-1-benzofuran-2-yl)methyl]pyrrolidine 270 mg of the title compound was obtained in the same manner as described for Reference Example 141 using 5-bromo-2-(iodomethyl)-2,4,6,7-tetramethyl-2,3-dihydro-1-benzofuran (400 mg, 1.01 mmol) synthesized in Reference Example 133 and pyrrolidine (359 mg, 5.05 mmol) (yield: 79%).
$^1$H-NMR (CDCl$_3$): δ1.45 (3H, s), 1.67-1.80 (4H, m), 2.15 (3H, s), 2.27 (3H, s), 2.35 (3H, s), 2.46-2.74 (6H, m), 2.85 (1H, d, J=15.3 Hz), 3.24 (1H, d, J=15.3 Hz).

Reference Example 143

N-benzyl-2,2,4,6,7-pentamethyl-2,3-dihydro-1-benzofuran-5-amine 13.3 g of the title compound was synthesized in the same manner as described for Reference Example 19 using 5-bromo-2,2,4,6,7-pentamethyl-2,3-dihydro-1-benzofuran (26.9 g, 0.10 mol) synthesized in Reference Example 4 and benzylamine (21.8 mL, 0.20 mol) (yield: 45%).
$^1$H-NMR (CDCl$_3$): δ1.46 (6H, s), 2.12 (3H, s), 2.14 (3H, s), 2.23 (3H, s), 2.88 (1H, brs), 2.93 (2H, s), 3.93 (2H, s), 7.25-7.47 (5H, m).

Reference Example 144

2,2,4,6,7-pentamethyl-2,3-dihydro-1-benzofuran-5-amine 9.0 g of the title compound was synthesized in the same manner as described for Reference Example 20 using N-benzyl-2,2,4,6,7-pentamethyl-2,3-dihydro-1-benzofuran-5-amine (13.0 g, 44.1 mmol) synthesized in Reference Example 143 (yield: 100%).
$^1$H-NMR (CDCl$_3$): δ1.44 (6H, s), 2.00-2.11 (6H, m), 2.12 (3H, s), 2.93 (2H, s), 3.22 (2H, brs).

Reference Example 145

2,2'-[(2,2,4,6,7-pentamethyl-2,3-dihydro-1-benzofuran-5-yl)imino]diethanol 2,2,4,6,7-pentamethyl-2,3-dihydro-1-benzofuran-5-amine (6.15 g, 30.0 mmol) synthesized in Reference Example 144 was dissolved in 2-chloroethanol (40.5 mL). N-ethyldiisopropylamine (15.6 mL, 90 mmol) and potassium iodide (4.98 g, 30.0 mmol) were added thereto, and the mixture was stirred at 120° C. for 3 hours. The reaction solution was cooled and then diluted with ethyl acetate, and the mixture was washed with water and saturated saline. The organic layer was dried using sodium sulfate, and after that, the solvent was removed under reduce pressure. The obtained residue was purified by silica gel column chromatography (hexane-ethyl acetate 30:70) to give 6.94 g of the title compound (yield: 79%).
$^1$H-NMR (CDCl$_3$): δ1.46 (6H, s), 2.08 (3H, s), 2.20 (3H, s), 2.24 (3H, s), 2.91 (2H, s), 3.14-3.27 (4H, m), 3.46-3.63 (4H, m), 3.86 (2H, brs).

Reference Example 146

N,N-bis(2-chloroethyl)-2,2,4,6,7-pentamethyl-2,3-dihydro-1-benzofuran-5-amine

Methanesulfonyl chloride (6.4 mL, 81.9 mmol) was slowly added to a solution of pyridine (60 mL) containing 2,2'-[(2,2,4,6,7-pentamethyl-2,3-dihydro-1-benzofuran-5-yl)imino]diethanol (6.0 g, 20.5 mmol) synthesized in Reference Example 145 under ice-cooling condition. The mixture was warmed to room temperature and stirred for 16 hours. A sodium hydrogencarbonate aqueous solution was added to the reaction solution, and after that, extraction was performed using ethyl acetate. The organic layer was washed with 3N hydrochloric acid, sodium hydrogencarbonate aqueous solution and saturated saline, and dried using sodium sulfate. The solvent was removed under reduced pressure, and the obtained residue was purified by silica gel column chromatography (hexane-ethyl acetate 9:1) to give 5.1 g of the title compound as an oily product (yield: 81%).
$^1$H-NMR (CDCl$_3$): δ1.48 (6H, s), 2.08 (3H, s), 2.16 (3H, s), 2.20 (3H, s), 2.91 (2H, s), 3.33-3.55 (8H, m).

Reference Example 147

1-(2,2,4,6,7-pentamethyl-2,3-dihydro-1-benzofuran-5-yl)piperazine hydrochloride

The mother liquor after crystallization obtained in Reference Example 61 was concentrated, and the residue was treated with 2N hydrogen chloride-ethyl acetate solution to give 2.52 g of the title compound as amorphous powder (yield: 62.3%).
$^1$H-NMR (DMSO-d6): δ1.36 (6H, s), 2.10 (3H, s), 2.11 (3H, s), 2.86 (2H, s), 3.02-3.27 (8H, m), 9.14 (2H, brs).

Reference Example 148

N-benzyl-2,2,4,7-tetramethyl-2,3-dihydro-1-benzofuran-5-amine 28.6 g of the title compound was obtained as an amorphous solid in the same manner as described for Reference Example 19 using 5-bromo-2,2,4,7-tetramethyl-2,3-dihydro-1-benzofuran (26.0 g, 102 mmol) synthesized in Reference Example 103 and benzylamine (16.4 g, 153 mmol) (yield: 100%).

$^1$H-NMR (CDCl$_3$): δ1.46 (6H, s), 2.01 (3H, s), 2.14 (3H, s), 2.93 (2H, s), 3.36 (1H, s), 4.27 (2H, s), 6.31 (1H, s), 7.25-7.45 (5H, m).

Reference Example 149

2,2,4,7-tetramethyl-2,3-dihydro-1-benzofuran-5-amine 19.0 g of the title compound was obtained as an amorphous solid in the same manner as described for Reference Example 20 using N-benzyl-2,2,4,7-tetramethyl-2,3-dihydro-1-benzofuran-5-amine (28.6 g, 102 mmol) synthesized in Reference Example 148 (yield: 97%).

$^1$H-NMR (CDCl$_3$): δ1.45 (6H, s), 2.02 (3H, s), 2.10 (3H, s), 2.91 (2H, s), 6.34 (1H, s).

Reference Example 150

6-bromo-2,2,4,7-tetramethyl-2,3-dihydro-1-benzofuran-5-amine 1.14 g of the title compound was obtained as an amorphous solid in the same manner as described for Reference Example 4 using 2,2,4,7-tetramethyl-2,3-dihydro-1-benzofuran-5-amine (2.00 g, 10.5 mmol) synthesized in Reference Example 149 (yield: 40%).

$^1$H-NMR (CDCl$_3$): δ1.44 (6H, s), 2.08 (3H, s), 2.21 (3H, s), 2.90 (2H, s), 3.58-4.00 (2H, m).

Reference Example 151

2,2'-[(6-bromo-2,2,4,7-tetramethyl-2,3-dihydro-1-benzofuran-5-yl)imino]diethanol 970 mg of the title compound was obtained as an amorphous solid in the same manner as described for Reference Example 145 using 6-bromo-2,2,4,7-tetramethyl-2,3-dihydro-1-benzofuran-5-amine (1.14 g, 4.22 mmol) synthesized in Reference Example 150 (yield: 64%).

$^1$H-NMR (CDCl$_3$): δ1.47 (6H, s), 2.22 (3H, s), 2.24 (3H, s), 2.88 (2H, s), 3.01 (2H, s), 3.15-3.38 (4H, m), 3.55-3.70 (4H, m).

Reference Example 152

6-bromo-N,N-bis(2-chloroethyl)-2,2,4,7-tetramethyl-2,3-dihydro-1-benzofuran-5-amine 492 mg of the title compound was obtained as an oily product in the same manner as described for Reference Example 146 using 2,2'-[(6-bromo-2,2,4,7-tetramethyl-2,3-dihydro-1-benzofuran-5-yl)imino]diethanol (970 mg, 2.71 mmol) synthesized in Reference Example 151 (yield: 46%).

$^1$H-NMR (CDCl$_3$): δ1.47 (6H, s), 2.21 (6H, s), 2.87 (2H, s), 3.26-3.59 (8H, m).

Reference Example 153

1-chloro-2-methyl-3-[(2-methylprop-2-en-1-yl)oxy]benzene 3-bromo-2-methylpropene (8.5 mL, 84.2 mmol) was added to a mixture of DMF (200 mL) containing 3-chloro-2-methylphenol (10.0 g, 70.1 mmol) and potassium carbonate (19.4 g, 140 mmol), and the mixture was stirred at room temperature for 15 hours. The reaction solution was distributed using ethyl acetate and water, and the organic layer was washed with water and saturated saline, and then dried using anhydrous magnesium sulfate. The solvent was removed under reduced pressure, and the obtained residue was purified by silica gel column chromatography (hexane-ethyl acetate 10:1) to give 13.7 g of the title compound as an amorphous solid (yield: 99%).

$^1$H-NMR (CDCl$_3$): δ1.84 (3H, s), 2.31 (3H, s), 4.42 (2H, s), 4.97-5.02 (1H, m) 5.08-5.12 (1H, m), 6.72 (1H, dd, J=0.8, 8.0 Hz), 6.97 (1H, dd, J=0.8, 8.0 Hz), 7.05 (1H, t, J=8.0 Hz).

Reference Example 154

3-chloro-2-methyl-6-(2-methylprop-2-en-1-yl)phenol

A solution of N,N-diethylaniline (12.1 mL) containing 1-chloro-2-methyl-3-[(2-methylprop-2-en-1-yl)oxy]benzene (3.00 mg, 15.3 mmol) synthesized in Reference Example 153 was reacted under microwave irradiation at 220° C. for 20 minutes. After cooled to room temperature, the reaction solution was diluted with ethyl acetate, and washed serially with 1N hydrochloric acid, saturated sodium bicarbonate water and saturated saline. It was dried using anhydrous magnesium sulfate, and the solvent was removed under reduced pressure. After that, the obtained residue was purified by silica gel column chromatography (hexane-ethyl acetate 10:1) to give 2.89 g of the title compound as a yellow solid (yield: 96%).

$^1$H-NMR (CDCl$_3$): δ1.72 (3H, s), 2.28 (3H, s), 3.34 (2H, s), 4.89-4.93 (1H, m), 4.95-4.99 (1H, m), 5.42 (1H, s), 6.86 (1H, d, J=8.0 Hz), 6.91 (1H, d, J=8.4 Hz).

Reference Example 155

2,2,7-trimethyl-2,3-dihydro-1-benzofuran 7.89 g of the title compound was obtained as an oily product in the same manner as described for Reference Example 3 using 3-chloro-2-methyl-6-(2-methylprop-2-en-1-yl)phenol (10.0 g, 50.8 mmol) synthesized in Reference Example 154 (yield: 79%).

$^1$H-NMR (CDCl$_3$): δ1.46 (6H, s), 2.21 (3H, s), 2.97 (2H, s), 6.81 (1H, d, J=8.0 Hz), 6.87 (1H, d, J=7.6 Hz).

Reference Example 156

2,2,7-trimethyl-6-(4-methylphenyl)-2,3-dihydro-1-benzofuran

Tripotassium phosphate (28.1 g, 132 mmol) was added to a solution of toluene (200 mL) containing 2,2,7-trimethyl-2,3-dihydro-1-benzofuran (10.0 g, 5.08 mmol) synthesized in Reference Example 155, bis(triphenylphosphine)nickel (II) dichloride (0.998 g, 1.53 mmol), triphenylphosphine (0.800 g, 3.05 mmol) and 4-methylphenyl borate (8.99 g, 66.1 mmol), and the mixture was stirred under heated reflux for 2 hours. After cooled to room temperature, the reaction solution was filtered using Celite. Water was added to the obtained filtrate, and it was subjected to extraction using ethyl acetate. The extract was dried using anhydrous magnesium sulfate, and the solvent was removed under reduced pressure. After that, the obtained residue was purified by silica gel column chromatography (hexane-ethyl acetate 20:1) to give 12.1 g of the title compound as a brown solid (yield: 94%).

$^1$H-NMR (CDCl$_3$): δ1.51 (6H, s), 2.11 (3H, s), 2.39 (3H, s), 3.06 (2H, s), 6.73 (1H, d, J=7.2 Hz), 7.00 (1H, d, J=7.2 Hz), 7.19-7.23 (4H, m).

Reference Example 157

5-bromo-2,2,7-trimethyl-6-(4-methylphenyl)-2,3-dihydro-1-benzofuran 8.25 g of the title compound was obtained as an oily product in the same manner as described for Reference Example 4 using 2,2,7-trimethyl-6-(4-methylphenyl)-2,3-dihydro-1-benzofuran (10.0 g, 30.9 mmol) synthesized in Reference Example 156 and N-bromosuccinimide (10.6 g, 59.4 mmol) (yield: 63%).

$^1$H-NMR (CDCl$_3$): δ1.50 (6H, s), 1.92 (3H, s), 2.41 (3H, s), 3.05 (2H, s), 7.06 (2H, d, J=8.0 Hz), 7.23-7.26 (3H, m).

Reference Example 158

2-[(benzyloxy)methyl]-2,4,6,7-tetramethyl-2,3-dihydro-1-benzofuran 740 mg of the title compound was obtained as an oily product in the same manner as described for Reference Example 124 using (2,4,6,7-tetramethyl-2,3-dihydro-1-benzofuran-2-yl)methanol (730 mg, 3.54 mmol) synthesized in Reference Example 122 and benzyl bromide (908 mg, 5.31 mmol) (yield: 71%).

$^1$H-NMR (CDCl$_3$): δ1.49 (3H, s), 2.08 (3H, s), 2.14 (3H, s), 2.19 (3H, s), 2.79 (1H, d, J=15.6 Hz), 3.12 (1H, d, J=15.6 Hz), 3.50 (1H, d, J=9.9 Hz), 3.53 (1H, d, J=9.9 Hz), 4.57 (1H, d, J=12.3 Hz), 4.63 (1H, d, J=12.3 Hz), 6.48 (1H, s), 7.21-7.39 (5H, m).

Reference Example 159

2-[(benzyloxy)methyl]-5-bromo-2,4,6,7-tetramethyl-2,3-dihydro-1-benzofuran 520 mg of the title compound was obtained as an oily product in the same manner as described for Reference Example 4 using 2-[(benzyloxy)methyl]-2,4,6,7-tetramethyl-2,3-dihydro-1-benzofuran (740 mg, 2.50 mmol) synthesized in Reference Example 158 and N-bromosuccinimide (488 mg, 2.75 mmol) (yield: 55%).

$^1$H-NMR (CDCl$_3$): δ1.47 (3H, s), 2.15 (3H, s), 2.25 (3H, s), 2.34 (3H, s), 2.86 (1H, d, J=15.3 Hz), 3.21 (1H, d, J=15.3 Hz), 3.51 (2H, s), 4.57 (1H, d, J=12.3 Hz), 4.62 (1H, d, J=12.3 Hz), 7.23-7.40 (5H, m).

Reference Example 160

4-bromo-2,3,5-trimethylphenol 15.1 g of the title compound was obtained as a white solid in the same manner as described for Reference Example 4 using 2,3,5-trimethylphenol (10.0 g, 73.4 mmol) and N-bromosuccinimide (13.7 g, 77.1 mmol) (yield: 96%).

$^1$H-NMR (CDCl$_3$): δ2.20 (3H, s), 2.33 (3H, s), 2.39 (3H, s), 4.62 (1H, s), 6.58 (1H, s).

Reference Example 161

2-bromo-1,3,4-trimethyl-5-[(2-methylprop-2-en-1-yl)oxy]benzene 18.3 g of the title compound was obtained as an amorphous solid in the same manner as described for Reference Example 1 using 4-bromo-2,3,5-trimethylphenol (15.1 g, 70.2 mmol) synthesized in Reference Example 160 and 3-chloro-2-methylpropene (10.3 mL, 105 mmol) (yield: 97%).

$^1$H-NMR (CDCl$_3$): δ1.84 (3H, s), 2.23 (3H, s), 2.38 (3H, s), 2.40 (3H, s), 4.38 (2H, s), 4.93-5.02 (1H, m), 5.07-5.15 (1H, m), 6.62 (1H, s).

Reference Example 162

4-bromo-2,3,5-trimethyl-6-(2-methylprop-2-en-1-yl)phenol 1.81 g of the title compound was obtained as an amorphous solid in the same manner as described for Reference Example 2 using 2-bromo-1,3,4-trimethyl-5-[(2-methylprop-2-en-1-yl)oxy]benzene (5.00 g, 18.6 mmol) synthesized in Reference Example 161 (yield: 36%).

$^1$H-NMR (CDCl$_3$): δ1.79 (3H, s), 2.22 (3H, s), 2.39 (3H, s), 2.41 (3H, s), 3.42 (2H, s), 4.61-4.67 (1H, m), 4.84-4.90 (1H, m), 4.98 (1H, s).

Reference Example 163

5-bromo-2-[(methoxymethoxy)methyl]-2,4,6,7-tetramethyl-2,3-dihydro-1-benzofuran

Ethyldiisopropylamine (1.26 g, 9.74 mmol) and chloromethylmethylether (627 mg, 7.79 mmol) were serially added to a solution of THF (15 mL) containing (5-bromo-2,4,6,7-tetramethyl-2,3-dihydro-1-benzofuran-2-yl)methanol (1.85 g, 6.49 mmol) synthesized in Reference Example 123 under ice-cooling condition, and the mixture was warmed to room temperature and stirred for 15 hours. Ethyldiisopropylamine (1.26 g, 9.74 mmol) and chloromethylmethylether (523 mg, 6.49 mmol) were further added serially to the reaction solution under ice-cooling condition, and the mixture was warmed to room temperature and stirred for 15 hours. The reaction solution was poured into saturated sodium bicarbonate water, and THF was removed under reduced pressure, followed by extraction using ethyl acetate. The extract was washed with saturated saline and dried using anhydrous magnesium sulfate. After that, the solvent was removed under reduced pressure. The obtained residue was purified by silica gel column chromatography (hexane-ethyl acetate 96:4-80:20) to give 1.62 g of the title compound as an oily product (yield: 76%).

$^1$H-NMR (CDCl$_3$): δ1.47 (3H, s), 2.15 (3H, s), 2.26 (3H, s), 2.34 (3H, s), 2.87 (1H, d, J=15.6 Hz), 3.20 (1H, d, J=15.6 Hz), 3.56 (3H, s), 3.59 (2H, s), 4.64 (1H, d, J=6.3 Hz), 4.67 (1H, d, J=6.3 Hz).

Reference Example 164

7-methoxy-2,2,4,6-tetramethyl-2,3-dihydro-1-benzofuran-5-amine hydrochloride

A solution of water (100 mL) containing sodium nitrite (61.8 g, 895 mmol) was added dropwise to a suspension of 6N hydrochloric acid (1.74 L) containing p-nitroaniline (129 g, 933 mmol) under ice-cooling condition, with the inner temperature thereof being maintained at 10° C. or lower. The reaction solution was stirred under ice-cooling condition for 1 hour, and after that, a solution of acetic acid (1.74 L) containing 7-methoxy-2,2,4,6-tetramethyl-2,3-dihydro-1-benzofuran (crude, calculated as 746 mmol) synthesized in Reference Example 93 was added dropwise thereto. The obtained mixture was stirred at 45° C. for 4 hours. After cooled to room temperature, the precipitated solid was collected by filtration, and it was washed with 50% acetic acid aqueous solution (500 mL), water (500 mL) and cold methanol (500 mL) to give 1-(7-methoxy-2,2,4,6-tetramethyl-2,3-dihydro-1-benzofuran-5-yl)-2-(4-nitrophenyl)diazene as wet crystal. Sodium hydrosulfite (519 g, 2.98 mol) was added to a suspension of methanol (1.74 L)/water (580 mL) containing the obtained wet crystal (calculated as 746 mmol), and the mixture was refluxed for 2 hours. After cooled to room temperature, the precipitate was filtered. Saturated saline was added to the filtrate, and extraction was performed using ethyl acetate (1.5 L, 1 L). The organic layer was washed with saturated saline (1 L) and dried using anhydrous magnesium sulfate, and the solvent was removed under reduced pressure. The residue was purified by silica gel column chromatography (hexane-ethyl acetate 85:15-70:30). The obtained crude product was dissolved in ethyl acetate (1.74 L), and 4N hydrochloric acid/ethyl acetate (100 mL) was added thereto for conversion into hydrochloride salt. The obtained white solid was collected by filtration, and it was washed with ethyl acetate to give 87.7 g of the title compound as a white solid (yield: 46%).

$^1$H-NMR (DMSO-d$_6$): δ 1.43 (6H, s), 2.18 (3H, s), 2.19 (3H, s), 2.96 (2H, s), 3.72 (3H, s), 9.66 (3H, brs).

Example 1

1-(2,4-Dimethoxyphenyl)-4-(2,2,4,6,7-pentamethyl-2,3-dihydro-1-benzofuran-5-yl)piperazine To the toluene (10 mL) mixture solution of 5-bromo-2,2,4,6,7-pentamethyl-2,3-dihydro-1-benzofuran (400 mg, 1.49 mmol) synthesized in Reference example 4, 1-(2,4-dimethoxyphenyl)piperazine (495 mg, 2.23 mmol), palladium acetate (17 mg, 0.0745 mmol) and BINAP (139 mg, 0.224 mmol), sodium t-butoxide (286 mg, 2.98 mmol) was added and stirred for 15 hours under reflux. After cooling to room temperature, water was added to the reaction solution, and extracted with ethyl acetate. The organic layer was washed with saturated brine and dried over anhydrous magnesium sulfate. The solvent was removed by distillation under reduced pressure. The residue was purified by silica gel chromatography (hexane-ethyl acetate 95:5-85:15) and crystallized from ethyl acetate-hexane to obtain the title compound 340 mg (yield 56%). Melting point was 154 to 156° C.

$^1$H-NMR (CDCl$_3$): δ1.46 (6H, s), 2.09 (3H, s), 2.21 (3H, s), 2.26 (3H, s), 2.91 (2H, s), 2.97-3.14 (4H, m), 3.15-3.36 (4H, m), 3.79 (3H, s), 3.86 (3H, s), 6.44 (1H, dd, J=2.7, 8.7 Hz), 6.50 (1H, d, J=2.7 Hz), 6.93 (1H, d, J=8.7 Hz).

Example 2

1-[2,2-Dimethyl-6-(4-methylphenyl)-2,3-dihydro-1-benzofuran-5-yl]-4-(4-methoxyphenyl)piperazine By using 5-bromo-2,2-dimethyl-6-(4-methylphenyl)-2,3-dihydro-1-benzofuran (250 mg, 0.788 mmol) synthesized in Reference example 9 and 1-(4-methoxyphenyl)piperazine (455 mg, 2.36 mmol), the reaction was carried out in the same manner as Example 1 to synthesize the title compound 55 mg (yield 16%). Melting point was 187 to 190° C. (ethyl acetate-hexane).

$^1$H-NMR (CDCl$_3$): δ1.50 (6H, s), 2.35 (3H, s), 2.86-3.00 (8H, m), 3.04 (2H, s), 3.76 (3H, s), 6.68 (1H, s), 6.78-6.91 (4H, m), 6.94 (1H, s), 7.12-7.19 (2H, m), 7.48-7.54 (2H, m).

Example 3

1-(2,2-Dimethyl-6-pyridin-3-yl-2,3-dihydro-1-benzofuran-5-yl)-4-(4-methoxyphenyl)piperazine By using 3-(5-bromo-2,2-dimethyl-2,3-dihydro-1-benzofuran-6-yl)pyridine (160 mg, 0.526 mmol) synthesized in Reference example 11 and 1-(4-methoxyphenyl)piperazine (303 mg, 1.58 mmol), the reaction was carried out in the same manner as Example 1 to synthesize the title compound 100 mg (yield 46%).

Melting point was 177 to 180° C. (ethyl acetate-hexane).

$^1$H-NMR (CDCl$_3$): δ1.50 (6H, s), 2.35 (3H, s), 2.86-3.00 (8H, m), 3.04 (2H, s), 3.7.6 (3H, s), 6.68 (1H, s), 6.78-6.91 (4H, m), 6.94 (1H, s), 7.12-7.19 (2H, m), 7.48-7.54 (2H, m).

Example 4

1-(4-Methoxyphenyl)-4-(2,2,6,7-tetramethyl-2,3-dihydro-1-benzofuran-5-yl)piperazine By using 5-bromo-2,2,6,7-tetramethyl-2,3-dihydro-1-benzofuran (300 mg, 1.18 mmol) synthesized in Reference example 15 and 1-(4-methoxyphenyl)piperazine (678 mg, 3.53 mmol), the reaction was carried out in the same manner as Example 1 to obtain the title compound 250 mg (yield 58%). Melting point was 180 to 182° C. (ethyl acetate-hexane).

$^1$H-NMR (CDCl$_3$): δ1.46 (6H, s), 2.13 (3H, s), 2.23 (3H, s), 2.90-3.35 (10H, m), 3.78 (3H, s), 6.78-6.90 (3H, m), 6.91-7.00 (2H, m).

Example 5

4-{5-[4-(4-Methoxyphenyl)piperazin-1-yl]-2,2,6,7-tetramethyl-2,3-dihydro-1-benzofuran-4-yl}-N,N-dimethylaniline To the THF (15 mL) suspension of lithium aluminum hydride (342 mg, 9.00 mmol), aluminum chloride (1.20 g, 9.00 mmol) was added under ice cooling, and then the mixture was stirred for 10 minutes and added with the THF (25 mL) solution of 4-[4-(dimethylamino)phenyl]-5-[4-(4-methoxyphenyl)piperazin-1-yl]-2,2,6,7-tetramethyl-1-benzofuran-3(2H)-one (1.50 g, 3.00 mmol) synthesized in Reference example 31, followed by further stirring for 2.5 hours under reflux. After cooling the mixture solution on ice, water was added dropwise thereto and 0.5 N aqueous solution of sodium hydroxide was further added. The mixture was stirred for 10 minutes at room temperature. Undissolved residues were removed by filtration. The filtrate was extracted with the mixture solvent of ethyl acetate-ether (1:1). After washing with the saturated brine, the extract solution was dried over anhydrous magnesium sulfate. The solvent was removed by distillation under reduced pressure. The resulting residue was purified by silica gel chromatography (hexane-ethyl acetate 96:4-85:15) and crystallized from ethyl acetate and hexane to obtain the title compound 1.01 g (yield 69%). Melting point was 177 to 179° C. (ethyl acetate-hexane).

¹H-NMR (CDCl₃): δ1.41 (6H, s), 2.16 (3H, s), 2.29 (3H, s), 2.68-2.90 (6H, m), 2.91-3.10 (10H, m), 3.75 (3H, s), 6.68-6.88 (6H, m), 7.03-7.13 (2H, m).

Example 6

1-(4-Furan-3-yl-2,2,6,7-tetramethyl-2,3-dihydro-1-benzofuran-5-yl)-4-(4-methoxyphenyl)piperazine By using 4-furan-3-yl-5-[4-(4-methoxyphenyl)piperazin-1-yl]-2,2,6,7-tetramethyl-1-benzofuran-3(2H)-one (460 mg, 1.03 mmol) synthesized in Reference example 33, the reaction was carried out in the same manner as Example 5 to obtain the title compound 250 mg (yield 56%). Melting point was 192 to 195° C. (ethyl acetate-hexane).
¹H-NMR (CDCl₃): δ1.41 (6H, s), 2.26 (3H, s), 2.40 (3H, s), 2.83-3.05 (6H, m), 3.09-3.21 (2H, m), 3.77 (3H, s), 6.46 (1H, dd, J=0.9, 1.8 Hz), 6.78-6.92 (4H, m), 7.44 (1H, dd, J=0.9, 1.5 Hz), 7.52 (1H, dd, J=1.5, 1.8 Hz).

Example 7

1-(4-Cyclopropyl-2,2,6,7-tetramethyl-2,3-dihydro-1-benzofuran-5-yl)-4-(4-methoxyphenyl)piperazine By using 4-cyclopropyl-5-[4-(4-methoxyphenyl)piperazin-1-yl]-2,2,6,7-tetramethyl-1-benzofuran-3(2H)-one (80.0 mg, 0.190 mmol) synthesized in Reference example 26, the reaction was carried out in the same manner as Example 5 to synthesize the title compound 49.6 mg (yield 64%). Melting point was 121 to 122° C. (hexane).
¹H-NMR (CDCl₃): δ0.60-0.70 (2H, m), 0.84-0.94 (2H, m), 1.44 (6H, s), 1.83-1.98 (1H, m), 2.09 (3H, s), 2.24 (3H, s), 3.03 (2H, s), 3.06-3.31 (6H, m), 3.38-3.53 (2H, m), 3.78 (3H, s), 6.86 (2H, d, J=9.0 Hz), 6.97 (2H, d, J=9.0 Hz).

Example 8

1-(4-Ethenyl-2,2,6,7-tetramethyl-2,3-dihydro-1-benzofuran-5-yl)-4-(4-methoxyphenyl)piperazine By using 4-ethenyl-5-[4-(4-methoxyphenyl)piperazin-1-yl]-2,2,6,7-tetramethyl-1-benzofuran-3(2H)-one (70.0 mg, 0.172 mmol) synthesized in Reference example 23, the reaction was carried out in the same manner as Example 5 to synthesize the title compound 49.4 mg (yield 73%). Melting point was 135 to 136° C. (hexane).
¹H-NMR (CDCl₃): δ1.46 (6H, s), 2.12 (3H, s), 2.24 (3H, s), 3.06 (2H, s), 3.11-3.18 (4H, m), 3.21-3.30 (4H, m), 3.78 (3H, s), 5.24-5.37 (2H, m), 6.86 (2H, d, J=9.0 Hz), 6.97 (2H, d, J=9.0 Hz), 7.05-7.17 (1H, m).

Example 9

1-(4-Ethyl-2,2,6,7-tetramethyl-2,3-dihydro-1-benzofuran-5-yl)-4-(4-methoxyphenyl)piperazine By using 4-ethyl-5-[4-(4-methoxyphenyl)piperazin-1-yl]-2,2,6,7-tetramethyl-1-benzofuran-3(2H)-one (72.1 mg, 0.176 mmol) synthesized in Reference example 24, the reaction was carried out in the same manner as Example 5 to synthesize the title compound 34.4 mg (yield 50%). Melting point was 150 to 151° C. (methanol-hexane).
¹H-NMR (CDCl₃): δ1.11 (3H, t, J=7.8 Hz), 1.46 (6H, s), 2.08 (3H, s), 2.24 (3H, s), 2.61 (2H, q, J=7.8 Hz), 2.95 (2H, s), 3.00-3.17 (4H, m), 3.20-3.30 (2H, m), 3.34-3.45 (2H, m), 3.79 (3H, s), 6.86 (2H, d, J=9.0 Hz), 6.97 (2H, d, J=9.0 Hz).

Example 10

1-(4-Methoxyphenyl)-4-[2,2,6,7-tetramethyl-4-(1-methylethenyl)-2,3-dihydro-1-benzofuran-5-yl]piperazine By using 5-[4-(4-methoxyphenyl)piperazin-1-yl]-2,2,6,7-tetramethyl-4-(1-methylethenyl)-1-benzofuran-3(2H)-one (60.0 mg, 0.142 mmol) synthesized in Reference example 28, the reaction was carried out in the same manner as Example 5 to synthesize the title compound 20.0 mg (yield 35%). Melting point was 174 to 175° C. (methanol-hexane).
¹H-NMR (CDCl₃): δ1.45 (6H, s), 2.03 (3H, s), 2.11 (3H, s), 2.24 (3H, s), 2.88 (2H, s), 3.05-3.12 (4H, m), 3.19-3.26 (4H, m), 3.78 (3H, s), 4.77 (1H, s), 5.13 (1H, s), 6.85 (2H, d, J=9.0 Hz), 6.94 (2H, d, J=9.0 Hz).

Example 11

1-(4-Methoxyphenyl)-4-[2,2,6,7-tetramethyl-4-(1-methylethyl)-2,3-dihydro-1-benzofuran-5-yl]piperazine By using 5-[4-(4-methoxyphenyl)piperazin-1-yl]-2,2,6,7-tetramethyl-4-(1-methylethyl)-1-benzofuran-3(2H)-one (60.0 mg, 0.142 mmol) synthesized in Reference example 29, the reaction was carried out in the same manner as Example 5 to synthesize the title compound 27.0 mg (yield 47%). Melting point was 192 to 194° C. (hexane).
¹H-NMR (CDCl₃): δ1.22 (6H, d, J=5.7 Hz), 1.45 (6H, s), 2.08 (3H, s), 2.25 (3H, s), 3.04-3.25 (8H, m), 3.26-3.40 (2H, m), 3.58-3.76 (2H, m), 3.79 (3H, s), 6.86 (2H, d, J=9.0 Hz), 6.97 (2H, d, J=9.0 Hz).

Example 12

1-(4-Methylphenyl)-4-(2,2,4,6,7-pentamethyl-2,3-dihydro-1-benzofuran-5-yl)piperazine By using 2,2,4,6,7-pentamethyl-5-[4-(4-methylphenyl)piperazin-1-yl]-1-benzofuran-3(2H)-one (870 mg, 2.29 mmol) synthesized in Reference example 37, the reaction was carried out in the same manner as Example 5 to synthesize the title compound 100 mg (yield 12%). Melting point was 152 to 155° C. (ethyl acetate-hexane).
¹H-NMR (CDCl₃): δ1.46 (6H, s), 2.08 (3H, s), 2.19 (3H, s), 2.24 (3H, s), 2.28 (3H, s), 2.91 (2H, s), 3.11-3.34 (8H, m), 6.86-6.95 (2H, m), 7.04-7.13 (2H, m).

Example 13

2-(4-Methoxyphenyl)-1-methyl-4-(2,2,4,6,7-pentamethyl-2,3-dihydro-1-benzofuran-5-yl)piperazine By using 5-[3-(4-methoxyphenyl)-4-methylpiperazin-1-yl]-2,2,4,6,7-pentamethyl-1-benzofuran-3(2H)-one (200 mg, 0.490 mmol) synthesized in Reference example 36, the reaction was carried out in the same manner as Example 5 to obtain the title compound 184 mg (yield 94%) as a diastereomeric mixture (3:2).
¹H-NMR (CDCl₃): δ1.36-1.51 (6H, m), 2.02 (1.2H, s), 2.05-2.19 (7.8H, m), 2.22 (1.2H, s), 2.31 (1.8H, s), 2.43-2.59

(1H, m), 2.71-3.00 (5H, m), 3.04-3.17 (1H, m), 3.24-3.37 (1H, m), 3.53-3.67 (1H, m), 3.79 (3H, s), 6.77-6.91 (2H, m), 7.19-7.38 (2H, m).

Example 14

2-(3,4-Dimethoxyphenyl)-1-methyl-4-(2,2,4,6,7-pentamethyl-2,3-dihydro-1-benzofuran-5-yl)piperazine By using 5-[3-(3,4-dimethoxyphenyl)-4-methylpiperazin-1-yl]-2,2,4,6,7-pentamethyl-1-benzofuran-3(2H)-one (215 mg, 0.490 mmol) synthesized in Reference example 39, the reaction was carried out in the same manner as Example 5 to obtain the title compound 195 mg (yield 92%) as a diastereomeric mixture (3:2).
$^1$H-NMR (CDCl$_3$): δ1.38-1.50 (6H, m), 2.02 (1.2H, s), 2.06-2.18 (7.8H, m), 2.23 (1.2H, s), 2.31 (1.8H, s), 2.45-2.59 (1H, m), 2.72-3.01 (5H, m), 3.03-3.13 (1H, m), 3.25-3.37 (1H, m), 3.51-3.68 (1H, m), 3.86 (3H, s), 3.90 (3H, s), 6.75-6.85 (1H, m), 6.85-6.96 (2H, m).

Example 15

2-(4-Methoxyphenyl)-4-(2,2,4,6,7-pentamethyl-2,3-dihydro-1-benzofuran-5-yl)morpholine By using 5-[2-(4-methoxyphenyl)morpholin-4-yl]-2,2,4,6,7-pentamethyl-1-benzofuran-3(2H)-one (150 mg, 0.380 mmol) synthesized in Reference example 40, the reaction was carried out in the same manner as Example 5 to obtain the title compound 137 mg (yield 93%) as a diastereomeric mixture (3:2).
$^1$H-NMR (CDCl$_3$): δ1.36-1.51 (6H, m), 2.04 (1.2H, s), 2.07-2.21 (4.8H, m), 2.25 (1.8H, s), 2.34 (1.8H, s), 2.67-2.81 (1H, m), 2.82-2.98 (3H, m), 3.23-3.37 (1H, m), 3.42-3.59 (1H, m), 3.79 (3H, s), 3.87-4.12 (2H, m), 4.55-4.66 (1H, m), 6.79-6.96 (2H, m), 7.28-7.35 (2H, m).

Example 16

2-Benzyl-4-(2,2,4,6,7-pentamethyl-2,3-dihydro-1-benzofuran-5-yl)morpholine

By using 5-(2-benzylmorpholin-4-yl)-2,2,4,6,7-pentamethyl-1-benzofuran-3(2H)-one (150 mg, 0.395 mmol) synthesized in Reference example 41, the reaction was carried out in the same manner as Example 5 to obtain the title compound 97.1 mg (yield 67%) as a diastereomeric mixture (3:2).
$^1$H-NMR (CDCl$_3$): δ1.39-1.48 (6H, m), 2.01-2.07 (3H, m), 2.09 (1.8H, s), 2.14-2.21 (4.2H, m), 2.59-2.77 (3H, m), 2.82-2.99 (3H, m), 3.06-3.18 (1H, m), 3.34-3.53 (1H, m), 3.72-3.98 (3H, m), 7.15-7.31 (5H, m).

Example 17

1-(4-Methoxyphenyl)-4-(2,2,4,6,7-pentamethyl-2,3-dihydro-1-benzofuran-5-yl)piperazine By using 5-[4-(4-methoxyphenyl)piperazin-1-yl]-2,2,4,6,7-pentamethyl-1-benzofuran-3(2H)-one (2.00 g, 5.07 mmol) synthesized in Reference example 42, the reaction was carried out in the same manner as Example 5 to synthesize the title compound 1.60 g (yield 83%).

That is, to the THF (20 mL) suspension of lithium aluminum hydride (577 mg, 15.2 mmol), aluminum chloride (2.03 g, 15.2 mmol) was added under ice cooling, and then the mixture was stirred for 10 minutes and added with the THF (25 mL) solution of 5-[4-(4-methoxyphenyl)piperazin-1-yl]-2,2,4,6,7-pentamethyl-1-benzofuran-3(2H)-on (2.00 g, 5.07 mmol), and the mixture was stirred for 2 hours under reflux. After cooling the reaction solution on ice, water and 0.5 N aqueous solution of sodium hydroxide were serially added thereto. The mixture was stirred for 1 hour at room temperature, and then extraction was performed using ethyl acetate. The extract was washed with saturated saline and dried over anhydrous magnesium sulfate. After that, the solvent was removed by distillation under reduced pressure. The resulting residue was purified by silica gel chromatography (hexane-ethyl acetate 90:10-75:25) and crystallized from ethyl acetate and hexane to obtain the title compound 1.60 g as a colorless crystal (yield 83%). Melting point was 152 to 155° C.

In addition, synthesis was also performed according to the below-described method using 5-bromo-2,2,4,6,7-pentamethyl-2,3-dihydro-1-benzofuran (344.1 g, 1.28 mol) synthesized in Reference Example 4 and 1-(4-methoxyphenyl)piperazine (164 g, 853 mmol). That is, 1-(4-methoxyphenyl)piperazine (51.5 g, 268 mmol), palladium acetate (3.01 g, 13.4 mmol), BINAP (12.5 g, 20.1 mmol) and sodium tert-butoxide (38.6 g, 402 mmol) were added to a solution of toluene (775 mL) containing 5-bromo-2,2,4,6,7-pentamethyl-2,3-dihydro-1-benzofuran (108 g, 402 mmol), and the mixture was heated to reflux under argon atmosphere for 7 hours. After cooled to room temperature, water (775 mL) was added to the reaction solution for distribution. The organic layer was washed with saturated saline (515 mL) and dried using anhydrous magnesium sulfate, and after that, the solvent was removed under reduced pressure. The obtained residue was purified by basic silica gel column chromatography (hexane-ethyl acetate 98:2) and then silica gel column chromatography (hexane-ethyl acetate 100:0-94:6) to give a crudely purified product of the title compound as a yellow solid (68.0 g). Similarly, a crudely purified product of the title compound (136.6 g) was obtained from 5-bromo-2,2,4,6,7-pentamethyl-2,3-dihydro-1-benzofuran (213 g, 791 mmol) and 1-(4-methoxyphenyl)piperazine (101.5 g, 528 mmol). The obtained crudely purified products were put together and suspended in ethanol (2.3 L). This suspension was stirred at 65° C. for 30 minutes. After cooled to room temperature, it was further stirred for 1 hour, and crystals were collected by filtration to give a crude crystal of the title compound (181 g). Similarly, a crude crystal of the title compound was obtained from 5-bromo-2,2,4,6,7-pentamethyl-2,3-dihydro-1-benzofuran (23.1 g, 85.8 mmol) and 1-(4-methoxyphenyl)piperazine (11.0 g, 57.2 mmol). The obtained crude crystals were put together and recrystallized from acetone (2.82 L)/water (940 mL) to give 176 g of the title compound as a colorless crystal (yield: 54%). Melting point was 152 to 155° C.
$^1$H-NMR (CDCl$_3$): δ1.46 (6H, s), 2.08 (3H, s), 2.19 (3H, s), 2.24 (3H, s), 2.91 (2H, s), 3.06-3.34 (8H, m), 3.78 (3H, s), 6.81-6.90 (2H, m), 6.92-7.01 (2H, m).

Example 18

1-(4-Methoxyphenyl)-4-(4,6,7-trimethyl-2',3',5',6'-tetrahydro-3H-spiro[1-benzofuran-2,4'-pyran]-5-yl)piperazine By using 5-[4-(4-methoxyphenyl)piperazin-1-yl]-4,6,7-trimethyl-2',3',5',6'-tetrahydro-3H-spiro [1-benzofuran-2,4'-pyran]-3-one (125 mg, 0.286 mmol) synthesized in Reference example 47, the reaction was carried out in the same manner as Example 5 to synthesize the title compound 60 mg (yield 50%). Melting point was 153 to 155° C. (ethyl acetate-hexane).

$^1$H-NMR (CDCl$_3$): δ1.74-1.97 (4H, m), 2.11 (3H, m), 2.21 (3H, s), 2.24 (3H, s), 2.92 (2H, s), 3.07-3.33 (8H, m), 3.71-3.82 (5H, m), 3.88-3.99 (2H, m), 6.82-6.90 (2H, m), 6.92-7.00 (2H, m).

Example 19

1-(4-Methoxyphenyl)-4-(4,6,7-trimethyl-3H-spiro[1-benzofuran-2,1'-cyclopentan]-5-yl)piperazine By using 5-[4-(4-methoxyphenyl)piperazin-1-yl]-4,6,7-trimethyl-3H-spiro[1-benzofuran-2,1'-cyclopentan]-3-one (180 mg, 0.428 mmol) synthesized in Reference example 49, the reaction was carried out in the same manner as Example 5 to obtain the title compound 120 mg (yield 69%). Melting point was 137 to 139° C. (ethyl acetate-hexane).

$^1$H-NMR (CDCl$_3$): δ1.62-1.80 (4H, m), 1.81-1.96 (2H, m), 2.01-2.13 (5H, m), 2.20 (3H, s), 2.24 (3H, s), 3.06 (2H, s), 3.07-3.34 (8H, m), 3.78 (3H, s), 6.82-6.90 (2H, m), 6.92-7.00 (2H, m).

Example 20

1-(4-Methoxyphenyl)-4-[2,4,6,7-tetramethyl-2,3-dihydro-1-benzofuran-5-yl]piperazine By using 5-bromo-2,4,6,7-tetramethyl-2,3-dihydro-1-benzofuran (4.02 g, 15.8 mmol) synthesized in Reference example 53 and 1-(4-methoxyphenyl)piperazine (6.08 g, 31.6 mmol), the reaction was carried out in the same manner as Example 1 to obtain the title compound 2.25 g (yield 39%).

$^1$H-NMR (CDCl$_3$): δ1.47 (3H, d, J=6.1 Hz), 2.10 (3H, s), 2.22 (3H, s), 2.24 (3H, s), 2.71 (1H, dd, J=15.1, 7.6 Hz), 3.09-3.33 (9H, m), 3.78 (3H, s), 4.82-4.95 (1H, m), 6.83-6.89 (2H, m), 6.93-7.00 (2H, m).

Example 21

1-(4-Methoxyphenyl)-4-[(2R)-2,4,6,7-tetramethyl-2,3-dihydro-1-benzofuran-5-yl]piperazine To the toluene (10 mL) solution of (2R)-5-bromo-2,4,6,7-tetramethyl-2,3-dihydro-1-benzofuran (800 mg, 3.14 mmol) obtained in Reference example 54, 1-(4-methoxyphenyl)piperazine (1.81 g, 9.41 mmol), palladium acetate (35 mg, 0.157 mmol), BINAP (293 mg, 0.471 mmol) and sodium tert-butoxide (602 mg, 6.27 mmol) were added and irradiated with microwave. The mixture was stirred for 15 minutes at 160° C. To the mixture solution, water was added and extracted with ethyl acetate. The extract solution was washed with saturated brine and dried over anhydrous magnesium sulfate. The solvent was removed by distillation under reduced pressure. The resulting residue was purified by silica gel column chromatography (hexane-ethyl acetate 85:15). The resulting solids were recrystallized from hexane-ethyl acetate to obtain the title compound 354 mg (yield 31%). Melting point was 127 to 128° C. (hexane-ethyl acetate). [α]$_D^{20}$=+13.1° (c=0.51, chloroform).

Example 22

1-(4-Methoxyphenyl)-4-[(2S)-2,4,6,7-tetramethyl-2,3-dihydro-1-benzofuran-5-yl]piperazine By using (2S)-5-bromo-2,4,6,7-tetramethyl-2,3-dihydro-1-benzofuran (800 mg, 3.14 mmol) obtained in Reference example 54 and 1-(4-methoxyphenyl)piperazine (1.81 g, 9.41 mmol), the reaction was carried out in the same manner as Example 21 to synthesize the title compound 652 mg (yield 57%). Melting point was 127 to 128° C. (hexane-ethyl acetate). [α]$_D^{20}$=−13.6° (c=0.51, chloroform).

Example 23

1-(4-Methoxy-3-methylphenyl)-4-(2,4,6,7-tetramethyl-2,3-dihydro-1-benzofuran-5-yl)piperazine To the toluene (3.1 mL) solution of 1-(2,4,6,7-tetramethyl-2,3-dihydro-1-benzofuran-5-yl)piperazine (400 mg, 1.54 mmol) synthesized in Reference example 56, 4-bromo-1-methoxy-2-methylbenzene (464 mg, 2.31 mmol), palladium acetate (17 mg, 0.077 mmol), BINAP (143 mg, 0.231 mmol) and sodium tert-butoxide (296 mg, 3.08 mmol) were added and irradiated with microwave. The mixture was reacted for 15 minutes at 150° C. To the mixture solution, water was added and extracted with ethyl acetate. The extract solution was washed with saturated brine and dried over anhydrous magnesium sulfate. The solvent was removed by distillation under reduced pressure. The resulting residue was purified by silica gel column chromatography (hexane-ethyl acetate 85:15). The resulting solid was recrystallized from ethanol to obtain the title compound 114 mg (yield 19%). Melting point was 141 to 142° C. (ethanol).

$^1$H-NMR (CDCl$_3$): δ1.47 (3H, d, J=6.4 Hz), 2.10 (3H, s), 2.22 (6H, s), 2.24 (3H, s), 2.71 (1H, dd, J=15.1, 7.9 Hz), 3.07-3.33 (9H, m), 3.80 (3H, s), 4.82-4.95 (1H, m), 6.75-6.89 (3H, m).

Example 24

1-(4-Fluorophenyl)-4-(2,4,6,7-tetramethyl-2,3-dihydro-1-benzofuran-5-yl)piperazine By using 1-(2,4,6,7-tetramethyl-2,3-dihydro-1-benzofuran-5-yl)piperazine (400 mg, 1.54 mmol) synthesized in Reference example 56 and 1-fluoro-4-iodobenzene (1.54 g, 6.92 mmol), the reaction was carried out in the same manner as Example 23 to synthesize the title compound 119 mg (yield 16%).

Melting point was 137 to 138° C. (ethanol).

$^1$H-NMR (CDCl$_3$): δ1.47 (3H, d, J=6.0 Hz), 2.10 (3H, s), 2.21 (3H, s), 2.24 (3H, s), 2.71 (1H, dd, J=15.4, 7.9 Hz), 3.08-3.35 (9H, m), 4.82-4.95 (1H, m), 6.89-7.05 (4H, m)

Example 25

1-(4-Methylphenyl)-4-(2,4,6,7-tetramethyl-2,3-dihydro-1-benzofuran-5-yl)piperazine By using 1-(2,4,6,7-tetramethyl-2,3-dihydro-1-benzofuran-5-yl)piperazine (700 mg, 2.69 mmol) synthesized in Reference example 56 and 4-iodotoluene (1.76 g, 8.08 mmol), the reaction was carried out in the same manner as Example 23 to synthesize the title compound 310 mg (yield 33%). Melting point was 150 to 151° C. (ethanol).

$^1$H-NMR (CDCl$_3$): δ1.47 (3H, d, J=6.0 Hz), 2.10 (3H, s), 2.21 (3H, s), 2.24 (3H, s), 2.28 (3H, s), 2.71 (1H, dd, J=15.1, 7.9 Hz), 3.09-3.35 (9H, m), 4.82-4.95 (1H, m), 6.88-6.95 (2H, m), 7.07-7.13 (2H, m).

Example 26

1-(4-Bromophenyl)-4-(2,4,6,7-tetramethyl-2,3-dihydro-1-benzofuran-5-yl)piperazine By using 1-(2,4,6,7-tetramethyl-2,3-dihydro-1-benzofuran-5-yl)piperazine (2.60 g, 10.0 mmol) synthesized in Reference example 56 and 1,4-dibromobenzene (7.08 g, 30 mmol), the reaction was carried out in the same manner as Example 23 to synthesize the title compound 2.3 g (yield 55%). Melting point was 202 to 204° C. (hexane-ethyl acetate).
$^1$H-NMR (CDCl$_3$): δ1.47 (3H, d, J=6.4 Hz), 2.10 (3H, s), 2.20 (3H, s), 2.23 (3H, s), 2.71 (1H, dd, J=15.3, 7.7 Hz), 3.10-3.36 (9H, m), 4.80-4.96 (1H, m), 6.77-6.92 (2H, m), 7.29-7.41 (2H, m).

Example 27

1-[4-(Methylsulfanyl)phenyl]-4-(2,4,6,7-tetramethyl-2,3-dihydro-1-benzofuran-5-yl)piperazine By using 1-(2,4,6,7-tetramethyl-2,3-dihydro-1-benzofuran-5-yl)piperazine (130 mg, 0.50 mmol) synthesized in Reference example 56 and 4-bromothioanisole (203 mg, 1.0 mmol), the reaction was carried out in the same manner as Example 23 to obtain the title compound 78 mg (yield 41%).
$^1$H-NMR (CDCl$_3$): δ1.47 (3H, d, J=6.4 Hz), 2.10 (3H, s), 2.20 (3H, s), 2.23 (3H, s), 2.45 (3H, s), 2.70 (1H, dd, J=15.3, 7.8 Hz), 3.14-3.33 (9H, m), 4.82-4.95 (1H, m), 6.89-6.96 (2H, m), 7.23-7.30 (2H, m).

Example 28

1-[4-(Methylsulfonyl)phenyl]-4-(2,4,6,7-tetramethyl-2,3-dihydro-1-benzofuran-5-yl)piperazine To the mixture solution of ethyl acetate-DMF (1:1, 2.0 mL) of 1-[4-(methylsulfanyl)phenyl]-4-(2,4,6,7-tetramethyl-2,3-dihydro-1-benzofuran-5-yl)piperazine (60 mg, 0.157 mmol) synthesized in Example 27, m-chloroperbenzoic acid (70%, 85 mg) was added under ice cooling, followed by stirring for 1 hour. The mixture solution was diluted with ethyl acetate, and then washed with aqueous solution of sodium hydrogen carbonate, aqueous solution of sodium thiosulfate, and saturated brine. The organic layer was dried over anhydrous magnesium sulfate. The solvent was removed by distillation under reduced pressure. The resulting residue was crystallized from ethanol to obtain the title compound 24 mg (yield 37%). Melting point was 228 to 233° C. (ethanol).
$^1$H-NMR (CDCl$_3$): δ1.47 (3H, d, J=6.4 Hz), 2.10 (3H, s), 2.19 (3H, s), 2.23 (3H, s), 2.71 (1H, dd, J=15.1, 7.9 Hz), 3.02 (3H, s), 3.15-3.55 (9H, m), 4.83-4.95 (1H, m), 6.95-7.02 (2H, m), 7.75-7.82 (2H, m).

Example 29

4-[4-(2,4,6,7-Tetramethyl-2,3-dihydro-1-benzofuran-5-yl)piperazin-1-yl]benzonitrile By using 1-(2,4,6,7-tetramethyl-2,3-dihydro-1-benzofuran-5-yl)piperazine (130 mg, 0.50 mmol) synthesized in Reference example 56 and 4-bromobenzonitrile (182 mg, 1.0 mmol), the reaction was carried out in the same manner as Example 23 to obtain the title compound 71 mg (yield 39%).
$^1$H-NMR (CDCl$_3$): δ1.47 (3H, d, J=6.0 Hz), 2.10 (3H, s), 2.19 (3H, s), 2.22 (3H, s), 2.70 (1H, dd, J=15.3, 7.7 Hz), 3.11-3.52 (9H, m), 4.81-4.96 (1H, m), 6.86-6.96 (2H, m), 7.46-7.56 (2H, m).

Example 30

4-[4-(2,4,6,7-Tetramethyl-2,3-dihydro-1-benzofuran-5-yl)piperazin-1-yl]benzamide The mixture of 4-[4-(2,4,6,7-tetramethyl-2,3-dihydro-1-benzofuran-5-yl)piperazin-1-yl]benzonitrile (70 mg, 0.194 mmol) synthesized in Reference example 29 and potassium hydroxide (33 mg, 0.582 mmol) was stirred in tert-butanol (2.0 mL) at 80° C. for 20 hours. After adding water, solids obtained were filtered and washed with ethanol to obtain the title compound 35 mg (yield 48%). Melting point was 240 to 245° C. (ethanol).
$^1$H-NMR (CDCl$_3$): δ1.47 (3H, d, J=6.0 Hz), 2.10 (3H, s), 2.20 (3H, s), 2.23 (3H, s), 2.71 (1H, dd, J=15.1, 7.9 Hz), 3.12-3.50 (9H, m), 4.81-4.96 (1H, m), 5.69 (2H, br s), 6.90-6.99 (2H, m), 7.71-7.78 (2H, m).

Example 31

1-(4-Methoxy-3-methylphenyl)-4-(2,2,4,6,7-pentamethyl-2,3-dihydro-1-benzofuran-5-yl)piperazine By using 5-[4-(4-methoxy-3-methylphenyl)piperazin-1-yl]-2,2,4,6,7-pentamethyl-1-benzofuran-3(2H)-one (220 mg, 0.538 mmol) synthesized in Reference example 58, the reaction was carried out in the same manner as Example 5 to obtain the title compound 80 mg (yield 38%). Melting point was 137 to 141° C. (ethyl acetate-hexane).
$^1$H-NMR (CDCl$_3$): δ1.46 (6H, s), 2.08 (3H, s), 2.19 (3H, s), 2.22 (3H, s), 2.24 (3H, s), 2.91 (2H, s), 3.05-3.34 (8H, m), 3.80 (3H, s), 6.74-6.84 (2H, m), 6.85-6.89 (1H, m).

Example 32

1-(3-Fluoro-4-methoxyphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (311 mg, 1.0 mmol) synthesized in Reference example 61 and 4-bromo-2-fluoroanisole (0.194 mL, 1.5 mmol), the reaction was carried out in the same manner as Example 23 to synthesize the title compound 145 mg (yield 36%). Melting point was 161 to 163° C. (hexane).
$^1$H-NMR (CDCl$_3$): δ1.47 (6H, s), 2.09 (3H, s), 2.19 (3H, s), 2.24 (3H, s), 2.91 (2H, s), 3.08-3.33 (8H, m), 3.86 (3H, s), 6.67 (1H, ddd, J=8.9, 2.8, 1.2 Hz), 6.78 (1H, dd, J=14.0, 2.7 Hz), 6.86-6.96 (1H, m).

Example 33

1-(4-Chloro-3-methylphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (274 mg, 1.00 mmol) synthesized in Reference example 61 and 4-bromo-1-chloro-2-methylbenzene (308 mg, 1.50 mmol), the reaction was carried out in the same manner as Example 23 to obtain the title compound 60 mg (yield 15%).

Melting point was 168 to 171° C. (ethyl acetate-hexane).
¹H-NMR (CDCl₃): δ1.46 (6H, s), 2.08 (3H, s), 2.18 (3H, s), 2.23 (3H, s), 2.34 (3H, s), 2.91 (2H, s), 3.11-3.33 (8H, m), 6.75 (2H, dd, J=3.0, 8.7 Hz), 6.85 (1H, d, J=3.0 Hz), 7.21 (1H, d, J=8.7 Hz).

Example 34

1-(4-Chlorophenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (274 mg, 1.00 mmol) synthesized in Reference example 61 and 1-bromo-4-chlorobenzene (287 mg, 1.50 mmol), the reaction was carried out in the same manner as Example 23 to obtain the title compound 100 mg (yield 26%).
Melting point was 226 to 229° C. (ethyl acetate-hexane).
¹H-NMR (CDCl₃): δ1.46 (6H, s), 2.08 (3H, s), 2.18 (3H, s), 2.23 (3H, s), 2.91 (2H, s), 3.11-3.33 (8H, m), 6.85-6.94 (2H, m), 7.17-7.25 (2H, m).

Example 35

1-(4-Fluoro-3-methylphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (311 mg, 1.0 mmol) synthesized in Reference example 61 and 5-bromo-2-fluorotoluene (0.191 mL, 1.5 mmol), the reaction was carried out in the same manner as Example 23 to synthesize the title compound 231 mg (yield 60%).
Melting point was 143 to 145° C. (hexane).
¹H-NMR (CDCl₃): δ1.47 (6H, s), 2.09 (3H, s), 2.20 (3H, s), 2.24 (3H, s), 2.26 (3H, d, J=1.9 Hz), 2.92 (2H, s), 3.06-3.35 (8H, m), 6.71-6.85 (2H, m), 6.86-6.96 (1H, m).

Example 36

1-(3-Chloro-4-methylphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine hydrochloric acid salt (311 mg, 1.00 mmol) synthesized in Reference example 147 and 4-bromo-2-chloro-1-methylbenzene (308 mg, 1.50 mmol), the reaction was carried out in the same manner as Example 23 to obtain the title compound 213 mg (yield 58%).
Melting point was 146 to 148° C. (hexane).
¹H-NMR (CDCl₃): δ1.46 (6H, s), 2.08 (3H, s), 2.18 (3H, s), 2.23 (3H, s), 2.29 (3H, s), 2.91 (2H, s), 3.11-3.33 (8H, m), 6.79 (1H, dd, J=8.4, 2.7 Hz), 6.97 (1H, d, J=2.7 Hz), 7.10 (1H, d, J=8.4 Hz).

Example 37

1-(3,4-Dimethoxyphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine hydrochloric acid salt (311 mg, 1.00 mmol) synthesized in Reference example 147 and 4-bromo-1,2-dimethoxybenzene (326 mg, 1.50 mmol), the reaction was carried out in the same manner as Example 23 to synthesize the title compound 131 mg (yield 32%).
Melting point was 135 to 137° C. (hexane).
¹H-NMR (CDCl₃): δ1.46 (6H, s), 2.09 (3H, s), 2.20 (3H, s), 2.25 (3H, s), 2.91 (2H, s), 3.10-3.34 (8H, m), 3.85 (3H, s), 3.89 (3H, s), 6.52 (1H, dd, J=8.7, 2.4 Hz), 6.65 (1H, d, J=2.4 Hz), 6.81 (1H, d, J=8.7 Hz).

Example 38

1-(4-Fluoro-3-methoxyphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine hydrochloric acid salt (311 mg, 1.00 mmol) synthesized in Reference example 147 and 4-bromo-1-fluoro-2-methoxybenzene (308 mg, 1.50 mmol), the reaction was carried out in the same manner as Example 23 to synthesize the title compound 212 mg (yield 53%). Melting point was 152 to 155° C. (hexane).
¹H-NMR (CDCl₃): δ1.46 (6H, s), 2.09 (3H, s), 2.19 (3H, s), 2.24 (3H, s), 2.91 (2H, s), 3.10-3.37 (8H, m), 3.89 (3H, s), 6.48 (1H, dt, J=8.7, 3.3 Hz), 6.63 (1H, dd, J=7.2, 3.3 Hz), 6.98 (1H, dd, J=8.7, 7.7 Hz).

Example 39

1-(4-Ethylphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (210 mg, 0.765 mmol) synthesized in Reference example 61 and 1-bromo-4-ethylbenzene (212 mg, 1.15 mmol), the reaction was carried out in the same manner as Example 23 to synthesize the title compound 110 mg (yield 38%).
Melting point was 152 to 155° C. (hexane).
¹H-NMR (CDCl₃): δ1.22 (3H, t, J=7.8 Hz), 1.46 (6H, s), 2.08 (3H, s), 2.19 (3H, s), 2.24 (3H, s), 2.59 (2H, q, J=7.8 Hz), 2.91 (2H, s), 3.11-3.35 (8H, m), 6.93 (2H, d, J=8.7 Hz), 7.12 (2H, d, J=8.7 Hz).

Example 40

1-(6-Methoxypyridin-3-yl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (210 mg, 0.765 mmol) synthesized in Reference example 61 and 5-bromo-2-methoxypyridine (216 mg, 1.15 mmol), the reaction was carried out in the same manner as Example 23 to synthesize the title compound 109 mg (yield 37%).
Melting point was 178 to 180° C. (hexane).
¹H-NMR (CDCl₃): δ1.46 (6H, s), 2.09 (3H, s), 2.19 (3H, s), 2.24 (3H, s), 2.91 (2H, s), 3.05-3.35 (8H, m), 3.91 (3H, s), 6.70 (1H, d, J=9.0 Hz), 7.35 (1H, dd, J=9.0, 3.0 Hz), 7.85 (1H, d, J=3.0 Hz).

Example 41

1-(4-Fluorophenyl)-4-(2,2,4,6,7-pentamethyl-2,3-dihydro-1-benzofuran-5-yl)piperazine By using 5-bromo-2,2,4,6,7-pentamethyl-2,3-dihydro-1-benzofuran (269 mg, 0.999 mmol) synthesized in Reference example 4 and 1-(4-fluorophenyl)piperazine (541 mg, 3.00 mmol), the reaction was carried out in the same manner as Example 21 to synthesize the title compound 100 mg (yield 27%). Melting point was 175 to 177° C. (hexane).

$^{1}$H-NMR (CDCl$_{3}$): δ1.46 (6H, s), 2.08 (3H, s), 2.19 (3H, s), 2.24 (3H, s), 2.91 (2H, s), 3.10-3.36 (8H, m), 6.88-7.03 (4H, m).

Example 42

1-(4-Chloro-3-methoxyphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (274 mg, 1.00 mmol) synthesized in Reference example 61 and 4-bromo-1-chloro-2-methoxybenzene (332 mg, 1.50 mmol), the reaction was carried out in the same manner as Example 23 to obtain the title compound 100 mg (yield 24%). Melting point was 168 to 171° C. (ethyl acetate-hexane).

$^{1}$H-NMR (CDCl$_{3}$): δ1.46 (6H, s), 2.09 (3H, s), 2.19 (3H, s), 2.24 (3H, s), 2.91 (2H, s), 3.12-3.34 (8H, m), 3.90 (3H, s), 6.51 (1H, dd, J=2.4, 8.7 Hz), 6.57 (1H, d, J=2.4 Hz), 7.22 (1H, d, J=8.7 Hz).

Example 43

1-(3,4-Dimethylphenyl)-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (274 mg, 1.00 mmol) synthesized in Reference example 61 and 4-bromo-1,2-dimethylbenzene (278 mg, 1.50 mmol), the reaction was carried out in the same manner as Example 23 to obtain the title compound 70 mg (yield 18%).

Melting point was 137 to 139° C. (ethyl acetate-hexane).

$^{1}$H-NMR (CDCl$_{3}$): δ1.46 (6H, s), 2.08 (3H, s), 2.19 (3H, s), 2.20 (3H, s), 2.237 (3H, s), 2.243 (3H, s), 2.91 (2H, s), 3.11-3.33 (8H, m), 6.75 (1H, dd, J=2.7, 8.4 Hz), 6.82 (1H, d, J=2.7 Hz), 7.21 (1H, d, J=8.4 Hz).

Example 44

1-(2,2,4,6,7-Pentamethyl-2,3-dihydro-1-benzofuran-5-yl)-4-[4-(trifluoromethoxy)phenyl]piperazine By using 1-(2,2,4,6,7-pentamethyl-2,3-dihydro-1-benzofuran-5-yl)piperazine (311 mg, 1.0 mmol) synthesized in Reference example 61 and 1-bromo-4-(trifluoromethoxy)benzene (0.223 mL, 1.5 mmol), the reaction was carried out in the same manner as Example 1 to synthesize the title compound 221 mg (yield 51%). Melting point was 216 to 219° C. (hexane).

$^{1}$H-NMR (CDCl$_{3}$): δ1.44-1.50 (6H, m), 2.09 (3H, s), 2.19 (3H, s), 2.24 (3H, s), 2.92 (2H, s), 3.16-3.34 (8H, m), 6.91-6.99 (2H, m), 7.08-7.16 (2H, m).

Example 45

1-(4-Methoxyphenyl)-4-(2,2,4,6,7-pentamethyl-2,3-dihydro-1-benzofuran-5-yl)-1,4-diazepane By using 5-[4-(4-methoxyphenyl)-1,4-diazepan-1-yl]-2,2,4,6,7-pentamethyl-1-benzofuran-3(2H)-one synthesized in Reference example 64, the reaction was carried out in the same manner as Example 5 to synthesize the title compound 246 mg (yield 100%).

Melting point was 105 to 107° C. (methanol).

$^{1}$H-NMR (CDCl$_{3}$): δ1.44 (6H, s), 1.86-1.99 (2H, m), 2.03 (3H, s), 2.18 (3H, s), 2.05 (3H, s), 2.09 (3H, s), 2.87 (2H, s), 3.05-3.30 (2H, m), 3.55-3.72 (4H, m), 3.77 (3H, s), 6.71 (2H, d, J=9.3 Hz), 6.83 (2H, d, J=9.3 Hz).

Example 46

1-(7-Ethoxy-2,2,4,6-tetramethyl-2,3-dihydro-1-benzofuran-5-yl)-4-(4-methoxyphenyl)piperazine By using 7-ethoxy-5-[4-(4-methoxyphenyl)piperazin-1-yl]-2,2,4,6-tetramethyl-1-benzofuran-3(2H)-one (90 mg, 0.212 mmol) synthesized in Reference example 74, the reaction was carried out in the same manner as Example 5 to synthesize the title compound 50 mg (yield 57%). Melting point was 151 to 153° C. (ethyl acetate-hexane).

$^{1}$H-NMR (CDCl$_{3}$): δ1.33 (3H, t, J=7.2 Hz), 1.48 (6H, s), 2.17 (3H, s), 2.24 (3H, s), 2.89 (2H, s), 3.09-3.18 (4H, m), 3.20-3.29 (4H, m), 3.78 (3H, s), 4.03 (2H, q, J=7.2 Hz), 6.82-6.90 (2H, m), 6.92-7.00 (2H, m).

Example 47

1-(4-Methoxyphenyl)-4-(7-methoxy-2,2,4,6-tetramethyl-2,3-dihydro-1-benzofuran-5-yl)piperazine By using 7-methoxy-5-[4-(4-methoxyphenyl)piperazin-1-yl]-2,2,4,6-tetramethyl-1-benzofuran-3(2H)-one (110 mg, 0.268 mmol) synthesized in Reference example 76, the reaction was carried out in the same manner as Example 5 to synthesize the title compound 60 mg (yield 56%). Melting point was 161 to 163° C. (ethyl acetate-hexane). That is, to the THF (2.0 mL) suspension of lithium aluminum hydride (31 mg, 0.804 mmol), aluminum chloride (107 mg, 0.804 mmol) was added under ice cooling, and then the mixture was stirred for 10 minutes and added with the THF (3.0 mL) solution of 7-methoxy-5-[4-(4-methoxyphenyl)piperazin-1-yl]-2,2,4,6-tetramethyl-1-benzofuran-3(2H)-one (110 mg, 0.268 mmol), followed by further stirring for 2 hours under reflux. After cooling the mixture solution on ice, water and 0.5 N aqueous solution of sodium hydroxide was serially added, and extraction was performed using the mixture solvent of ethyl acetate-diethyl ether (1:1). After washing with the saturated brine, the extract solution was dried over anhydrous magnesium sulfate. The solvent was removed by distillation under reduced pressure. The resulting residue was purified by silica gel chromatography (hexane-ethyl acetate 96:4-85:15) and crystallized from ethyl acetate and hexane to obtain the title compound 60 mg (yield 56%). Melting point was 161 to 163° C. In addition, synthesis was also performed according to the below-described method using 7-methoxy-2,2,4,6-tetramethyl-2,3-dihydro-1-benzofuran-5-amine hydrochloride (155.2 g, 602 mmol) synthesized in Reference Example 164 and N,N-bis(2-chloroethyl)-4-methoxyaniline (164 g, 662 mmol). That is, a suspension of NMP (1.40 L)-water (155 mL) containing 7-methoxy-2,2,4,6-tetramethyl-2,3-dihydro-1-benzofuran-5-amine hydrochloride (155.2 g, 602 mmol), N,N-bis(2-chloroethyl)-4-methoxyaniline (164 g, 662 mmol), potassium carbonate (250 g, 1.81 mol), and sodium iodide (135 g, 903 mmol) was stirred at 90° C. for 8 hours. After cooled to room temperature, water (2.80 L) was added to the mixture with the inner temperature thereof being maintained at 45 to 50° C. After cooled to room temperature, the precipitated solid was collected by filtration and washed with water. The obtained wet crystals were suspended in ethanol, and it was stirred overnight. After cooled in ice bath, the solid was collected by filtration and washed with a mixture of ethanol-water (90-10) to give a crudely purified product of the title compound as a solid (148.4 g). Similarly, a crudely purified product (165.1 g) was obtained from 7-methoxy-2,2,4,6-tetramethyl-2,3-dihydro-1-benzofuran-5-amine hydrochloride (165.1 g, 640 mmol), and the crudely purified products were put together and dissolved in toluene (2.5 L) to be subjected to Celite filtration, thereby removing insolubles. The solvent was removed under reduced pressure, and the obtained residue was crystallized from acetonitrile (3.0 L)-water (600 mL) to obtain a crude crystal (277.8 g). The obtained crude crystals were recrystallized from acetone (2.7 L)-water (1.35 L) to give 268.9 g of the title compound as a white crystal (yield 55%).

Melting point was 163° C.

$^1$H-NMR (CDCl$_3$): δ1.49 (6H, s), 2.17 (3H, s), 2.25 (3H, s), 2.91 (2H, s), 3.08-3.32 (8H, m), 3.78 (3H, s), 3.81 (3H, s), 6.82-6.90 (2H, m), 6.92-7.00 (2H, m).

Example 48

1-(4-Methoxyphenyl)-4-(7-methoxy-2,4,6-trimethyl-2,3-dihydro-1-benzofuran-5-yl)piperazine By using 5-bromo-7-methoxy-2,4,6-trimethyl-2,3-dihydro-1-benzofuran (542 mg, 2.0 mmol) synthesized in Reference example 83 and 1-(4-methoxyphenyl)piperazine (768 mg, 4.0 mmol), the reaction was carried out in the same manner as Example 21 to synthesize the title compound 420 mg (yield 55%).

Melting point was 109 to 111° C. (ethanol-water).

$^1$H-NMR (CDCl$_3$): δ1.48 (3H, d, J=6.4 Hz), 2.19 (3H, s), 2.25 (3H, s), 2.70 (1H, dd, J=15.3, 7.7 Hz), 3.08-3.32 (9H, m), 3.78 (3H, s), 3.82 (3H, s), 4.88-5.02 (1H, m), 6.82-6.90 (2H, m), 6.92-7.01 (2H, m).

Example 49

1-(7-Methoxy-2,4,6-trimethyl-2,3-dihydro-1-benzofuran-5-yl)-4-(4-methylphenyl)piperazine By using 5-bromo-7-methoxy-2,4,6-trimethyl-2,3-dihydro-1-benzofuran (542 mg, 2.0 mmol) synthesized in Reference example 83 and 1-(4-methylphenyl)piperazine (704 mg, 4.0 mmol), the reaction was carried out in the same manner as Example 21 to synthesize the title compound 306 mg (yield 42%).

Melting point was 82 to 84° C. (ethanol-water).

$^1$H-NMR (CDCl$_3$): δ1.48 (3H, d, J=6.4 Hz), 2.19 (3H, s), 2.24 (3H, s), 2.28 (3H, s), 2.70 (1H, dd, J=15.1, 7.5 Hz), 3.13-3.30 (9H, m), 3.82 (3H, s), 4.88-5.02 (1H, m), 6.87-6.94 (2H, m), 7.05-7.13 (2H, m).

Example 50

1-(7-Ethoxy-2,4,6-trimethyl-2,3-dihydro-1-benzofuran-5-yl)-4-(4-methoxyphenyl)piperazine By using 5-bromo-7-ethoxy-2,4,6-trimethyl-2,3-dihydro-1-benzofuran (570 mg, 2.0 mmol) synthesized in Reference example 84 and 1-(4-methoxyphenyl)piperazine (768 mg, 4.0 mmol), the reaction was carried out in the same manner as Example 21 to synthesize the title compound 385 mg (yield 48%).

Melting point was 106 to 108° C. (ethanol-water).

$^1$H-NMR (CDCl$_3$): δ1.34 (3H, t, J=7.2 Hz), 1.47 (3H, d, J=6.4 Hz), 2.19 (3H, s), 2.24 (3H, s), 2.69 (1H, dd, J=15.3, 7.7 Hz), 3.10-3.29 (9H, m), 3.78 (3H, s), 4.05 (2H, q, J=7.2 Hz), 4.86-5.00 (1H, m), 6.82-6.89 (2H, m), 6.93-7.00 (2H, m).

Example 51

1-(4-Fluorophenyl)-4-(7-methoxy-2,4,6-trimethyl-2,3-dihydro-1-benzofuran-5-yl)piperazine By using 5-bromo-7-methoxy-2,4,6-trimethyl-2,3-dihydro-1-benzofuran (542 mg, 2.0 mmol) synthesized in Reference example 83 and 1-(4-fluorophenyl)piperazine (720 mg, 4.0 mmol), the reaction was carried out in the same manner as Example 21 to synthesize the title compound 417 mg (yield 56%). Melting point was 114 to 116° C. (ethanol-water).

$^1$H-NMR (CDCl$_3$): δ1.49 (3H, d, J=6.4 Hz), 2.19 (3H, s), 2.24 (3H, s), 2.70 (1H, dd, J=15.1, 7.5 Hz), 3.13-3.30 (9H, m), 3.82 (3H, s), 4.88-5.02 (1H, m), 6.90-7.03 (4H, m).

Example 52

1-(3-Methoxyphenyl)-4-(7-methoxy-2,4,6-trimethyl-2,3-dihydro-1-benzofuran-5-yl)piperazine By using 5-bromo-7-methoxy-2,4,6-trimethyl-2,3-dihydro-1-benzofuran (542 mg, 2.0 mmol) synthesized in Reference example 83 and 1-(3-methoxyphenyl)piperazine (768 mg, 4.0 mmol), the reaction was carried out in the same manner as Example 21 to obtain the title compound 340 mg (yield 44%) as an oily substance.

$^1$H-NMR (CDCl$_3$): δ1.48 (3H, d, J=6.4 Hz), 2.18 (3H, s), 2.24 (3H, s), 2.70 (1H, dd, J=15.3, 7.7 Hz), 3.15-3.32 (9H, m), 3.80 (3H, s), 3.82 (3H, s), 4.88-5.02 (1H, m), 6.39-6.64 (3H, m), 7.19 (1H, t, J=8.1 Hz).

Example 53

1-(7-Ethoxy-2,4,6-trimethyl-2,3-dihydro-1-benzofuran-5-yl)-4-(4-methylphenyl)piperazine By using 5-bromo-7-ethoxy-2,4,6-trimethyl-2,3-dihydro-1-benzofuran (570 mg, 2.0 mmol) synthesized in Reference example 84 and 1-(4-methylphenyl)piperazine (704 mg, 4.0 mmol), the reaction was carried out in the same manner as Example 21 to synthesize the title compound 327 mg (yield 43%).

Melting point was 96 to 98° C. (ethanol-water).

$^1$H-NMR (CDCl$_3$): δ1.34 (3H, t, J=6.9 Hz), 1.47 (3H, d, J=6.4 Hz), 2.18 (3H, s), 2.24 (3H, s), 2.28 (3H, s), 2.69 (1H, dd, J=15.1, 7.5 Hz), 3.13-3.32 (9H, m), 4.05 (2H, q, J=6.9 Hz), 4.86-5.01 (1H, m), 6.87-6.94 (2H, m), 7.05-7.13 (2H, m).

Example 54

1-(7-Ethoxy-2,4,6-trimethyl-2,3-dihydro-1-benzofuran-5-yl)-4-(4-fluorophenyl)piperazine By using 5-bromo-7-ethoxy-2,4,6-trimethyl-2,3-dihydro-1-benzofuran (570 mg, 2.0 mmol) synthesized in Reference example 84 and 1-(4-fluorophenyl)piperazine (720 mg, 4.0 mmol), the reaction was carried out in the same manner as Example 21 to synthesize the title compound 467 mg (yield 61%). Melting point was 136 to 138° C. (ethanol-water).

$^1$H-NMR (CDCl$_3$): δ1.34 (3H, t, J=6.9 Hz), 1.47 (3H, d, J=6.0 Hz), 2.18 (3H, s), 2.24 (3H, s), 2.69 (1H, dd, J=15.1, 7.5 Hz), 3.13-3.29 (9H, m), 4.05 (2H, q, J=6.9 Hz), 4.87-5.00 (1H, m), 6.90-7.02 (4H, m).

Example 55

1-(4-Methoxyphenyl)-4-[2,4,6-trimethyl-7-(1-methylethoxy)-2,3-dihydro-1-benzofuran-5-yl]piperazine By using 5-bromo-2,4,6-trimethyl-7-(1-methylethoxy)-2,3-dihydro-1-benzofuran (598 mg, 2.0 mmol) synthesized in Reference example 85 and 1-(4-methoxyphenyl)piperazine (768 mg, 4.0 mmol), the was carried out in the same manner as Example 21 to synthesize the title compound 276 mg (yield 34%). Melting point was 110 to 112° C. (ethanol-water).

$^1$H-NMR (CDCl$_3$): δ1.27 (3H, d, J=6.1 Hz), 1.27 (3H, d, J=6.1 Hz), 1.45 (3H, d, J=6.4 Hz), 2.18 (3H, s), 2.22 (3H, s), 2.68 (1H, dd, J=15.1, 7.6 Hz), 3.07-3.33 (9H, m), 3.78 (3H, s), 4.46 (1H, spt, J=6.1 Hz), 4.85-4.98 (1H, m), 6.82-6.89 (2H, m), 6.93-7.00 (2H, m).

Example 56

1-(4-Ethoxyphenyl)-4-(7-methoxy-2,4,6-trimethyl-2,3-dihydro-1-benzofuran-5-yl)piperazine By using 1-(7-methoxy-2,4,6-trimethyl-2,3-dihydro-1-benzofuran-5-yl)piperazine (552 mg, 2.0 mmol) synthesized in Reference example 88 and 1-bromo-4-ethoxybenzene (804 mg, 4.0 mmol), the reaction was carried out in the same manner as Example 23 to synthesize the title compound 265 mg (yield 33%). Melting point was 117 to 119° C. (ethanol-water).

$^1$H-NMR (CDCl$_3$): δ1.39 (3H, t, J=7.0 Hz), 1.49 (3H, d, J=6.4 Hz), 2.19 (3H, s), 2.24 (3H, s), 2.70 (1H, dd, J=15.1, 7.5 Hz), 3.10-3.30 (9H, m), 3.82 (3H, s), 4.00 (2H, q, J=7.0 Hz), 4.89-5.02 (1H, m), 6.82-6.89 (2H, m), 6.91-6.98 (2H, m).

Example 57

1-(4-Methoxy-3-methylphenyl)-4-(7-methoxy-2,4,6-trimethyl-2,3-dihydro-1-benzofuran-5-yl)piperazine By using 1-(7-methoxy-2,4,6-trimethyl-2,3-dihydro-1-benzofuran-5-yl)piperazine (552 mg, 2.0 mmol) synthesized in Reference example 88 and 4-bromo-1-methoxy-2-methylbenzene (804 mg, 4.0 mmol), the reaction was carried out in the same manner as Example 23 to synthesize the title compound 323 mg (yield 41%). Melting point was 94 to 96° C. (ethanol-water).

$^1$H-NMR (CDCl$_3$): δ1.48 (3H, d, J=6.0 Hz), 2.19 (3H, s), 2.22 (3H, s), 2.25 (3H, s), 2.70 (1H, dd, J=15.1, 7.5 Hz), 3.08-3.32 (9H, m), 3.80 (3H, s), 3.82 (3H, s), 4.89-5.02 (1H, m), 6.74-6.89 (3H, m).

Example 58

1-(7-Methoxy-2,4,6-trimethyl-2,3-dihydro-1-benzofuran-5-yl)-4-[4-(trifluoromethyl)phenyl]piperazine By using 1-(7-methoxy-2,4,6-trimethyl-2,3-dihydro-1-benzofuran-5-yl)piperazine (552 mg, 2.0 mmol) synthesized in Reference example 88 and 1-bromo-4-(trifluoromethyl)benzene (900 mg, 4.0 mmol), the reaction was carried out in the same manner as Example 23 to synthesize the title compound 463 mg (yield 55%). Melting point was 142 to 145° C. (ethanol-water).

$^1$H-NMR (CDCl$_3$): δ1.49 (3H, d, J=6.0 Hz), 2.18 (3H, s), 2.24 (3H, s), 2.70 (1H, dd, J=15.3, 7.7 Hz), 3.16-3.41 (9H, m), 3.83 (3H, s), 4.89-5.03 (1H, m), 6.93-7.02 (2H, m), 7.47-7.54 (2H, m).

Example 59

1-(3-Fluoro-4-methoxyphenyl)-4-(7-methoxy-2,4,6-trimethyl-2,3-dihydro-1-benzofuran-5-yl)piperazine By using 1-(7-methoxy-2,4,6-trimethyl-2,3-dihydro-1-benzofuran-5-yl)piperazine (552 mg, 2.0 mmol) synthesized in Reference example 88 and 4-bromo-2-fluoro-1-methoxybenzene (720 mg, 4.0 mmol), the reaction was carried out in the same manner as Example 23 to synthesize the title compound 309 mg (yield 39%). Melting point was 120 to 122° C. (ethanol-water).

$^1$H-NMR (CDCl$_3$): δ1.48 (3H, d, J=6.4 Hz), 2.18 (3H, s), 2.24 (3H, s), 2.70 (1H, dd, J=15.1, 7.5 Hz), 3.09-3.29 (9H, m), 3.82 (3H, s), 3.85 (3H, s), 4.88-5.03 (1H, m), 6.64-6.70 (1H, m), 6.78 (1H, dd, J=14.1, 2.8 Hz), 6.90 (1H, t, J=9.2 Hz).

Example 60

1-(7-Ethoxy-2,4,6-trimethyl-2,3-dihydro-1-benzofuran-5-yl)-4-(4-methoxy-3-methylphenyl)piperazine By using 1-(7-ethoxy-2,4,6-trimethyl-2,3-dihydro-1-benzofuran-5-yl)piperazine (580 mg, 2.0 mmol) synthesized in Reference example 88 and 4-bromo-1-methoxy-2-methylbenzene (804 mg, 4.0 mmol), the reaction was carried out in the same manner as Example 23 to synthesize the title compound 375 mg (yield 46%). Melting point was 80 to 83° C. (ethanol-water).

$^1$H-NMR (CDCl$_3$): δ1.34 (3H, t, J=7.2 Hz), 1.47 (3H, d, J=6.4 Hz), 2.19 (3H, s), 2.22 (3H, s), 2.24 (3H, s), 2.69 (1H, dd, J=15.1, 7.5 Hz), 3.08-3.29 (9H, m), 3.80 (3H, s), 4.05 (2H, q, J=7.2 Hz), 4.86-5.00 (1H, m), 6.73-6.90 (3H, m).

Example 61

1-(4-Ethoxyphenyl)-4-(7-ethoxy-2,4,6-trimethyl-2,3-dihydro-1-benzofuran-5-yl)piperazine By using 1-(7-ethoxy-2,4,6-trimethyl-2,3-dihydro-1-benzofuran-5-yl)piperazine (580 mg, 2.0 mmol) synthesized in Reference example 89 and 1-bromo-4-ethoxybenzene (804 mg, 4.0 mmol), the reaction was carried out in the same manner as Example 23 to synthesize the title compound 532 mg (yield 65%). Melting point was 121 to 122° C. (ethanol-water).

$^1$H-NMR (CDCl$_3$): δ1.34 (3H, t, J=7.0 Hz), 1.39 (3H, t, J=7.0 Hz), 1.47 (3H, d, J=6.4 Hz), 2.19 (3H, s), 2.24 (3H, s), 2.69 (1H, dd, J=15.1, 7.5 Hz), 3.08-3.30 (9H, m), 3.95-4.10 (4H, m), 4.86-5.00 (1H, m), 6.81-6.99 (4H, m).

Example 62

1-(7-Methoxy-2,2,4,6-tetramethyl-2,3-dihydro-1-benzofuran-5-yl)-4-(4-methylphenyl)piperazine By using 5-bromo-7-methoxy-2,2,4,6-tetramethyl-2,3-dihydro-1-benzofuran (1.80 g, 6.31 mmol) synthesized in Reference example 94 and 1-(4-methylphenyl)piperazine (2.22 g, 12.6 mmol), the reaction was carried out in the same manner as Example 1 to synthesize the title compound 1.32 g (yield 55%).

Melting point was 150 to 152° C. (hexane-ethyl acetate).

$^1$H-NMR (CDCl$_3$): δ1.49 (6H, s), 2.17 (3H, s), 2.24 (3H, s), 2.28 (3H, s), 2.90 (2H, s), 3.12-3.28 (8H, m), 3.81 (3H, s), 6.90 (2H, d, J=8.4 Hz), 7.09 (2H, d, J=8.4 Hz).

Example 63

1-(4-Fluorophenyl)-4-(7-methoxy-2,2,4,6-tetramethyl-2,3-dihydro-1-benzofuran-5-yl)piperazine By using 5-bromo-7-methoxy-2,2,4,6-tetramethyl-2,3-dihydro-1-benzofuran (600 mg, 2.10 mmol) synthesized in Reference example 94 and 1-(4-fluorophenyl)piperazine (757 mg, 4.20 mmol), the reaction was carried out in the same manner as Example 1 to synthesize the title compound 397 mg (yield 49%).

Melting point was 137 to 139° C. (hexane-ethyl acetate).
$^1$H-NMR (CDCl$_3$): δ1.49 (6H, s), 2.17 (3H, s), 2.24 (3H, s), 2.94 (2H, s), 3.10-3.30 (8H, m), 3.81 (3H, s), 6.88-7.05 (4H, m).

Example 64

1-(4-Ethylphenyl)-4-(7-methoxy-2,2,4,6-tetramethyl-2,3-dihydro-1-benzofuran-5-yl)piperazine By using 1-(7-methoxy-2,2,4,6-tetramethyl-2,3-dihydro-1-benzofuran-5-yl)piperazine (400 mg, 1.38 mmol) synthesized in Reference example 96 and 1-bromo-4-ethylbenzene (383 mg, 2.07 mmol), the reaction was carried out in the same manner as Reference example 59 to synthesize the title compound 133 mg (yield 25%). Melting point was 157 to 160° C. (hexane-ethyl acetate).

$^1$H-NMR (CDCl$_3$): δ1.22 (3H, t, J=7.5 Hz), 1.49 (6H, s), 2.17 (3H, s), 2.24 (3H, s), 2.59 (2H, q, J=7.5 Hz), 2.91 (2H, s), 3.15-3.30 (8H, m), 3.81 (3H, s), 6.93 (2H, d, J=8.7 Hz), 7.12 (2H, d, J=8.7 Hz).

Example 65

1-(4-Ethoxyphenyl)-4-(7-methoxy-2,2,4,6-tetramethyl-2,3-dihydro-1-benzofuran-5-yl)piperazine By using 1-(7-methoxy-2,2,4,6-tetramethyl-2,3-dihydro-1-benzofuran-5-yl)piperazine (400 mg, 1.38 mmol) synthesized in Reference example 96 and 1-bromo-4-ethoxybenzene (416 mg, 2.07 mmol), the reaction was carried out in the same manner as Reference example 59 to synthesize the title compound 123 mg (yield 22%). That is, sodium t-butoxide (398 mg, 4.14 mmol) was added to a mixture of toluene (30 mL) containing 1-(7-methoxy-2,2,4,6-tetramethyl-2,3-dihydro-1-benzofuran-5-yl)piperazine (400 mg, 1.38 mmol), 1-bromo-4-ethoxybenzene (416 mg, 2.07 mmol), palladium acetate (15 mg, 0.069 mmol) and BINAP (129 mg, 0.207 mmol), and the mixture was stirred under argon atmosphere and under heated reflux for 12 hours. After cooled to room temperature, saturated saline was added to the reaction solution, and extraction was performed using ethyl acetate. The organic layer was dried using anhydrous magnesium sulfate. The solvent was removed under reduced pressure, and the obtained residue was purified by silica gel chromatography (hexane-ethyl acetate 100:0-80:20). Crystallization was performed using ethyl acetate-hexane to give 123 mg of the title compound as a colorless crystal (yield: 22%). Melting point was 152 to 154° C.

$^1$H-NMR (CDCl$_3$): δ1.39 (3H, t, J=7.2 Hz), 1.49 (6H, s), 2.17 (3H, s), 2.24 (3H, s), 2.90 (2H, s), 3.06-3.30 (8H, m), 3.81 (3H, s), 4.00 (2H, q, J=7.2 Hz), 6.85 (2H, d, J=9.0 Hz), 6.95 (2H, d, J=9.0 Hz).

Example 66

1-(7-Methoxy-2,2,4,6-tetramethyl-2,3-dihydro-1-benzofuran-5-yl)-4-[4-(trifluoromethoxy)phenyl]piperazine By using 1-(7-methoxy-2,2,4,6-tetramethyl-2,3-dihydro-1-benzofuran-5-yl)piperazine (436 mg, 1.50 mmol) synthesized in Reference example 96 and 1-bromo-4-(trifluoromethoxy)benzene (542 mg, 2.25 mmol), the reaction was carried out in the same manner as Reference example 59 to synthesize the title compound 160 mg (yield 16%). Melting point was 162 to 164° C. (hexane).

$^1$H-NMR (CDCl$_3$): δ1.50 (6H, s), 2.16 (3H, s), 2.24 (3H, s), 2.91 (2H, s), 3.20-3.28 (8H, m), 3.81 (3H, s), 6.94 (2H, d, J=9.0 Hz), 7.12 (2H, d, J=9.0 Hz).

Example 67

1-[4-(Difluoromethoxy)phenyl]-4-(7-methoxy-2,2,4,6-tetramethyl-2,3-dihydro-1-benzofuran-5-yl)piperazine By using 1-(7-methoxy-2,2,4,6-tetramethyl-2,3-dihydro-1-benzofuran-5-yl)piperazine (436 mg, 1.50 mmol) synthesized in Reference example 96 and 1-bromo-4-(difluoromethoxy)benzene (524 mg, 2.25 mmol), the reaction was carried out in the same manner as Reference example 59 to synthesize the title compound 12.9 mg (yield 1%). Melting point was 151 to 152° C. (hexane).

$^1$H-NMR (CDCl$_3$): δ1.50 (6H, s), 2.16 (3H, s), 2.24 (3H, s), 2.91 (2H, s), 3.17-3.28 (8H, m), 3.81 (3H, s), 6.43 (1H, s), 6.95 (2H, d, J=9.0 Hz), 7.06 (2H, d, J=9.0 Hz).

Example 68

1-(7-Methoxy-2,2,4,6-tetramethyl-2,3-dihydro-1-benzofuran-5-yl)-4-[4-(trifluoromethyl)phenyl]piperazine By using 1-(7-methoxy-2,2,4,6-tetramethyl-2,3-dihydro-1-benzofuran-5-yl)piperazine (436 mg, 1.50 mmol) synthesized in Reference example 96 and 1-bromo-4-(trifluoromethyl)benzene (506 mg, 2.25 mmol), the reaction was carried out in the same manner as Reference example 59 to synthesize the title compound 389 mg (yield 40%). Melting point was 186 to 187° C. (hexane).

$^1$H-NMR (CDCl$_3$): δ1.50 (6H, s), 2.16 (3H, s), 2.24 (3H, s), 2.91 (2H, s), 3.16-3.43 (8H, m), 3.81 (3H, s), 6.97 (2H, d, J=8.7 Hz), 7.49 (2H, d, J=8.7 Hz).

Example 69

1-(2,3-Dihydro-1,4-benzodioxin-6-yl)-4-(7-methoxy-2,2,4,6-tetramethyl-2,3-dihydro-1-benzofuran-5-yl)piperazine By using 1-(7-methoxy-2,2,4,6-tetramethyl-2,3-dihydro-1-benzofuran-5-yl)piperazine (436 mg, 1.50 mmol) synthesized in Reference example 96 and 6-bromo-2,3-dihydro-1,4-benzodioxine (484 mg, 2.25 mmol), the reaction was carried out in the same manner as Reference example 59 to synthesize the title compound 143 mg (yield 15%). Melting point was 167 to 168° C. (hexane).

$^1$H-NMR (CDCl$_3$): δ1.49 (6H, s), 2.16 (3H, s), 2.24 (3H, s), 2.90 (2H, s), 3.08-3.28 (8H, m), 3.80 (3H, s), 4.17-4.28 (4H, m), 6.49-6.57 (2H, m), 6.75-6.83 (1H, m).

Example 70

1-(7-Ethoxy-2,2,4,6-tetramethyl-2,3-dihydro-1-benzofuran-5-yl)-4-(4-methylphenyl)piperazine By using 5-bromo-7-ethoxy-2,2,4,6-tetramethyl-2,3-dihydro-1-benzofuran (500 mg, 1.67 mmol) synthesized in Reference example 98 and 1-(4-methylphenyl)piperazine (589 mg, 3.34 mmol), the reaction was carried out in the same manner as Example 1 to synthesize the title compound 149 mg (yield 23%).

Melting point was 152 to 155° C. (hexane).
$^1$H-NMR (CDCl$_3$): δ1.33 (3H, t, J=6.9 Hz), 1.48 (6H, s), 2.16 (3H, s), 2.24 (3H, s), 2.28 (3H, s), 2.89 (2H, s), 3.10-3.30 (8H, m), 4.04 (2H, q, J=6.9 Hz), 6.90 (2H, d, J=8.7 Hz), 7.09 (2H, d, J=8.7 Hz).

Example 71

1-(7-Ethoxy-2,2,4,6-tetramethyl-2,3-dihydro-1-benzofuran-5-yl)-4-(4-fluorophenyl)piperazine By using 5-bromo-7-ethoxy-2,2,4,6-tetramethyl-2,3-dihydro-1-benzofuran (600 mg, 2.01 mmol) synthesized in Reference example 98 and 1-(4-fluorophenyl)piperazine (723 mg, 4.01 mmol), the reaction was carried out in the same manner as Example 1 to synthesize the title compound 327 mg (yield 41%).

Melting point was 163 to 165° C. (hexane-ethyl acetate).
$^1$H-NMR (CDCl$_3$): δ1.33 (3H, t, J=7.2 Hz), 1.48 (6H, s), 2.16 (3H, s), 2.24 (3H, s), 2.89 (2H, s), 3.10-3.30 (8H, m), 4.05 (2H, q, J=7.2 Hz), 6.85-7.05 (4H, m).

Example 72

2,2,4,6-Tetramethyl-5-[4-(4-methylphenyl)piperazin-1-yl]-2,3-dihydro-1-benzofuran-7-ol To 1-(7-methoxy-2,2,4,6-tetramethyl-2,3-dihydro-1-benzofuran-5-yl)-4-(4-methylphenyl)piperazine (444 mg, 1.18 mmol) synthesized in Example 62, acetic acid (7 mL) and 48% aqueous solution of hydrobromic acid (7 ml) were added, followed by stirring at 100° C. for 12 hours. After cooling to room temperature, aqueous solution of saturated sodium hydrogen carbonate was added to the mixture solution, and then the mixture solution was extracted with ethyl acetate. The extract solution was dried over anhydrous magnesium sulfate. The solvent was removed by distillation under reduced pressure. The resulting residue was purified by silica gel column chromatography (hexane-ethyl acetate 100:0-90:10) and the resulting solids were recrystallized from hexane-ethyl acetate to obtain the title compound 71.0 mg (yield 16%). Melting point was 185 to 189° C.
$^1$H-NMR (CDCl$_3$): δ1.48 (6H, s), 2.15 (3H, s), 2.24 (3H, s), 2.28 (3H, s), 2.94 (2H, s), 3.12-3.35 (8H, m), 4.64 (1H, br s), 6.91 (2H, d, J=8.7 Hz), 7.09 (2H, d, J=8.7 Hz).

Example 73

2-(4-Methoxyphenyl)-4-(2,2,6,7-tetramethyl-2,3-dihydro-1-benzofuran-5-yl)morpholine By using 5-[2-(4-methoxyphenyl)morpholin-4-yl]-2,2,6,7-tetramethyl-1-benzofuran-3(2H)-one (200 mg, 0.524 mmol) synthesized in Reference example 99, the reaction was carried out in the same manner as Example 5 to synthesize the title compound 96.1 mg (yield 50%).

$^1$H-NMR (CDCl$_3$): δ1.43 (3H, s), 1.45 (3H, s), 2.12 (3H, s), 2.26 (3H, s), 2.76 (1H, dd, J=11.7, 9.9 Hz), 2.81-2.90 (2H, m), 2.90-3.04 (3H, m), 3.80 (3H, s), 3.94-4.04 (1H, m), 4.05-4.13 (1H, m), 4.66 (1H, dd, J=10.2, 2.4 Hz), 6.76 (1H, s), 6.88 (2H, d, J=8.7 Hz), 7.32 (2H, d, J=8.7 Hz).

Example 74

1-(4-Methoxyphenyl)-4-(2,2,4,7-tetramethyl-2,3-dihydro-1-benzofuran-5-yl)piperazine By using 5-bromo-2,2,4,7-tetramethyl-2,3-dihydro-1-benzofuran (510 mg, 2.00 mmol) synthesized in Reference example 103 and 1-(4-methoxyphenyl)piperazine (769 mg, 4.00 mmol), the reaction was carried out in the same manner as Example 1 to synthesize the title compound 540 mg (yield 74%).

Melting point was 174 to 175° C. (hexane-ethyl acetate).
$^1$H-NMR (CDCl$_3$): δ1.47 (6H, s), 2.16 (6H, s), 2.92 (2H, s), 3.05 (4H, m), 3.13-3.27 (4H, m), 3.78 (3H, s), 6.71 (1H, s), 6.86 (2H, d, J=9.0 Hz), 6.96 (2H, d, J=8.7 Hz).

Example 75

2-(4-Methoxyphenyl)-4-(2,2,4,7-tetramethyl-2,3-dihydro-1-benzofuran-5-yl)morpholine By using 5-bromo-2,2,4,7-tetramethyl-2,3-dihydro-1-benzofuran (510 mg, 2.00 mmol) synthesized in Reference example 103 and 2-(4-methoxyphenyl)morpholine (773 mg, 4.00 mmol), the reaction was carried out in the same manner as Example 1 to synthesize the title compound 412 mg (yield 56%).

Melting point was 107 to 108° C. (methanol).
$^1$H-NMR (CDCl$_3$): δ1.45 (3H, s), 1.47 (3H, s), 2.13 (3H, s), 2.18 (3H, s), 2.72-2.81 (1H, m), 2.84-2.95 (4H, m), 2.96-3.05 (1H, m), 3.80 (3H, s), 3.91-4.04 (1H, m), 4.06-4.15 (1H, m), 4.58-4.70 (1H, m), 6.64 (1H, s), 6.88 (2H, d, J=8.7 Hz), 7.33 (2H, d, J=8.7 Hz).

Example 76

1-(3-Tert-butyl-2,2,4,6,7-pentamethyl-2,3-dihydro-1-benzofuran-5-yl)-4-(4-methoxyphenyl)piperazine To trifluoroacetic acid (4 mL), 3-tert-butyl-5-[4-(4-methoxyphenyl)piperazin-1-yl]-2,2,4,6,7-pentamethyl-2,3-dihydro-1-benzofuran-3-ol (400 mg, 0.883 mmol) obtained in Reference example 104 was added under ice cooling. After adding triethylsilane (0.6 mL, 3.76 mmol) thereto, the temperature was raised to room temperature. The reaction solution was stirred for 15 minutes at room temperature and concentrated under reduced pressure. To the residue, 2M aqueous solution of potassium carbonate was added to alkalify the aqueous layer, followed by extraction with ethyl acetate. The organic layer was washed with water and saturated brine and dried over anhydrous sodium sulfate. After the concentration under reduced pressure, the resulting residue was purified by thin layer silica gel column chromatography (hexane:ethyl acetate=10:1) and crystallized from ethanol to obtain the title compound 120 mg (yield 31%). Melting point was 144 to 146° C.
$^1$H-NMR (CDCl$_3$) δ: 0.94 (9H, s), 1.17 (3H, s), 1.73 (3H, s), 2.07 (3H, s), 2.21 (3H, s), 2.24 (3H, s), 2.53 (1H, s), 3.02-3.44 (8H, m), 3.79 (3H, s), 6.86 (2H, d, J=9.2 Hz), 6.98 (2H, d, J=9.2 Hz).

Example 77

1-(2,2,3,4,6,7-Hexamethyl-2,3-dihydro-1-benzofuran-5-yl)-4-(4-methoxyphenyl)piperazine To the ethyl acetate (5 mL) suspension of 1-(4-methoxyphenyl)-4-(2,2,4,6,7-pentamethyl-3-methyliene-2,3-dihydro-1-benzofuran-5-yl)piperazine (400 mg, 1.02 mmol) obtained in Reference example 106, 10%-hydrogen chloride/methanol solution (5 mL) was added and the mixture was concentrated under reduced pressure. The residue was dissolved in methanol (20 mL), added with 10%-palladium carbon (comprising 50% moisture, 100 mg), and then stirred at room temperature for 6 hours under 4 to 5 atm of hydrogen. The catalyst was removed by filtration and the filtrate was concentrated under reduced pressure. To the residue, 10% aqueous solution of potassium carbonate was added to alkalify the aqueous layer, followed by extraction with ethyl acetate. The organic layer was washed with water and saturated brine and dried over anhydrous sodium sulfate. After the concentration under reduced pressure, the resulting residue was crystallized from ethanol to obtain the title compound 340 mg (yield 85%). Melting point was 141 to 143° C.

$^1$H-NMR (CDCl$_3$) δ: 1.12 (3H, d, J=7.0 Hz), 1.31 (3H, s), 1.43 (3H, s), 2.08 (3H, s), 2.23 (3H, s), 2.26 (3H, s), 2.96 (1H, q, J=7.0 Hz), 3.04-3.38 (8H, m), 3.78 (3H, s), 6.86 (2H, d, J=9.2 Hz), 6.98 (2H, d, J=9.2 Hz).

Example 78

1-(4-Methoxyphenyl)-4-(4,6,7-trimethyl-2,3-dihydro-1-benzofuran-5-yl)piperazine

To the THF (2 ml) solution of lithium aluminum hydride (68 mg, 1.80 mmol), aluminum chloride (240 mg, 1.80 mmol) was added under ice cooling. After stirring for 10 minutes at 0° C., THF (4 ml) solution of 5-[4-(4-methoxyphenyl)piperazin-1-yl]-4,6,7-trimethyl-1-benzofuran-3(2H)-one (220 mg, 0.600 mmol) synthesized in Reference example 109 was added. The mixture was stirred for 3 hours under reflux. After cooling to room temperature, water was added to the reaction solution, and 0.5 N aqueous solution of sodium hydroxide was further added to the reaction solution. The mixture was stirred for 30 minutes at room temperature and extracted with ethyl acetate-diethyl ether (1/1) mixture solvent. The extract solution was washed with saturated brine, dried over anhydrous magnesium sulfate, and then concentrated under reduced pressure. The residue was dissolved in ethyl acetate (20 ml), added with 10%-palladium carbon (comprising 50% moisture, 200 mg), and then the mixture was stirred at 60° C. for 15 hours under hydrogen atmosphere. After cooling to room temperature, palladium carbon was removed by filtration and the filtrate was concentrated under reduced pressure. The residue was purified by silica gel chromatography (hexane-ethyl acetate 95:5-80/20) to obtain the title compound 35 mg (yield 17%).

$^1$H-NMR (CDCl$_3$): δ2.10 (3H, s), 2.25 (6H, s), 3.05-3.35 (10H, m), 3.78 (3H, s), 4.54 (2H, t, J=8.7 Hz), 6.82-6.91 (2H, m), 6.92-7.01 (2H, m).

Example 79

1-(2-Ethyl-2,4,6,7-tetramethyl-2,3-dihydro-1-benzofuran-5-yl)-4-(4-methoxyphenyl)piperazine By using 2-ethyl-5-[4-(4-methoxyphenyl)piperazin-1-yl]-2,4,6,7-tetramethyl-1-benzofuran-3(2H)-one (120 mg, 0.294 mmol) synthesized in Reference example 116, the reaction was carried out in the same manner as Example 5 to obtain the title compound 50 mg (yield 43%). Melting point was 106 to 110° C. (ethyl acetate-hexane).

$^1$H-NMR (CDCl$_3$): δ0.96 (3H, t, J=7.2 Hz), 1.40 (3H, s), 1.66-1.81 (2H, m), 2.09 (3H, s), 2.20 (3H, s), 2.24 (3H, s), 2.80 (1H, d, J=15.3 Hz), 2.95 (1H, d, J=15.3 Hz), 3.07-3.34 (8H, m), 3.78 (3H, s), 6.81-6.91 (2H, m), 6.92-7.02 (2H, m).

Example 80

1-{5-[4-(4-Methoxyphenyl)piperazin-1-yl]-2,2,4,6-tetramethyl-2,3-dihydro-1-benzofuran-7-yl}ethanone By using 1-(5-bromo-2,2,4,6-tetramethyl-2,3-dihydro-1-benzofuran-7-yl)ethanone (440 mg, 1.48 mmol) synthesized in Reference example 121, the reaction was carried out in the same manner as Example 1 to obtain the title compound 100 mg (yield 17%).

Melting point was 156 to 159° C. (ethyl acetate-hexane).

$^1$H-NMR (CDCl$_3$): δ1.48 (6H, s), 2.22 (3H, s), 2.30 (3H, s), 2.54 (3H, s), 2.89 (2H, s), 3.07-3.30 (8H, m), 3.78 (3H, s), 6.82-6.90 (2H, m), 6.92-7.00 (2H, m).

Example 81

1-{5-[4-(4-Methoxyphenyl)piperazin-1-yl]-2,2,4,6-tetramethyl-2,3-dihydro-1-benzofuran-7-yl}ethanol To the THF (1.5 ml)/methanol (1.5 ml) mixture solution of 1-{5-[4-(4-methoxyphenyl)piperazin-1-yl]-2,2,4,6-tetramethyl-2,3-dihydro-1-benzofuran-7-yl}ethanone (120 mg, 0.294 mmol) synthesized in Example 80, sodium borohydride (133 mg, 3.52 mmol) was added and the mixture was stirred for 3 hours at room temperature. After diluting the reaction solution with water, THF and methanol in the reaction solution was removed by distillation under reduced pressure. The residue was extracted with ethyl acetate. The extract solution was washed with saturated brine, dried over anhydrous magnesium sulfate, and then solvent was removed by distillation under reduced pressure. The residue was purified by silica gel chromatography (hexane-ethyl acetate 99:1-80/20) and crystallized from ethyl acetate-hexane to obtain the title compound 60 mg (yield 50%). Melting point was 183 to 186° C.

$^1$H-NMR (CDCl$_3$): δ1.48 (3H, d, J=6.6 Hz), 1.49 (3H, s), 1.50 (3H, s), 2.20 (3H, s), 2.27 (3H, s), 2.88 (2H, s), 3.03-3.38 (8H, m), 3.78 (3H, s), 3.80 (1H, d, J=11.1 Hz), 4.89-5.03 (1H, m), 6.82-6.90 (2H, m), 6.92-7.00 (2H, m).

Example 82

2-Chloro-4-[4-(2,2,4,6,7-pentamethyl-2,3-dihydro-1-benzofuran-5-yl)piperazin-1-yl]pyrimidine

Example 83

4-Chloro-2-[4-(2,2,4,6,7-pentamethyl-2,3-dihydro-1-benzofuran-5-yl)piperazin-1-yl]pyrimidine To the DMF (10 mL) solution of 1-(2,2,4,6,7-pentamethyl-2,3-dihydro-1-benzofuran-5-yl)piperazine (1.92 g, 7.00 mmol) synthesized in Reference example 61, 2,4-dichloropyrimidine (1.04 g, 7.00 mmol) and triethylamine (1.07 mL, 7.70 mmol) were added and the mixture was stirred at room temperature for 1 hour. To the mixture solution, water was added. The extraction was carried out by using ethyl acetate, and the extract was dried over anhydrous magnesium sulfate.

Then, the solvent was removed by distillation under reduced pressure. The resulting residue was purified by silica gel column chromatography (hexane-ethyl acetate 95:5-85:15) to obtain 2-chloro-4-[4-(2,2,4,6,7-pentamethyl-2,3-dihydro-1-benzofuran-5-yl)piperazin-1-yl]pyrimidine 1.68 g (ethyl acetate/hexane=4:1, Rf=0.1, yield 62%) and 4-chloro-2-[4-(2,2,4,6,7-pentamethyl-2,3-dihydro-1-benzofuran-5-yl)piperazin-1-yl]pyrimidine 100 mg (ethyl acetate/hexane=4:1, Rf=0.5, yield 4%).

2-Chloro-4-[4-(2,2,4,6,7-pentamethyl-2,3-dihydro-1-benzofuran-5-yl)piperazin-1-yl]pyrimidine Melting point was 192 to 193° C. (ethyl acetate-hexane).
$^1$H-NMR (CDCl$_3$): δ1.46 (6H, s), 2.08 (3H, s), 2.15 (3H, s), 2.21 (3H, s), 2.90 (3H, s), 3.05-3.25 (4H, m), 3.60-3.97 (4H, m), 6.42 (1H, d, J=6.3 Hz), 8.04 (1H, d, J=6.3 Hz).

4-Chloro-2-[4-(2,2,4,6,7-pentamethyl-2,3-dihydro-1-benzofuran-5-yl)piperazin-1-yl]pyrimidine $^1$H-NMR (CDCl$_3$): δ1.46 (6H, s), 2.08 (3H, s), 2.16 (3H, s), 2.22 (3H, s), 2.90 (3H, s), 3.05-3.22 (4H, m), 3.78-3.90 (2H, m), 3.95-4.05 (2H, m), 6.49 (1H, d, J=5.1 Hz), 8.16 (1H, d, J=5.1 Hz).

Example 84

2-(4-Methoxyphenyl)-4-[4-(2,2,4,6,7-pentamethyl-2,3-dihydro-1-benzofuran-5-yl)piperazin-1-yl]pyrimidine By using 2-chloro-4-[4-(2,2,4,6,7-pentamethyl-2,3-dihydro-1-benzofuran-5-yl)piperazin-1-yl]pyrimidine (200 mg, 0.517 mmol) synthesized in Example 82 and (4-methoxyphenyl)borate (157 mg, 1.03 mmol), the reaction was carried out in the same manner as Reference example 22 to synthesis the title compound 54.9 mg (yield 12%). Melting point was 240 to 242° C. (ethyl acetate-hexane).
$^1$H-NMR (CDCl$_3$): δ1.46 (6H, s), 2.09 (3H, s), 2.17 (3H, s), 2.23 (3H, s), 2.91 (3H, s), 3.10-3.30 (4H, m), 3.70-4.00 (7H, m), 6.41 (1H, d, J=6.0 Hz), 6.97 (2H, d, J=9.0 Hz), 8.29 (1H, d, J=6.0 Hz), 8.36 (2H, d, J=9.0 Hz).

Example 85

4-(4-Methoxyphenyl)-2-[4-(2,2,4,6,7-pentamethyl-2,3-dihydro-1-benzofuran-5-yl)piperazin-1-yl]pyrimidine By using 1-(2,2,4,6,7-pentamethyl-2,3-dihydro-1-benzofuran-5-yl)piperazine (100 mg, 0.258 mmol) synthesized in Example 83 and (4-methoxyphenyl)borate (78.4 mg, 0.516 mmol), the reaction was carried out in the same manner as Reference example 22 to obtain the title compound 47.9 mg (yield 40%). Melting point was 156 to 159° C. (ethyl acetate-hexane).
$^1$H-NMR (CDCl$_3$): δ1.46 (6H, s), 2.09 (3H, s), 2.18 (3H, s), 2.24 (3H, s), 2.91 (3H, s), 3.07-3.30 (4H, m), 3.80-4.00 (5H, m), 4.40-4.20 (2H, m), 6.88 (1H, d, J=5.1 Hz), 6.98 (2H, d, J=8.7 Hz), 8.05 (2H, d, J=8.7 Hz), 8.34 (1H, d, J=5.1 Hz).

Example 86

1-(2,4,6,7-Tetramethyl-2,3-dihydro-1-benzofuran-5-yl)-4-(1,3,4-thiadiazol-2-yl)piperazine By using 1-(2,4,6,7-tetramethyl-2,3-dihydro-1-benzofuran-5-yl)piperazine (130 mg, 0.50 mmol) synthesized in Reference example 56 and 2-bromo-1,3,4-thiadiazole (165 mg, 1.0 mmol), the reaction was carried out in the same manner as Example 23 to synthesis the title compound 24 mg (yield 14%).
Melting point was 203 to 205° C. (hexane-ethyl acetate).
$^1$H-NMR (CDCl$_3$): δ1.46 (3H, d, J=6.0 Hz), 2.09 (3H, s), 2.18 (3H, s), 2.22 (3H, s), 2.70 (1H, dd, J=15.1, 7.9 Hz), 3.12-3.31 (5H, m), 3.60-3.76 (4H, m), 4.82-4.96 (1H, m), 8.47 (1H, s).

Example 87

1-(2,2,4,6,7-Pentamethyl-2,3-dihydro-1-benzofuran-5-yl)-4-(3-phenyl-1,2,4-thiadiazol-5-yl)piperazine By using 5-bromo-2,2,4,6,7-pentamethyl-2,3-dihydro-1-benzofuran (269 mg, 0.999 mmol) synthesized in Reference example 4 and 1-(3-phenyl-1,2,4-thiadiazol-5-yl)piperazine 2 hydrochloric acid salt (640 mg, 2.00 mmol), the reaction was carried out in the same manner as Example 21 to synthesis the title compound 50.4 mg (yield 12%). Melting point was 204 to 205° C. (hexane-acetone).
$^1$H-NMR (CDCl$_3$): δ1.46 (6H, s), 2.09 (3H, s), 2.17 (3H, s), 2.23 (3H, s), 2.91 (2H, s), 3.15-3.34 (4H, m), 3.60-3.80 (4H, m), 7.37-7.50 (3H, m), 8.15-8.25 (2H, m).

Example 88

1-(2,2,4,6,7-Pentamethyl-2,3-dihydro-1-benzofuran-5-yl)-4-(1,3-thiazol-2-yl)piperazine By using 5-bromo-2,2,4,6,7-pentamethyl-2,3-dihydro-1-benzofuran (404 mg, 1.50 mmol) synthesized in Reference example 4 and 1-(1,3-thiazol-2-yl)piperazine (508 mg, 3.00 mmol), the reaction was carried out in the same manner as Example 21 to synthesis the title compound 196 mg (yield 36%). Melting point was 150 to 151° C. (hexane-ethyl acetate).
$^1$H-NMR (CDCl$_3$): δ1.46 (6H, s), 2.08 (3H, s), 2.16 (3H, s), 2.22 (3H, s), 2.90 (2H, s), 3.10-3.30 (4H, m), 3.50-3.70 (4H, m), 6.88-7.03 (4H, m), 6.58 (1H, d, J=3.6 Hz), 7.22 (1H, d, J=3.6 Hz).

Example 89

1-[4-(Methylsulfanyl)phenyl]-4-(2,2,4,6,7-pentamethyl-2,3-dihydro-1-benzofuran-5-yl)piperazine By using 1-(2,2,4,6,7-pentamethyl-2,3-dihydro-1-benzofuran-5-yl)piperazine (1.37 g, 5.0 mmol) synthesized in Reference example 61 and 4-bromothioanisole (1.52 g, 7.5 mmol), the reaction was carried out in the same manner as Example 23 to synthesize the title compound 1.2 g (yield 60%). Melting point was 211 to 213° C. (ethanol).
$^1$H-NMR (CDCl$_3$): δ1.46 (6H, s), 2.08 (3H, s), 2.18 (3H, s), 2.23 (3H, s), 2.45 (3H, s), 2.91 (2H, s), 3.15-3.33 (8H, m), 6.89-6.97 (2H, m), 7.23-7.31 (2H, m).

Example 90

4-[4-(2,2,4,6,7-Pentamethyl-2,3-dihydro-1-benzofuran-5-yl)piperazin-1-yl]benzonitrile By using 1-(2,2,4,6,7-pentamethyl-2,3-dihydro-1-benzofuran-5-yl)piperazine (2.74 g, 10.0 mmol) synthesized in Reference example 61 and 4-bromobenzonitrile (2.73 g, 15 mmol), the reaction was carried out in the same manner as Example 23 to synthesis the title compound 700 mg (yield 19%). Melting point was 255 to 257° C. (ethanol).

¹H-NMR (CDCl₃): δ1.46 (6H, s), 2.08 (3H, s), 2.17 (3H, s), 2.22 (3H, s), 2.91 (2H, s), 3.14-3.51 (8H, m), 6.87-6.95 (2H, m), 7.46-7.55 (2H, m).

Example 91

1-[4-(Methylsulfinyl)phenyl]-4-(2,2,4,6,7-pentamethyl-2,3-dihydro-1-benzofuran-5-yl)piperazine To the THF/ethyl acetate (1:1, 6.0 mL) solution of 1-[4-(methylsulfanyl)phenyl]-4-(2,2,4,6,7-pentamethyl-2,3-dihydro-1-benzofuran-5-yl)piperazine (200 mg, 0.50 mmol) synthesized in Example 89, m-chloroperbenzoic acid (70%, 124 mg, 0.50 mmol) was added under ice cooling, followed by stirring for 2 hours. The reaction solution was added with an aqueous solution of sodium hydrogen carbonate, and extracted with ethyl acetate. The organic layer was washed with saturated brine, and then dried over sodium sulfate. The solvent was removed by distillation under reduced pressure. The resulting residue was purified by silica gel column chromatography (ethyl acetate) and the resulting solids were recrystallized from hexane-THF to obtain the title compound 94 mg (yield 46%). Melting point was 223 to 227° C. (hexane-THF).

¹H-NMR (CDCl₃): δ1.46 (6H, s), 2.09 (3H, s), 2.18 (3H, s), 2.23 (3H, s), 2.71 (3H, s), 2.91 (2H, s), 3.14-3.47 (8H, m), 7.02-7.08 (2H, m), 7.52-7.59 (2H, m).

Example 92

1-[4-(Methylsulfonyl)phenyl]-4-(2,2,4,6,7-pentamethyl-2,3-dihydro-1-benzofuran-5-yl)piperazine By using 1-[4-(methylsulfinyl)phenyl]-4-(2,2,4,6,7-pentamethyl-2,3-dihydro-1-benzofuran-5-yl)piperazine (200 mg, 0.50 mmol) synthesized in Example 91 and 70% m-chloroperbenzoic acid (272 mg, 1.1 mmol), the reaction was carried out in the same manner as Example 91 to synthesis the title compound 67 mg (yield 31%). Melting point was 256 to 260° C. (hexane-THF).

¹H-NMR (CDCl₃): δ1.46 (6H, s), 2.09 (3H, s), 2.17 (3H, s), 2.22 (3H, s), 2.91 (2H, s), 3.02 (3H, s), 3.15-3.55 (8H, m), 6.94-7.02 (2H, m), 7.75-7.82 (2H, m).

Example 93

1-{-4-[4-(2,2,4,6,7-Pentamethyl-2,3-dihydro-1-benzofuran-5-yl)piperazin-1-yl]phenyl}methaneamine To the THF (5.0 mL) solution of 4-[4-(2,2,4,6,7-pentamethyl)-2,3-dihydro-1-benzofuran-5-yl)piperazin-1-yl]benzonitrile (180 mg, 0.479 mmol) synthesized in Example 90, lithium aluminum hydride (91 mg, 2.39 mmol) was slowly added under ice cooling, followed by stirring for 1.5 hours. To the reaction solution, sodium sulfate•10 hydrate (500 mg) was added. The temperature was raised to room temperature and the mixture was stirred for 16 hours. Undissolved residues were removed by filtration and the filtrate was concentrated under reduced pressure. To the resulting residue, hexane was added. The resulting solids were filtered to obtain the title compound 120 mg (yield 66%). Melting point was 156 to 158° C. (hexane-THF).

¹H-NMR (CDCl₃): δ1.46 (6H, s), 2.08 (3H, s), 2.19 (3H, s), 2.24 (3H, s), 2.91 (2H, s), 3.15-3.33 (8H, m), 3.79 (2H, s), 6.93-7.00 (2H, m), 7.19-7.24 (2H, m).

Example 94

N,N-Dimethyl-1-{-4-[4-(2,2,4,6,7-pentamethyl)-2,3-dihydro-1-benzofuran-5-yl)piperazin-1-yl]phenyl}methaneamine To the THF (2.0 mL) solution of 1-{-4-[4-(2,2,4,6,7-pentamethyl)-2,3-dihydro-1-benzofuran-5-yl)piperazin-1-yl]phenyl}methaneamine (23 mg, 0.061 mmol) synthesized in Example 93, 37% aqueous solution of formaldehyde (49 mg, 0.61 mmol) and acetic acid (0.010 mL, 0.18 mmol), sodium triacetoxyborohydride (65 mg, 0.31 mmol) was added under ice cooling. The temperature was raised to room temperature and the mixture was stirred for 16 hours. The reaction solution was added with water, and extracted with ethyl acetate. The organic layer was washed with water and saturated brine and dried over sodium sulfate. The solvent was removed by distillation under reduced pressure. The resulting residue was purified by basic silica gel column chromatography (hexane-ethyl acetate 80:20) to obtain the title compound 12 mg (yield 48%).

Melting point was 134 to 138° C. (hexane-ethyl acetate).

¹H-NMR (CDCl₃): δ1.46 (6H, s), 2.08 (3H, s), 2.19 (3H, s), 2.23 (6H, s), 2.24 (3H, s), 2.91 (2H, s), 3.16-3.34 (8H, m), 3.35 (2H, s), 6.91-6.98 (2H, m), 7.17-7.24 (2H, m).

Example 95

1-{4-[4-(2,2,4,6,7-Pentamethyl-2,3-dihydro-1-benzofuran-5-yl)piperazin-1-yl]phenyl}ethanone To the THF (2.0 mL) solution of 4-[4-(2,2,4,6,7-pentamethyl-2,3-dihydro-1-benzofuran-5-yl)piperazin-1-yl]benzonitrile (75 mg, 0.20 mmol) synthesized in Example 90, 1.6 M-methyl lithium/diethyl ether solution (0.25 mL, 0.40 mmol) was slowly added under ice cooling, followed by stirring for 2 hours. 1.6 M-Methyl lithium/diethyl ether solution (1.0 mL, 1.6 mmol) was again added and stirred for 1 hour. The reaction solution was added with water, and extracted with ethyl acetate. The organic layer was washed with saturated brine and dried over sodium sulfate. The solvent was removed by distillation under reduced pressure. The resulting residue was purified by silica gel column chromatography (hexane-ethyl acetate 70:30) to obtain the title compound 39 mg (yield 50%). Melting point was 192 to 196° C. (hexane-ethyl acetate).

¹H-NMR (CDCl₃): δ1.46 (6H, s), 2.09 (3H, s), 2.17 (3H, s), 2.23 (3H, s), 2.53 (3H, s), 2.91 (2H, s), 3.23 (8H, s), 6.88-6.96 (2H, m), 7.85-7.93 (2H, m).

Example 96

1-{-4-[4-(2,2,4,6,7-Pentamethyl-2,3-dihydro-1-benzofuran-5-yl)piperazin-1-yl]phenyl}ethanol To the methanol (1.0 mL) solution of 1-{4-[4-(2,2,4,6,7-pentamethyl-2,3-dihydro-1-benzofuran-5-yl)piperazin-1-yl]phenyl}ethanone (39 mg, 0.10 mmol) synthesized in Example 95, sodium borohydride (11 mg, 0.30 mmol) was added under ice cooling. The mixture was stirred for 2 hours. The reaction solution was added with water, and extracted with ethyl acetate. The organic layer was washed with saturated brine and dried over sodium sulfate. The solvent was removed by distillation under reduced pressure. The resulting residue was crystallized from hexane to obtain the title compound 24 mg (yield 60%). Melting point was 133 to 136° C. (hexane-ethyl acetate).

Example 97

{5-[4-(4-Methoxyphenyl)piperazin-1-yl]-2,4,6,7-tetramethyl-2,3-dihydro-1-benzofuran-2-yl}methanol By using (5-bromo-2,4,6,7-tetramethyl-2,3-dihydro-1-benzofuran-2-yl)methanol (330 mg, 1.16 mmol) synthesized in Reference example 123, the reaction was carried out in the same manner as Example 1 to obtain the title compound 100 mg (yield 22%). That is, to the toluene (6.0 mL) mixture solution of (5-bromo-2,4,6,7-tetramethyl-2,3-dihydro-1-benzofuran-2-yl)methanol (330 mg, 1.16 mmol), 1-(4-methoxyphenyl)piperazine (667 mg, 3.47 mmol), palladium acetate (13 mg, 0.058 mmol) and BINAP (108 mg, 0.174 mmol), sodium t-butoxide (334 mg, 3.47 mmol) was added and stirred for 15 hours under reflux. After cooling to room temperature, water was added to the reaction solution, and extracted with ethyl acetate. The organic layer was washed with saturated brine and dried over anhydrous magnesium sulfate. The solvent was removed by distillation under reduced pressure. The residue was purified by silica gel chromatography (hexane-ethyl acetate 95:5-70:30) and crystallized from ethyl acetate-hexane to obtain the title compound 100 mg as a colorless crystal (yield 22%). Melting point was 145 to 148° C.

$^1$H-NMR (CDCl$_3$): δ1.44 (3H, s), 1.87 (1H, dd, J=6.3, 6.9 Hz), 2.09 (3H, s), 2.21 (3H, s), 2.24 (3H, s), 2.81 (1H, d, J=15.3 Hz), 3.06-3.34 (9H, m), 3.61 (1H, dd, J=6.9, 11.7 Hz), 3.67 (1H, dd, J=6.3, 11.7 Hz), 3.78 (3H, s), 6.82-6.91 (2H, m), 6.92-7.01 (2H, m).

Example 98

(2,4,6,7-Tetramethyl-5-{4-[4-(1-methylethyl)phenyl]piperazin-1-yl}-2,3-dihydro-1-benzofuran-2-yl)methanol By using (5-bromo-2,4,6,7-tetramethyl-2,3-dihydro-1-benzofuran-2-yl)methanol (330 mg, 1.16 mmol) synthesized in Reference example 123 and 1-(4-isopropylphenyl)piperazine (774 mg, 3.78 mmol), the reaction was carried out in the same manner as Example 1 to obtain the title compound 30 mg (yield 6%). Melting point was 160 to 163° C. (ethyl acetate-hexane).

$^1$H-NMR (CDCl$_3$): δ1.23 (6H, d, J=6.6 Hz), 1.44 (3H, s), 1.87 (1H, dd, J=6.3, 7.2 Hz), 2.09 (3H, s), 2.20 (3H, s), 2.23 (3H, s), 2.76-2.92 (2H, m), 3.08-3.33 (9H, m), 3.61 (1H, dd, J=7.2, 11.7 Hz), 3.66 (1H, dd, J=6.3, 11.7 Hz), 6.90-6.98 (2H, m), 7.01-7.09 (2H, m).

Example 99

{2,4,6,7-Tetramethyl-5-[4-(4-methylphenyl)piperazin-1-yl]-2,3-dihydro-1-benzofuran-2-yl}methanol By using (5-bromo-2,4,6,7-tetramethyl-2,3-dihydro-1-benzofuran-2-yl)methanol (360 mg, 1.16 mmol) synthesized in Reference example 123 and 1-(4-methylphenyl)piperazine (668 mg, 3.79 mmol), the reaction was carried out in the same manner as Example 1 to obtain the title compound 30 mg (yield 6%). Melting point was 152 to 155° C. (ethyl acetate-hexane).

$^1$H-NMR (CDCl$_3$): δ1.43 (3H, s), 1.87 (1H, dd, J=6.3, 7.2 Hz), 2.09 (3H, s), 2.20 (3H, s), 2.24 (3H, s), 2.28 (3H, s), 2.81 (1H, d, J=15.0 Hz), 3.08-3.35 (9H, m), 3.61 (1H, dd, J=7.2, 11.7 Hz), 3.66 (1H, dd, J=6.3, 11.7 Hz), 6.87-6.95 (2H, m), 7.05-7.13 (2H, m).

Example 100

1-(2,4-Dimethoxyphenyl)-4-(2,4,6,7-tetramethyl-2,3-dihydro-1-benzofuran-5-yl)piperazine By using 5-bromo-2,4,6,7-tetramethyl-2,3-dihydro-1-benzofuran (480 mg, 1.88 mmol) synthesized in Reference example 53 and 1-(2,4-dimethoxyphenyl)piperazine (627 mg, 2.82 mmol), the reaction was carried out in the same manner as Example 1 to obtain the title compound 400 mg (yield 54%).

Melting point was 142 to 144° C. (ethyl acetate-hexane).

$^1$H-NMR (CDCl$_3$): δ1.46 (3H, d, J=6.3 Hz), 2.10 (3H, s), 2.24 (3H, s), 2.26 (3H, s), 2.71 (1H, dd, J=7.8, 15.0 Hz), 2.97-3.37 (9H, m), 3.79 (3H, s), 3.86 (3H, s), 4.81-4.96 (1H, m), 6.44 (1H, dd, J=2.7, 8.4 Hz), 6.50 (1H, d, J=2.7 Hz), 6.93 (1H, d, J=8.4 Hz).

Example 101

1-[2-(Methoxymethyl)-2,4,6,7-tetramethyl-2,3-dihydro-1-benzofuran-5-yl]-4-(4-methoxyphenyl)piperazine hydrochloric acid salt By using 1-[(5-bromo-2,4,6,7-tetramethyl-2,3-dihydro-1-benzofuran-2-yl)methyl]-1H-pyrazole (120 mg, 0.401 mmol) synthesized in Reference example 125, the reaction was carried out in the same manner as Example 1 to give 1-[2-(methoxymethyl)-2,4,6,7-tetramethyl-2,3-dihydro-1-benzofuran-5-yl]-4-(4-methoxyphenyl)piperazine 64 mg (yield 39%). The resultant was dissolved in ethyl acetate (3 ml), added with 4 N hydrochloric acid-ethyl acetate solution (0.5 ml), and the solvent was removed by distillation under reduced pressure. The residue was crystallized from ethyl acetate and hexane to obtain the title compound 70 mg (yield 39%).

$^1$H-NMR (DMSO-d$_6$): δ1.34 (3H, s), 1.98 (3H, s), 2.20 (3H, s), 2.21 (3H, s), 2.77 (1H, d, J=15.6 Hz), 3.06 (1H, d, J=15.6 Hz), 3.31 (3H, s), 3.34-3.74 (10H, m), 3.80 (3H, s), 7.02-7.14 (2H, m), 7.55-7.95 (2H, m), 12.80 (1H, brs).

Example 102

1-{5-[4-(4-Methoxyphenyl)piperazin-1-yl]-2,4,6,7-tetramethyl-2,3-dihydro-1-benzofuran-2-yl}-N,N-dimethylmethaneamine By using 1-(5-bromo-2,4,6,7-tetramethyl-2,3-dihydro-1-benzofuran-2-yl)-N,N-dimethylmethaneamine (220 mg, 0.705 mmol) synthesized in Reference example 130, the reaction was carried out in the same manner as Example 1 to obtain the title compound 100 mg (yield 33%). Melting point was 145 to 148° C. (ethyl acetate-hexane).

$^1$H-NMR (CDCl$_3$): δ1.44 (3H, s), 2.07 (3H, s), 2.20 (3H, s), 2.23 (3H, s), 2.34 (6H, s), 2.51 (2H, s), 2.80 (1H, d, J=15.0 Hz), 3.01-3.34 (9H, m), 3.78 (3H, s), 6.81-6.90 (2H, m), 6.92-7.01 (2H, m).

---

Page 179 begins:

$^1$H-NMR (CDCl$_3$): δ1.46 (6H, s), 1.49 (3H, d, J=6.4 Hz), 2.08 (3H, s), 2.19 (3H, s), 2.24 (3H, s), 2.91 (2H, s), 3.15-3.37 (8H, m), 4.85 (1H, q, J=6.4 Hz), 6.93-7.01 (2H, m), 7.26-7.34 (2H, m).

Example 103

N-Benzyl-1-{5-[4-(4-methoxyphenyl)piperazin-1-yl]-2,4,6,7-tetramethyl-2,3-dihydro-1-benzofuran-2-yl}-N-methylmethaneamine By using N-benzyl-1-(5-bromo-2,4,6,7-tetramethyl-2,3-dihydro-1-benzofuran-2-yl)-N-methylmethaneamine (360 mg, 0.927 mmol) synthesized in Reference example 132, the reaction was carried out in the same manner as Example 1 to obtain the title compound 270 mg (yield 58%).
$^1$H-NMR (CDCl$_3$): δ1.44 (3H, s), 2.04 (3H, s), 2.20 (3H, s), 2.22 (3H, s), 2.31 (3H, s), 2.61 (2H, s), 2.77 (1H, d, J=15.3 Hz), 3.02-3.36 (9H, m), 3.55 (1H, d, J=13.2 Hz), 3.67 (1H, d, J=13.2 Hz), 3.78 (3H, s), 6.82-6.91 (2H, m), 6.92-7.01 (2H, m), 7.16-7.33 (5H, m).

Example 104

1-{5-[4-(4-Methoxyphenyl)piperazin-1-yl]-2,4,6,7-tetramethyl-2,3-dihydro-1-benzofuran-2-yl}-N-methylmethaneamine To the ethyl acetate (6 mL) solution of N-benzyl-1-{5-[4-(4-methoxyphenyl)piperazin-1-yl]-2,4,6,7-tetramethyl-2,3-dihydro-1-benzofuran-2-yl}-N-methylmethaneamine (190 mg, 0.380 mmol) synthesized in Example 103, 10%-palladium carbon (comprising 50% moisture, 70 mg) was added, and then the mixture was stirred at room temperature for 15 hours under hydrogen atmosphere. The reaction mixture was filtered to remove the palladium carbon, and the filtrate was concentrated under reduced pressure. The residue was purified by basic silica gel chromatography (hexane-ethyl acetate 95:5-50:50), and recrystallized from ethyl acetate-hexane to obtain the title compound 50 mg (yield 32%). Melting point was 107 to 113° C. (ethyl acetate-hexane).
$^1$H-NMR (CDCl$_3$): δ1.27 (1H, brs), 1.45 (3H, s), 2.08 (3H, s), 2.19 (3H, s), 2.23 (3H, s), 2.48 (3H, s), 2.73 (1H, d, J=12.0 Hz), 2.79 (1H, d, J=12.0 Hz), 2.80 (1H, d, J=15.3 Hz), 3.04-3.34 (9H, m), 3.78 (3H, s), 6.81-6.90 (2H, m), 6.92-7.01 (2H, m).

Example 105

1-(4-Methoxyphenyl)-4-{2,4,6,7-tetramethyl-2-[(methylsulfanyl)methyl]-2,3-dihydro-1-benzofuran-5-yl}piperazine By using 5-bromo-2,4,6,7-tetramethyl-2-[(methylsulfanyl)methyl]-2,3-dihydro-1-benzofuran (130 mg, 0.412 mmol) synthesized in Reference example 134, the reaction was carried out in the same manner as Example 1 to obtain the title compound 60 mg (yield 34%).
$^1$H-NMR (CDCl$_3$): δ1.53 (3H, s), 2.07 (3H, s), 2.21 (6H, s), 2.24 (3H, s), 2.79 (1H, d, J=13.8 Hz), 2.84 (1H, d, J=13.8 Hz), 2.89 (1H, d, J=15.3 Hz), 3.05-3.35 (9H, m), 3.78 (3H, s), 6.81-6.90 (2H, m), 6.92-7.01 (2H, m).

Example 106

1-(4-Methoxyphenyl)-4-{2,4,6,7-tetramethyl-2-[(methylsulfonyl)methyl]-2,3-dihydro-1-benzofuran-5-yl}piperazine To the toluene (4 ml) solution of 1-(4-methoxyphenyl)-4-{2,4,6,7-tetramethyl-2-[(methylsulfanyl)methyl]-2,3-dihydro-1-benzofuran-5-yl}piperazine (50 mg, 0.117 mmol) synthesized in Example 105, m-chloroperbenzoic acid (70%, 87 mg, 0.352 mmol) was added under ice cooling, followed by stirring for 15 hours after warming to room temperature. The reaction solution was added with saturated sodium bicarbonate solution and ethyl acetate to separate the organic layer. The organic layer was washed with 10% aqueous sodium sulfite solution and saturated brine and dried over anhydrous magnesium sulfate. After concentration under reduced pressure, the residue was purified by silica gel chromatography (hexane-ethyl acetate 94:6-60:40) to obtain the title compound 5 mg (yield 9%).
$^1$H-NMR (CDCl$_3$): δ1.71 (3H, s), 2.07 (3H, s), 2.21 (3H, s), 2.24 (3H, s), 2.95-3.56 (15H, m), 3.79 (3H, s), 6.83-6.91 (2H, m), 6.93-7.01 (2H, m).

Example 107

N,N-Dibenzyl-1-{5-[4-(4-methoxyphenyl)piperazin-1-yl]-2,4,6,7-tetramethyl-2,3-dihydro-1-benzofuran-2-yl}methaneamine By using N,N-dibenzyl-1-(5-bromo-2,4,6,7-tetramethyl-2,3-dihydro-1-benzofuran-2-yl)methaneamine (330 mg, 0.711 mmol) synthesized in Reference example 135, the reaction was carried out in the same manner as Example 1 to obtain the title compound 210 mg (yield 51%). Melting point was 168 to 170° C. (ethyl acetate-hexane).
$^1$H-NMR (CDCl$_3$): δ1.37 (3H, s), 1.97 (3H, s), 2.18 (3H, s), 2.19 (3H, s), 2.59-2.71 (3H, m), 2.84 (1H, d, J=15.0 Hz), 3.07-3.40 (8H, m), 3.58 (2H, d, J=13.5 Hz), 3.71 (2H, d, J=13.5 Hz), 3.79 (3H, s), 6.82-6.91 (2H, m), 6.93-7.02 (2H, m), 7.15-7.32 (10H, m).

Example 108

1-{5-[4-(4-Methoxyphenyl)piperazin-1-yl]-2,4,6,7-tetramethyl-2,3-dihydro-1-benzofuran-2-yl}methaneamine By using N,N-dibenzyl-1-{5-[4-(4-methoxyphenyl)piperazin-1-yl]-2,4,6,7-tetramethyl-2,3-dihydro-1-benzofuran-2-yl}methaneamine (220 mg, 0.382 mmol) synthesized in Example 107, the reaction was carried out in the same manner as Example 104 to obtain the title compound 40 mg (yield 26%). Melting point was 134 to 137° C. (ethyl acetate-hexane).
$^1$H-NMR (CDCl$_3$): δ1.42 (3H, s), 2.09 (3H, s), 2.21 (3H, s), 2.24 (3H, s), 2.77-2.88 (3H, m), 3.03 (1H, d, J=15.6 Hz), 3.07-3.34 (8H, m), 3.78 (3H, s), 6.82-6.91 (2H, m), 6.92-7.01 (2H, m).

Example 109

N-Ethyl-N-({5-[4-(4-methoxyphenyl)piperazin-1-yl]-2,4,6,7-tetramethyl-2,3-dihydro-1-benzofuran-2-yl}methyl)ethaneamine By using 1-{5-[4-(4-methoxyphenyl)piperazin-1-yl]-2,4,6,7-tetramethyl-2,3-dihydro-1-benzofuran-2-yl}methaneamine (60 mg, 0.152 mmol) synthesized in Example 108 and acetaldehyde (0.1 ml), the reaction was carried out in the same manner as Reference example 130 to obtain the title compound 25 mg (yield 36%). Melting point was 103 to 106° C. (ethyl acetate-hexane).
$^1$H-NMR (CDCl$_3$): δ1.53 (3H, s), 2.07 (3H, s), 2.21 (6H, s), 2.24 (3H, s), 2.79 (1H, d, J=13.8 Hz), 2.84 (1H, d, J=13.8 Hz), 2.89 (1H, d, J=15.3 Hz), 3.05-3.35 (9H, m), 3.78 (3H, s), 6.81-6.90 (2H, m), 6.92-7.01 (2H, m).

Example 110

4-({5-[4-(4-Methoxyphenyl)piperazin-1-yl]-2,4,6,7-tetramethyl-2,3-dihydro-1-benzofuran-2-yl}methyl)morpholine By using 4-[(5-bromo-2,4,6,7-tetramethyl-2,3-dihydro-1-benzofuran-2-yl)methyl]morpholine (220 mg, 0.382 mmol) synthesized in Reference example 136, the reaction was carried out in the same manner as Example 1 to obtain the title compound 140 mg (yield 48%).

Melting point was 137 to 142° C. (ethyl acetate-hexane).
$^1$H-NMR (CDCl$_3$): δ1.45 (3H, s), 2.05 (3H, s), 2.20 (3H, s), 2.23 (3H, s), 2.43-2.61.
(4H, m), 2.62-2.74 (2H, m), 2.80 (1H, d, J=15.3 Hz), 3.00-3.34 (9H, m), 3.62-3.73 (4H, m), 3.78 (3H, s), 6.82-6.91 (2H, m), 6.92-7.01 (2H, m).

Example 111

1-(4-Methoxyphenyl)-4-[2,4,6,7-tetramethyl-2-(piperidin-1-ylmethyl)-2,3-dihydro-1-benzofuran-5-yl]piperazine By using 1-[(5-bromo-2,4,6,7-tetramethyl-2,3-dihydro-1-benzofuran-2-yl)methyl]piperidine (160 mg, 0.454 mmol) synthesized in Reference example 137, the reaction was carried out in the same manner as Example 1 to obtain the title compound 60 mg (yield 29%).

Melting point was 122 to 125° C. (ethyl acetate-hexane).
$^1$H-NMR (CDCl$_3$): δ1.33-1.43 (2H, m), 1.44 (3H, s), 1.48-1.59 (4H, m), 2.06 (3H, s), 2.20 (3H, s), 2.23 (3H, s), 2.36-2.66 (6H, m), 2.78 (1H, d, J=15.3 Hz), 3.04 (1H, d, J=15.3 Hz), 3.78 (3H, s), 6.82-6.91 (2H, m), 6.92-7.01 (2H, m).

Example 112

4-({5-[4-(4-Methoxyphenyl)piperazin-1-yl]-2,4,6,7-tetramethyl-2,3-dihydro-1-benzofuran-2-yl}methyl)thiomorpholine 1,1-dioxide By using 4-[5-bromo-2,4,6,7-tetramethyl-2,3-dihydro-1-benzofuran-2-yl)methyl]thiomorpholine 1,1-dioxide (260 mg, 0.646 mmol) synthesized in Reference example 138, the reaction was carried out in the same manner as Example 1 to obtain the title compound 90 mg (yield 27%). Melting point was 145 to 164° C. (ethyl acetate-hexane).
$^1$H-NMR (CDCl$_3$): δ1.44 (3H, s), 2.04 (3H, s), 2.21 (3H, s), 2.23 (3H, s), 2.68 (1H, d, J=14.1 Hz), 2.74 (1H, d, J=14.1 Hz), 2.79-3.34 (18H, m), 3.78 (3H, s), 6.82-6.91 (2H, m), 6.92-7.01 (2H, m).

Example 113

1-(4-Methoxyphenyl)-4-[2,4,6,7-tetramethyl-2-(1H-pyrazole-1-ylmethyl)-2,3-dihydro-1-benzofuran-5-yl]piperazine By using 1-[(5-bromo-2,4,6,7-tetramethyl-2,3-dihydro-1-benzofuran-2-yl)methyl]-1H-pyrazole (180 mg, 0.537 mmol) synthesized in Reference example 139, the reaction was carried out in the same manner as Example 1 to obtain the title compound 100 mg (yield 42%).

Melting point was 117 to 120° C. (ethyl acetate-hexane).
$^1$H-NMR (CDCl$_3$): δ1.38 (3H, s), 2.12 (3H, s), 2.18 (3H, s), 2.24 (3H, s), 2.89 (1H, d, J=15.9 Hz), 3.05-3.33 (9H, m), 3.78 (3H, s), 4.31 (1H, d, J=14.7 Hz), 4.36 (1H, d, J=14.7 Hz), 6.22-6.26 (1H, m), 6.81-6.90 (2H, m), 6.92-7.01 (2H, m), 7.47-7.54 (2H, m).

Example 114

1-(4-Methoxyphenyl)-4-{2,4,6,7-tetramethyl-2-[(2-methyl-1H-imidazol-1-yl)methyl]-2,3-dihydro-1-benzofuran-5-yl}piperazine By using 1-[(5-bromo-2,4,6,7-tetramethyl-2,3-dihydro-1-benzofuran-2-yl)methyl]-2-methyl-1H-imidazole (110 mg, 0.315 mmol) synthesized in Reference example 139, the reaction was carried out in the same manner as Example 1 to obtain the title compound 60 mg (yield 41%). Melting point was 86 to 90° C. (ethyl acetate-hexane).
$^1$H-NMR (CDCl$_3$): δ1.39 (3H, s), 2.10 (3H, s), 2.19 (3H, s), 2.24 (3H, s), 2.41 (3H, s), 2.93 (1H, d, J=16.5 Hz), 2.98 (1H, d, J=16.5 Hz), 3.07-3.34 (8H, m), 3.78 (3H, s), 3.94 (1H, d, J=14.4 Hz), 4.08 (1H, d, J=14.4 Hz), 6.82-6.92 (3H, m), 6.93-7.01 (3H, m).

Example 115

8-({5-[4-(4-Methoxyphenyl)piperazin-1-yl]-2,4,6,7-tetramethyl-2,3-dihydro-1-benzofuran-2-yl}methyl)-1,4-dioxa-8-azaspiro[4.5]decane By using 8-[(5-bromo-2,4,6,7-tetramethyl-2,3-dihydro-1-benzofuran-2-yl)methyl]-1,4-dioxa-8-azaspiro[4.5]decane (300 mg, 0.731 mmol) synthesized in Reference example 141, the reaction was carried out in the same manner as Example 21 to obtain the title compound 100 mg (yield 26%). Melting point was 165 to 167° C. (ethyl acetate-hexane).
$^1$H-NMR (CDCl$_3$): δ1.45 (3H, s), 1.64-1.77 (4H, m), 2.05 (3H, s), 2.20 (3H, s), 2.23 (3H, s), 2.49-2.87 (7H, m), 2.98-3.37 (9H, m), 3.78 (3H, s), 3.90-3.42 (4H, m), 6.82-6.92 (2H, m), 6.93-7.03 (2H, m).

Example 116

1-(4-Methoxyphenyl)-4-[2,4,6,7-tetramethyl-2-(pyrrolidin-1-ylmethyl)-2,3-dihydro-1-benzofuran-5-yl]piperazine By using 1-[(5-bromo-2,4,6,7-tetramethyl-2,3-dihydro-1-benzofuran-2-yl)methyl]pyrrolidine (270 mg, 0.798 mmol) synthesized in Reference example 142, the reaction was carried out in the same manner as Example 21 to obtain the title compound 60 mg (yield 17%).

Melting point was 129 to 132° C. (ethyl acetate-hexane).
$^1$H-NMR (CDCl$_3$): δ1.46 (3H, s), 1.66-1.80 (4H, m), 2.07 (3H, s), 2.20 (3H, s), 2.23 (3H, s), 2.49-2.75 (6H, m), 2.80 (1H, d, J=15.5 Hz), 3.03-3.34 (9H, m), 3.78 (3H, s), 6.81-6.91 (2H, m), 6.92-7.01 (2H, m).

Example 117

1-(2,2,4,6,7-Pentamethyl-2,3-dihydro-1-benzofuran-5-yl)-4-(1,3,5-trimethyl-1H-pyrazole-4-yl)piperazine To 1-methyl-2-pyrrolidone (5.0 mL) solution of N,N-bis (2-chloroethyl)-2,2,4,6,7-pentamethyl-2,3-dihydro-1-benzofuran-5-mine (660 mg, 2.0 mmol) synthesized in Reference example 146, 1,3,5-trimethyl-1H-pyrazole-4-amine (300 mg, 2.4 mmol), sodium hydrogen carbonate (400 mg, 4.8 mmol) and sodium iodide (300 mg, 2.0 mmol) were added, and stirred at 120° C. for 16 hours. The reaction solution was diluted with ethyl acetate, washed with water and saturated brine, and dried over sodium sulfate. The solvent was removed by distillation under reduced pressure, and the resulting residue was purified by silica gel column chromatography (hexane-ethyl acetate 9:1). The resulting solids were recrystallized from ethanol-water to obtain the title compound 320 mg (yield 42%). Melting point was 162 to 164° C. (ethanol-water).

$^1$H-NMR (CDCl$_3$): δ1.46 (6H, s), 2.09 (3H, s), 2.22 (3H, s), 2.22 (3H, s), 2.27 (3H, s), 2.30 (3H, s), 2.92 (2H, s), 2.95-3.22 (8H, m), 3.67 (3H, s).

Example 118

1-(2,2-difluoro-1,3-benzodioxole-5-yl)-4-(7-methoxy-2,2,4,6-tetramethyl-2,3-dihydro-1-benzofuran-5-yl)piperazine By using 1-(7-methoxy-2,2,4,6-tetramethyl-2,3-dihydro-1-benzofuran-5-yl)piperazine (436 mg, 1.50 mmol) synthesized in Reference Example 96 and 5-bromo-2,2-difluoro-1,3-benzodioxole (614 mg, 2.25 mmol), the reaction was carried out in the same manner as Reference Example 59 to synthesize 321 mg of the title compound (yield 48%). Melting point was 149 to 151° C. (hexane).

$^1$H-NMR (CDCl$_3$): δ1.50 (6H, s), 2.16 (3H, s), 2.24 (3H, s), 2.91 (2H, s), 3.10-3.30 (8H, m), 3.81 (3H, s), 6.63 (1H, dd, J=9.3, 3.0 Hz), 6.75 (1H, d, J=3.0 Hz), 6.94 (1H, d, J=9.3 Hz).

Example 119

1-[7-(2-methoxyethoxy)-2,2,4,6-tetramethyl-2,3-dihydro-1-benzofuran-5-yl]-4-(4-methylphenyl)piperazine To a solution of DMF (5 mL) containing 2,2,4,6-tetramethyl-5-[4-(4-methylphenyl)piperazin-1-yl]-2,3-dihydro-1-benzofuran-7-ol (200 mg, 0.546 mmol) synthesized in Example 72, 1-bromo-2-methoxyethane (382 mg, 2.75 mmol) and potassium carbonate (380 mg, 2.75 mmol) were added, and the mixture was stirred at 100° C. for 24 hours. After cooled to room temperature, water was added to the mixture, and extraction was performed using ethyl acetate. The extract was dried using anhydrous magnesium sulfate, and the solvent was removed under reduced pressure. The obtained residue was purified by silica gel column chromatography (hexane-ethyl acetate 100:0-90:10) to obtain 33.5 mg of the title compound (yield 14%). Melting point was 118 to 120° C. (hexane).

$^1$H-NMR (CDCl$_3$): δ1.47 (6H, s), 2.16 (3H, s), 2.25 (3H, s), 2.28 (3H, s), 2.89 (2H, s), 3.15-3.31 (8H, m), 3.43 (3H, s), 3.61-3.72 (2H, m), 4.12-4.19 (2H, m), 6.90 (2H, d, J=8.5 Hz), 7.09 (2H, d, J=8.7 Hz).

Example 120

1-(6-bromo-2,2,4,7-tetramethyl-2,3-dihydro-1-benzofuran-5-yl)-4-(4-methoxyphenyl)piperazine By using 6-bromo-N,N-bis(2-chloroethyl)-2,2,4,7-tetramethyl-2,3-dihydro-1-benzofuran-5-amine (492 mg, 1.25 mmol) synthesized in Reference Example 152 and 4-methoxyaniline (185 mg, 1.50 mmol), the reaction was carried out in the same manner as Example 117 to synthesize 138 mg of the title compound (yield 25%).

Melting point was 180 to 181° C. (hexane).

$^1$H-NMR (CDCl$_3$): δ1.46 (6H, s), 2.21 (6H, s), 2.88 (2H, s), 3.03-3.17 (4H, m), 3.21-3.34 (2H, m), 3.47-3.61 (2H, m), 3.78 (3H, s), 6.85 (2H, d, J=9.0 Hz), 6.97 (2H, d, J=9.0 Hz).

Example 121

1,4-bis(2,2,4,6,7-pentamethyl-2,3-dihydro-1-benzofuran-5-yl)piperazine

To a solution of toluene (2.0 mL) containing 2,2,4,6,7-pentamethyl-2,3-dihydro-1-benzofuran-5-amine (410 mg, 2.0 mmol) synthesized in Reference Example 144, 1,2-dibromoethane (1.72 mL, 20 mmol), benzyl triethyl ammonium chloride (56 mg, 0.20 mmol) and 8N sodium hydroxide aqueous solution (2 mL) were added, and the mixture was stirred at 100° C. for 16 hours. The organic layer was washed with saturated saline and then dried using sodium sulfate. The solvent was removed under reduced pressure, and the obtained solid was recrystallized from hexane-ethyl acetate to give 150 mg of the title compound (yield 32%). Melting point was 256 to 260° C. (hexane-ethyl acetate).

$^1$H-NMR (CDCl$_3$): δ1.47 (12H, s), 2.10 (6H, s), 2.24 (6H, s), 2.29 (3H, s), 2.30 (3H, s), 2.92 (4H, s), 3.02-3.28 (8H, m).

Example 122

1-isoxazol-3-yl-4-(2,2,4,6,7-pentamethyl-2,3-dihydro-1-benzofuran-5-yl)piperazine By using N,N-bis(2-chloroethyl)-2,2,4,6,7-pentamethyl-2,3-dihydro-1-benzofuran-5-amine (165 mg, 0.50 mmol) synthesized in Reference Example 146 and isoxazol-3-amine (0.044 mL, 0.60 mmol), the reaction was carried out in the same manner as Example 117 to obtain 15 mg of the title compound as a colorless solid (yield 9%).

$^1$H-NMR (CDCl$_3$): δ1.46 (6H, s), 2.08 (3H, s), 2.17 (3H, s), 2.22 (3H, s), 2.90 (2H, s), 3.11-3.46 (8H, m), 6.01 (1H, d, J=1.9 Hz), 8.13 (1H, d, J=1.9 Hz).

Example 123

2-[4-(2,2,4,6,7-pentamethyl-2,3-dihydro-1-benzofuran-5-yl)piperazine-1-yl]pyrimidine To a solution of DMSO (12 mL) containing 1-(2,2,4,6,7-pentamethyl-2,3-dihydro-1-benzofuran-5-yl)piperazine (1.1 g, 4.00 mmol) synthesized in Reference Example 61, 2-bromopyrimidine (954 mg, 6.0 mmol) and diisopropylethylamine (2.09 mL) were added, and the mixture was stirred at 120° C. for 2 hours. The reaction solution was diluted with ethyl acetate, and washed with water and saturated saline. The organic layer was dried using magnesium sulfate. The solvent was removed under reduced pressure, and the obtained residue was purified by silica gel column chromatography (hexane-ethyl acetate 9:1). The obtained solid was recrystallized from ethanol-water to obtain 600 mg of the title compound (yield 42%).

Melting point was 145 to 147° C. (ethanol-water).

$^1$H-NMR (CDCl$_3$): δ1.46 (6H, s), 2.08 (3H, s), 2.17 (3H, s), 2.23 (3H, s), 2.90 (2H, s), 3.06-3.22 (4H, m), 3.79-4.06 (4H, m), 6.47 (1H, t, J=4.8 Hz), 8.32 (2H, d, J=4.8 Hz).

Example 124

1-(2,2,4,6,7-pentamethyl-2,3-dihydro-1-benzofuran-5-yl)-4-(1H-pyrazole-3-yl)piperazine By using N,N-bis(2-chloroethyl)-2,2,4,6,7-pentamethyl-2,3-dihydro-1-benzofuran-5-amine (165 mg, 0.50 mmol) synthesized in Reference Example 146 and 1H-pyrazole-5-amine (59 mg, 0.60 mmol), the reaction was carried out in the same manner as Example 117 to obtain 23 mg of the title compound as a colorless solid (yield 12%).

$^1$H-NMR (CDCl$_3$): δ1.47 (6H, s), 2.09 (3H, s), 2.19 (3H, s), 2.24 (3H, s), 2.91 (2H, s), 3.14-3.40 (8H, m), 5.80 (1H, d, J=2.4 Hz), 7.42 (1H, d, J=2.4 Hz).

Example 125

1-(1-methyl-1H-imidazole-2-yl)-4-(2,2,4,6,7-pentamethyl-2,3-dihydro-1-benzofuran-5-yl)piperazine By using N,N-bis(2-chloroethyl)-2,2,4,6,7-pentamethyl-2,3-dihydro-1-benzofuran-5-amine (330 mg, 1.0 mmol) synthesized in Reference Example 146 and 1-methyl-1H-imidazole-2-amine (146 mg, 1.5 mmol), the reaction was carried out in the same manner as Example 117 to obtain 184 mg of the title compound as an oily product (yield 52%).

$^1$H-NMR (CDCl$_3$): δ1.43 (6H, s), 1.82 (3H, s), 1.87 (3H, s), 2.02 (3H, s), 2.84 (2H, s), 3.29-3.46 (4H, m), 3.58-3.72 (5H, m), 4.29 (2H, t, J=6.3 Hz), 6.61 (1H, d, J=2.5 Hz), 6.70 (1H, d, J=2.5 Hz), 7.62 (4H, brs).

Example 126

5-methyl-7-[4-(2,2,4,6,7-pentamethyl-2,3-dihydro-1-benzofuran-5-yl)piperazin-1-yl]pyrazolo[1,5-a]pyrimidine To a solution of THF (2 mL) containing 1-(2,2,4,6,7-pentamethyl-2,3-dihydro-1-benzofuran-5-yl)piperazine (274 mg, 1.0 mmol) synthesized in Reference Example 61, 7-chloro-5-methylpyrazolol[1,5-a]pyrimidine (200 mg, 1.2 mmol) and diisopropylethylamine (0.42 mL) were added, and the mixture was heated to reflux for 2 hours. After addition of piperazine (42 mg, 0.50 mmol) thereto, the mixture was further heated to reflux for 1 hour. The reaction solution was diluted with ethyl acetate, and washed with water and saturated saline. The organic layer was dried using magnesium sulfate. The solvent was removed under reduced pressure, and the obtained residue was purified by silica gel column chromatography (hexane-ethyl acetate 7:3). The obtained solid was recrystallized from ethanol-water to obtain 140 mg of the title compound (yield 35%). Melting point was 180 to 182° C. (ethanol-water).

$^1$H-NMR (CDCl$_3$): δ1.47 (6H, s), 2.10 (3H, s), 2.22 (3H, s), 2.27 (3H, s), 2.55 (3H, s), 2.92 (2H, s), 3.25-3.44 (4H, m), 3.66-3.91 (4H, m), 6.06 (1H, s), 6.47 (1H, d, J=2.2 Hz), 8.02 (1H, d, J=2.2 Hz).

Example 127

1-(1-methyl-1H-pyrazole-3-yl)-4-(2,2,4,6,7-pentamethyl-2,3-dihydro-1-benzofuran-5-yl)piperazine By using N,N-bis(2-chloroethyl)-2,2,4,6,7-pentamethyl-2,3-dihydro-1-benzofuran-5-amine (660 mg, 2.0 mmol) synthesized in Reference Example 146 and 1-methyl-1H-pyrazole-3-amine (291 mg, 3.0 mmol), the reaction was carried out in the same manner as Example 117 to obtain 341 mg of the title compound as a colorless solid (yield 48%). Melting point was 147 to 149° C. (ethanol-water).

$^1$H-NMR (CDCl$_3$): δ1.47 (6H, s), 2.09 (3H, s), 2.19 (3H, s), 2.24 (3H, s), 2.91 (2H, s), 3.13-3.38 (8H, m), 3.78 (3H, s), 5.69 (1H, d, J=2.4 Hz), 7.18 (1H, d, J=2.4 Hz).

Example 128

1-(1-methyl-1H-pyrazole-5-yl)-4-(2,2,4,6,7-pentamethyl-2:3-dihydro-1-benzofuran-5-yl)piperazine By using N,N-bis(2-chloroethyl)-2,2,4,6,7-pentamethyl-2,3-dihydro-1-benzofuran-5-amine (660 mg, 2.0 mmol) synthesized in Reference Example 146 and 1-methyl-1H-pyrazole-5-amine (233 mg, 2.4 mmol), the reaction was carried out in the same manner as Example 117 to obtain 26 mg of the title compound as a colorless solid (yield 4%). Melting point was 126 to 128° C. (ethanol-water).

$^1$H-NMR (CDCl$_3$): δ1.48 (6H, s), 2.10 (3H, s), 2.22 (3H, s), 2.26 (3H, s), 2.93 (2H, s), 2.97-3.03 (4H, m), 3.14-3.31 (4H, m), 3.78 (3H, s), 5.86 (1H, d, J=1.9 Hz), 7.40 (1H, d, J=1.9 Hz).

Example 129

1-[2,2,7-trimethyl-6-(4-methylphenyl)-2,3-dihydro-1-benzofuran-5-yl]-4-(4-methylphenyl)piperazine To a solution of toluene (10 mL) containing 5-bromo-2,2,7-trimethyl-6-(4-methylphenyl)-2,3-dihydro-1-benzofuran (300 mg, 0.910 mmol) synthesized in Reference Example 157, 1-(4-methylphenyl)piperazine (160 mg, 0.910 mmol), Tris(dibenzylideneacetone)dipalladium (0) (24.9 mg, 0.027 mmol) and Xantphos (47.2 mg, 0.082 mmol), sodium tert-butoxide (131 mg, 1.36 mmol) was added, and the mixture was stirred under heated reflux for 15 hours. After cooled to room temperature, the reaction solution was subjected to Celite filtration. Water was added to the filtration, and extraction was performed using ethyl acetate. The extract was dried using anhydrous magnesium sulfate, and the solvent was removed under reduced pressure. After that, the residue was purified by silica gel chromatography (hexane-ethyl acetate 10:1), and it was crystallized from acetonitrile to obtain 12.0 mg of the title compound as a white solid (yield 3%).

$^1$H-NMR (CDCl$_3$): δ1.50 (6H, s), 1.95 (3H, s), 2.24 (3H, s), 2.35 (3H, s), 2.80-2.90 (8H, m), 3.05 (2H, s), 6.77 (2H, d, J=8.8 Hz), 6.83 (1H, brs), 7.03 (2H, d, J=8.0 Hz), 7.10-7.20 (4H, m).

Example 130

1-[2,2,7-trimethyl-6-(4-methylphenyl)-2,3-dihydro-1-benzofuran-5-yl]-4-phenylpiperazine By using 5-bromo-2,2,7-trimethyl-6-(4-methylphenyl)-2,3-dihydro-1-benzofuran (150 mg, 1.49 mmol) synthesized in Reference Example 157 and 1-phenylpiperazine (73.5 mg, 2.23 mmol), the reaction was carried out in the same manner as Example 129 to obtain 20 mg of the title compound as a colorless solid (yield 11%).

$^1$H-NMR (CDCl$_3$): δ1.50 (6H, s), 1.91 (3H, s), 2.40 (3H, s), 3.06 (2H, s), 3.15-3.30 (8H, m), 6.94 (1H, brs), 7.12 (2H, d, J=8.0 Hz), 7.21 (2H, d, J=8.0 Hz), 7.26-7.50 (5H, m).

Example 131

1-[2,2,7-trimethyl-6-(4-methylphenyl)-2,3-dihydro-1-benzofuran-5-yl]-4-(4-fluorophenyl)piperazine By using 5-bromo-2,2,7-trimethyl-6-(4-methylphenyl)-2,3-dihydro-1-benzofuran (150 mg, 1.49 mmol) synthesized in Reference Example 157 and 1-(4-fluorophenyl)piperazine (82.0 mg, 0.450 mmol), the reaction was carried out in the same manner as Example 129 to obtain 300 mg of the title compound as a colorless solid (yield 15%).

$^1$H-NMR (CDCl$_3$): δ1.50 (6H, s), 1.95 (3H, s), 2.36 (3H, s), 2.78-2.90 (8H, m), 3.05 (2H, s), 6.77-6.81 (2H, m), 6.83 (1H, brs), 6.92 (2H, t, J=8.6 Hz), 7.05-7.25 (4H, m).

Example 132

1-({5-[4-(4-methoxyphenyl)piperazin-1-yl]-2,4,6,7-tetramethyl-2,3-dihydro-1-benzofuran-2-yl}methyl)piperidine-4-one To a solution of ethyl acetate (2.0 mL) containing 8-({5-[4-(4-Methoxyphenyl)piperazin-1-yl]-2,4,6,7-tetramethyl-2,3-dihydro-1-benzofuran-2-yl}methyl)-1,4-dioxa-8-azaspiro[4.5]decane (55 mg, 0.105 mmol) synthesized in Example 115, a solution of 4N hydrochloric acid-ethyl acetate (2.0 mL) was added, and the mixture was stirred at room temperature for 5 hours and at 50° C. for 2 hours. After that, 6N hydrochloric acid was (1.0 mL) was added thereto, and the mixture was further stirred at 70° C. for 2 hours. After cooled to room temperature, the reaction solution was poured into saturated sodium bicarbonate water, and extraction was performed using ethyl acetate. The extract was washed saturated saline, and then dried using anhydrous magnesium sulfate. The solvent was removed under reduced pressure, and the obtained residue was purified by silica gel chromatography (hexane-ethyl acetate 95:5-72:28) and crystallized from ethyl acetate-hexane to give 25 mg of the title compound (yield 50%). Melting point was 123 to 127° C.

$^1$H-NMR (CDCl$_3$) δ: 1.49 (3H, s), 2.06 (3H, s), 2.21 (3H, s), 2.24 (3H, s), 2.31-2.49 (4H, m), 2.65 (1H, d, J=13.8 Hz), 2.72 (1H, d, J=13.8 Hz), 2.80-3.35 (14H, m), 3.78 (3H, s), 6.81-6.90 (2H, m), 6.92-7.01 (2H, m).

Example 133

1-({5-[4-(4-methoxyphenyl)piperazin-1-yl]-2,4,6,7-tetramethyl-2,3-dihydro-1-benzofuran-2-yl}methyl)piperidine-4-ol To a solution of ethanol (2.0 mL) containing 1-({5-[4-(4-methoxyphenyl)piperazin-1-yl]-2,4,6,7-tetramethyl-2,3-dihydro-1-benzofuran-2-yl}methyl)piperidine-4-one (30 mg, 0.0628 mmol) synthesized in Example 132, sodium boron hydride (10 mg, 0.264 mmol) was added, and the mixture was stirred at room temperature for 1 hour. After that, the reaction solution was concentrated under reduced pressure, and the residue was distributed using ethyl acetate and water. The organic layer was washed with water and saturated saline, and then dried using anhydrous magnesium sulfate. The solvent was removed under reduced pressure, and the obtained residue was purified by silica gel chromatography (hexane-ethyl acetate 65:35-0:100) and crystallized from ethyl acetate-hexane to give 15 mg of the title compound (yield 50%). Melting point was 139 to 143° C.

$^1$H-NMR (CDCl$_3$) δ: 1.44 (3H, s), 1.46-1.67 (2H, m), 1.77-1.90 (2H, m), 2.06 (3H, s), 2.20 (3H, s), 2.23 (3H, s), 2.24-2.42 (2H, m), 2.50 (1H, d, J=13.8 Hz), 2.57 (1H, d, J=13.8 Hz), 2.74-2.85 (2H, m), 2.94-3.71 (1H, m), 3.78 (3H, s), 6.81-6.90 (2H, m), 6.92-7.01 (2H, m).

Example 134

1-{2-[(benzyloxy)methyl]-2,4,6,7-tetramethyl-2,3-dihydro-1-benzofuran-5-yl}-4-(4-methoxyphenyl)piperazine By using 2-[(benzyloxy)methyl]-5-bromo-2,4,6,7-tetramethyl-2,3-dihydro-1-benzofuran (690 mg, 1.84 mmol) synthesized in Reference Example 159 and 1-(4-methoxyphenyl)piperazine (707 mg, 3.68 mmol), the reaction was carried out in the same manner as Example 1 to synthesize 580 mg of the title compound (yield 65%). An oily product.

$^1$H-NMR (CDCl$_3$): δ1.49 (3H, s), 2.09 (3H, s), 2.19 (3H, s), 2.23 (3H, s), 2.81 (1H, d, J=15.6 Hz), 3.05-3.35 (9H, m), 3.52 (2H, s), 3.78 (3H, s), 4.58 (1H, d, J=12.3 Hz), 4.64 (1H, d, J=12.3 Hz), 6.81-6.91 (2H, m), 6.92-7.02 (2H, m), 7.23-7.39 (5H, m).

Example 135

{5-[4-(4-methoxyphenyl)piperazin-1-yl]-2,4,6,7-tetramethyl-2,3-dihydro-1-benzofuran-2-yl}methyl formate To a solution of ethanol (7.0 mL) containing 1-{2-[(benzyloxy)methyl]-2,4,6,7-tetramethyl-2,3-dihydro-1-benzofuran-5-yl}-4-(4-methoxyphenyl)piperazine (30 mg, 0.0628 mmol) synthesized in Example 134, 10% palladium carbon (500 mg) and formic acid (7.0 mL) were serially added, and the mixture was stirred at 100° C. for 15 hours. After cooled to room temperature, palladium carbon was removed by filtration, and the solvent was removed under reduced pressure. The obtained residue was purified by silica gel column chromatography (hexane-ethyl acetate 97:3-80:20) and crystallized from ethyl acetate-hexane to obtain 290 mg of the title compound (yield: 49%). Melting point was 120 to 124° C.

$^1$H-NMR (CDCl$_3$) δ: 1.43 (3H, s), 2.09 (3H, s), 2.21 (3H, s), 2.24 (3H, s), 2.80 (1H, d, J=15.3 Hz), 3.07-3.33 (9H, m), 3.60 (1H, d, J=11.7 Hz), 3.66 (1H, d, J=11.7 Hz), 3.78 (3H, s), 6.81-6.91 (1H, m), 6.92-7.02 (1H, m).

Example 136

1-{2-[(methoxymethoxy)methyl]-2,4,6,7-tetramethyl-2,3-dihydro-1-benzofuran-5-yl}-4-(4-methoxyphenyl)piperazine By using 5-bromo-2-[(methoxymethoxy)methyl]-2,4,6,7-tetramethyl-2,3-dihydro-1-benzofuran (1.62 g, 4.92 mmol) synthesized in Reference Example 163 and 1-(4-methoxyphenyl)piperazine (1.89 g, 9.84 mmol), the reaction was carried out in the same manner as Example 1 to synthesize 1.03 g of the title compound (yield 48%).

Melting point was 111 to 114° C.

$^1$H-NMR (CDCl$_3$): δ1.48 (3H, s), 2.08 (3H, s), 2.20 (3H, s), 2.23 (3H, s), 2.82 (1H, d, J=15.9 Hz), 3.04-3.35 (9H, m), 3.37

(3H, s), 3.57 (1H, d, J=9.9 Hz), 3.61 (1H, d, J=9.9 Hz), 3.78 (3H, s), 4.68 (1H, s), 6.81-6.90 (2H, m), 6.92-7.01 (2H, m).

Example 137

N-({5-[4-(4-methoxyphenyl)piperazin-1-yl]-2,4,6,7-tetramethyl-2,3-dihydro-1-benzofuran-2-yl}methyl)acetamide To a solution of THF (2.0 mL) containing 1-{5-[4-(4-Methoxyphenyl)piperazin-1-yl]-2,4,6,7-tetramethyl-2,3-dihydro-1-benzofuran-2-yl}methaneamine (110 mg, 0.278 mmol) synthesized in Example 108, triethylamine (42 mg, 0.417 mmol) and acetylchloride (26 mg, 0.337 mmol) were serially added under ice-cooling condition, and the mixture was stirred at 0° C. for 30 minutes. The reaction solution was diluted with water, and THF was removed under reduced pressure, followed by extraction using ethyl acetate. The extract was washed with saturated saline and dried using anhydrous magnesium sulfate. After that, the solvent was removed under reduced pressure. The obtained residue was purified by silica gel chromatography (hexane-ethyl acetate 7:3-3:7) and crystallized from ethyl acetate-hexane to obtain 90 mg of the title compound (yield 74%). Melting point was 146 to 152° C.
$^1$H-NMR (CDCl$_3$) δ: 1.41 (3H, s), 2.00 (3H, s), 2.09 (3H, s), 2.19 (3H, s), 2.25 (3H, s), 2.83 (1H, d, J=15.3 Hz), 2.99 (1H, d, J=15.3 Hz), 3.05-3.34 (8H, m), 3.49 (1H, dd, J=5.7, 13.8 Hz), 3.58 (1H, dd, J=6.0, 13.8 Hz), 3.78 (3H, s), 5.76 (1H, dd, J=5.7, 6.0 Hz), 6.82-6.91 (2H, m), 6.92-7.01 (2H, m).

Example 138

N-({5-[4-(4-methoxyphenyl)piperazin-1-yl]-2,4,6,7-tetramethyl-2,3-dihydro-1-benzofuran-2-yl}methyl)butanamide By using 1-{5-[4-(4-Methoxyphenyl)piperazin-1-yl]-2,4,6,7-tetramethyl-2,3-dihydro-1-benzofuran-2-yl}methaneamine (110 mg, 0.278 mmol) synthesized in Example 108 and butyryl chloride (32 mg, 0.304 mmol), the reaction was carried out in the same manner as Example 137 to synthesize 80 mg of the title compound (yield 68%). Melting point was 140 to 142° C.
$^1$H-NMR (CDCl$_3$): δ0.90 (3H, t, J=7.2 Hz), 1.42 (3H, s), 1.53-1.68 (2H, m), 2.05-2.21 (8H, m), 2.24 (3H, s), 2.84 (1H, d, J=15.6 Hz), 2.99 (1H, d, J=15.6 Hz), 3.06-3.34 (8H, m), 3.48 (1H, dd, J=5.7, 13.8 Hz), 3.60 (1H, dd, J=6.3, 13.8 Hz), 3.78 (3H, s), 5.71 (1H, dd, J=5.7, 6.3 Hz), 6.82-6.91 (2H, m), 6.92-7.01 (2H, m).

Example 139

{5-[4-(4-methoxyphenyl)piperazin-1-yl]-2,4,6,7-tetramethyl-2,3-dihydro-1-benzofuran-2-yl}methyl methanesulfonate To a solution of THF (2.0 mL) containing {5-[4-(4-Methoxyphenyl)piperazin-1-yl]-2,4,6,7-tetramethyl-2,3-dihydro-1-benzofuran-2-yl}methanol (200 mg, 0.504 mmol) synthesized in Example 97, triethylamine (102 mg, 1.01 mmol) and methanesulfonyl chloride (87 mg, 0.756 mmol) were serially added under ice-cooling condition, and the mixture was warmed to room temperature and stirred for 15 hours. The reaction solution was diluted with water, and extraction was performed using ethyl acetate. The extract was washed with saturated saline and dried using anhydrous magnesium sulfate. After that, the solvent was removed under reduced pressure. The obtained residue was purified by silica gel chromatography (hexane-ethyl acetate 95:5-75:25) to give 220 mg of the title compound (yield: 92%). An amorphous solid.
$^1$H-NMR (CDCl$_3$) δ: 1.52 (3H, s), 2.06 (3H, s), 2.20 (3H, s), 2.23 (3H, s), 2.89 (1H, d, J=15.3 Hz), 3.04 (3H, s), 3.07-3.33 (9H, m), 3.78 (3H, s), 4.22 (1H, d, J=10.8 Hz), 4.27 (1H, d, J=10.8 Hz), 6.82-6.91 (2H, m), 6.92-7.01 (2H, m).

Example 140

{5-[4-(4-methoxyphenyl)piperazin-1-yl]-2,4,6,7-tetramethyl-2,3-dihydro-1-benzofuran-2-yl}acetonitrile A suspension of DMSO (2.2 mL) containing {5-[4-(4-methoxyphenyl)piperazin-1-yl]-2,4,6,7-tetramethyl-2,3-dihydro-1-benzofuran-2-yl}methyl methanesulfonate (190 mg, 0.400 mmol) synthesized in Example 139, potassium cyanide (130 mg, 2.00 mmol) and potassium iodide (66 mg, 0.400 mmol) was stirred at 140° C. for 15 hours. After cooled to room temperature, the reaction solution was distributed using water and ethyl acetate, and the organic layer was washed with water and saturated saline, and then dried using anhydrous magnesium sulfate. The solvent was removed under reduced pressure, and the obtained residue was purified by silica gel chromatography (hexane-ethyl acetate 96:4-82:18) and crystallized from ethyl acetate-hexane to give 80 mg of the title compound (yield: 49%). Melting point was 161 to 163° C.
$^1$H-NMR (CDCl$_3$) δ: 1.66 (3H, s), 2.08 (3H, s), 2.21 (3H, s), 2.21 (3H, s), 2.24 (3H, s), 2.69 (1H, d, J=16.5 Hz), 2.75 (1H, d, J=16.5 Hz), 3.02 (1H, d, J=15.9 Hz), 3.07-3.33 (9H, m), 3.78 (3H, s), 6.82-6.91 (2H, m), 6.92-7.01 (2H, m).

Example 141

{5-[4-(4-methoxyphenyl)piperazin-1-yl]-2,4,6,7-tetramethyl-2,3-dihydro-1-benzofuran-2-yl}acetic acid A mixture of {5-[4-(4-methoxyphenyl)piperazin-1-yl]-2,4,6,7-tetramethyl-2,3-dihydro-1-benzofuran-2-yl}acetonitrile (260 mg, 0.641 mmol) synthesized in Example 140, 8N sodium hydroxide aqueous solution (2.0 mL) and ethanol (10 mL) was stirred under heated reflux for 15 hours. After cooled to room temperature, 1N hydrochloric acid (16 mL) was added thereto, and the reaction solution was distributed using water and ethyl acetate. The organic layer was washed with saturated saline and dried using anhydrous magnesium sulfate, and then the solvent was removed under reduced pressure. The obtained residue was purified by silica gel chromatography (hexane-ethyl acetate 90:10-70:30) and crystallized from ethyl acetate-hexane to obtain 150 mg of the title compound (yield 55%). Melting point was 171 to 174° C. (decomposition).
$^1$H-NMR (CDCl$_3$) δ: 1.60 (3H, s), 2.08 (3H, s), 2.20 (3H, s), 2.24 (3H, s), 2.77 (1H, d, J=15.0 Hz), 2.85 (1H, d, J=15.0 Hz), 2.98 (1H, d, J=15.6 Hz), 3.06-3.35 (9H, m), 3.78 (3H, s), 6.81-6.91 (2H, m), 6.92-7.02 (2H, m).

Example 142

2-{5-[4-(4-methoxyphenyl)piperazin-1-yl]-2,4,6,7-tetramethyl-2,3-dihydro-1-benzofuran-2-yl}-N-propylacetamide A solution of DMF (1.0 mL) containing {5-[4-(4-methoxyphenyl)piperazin-1-yl]-2,4,6,7-tetramethyl-2,3-dihydro-1- benzofuran-2-yl}acetic acid (50 mg, 0.118 mmol) synthesized in Example 141, propylamine (45 mg, 0.236 mmol), 1-ethyl-3-(3-dimethylaminopropyl)carbodiimide hydrochloride (45 mg, 0.236 mmol), 1-hydroxybenzotriazol monohydrate (36 mg, 0.236 mmol) and triethylamine (60 mg, 0.590 mmol) was stirred at room temperature for 15 hours, and the reaction solution was distributed using water and ethyl acetate. The organic layer was washed with saturated saline and dried using anhydrous magnesium sulfate, and then the solvent was removed under reduced pressure. The obtained residue was purified by silica gel chromatography (hexane-ethyl acetate 90:10-70:30) and crystallized from ethyl acetate-hexane to obtain 20 mg of the title compound (yield 36%). Melting point was 135 to 138° C.

Example 143

(−)-{5-[4-(4-methoxyphenyl)piperazin-1-yl]-2,4,6,7-tetramethyl-2,3-dihydro-1-benzofuran-2-yl}methanol {5-[4-(4-Methoxyphenyl)piperazin-1-yl]-2,4,6,7-tetramethyl-2,3-dihydro-1-benzofuran-2-yl}methanol (152 mg) obtained in Example 97 was fractionated using high-performance liquid chromatography (column: CHIRALPAK IC manufactured by Daicel Chemical Industries, Ltd.; mobile phase: hexane/2-propanol=400/600 (v/v)), and a fractionated solution containing an optically-active substance having a shorter retention time was concentrated, followed by crystallization from ethyl acetate-hexane to obtain 52 mg of the title compound (99.9% ee). Melting point was 137 to 139° C. Specific optical rotation $[\alpha]_D^{25}=-11.0°$ (c=0.462, chloroform)

Example 144

(+)-{5-[4-(4-methoxyphenyl)piperazin-1-yl]-2,4,6,7-tetramethyl-2,3-dihydro-1-benzofuran-2-yl}methanol A fractionated solution containing an optically-active substance having a longer retention time obtained in Example 143 was concentrated, and crystallization was performed using ethyl acetate-hexane to give 47 mg of the title compound (99.9% ee). Melting point was 138 to 143° C. Specific optical rotation $[\alpha]_D^{25}=+11.8°$ (c=0.456, chloroform)

Chemical structural formulae of the compounds obtained in Examples 1-144 are shown in Tables 1-8 below.

TABLE 1

| Example No. | structural formula |
| --- | --- |
| 1 | |
| 2 | |
| 3 | |

TABLE 1-continued

| Example No. | structural formula |
|---|---|
| 4 | (4-methoxyphenyl)piperazinyl-2,2,6,7-tetramethyl-2,3-dihydrobenzofuran |
| 5 | 4-[4-(dimethylamino)phenyl]-5-[4-(4-methoxyphenyl)piperazin-1-yl]-2,2,6,7-tetramethyl-2,3-dihydrobenzofuran |
| 6 | 4-(furan-3-yl)-5-[4-(4-methoxyphenyl)piperazin-1-yl]-2,2,6,7-tetramethyl-2,3-dihydrobenzofuran |
| 7 | 4-cyclopropyl-5-[4-(4-methoxyphenyl)piperazin-1-yl]-2,2,6,7-tetramethyl-2,3-dihydrobenzofuran |
| 8 | 4-vinyl-5-[4-(4-methoxyphenyl)piperazin-1-yl]-2,2,6,7-tetramethyl-2,3-dihydrobenzofuran |

TABLE 1-continued
| Example No. | structural formula |
|---|---|
| 9 | 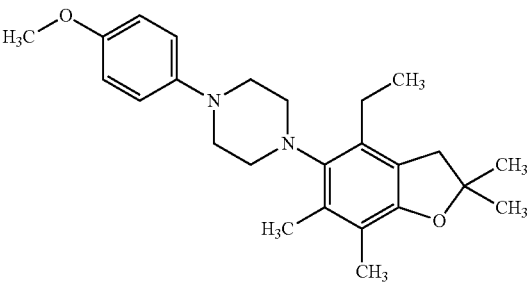 |
| 10 | 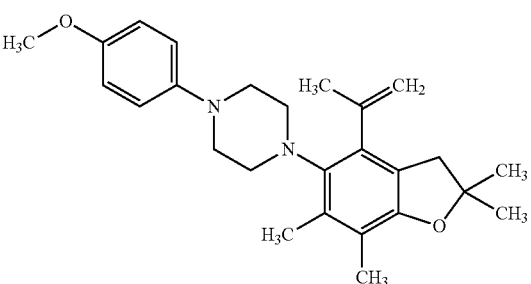 |
| 11 | 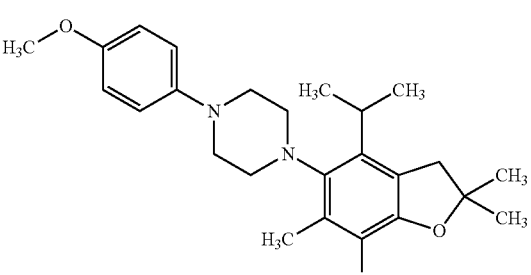 |
| 12 | 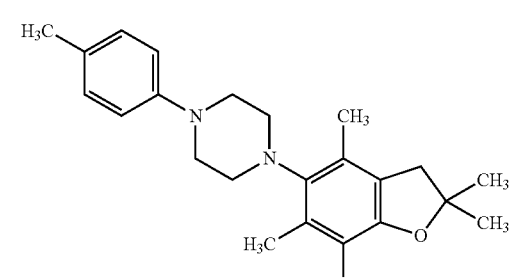 |
| 13 | 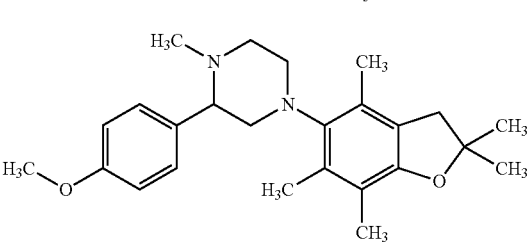 |
| 14 | 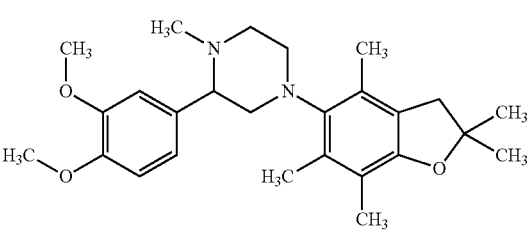 |

TABLE 1-continued

| Example No. | structural formula |
| --- | --- |
| 15 | |
| 16 | |
| 17 | |
| 18 | |
| 19 | |

TABLE 1-continued
| Example No. | structural formula |
| --- | --- |
| 20 | 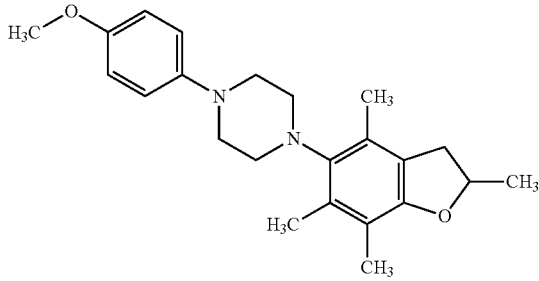 |
TABLE 2
| Example No. | structural formula |
| --- | --- |
| 21 | 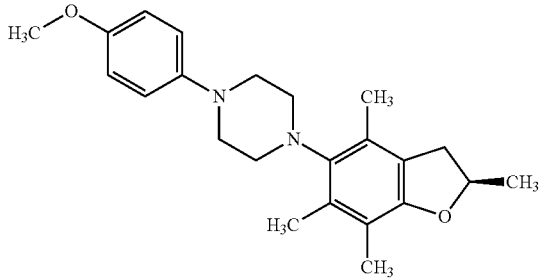 |
| 22 | 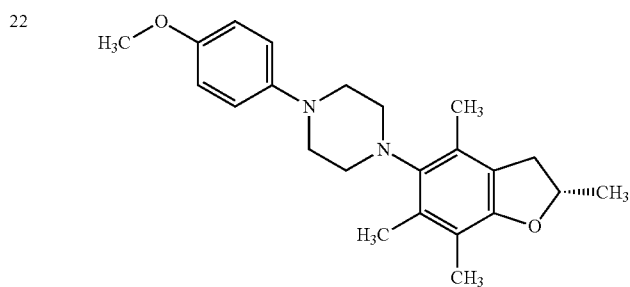 |
| 23 | 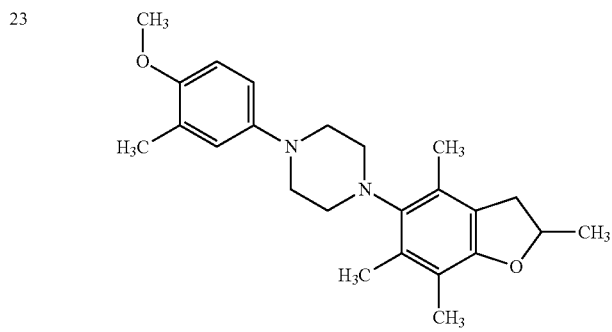 |

TABLE 2-continued

| Example No. | structural formula |
|---|---|
| 24 | (4-fluorophenyl)piperazine linked to 2,4,6,7-tetramethyl-2,3-dihydrobenzofuran at 5-position |
| 25 | (4-methylphenyl)piperazine linked to 2,4,6,7-tetramethyl-2,3-dihydrobenzofuran at 5-position |
| 26 | (4-bromophenyl)piperazine linked to 2,4,6,7-tetramethyl-2,3-dihydrobenzofuran at 5-position |
| 27 | (4-methylthiophenyl)piperazine linked to 2,4,6,7-tetramethyl-2,3-dihydrobenzofuran at 5-position |
| 28 | (4-methylsulfonylphenyl)piperazine linked to 2,4,6,7-tetramethyl-2,3-dihydrobenzofuran at 5-position |

TABLE 2-continued

| Example No. | structural formula |
| --- | --- |
| 29 | 4-[4-(2,4,6,7-tetramethyl-2,3-dihydro-1-benzofuran-5-yl)piperazin-1-yl]benzonitrile |
| 30 | 4-[4-(2,4,6,7-tetramethyl-2,3-dihydro-1-benzofuran-5-yl)piperazin-1-yl]benzamide |
| 31 | 1-(4-methoxy-3-methylphenyl)-4-(2,2,4,6,7-pentamethyl-2,3-dihydro-1-benzofuran-5-yl)piperazine |
| 32 | 1-(3-fluoro-4-methoxyphenyl)-4-(2,2,4,6,7-pentamethyl-2,3-dihydro-1-benzofuran-5-yl)piperazine |
| 33 | 1-(4-chloro-3-methylphenyl)-4-(2,2,4,6,7-pentamethyl-2,3-dihydro-1-benzofuran-5-yl)piperazine |

TABLE 2-continued

| Example No. | structural formula |
|---|---|
| 34 | (4-chlorophenyl)piperazinyl-4,6,7-trimethyl-2,2-dimethyl-2,3-dihydrobenzofuran |
| 35 | (4-fluoro-3-methylphenyl)piperazinyl-4,6,7-trimethyl-2,2-dimethyl-2,3-dihydrobenzofuran |
| 36 | (3-chloro-4-methylphenyl)piperazinyl-4,6,7-trimethyl-2,2-dimethyl-2,3-dihydrobenzofuran |
| 37 | (3,4-dimethoxyphenyl)piperazinyl-4,6,7-trimethyl-2,2-dimethyl-2,3-dihydrobenzofuran |
| 38 | (4-fluoro-3-methoxyphenyl)piperazinyl-4,6,7-trimethyl-2,2-dimethyl-2,3-dihydrobenzofuran |

TABLE 2-continued
| Example No. | structural formula |
|---|---|
| 39 | 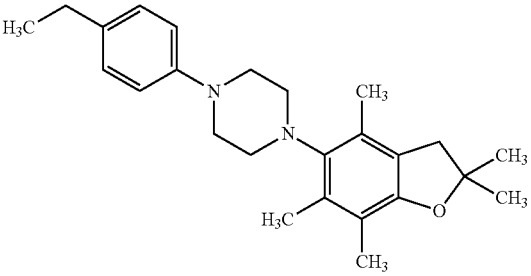 |
| 40 | 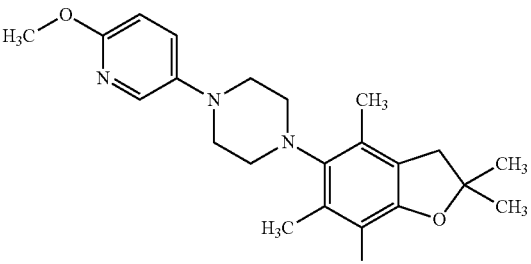 |
TABLE 3
| Example No. | structural formula |
|---|---|
| 41 | 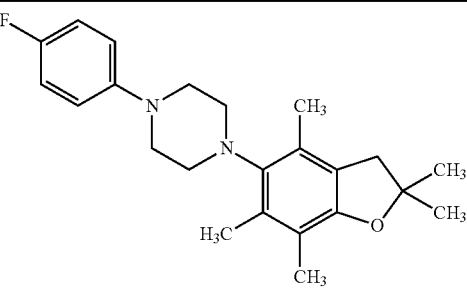 |
| 42 | 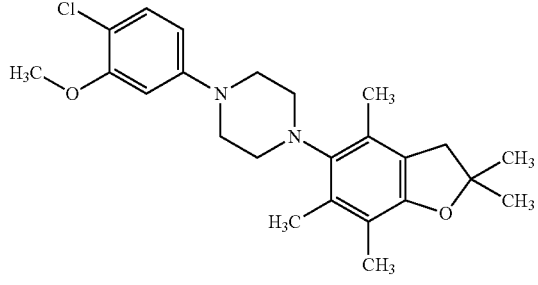 |
| 43 | 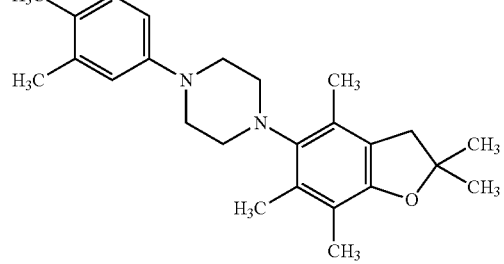 |

TABLE 3-continued

| Example No. | structural formula |
| --- | --- |
| 44 | |
| 45 | |
| 46 | |
| 47 | |
| 48 | |

TABLE 3-continued

| Example No. | structural formula |
|---|---|
| 49 | |
| 50 | |
| 51 | |
| 52 | |
| 53 | |

TABLE 3-continued
| Example No. | structural formula |
| --- | --- |
| 54 | 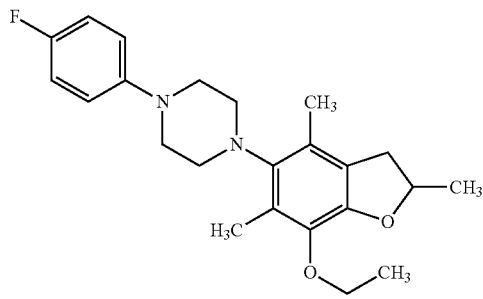 |
| 55 | 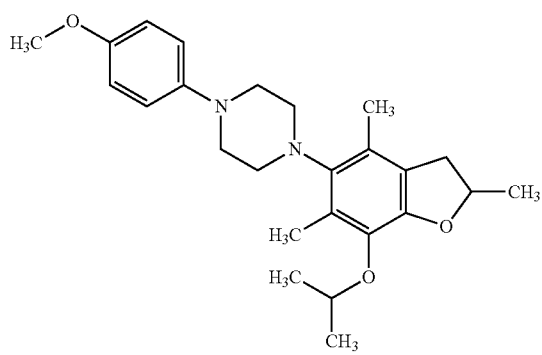 |
| 56 | 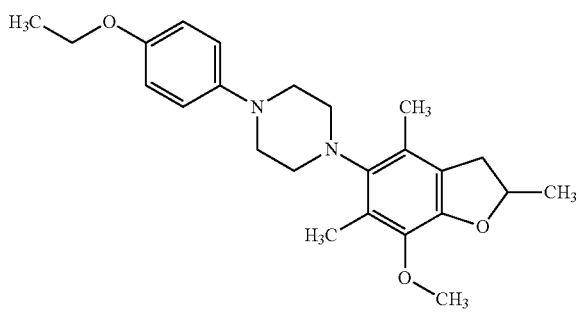 |
| 57 | 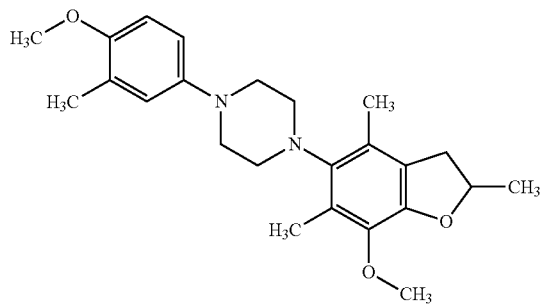 |

TABLE 3-continued
| Example No. | structural formula |
|---|---|
| 58 | 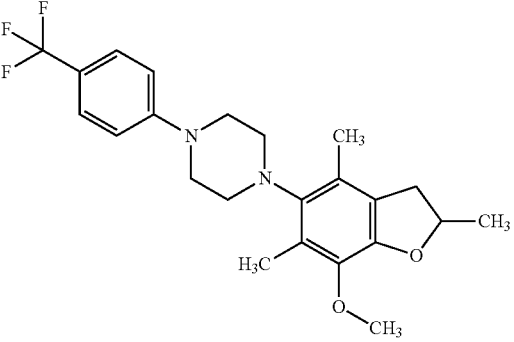 |
| 59 | 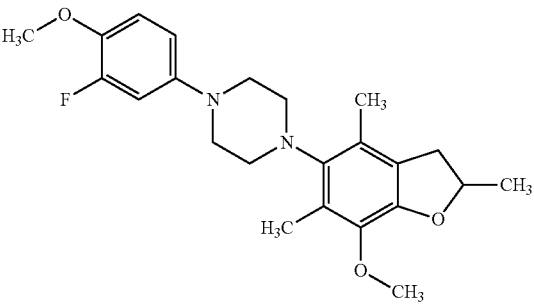 |
| 60 | 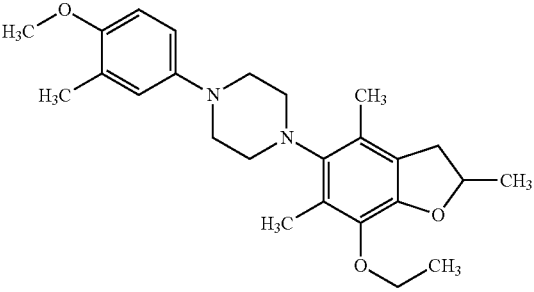 |
TABLE 4
| Example No. | structural formula |
|---|---|
| 61 | 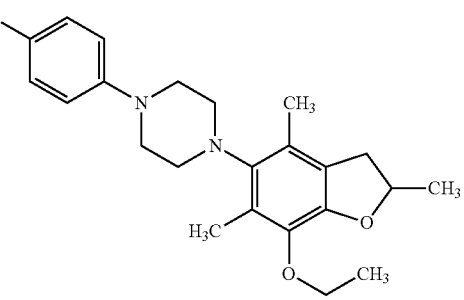 |

TABLE 4-continued

| Example No. | structural formula |
|---|---|
| 62 | 1-(4-methylphenyl)-4-(4,6,2,2-tetramethyl-7-methoxy-2,3-dihydrobenzofuran-5-yl)piperazine |
| 63 | 1-(4-fluorophenyl)-4-(4,6,2,2-tetramethyl-7-methoxy-2,3-dihydrobenzofuran-5-yl)piperazine |
| 64 | 1-(4-ethylphenyl)-4-(4,6,2,2-tetramethyl-7-methoxy-2,3-dihydrobenzofuran-5-yl)piperazine |
| 65 | 1-(4-ethoxyphenyl)-4-(4,6,2,2-tetramethyl-7-methoxy-2,3-dihydrobenzofuran-5-yl)piperazine |
| 66 | 1-(4-trifluoromethoxyphenyl)-4-(4,6,2,2-tetramethyl-7-methoxy-2,3-dihydrobenzofuran-5-yl)piperazine |

TABLE 4-continued

| Example No. | structural formula |
|---|---|
| 67 | (4-(difluoromethoxy)phenyl)piperazinyl linked to 4,6-dimethyl-7-methoxy-2,2-dimethyl-2,3-dihydrobenzofuran-5-yl |
| 68 | (4-(trifluoromethyl)phenyl)piperazinyl linked to 4,6-dimethyl-7-methoxy-2,2-dimethyl-2,3-dihydrobenzofuran-5-yl |
| 69 | (2,3-dihydro-1,4-benzodioxin-6-yl)piperazinyl linked to 4,6-dimethyl-7-methoxy-2,2-dimethyl-2,3-dihydrobenzofuran-5-yl |
| 70 | (4-methylphenyl)piperazinyl linked to 4,6-dimethyl-7-ethoxy-2,2-dimethyl-2,3-dihydrobenzofuran-5-yl |
| 71 | (4-fluorophenyl)piperazinyl linked to 4,6-dimethyl-7-ethoxy-2,2-dimethyl-2,3-dihydrobenzofuran-5-yl |

TABLE 4-continued
| Example No. | structural formula |
|---|---|
| 72 | 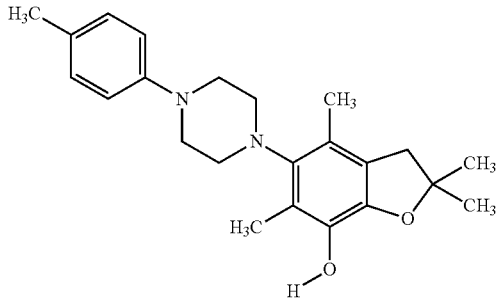 |
| 73 | 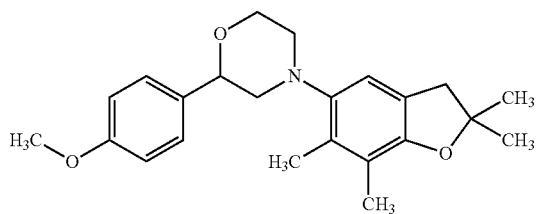 |
| 74 | 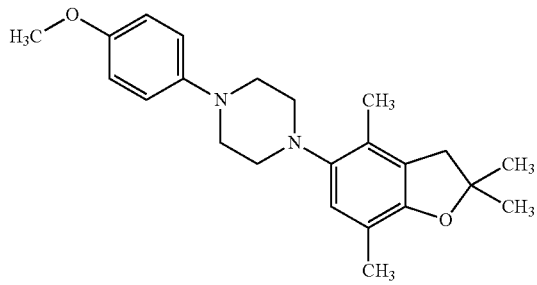 |
| 75 | 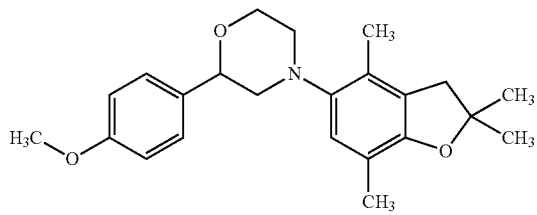 |
| 76 | 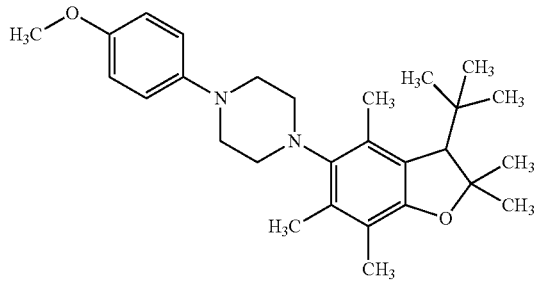 |

TABLE 4-continued

| Example No. | structural formula |
| --- | --- |
| 77 | |
| 78 | |
| 79 | |
| 80 | |

TABLE 5
| Example No. | structural formula |
|---|---|
| 81 | 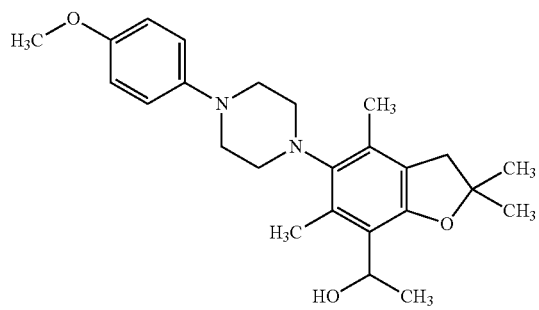 |
| 82 | 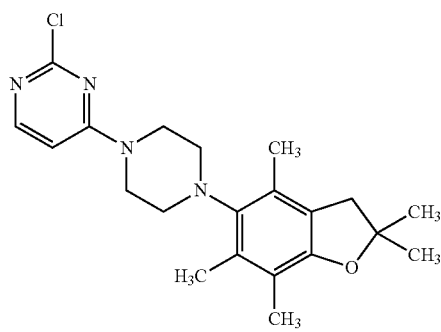 |
| 83 | 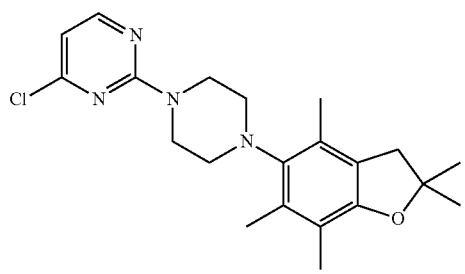 |
| 84 | 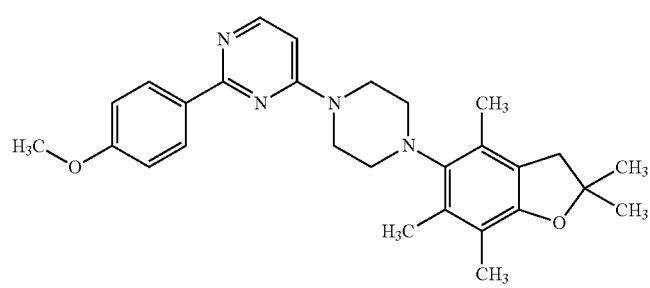 |
| 85 | 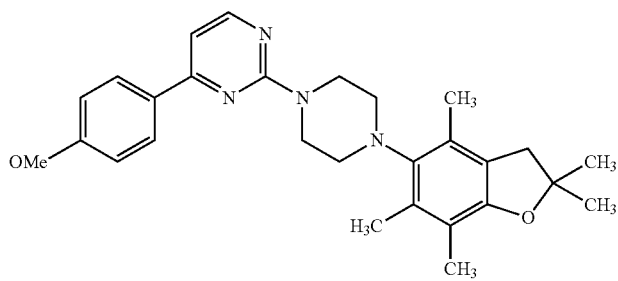 |

TABLE 5-continued
| Example No. | structural formula |
|---|---|
| 86 | 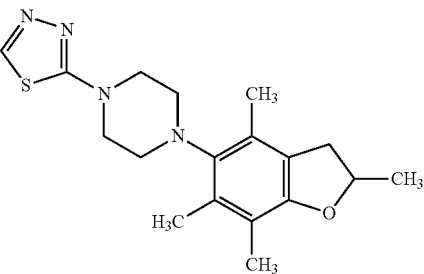 |
| 87 | 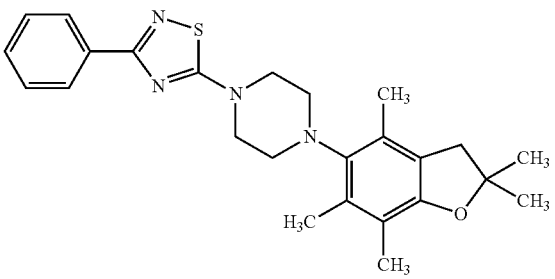 |
| 88 | 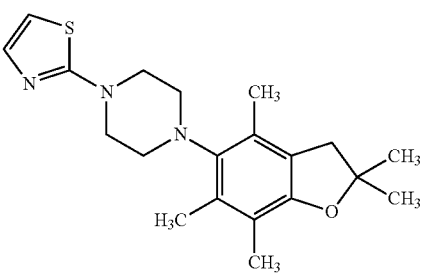 |
| 89 | 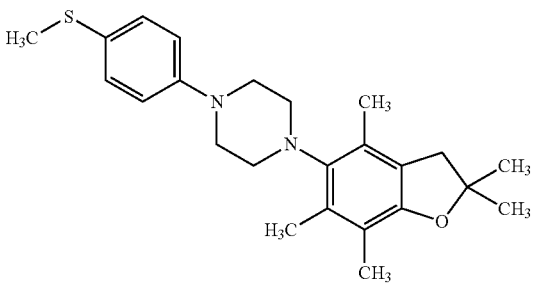 |
| 90 | 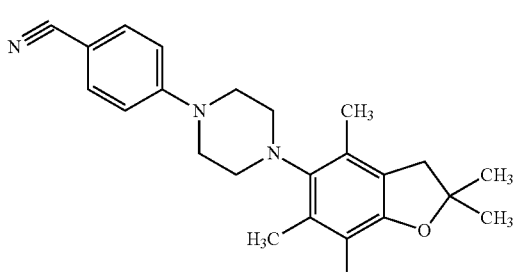 |

TABLE 5-continued
| Example No. | structural formula |
|---|---|
| 91 | 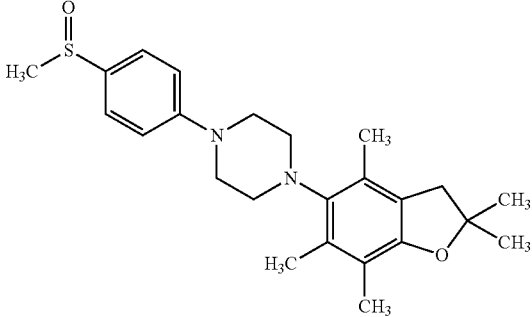 |
| 92 | 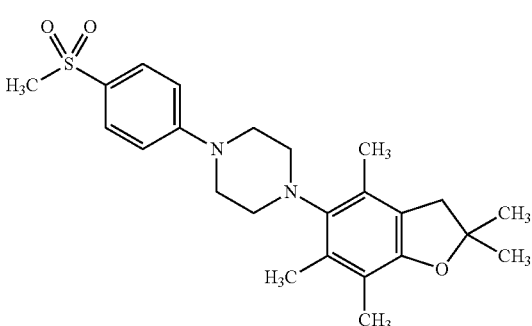 |
| 93 | 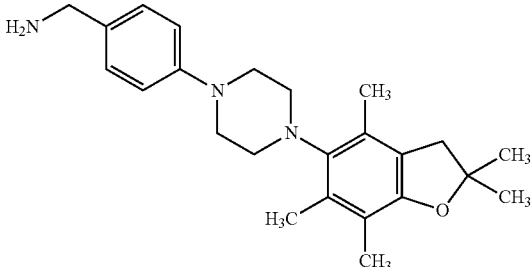 |
| 94 | 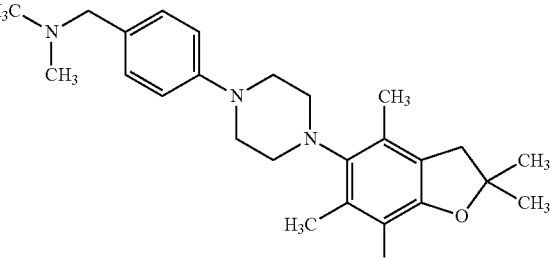 |
| 95 | 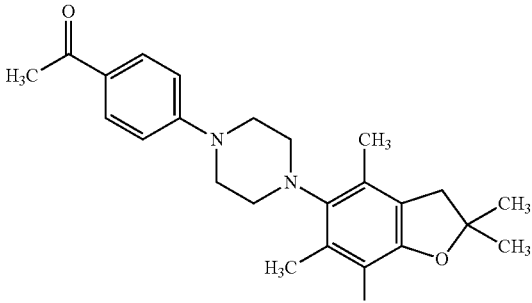 |

TABLE 5-continued
| Example No. | structural formula |
|---|---|
| 96 | 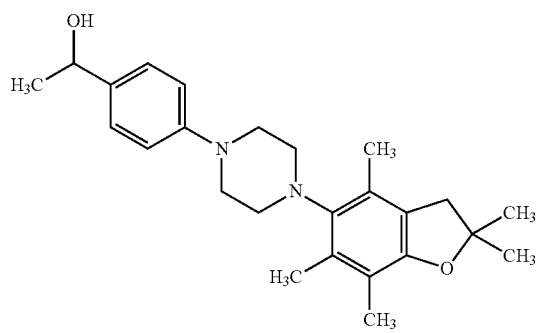 |
| 97 | 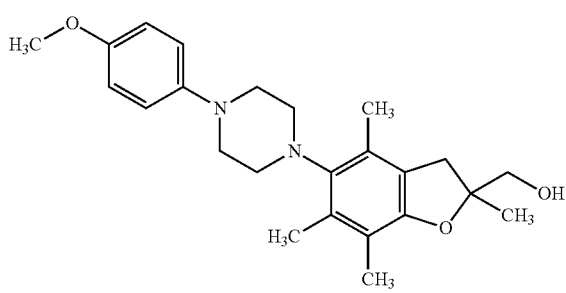 |
| 98 | 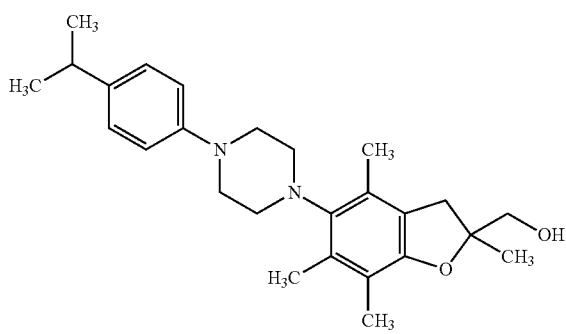 |
| 99 | 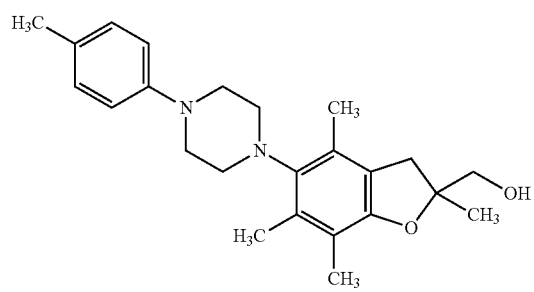 |
| 100 | 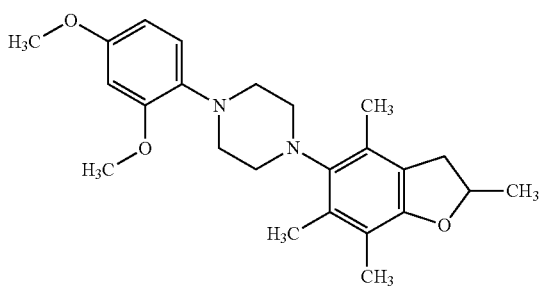 |

TABLE 6
| Example No. | structural formula |
|---|---|
| 101 | 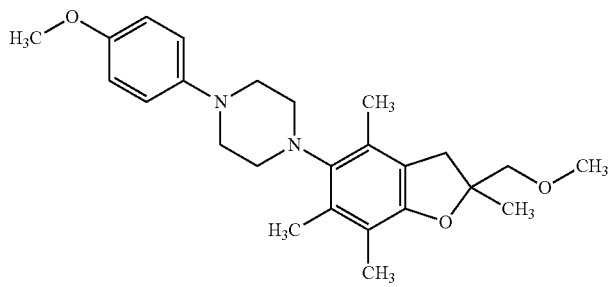 |
| 102 | 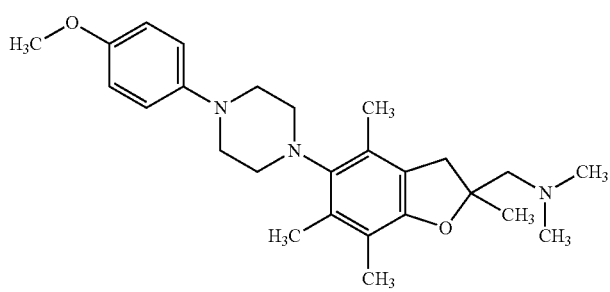 |
| 103 | 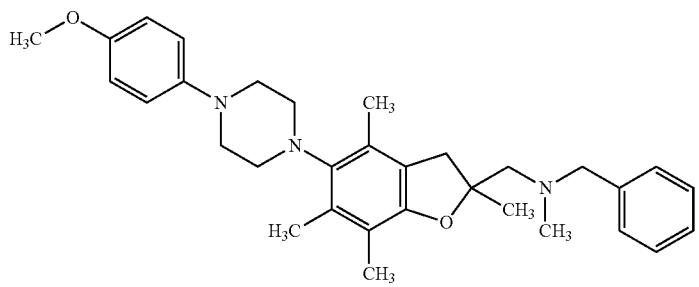 |
| 104 | 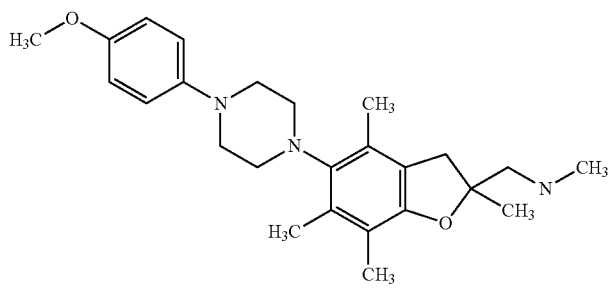 |
| 105 | 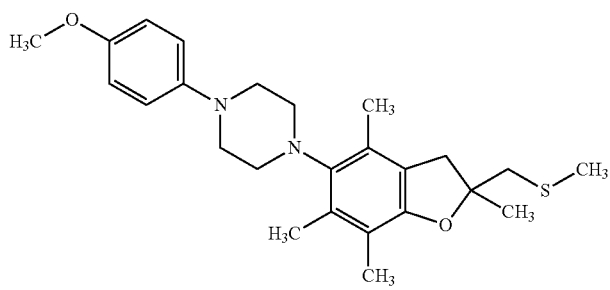 |

TABLE 6-continued
| Example No. | structural formula |
| --- | --- |
| 106 | 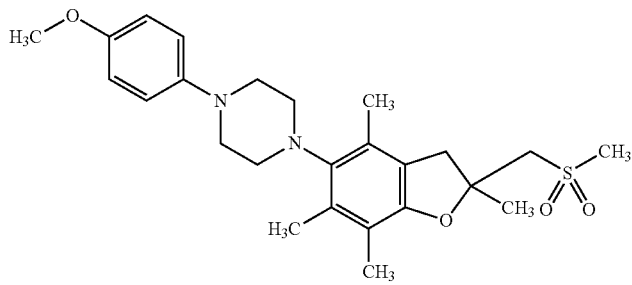 |
| 107 | 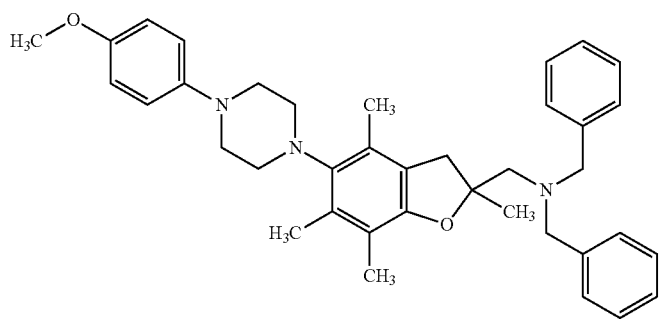 |
| 108 | 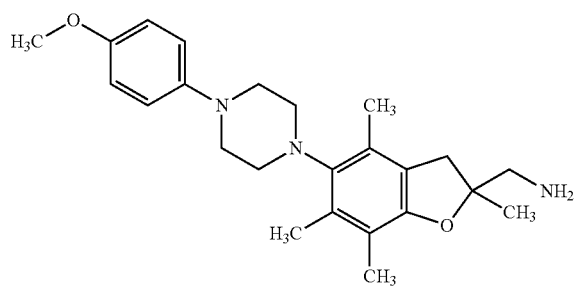 |
| 109 | 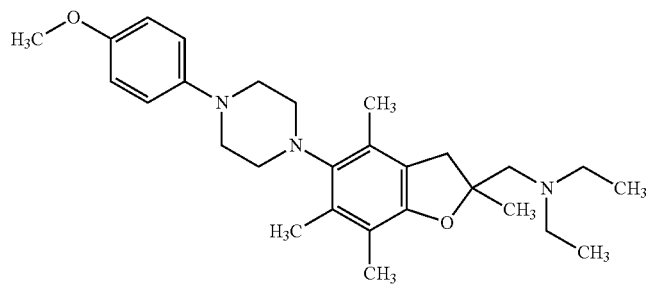 |
| 110 | 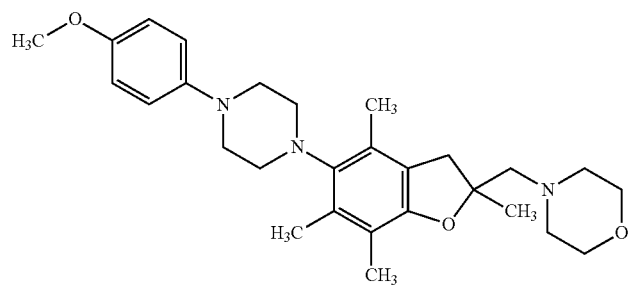 |

TABLE 6-continued

| Example No. | structural formula |
|---|---|
| 111 | |
| 112 | |
| 113 | |
| 114 | |
| 115 | |

TABLE 6-continued
| Example No. | structural formula |
|---|---|
| 116 | 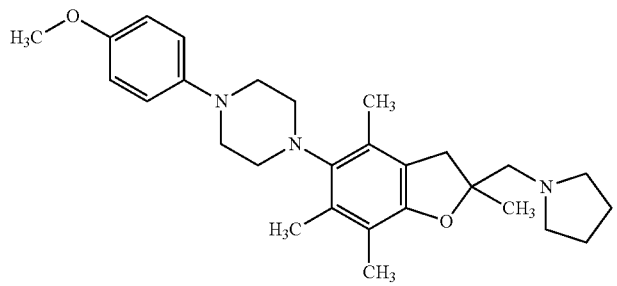 |
| 117 | 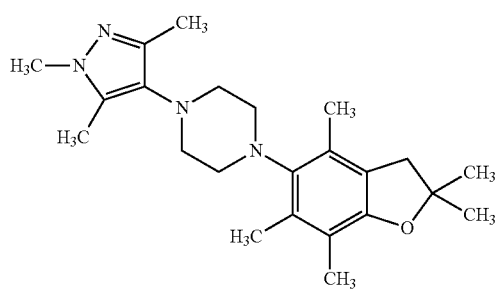 |
| 118 | 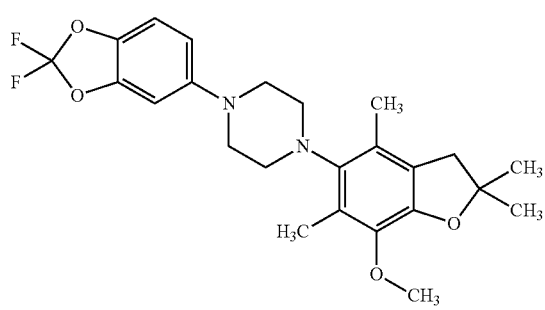 |
| 119 | 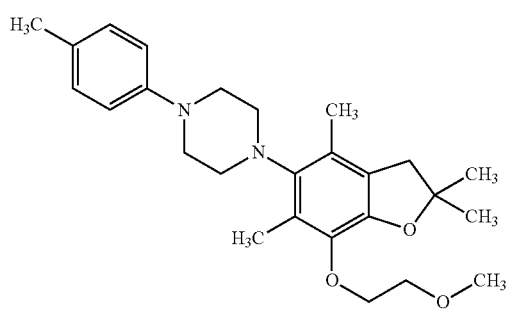 |
| 120 | 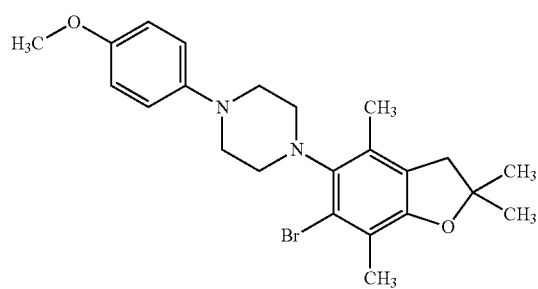 |

TABLE 7
| Example No. | structural formula |
|---|---|
| 121 | 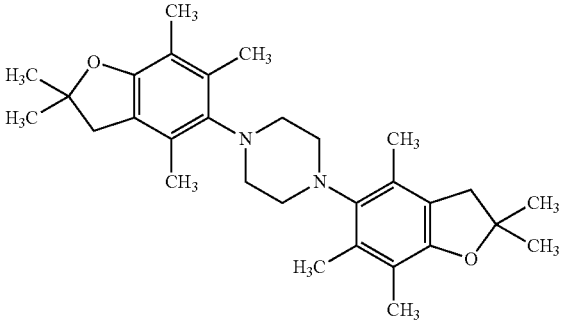 |
| 122 | 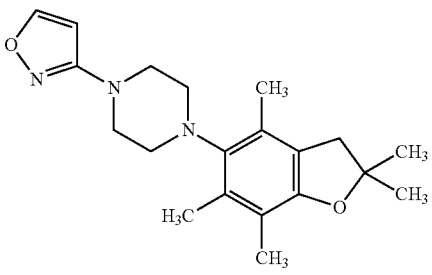 |
| 123 | 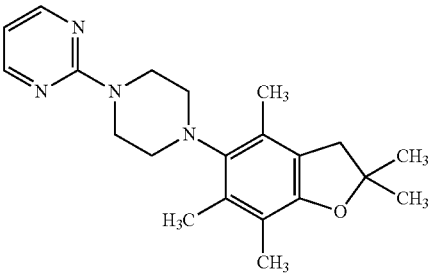 |
| 124 | 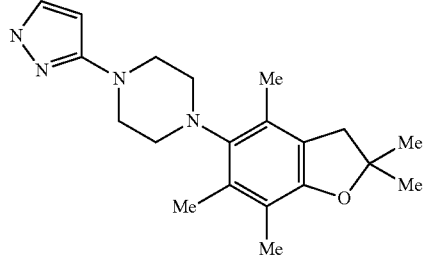 |
| 125 | 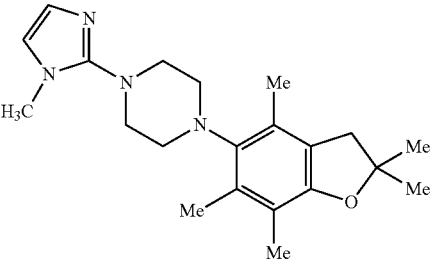 |

TABLE 7-continued
| Example No. | structural formula |
|---|---|
| 126 | 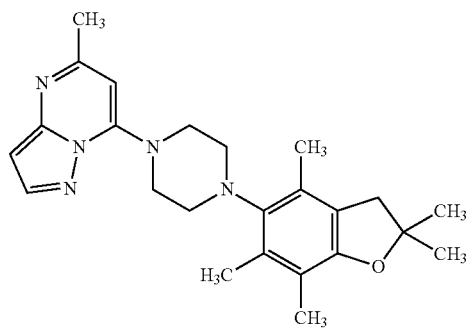 |
| 127 | 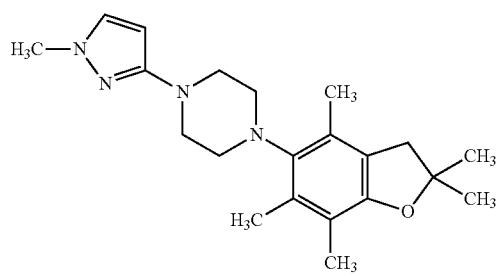 |
| 128 | 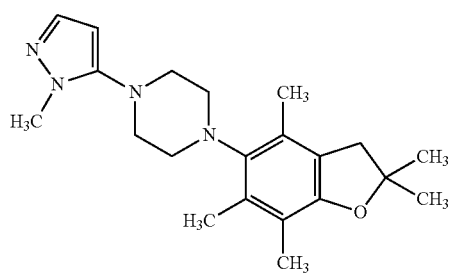 |
| 129 | 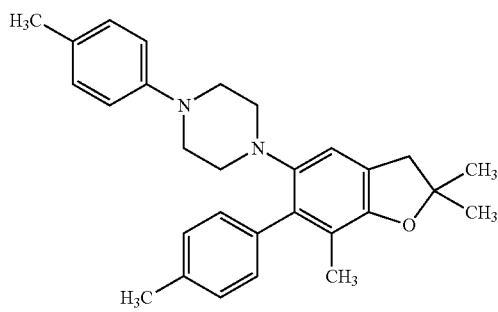 |
| 130 | 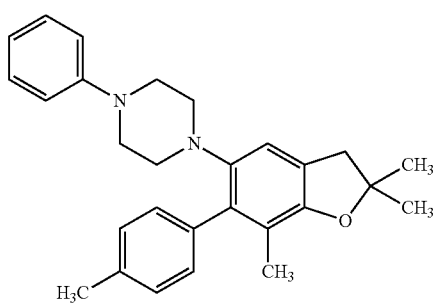 |

TABLE 7-continued
| Example No. | structural formula |
|---|---|
| 131 | 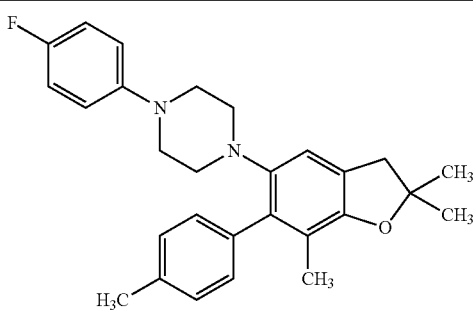 |
| 132 | 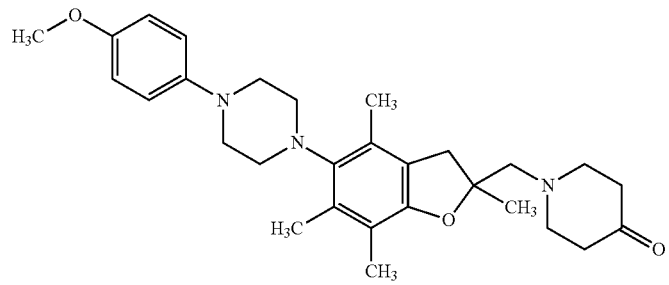 |
| 133 | 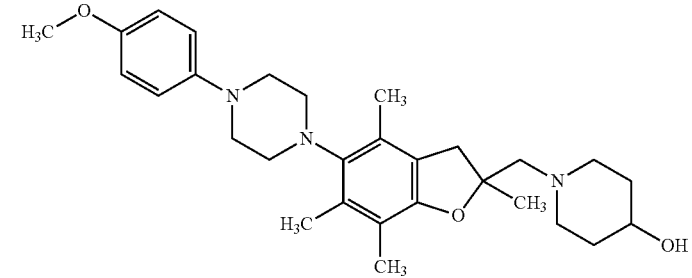 |
| 134 | 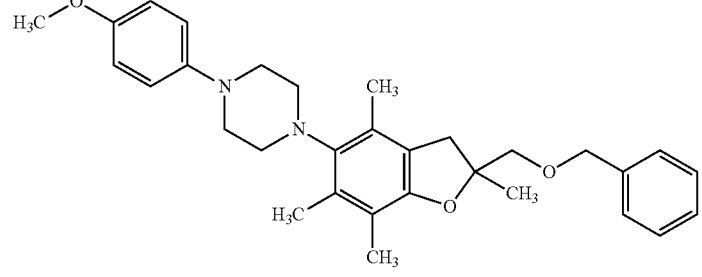 |
| 135 | 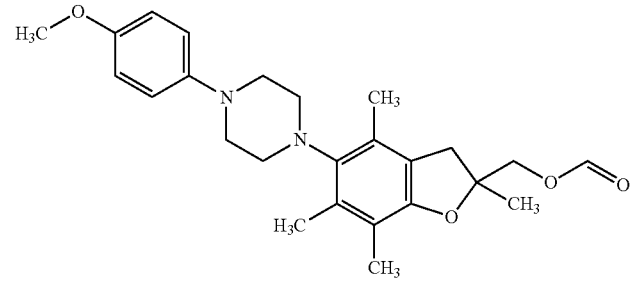 |

TABLE 7-continued
| Example No. | structural formula |
|---|---|
| 136 | 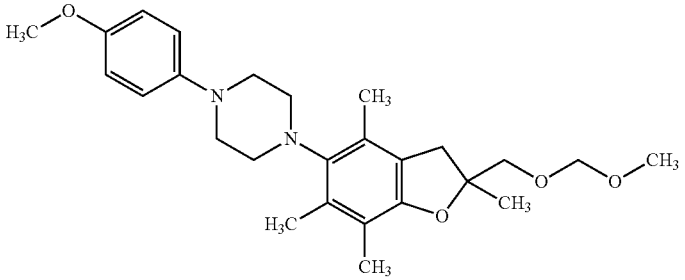 |
| 137 | 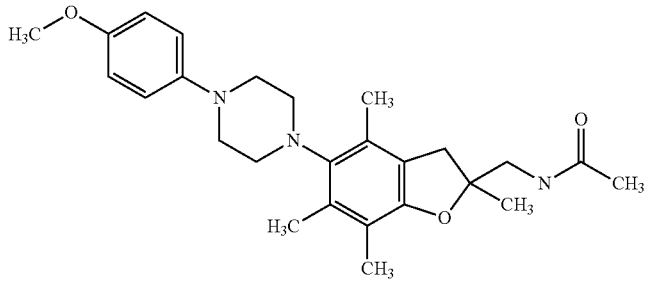 |
| 138 | 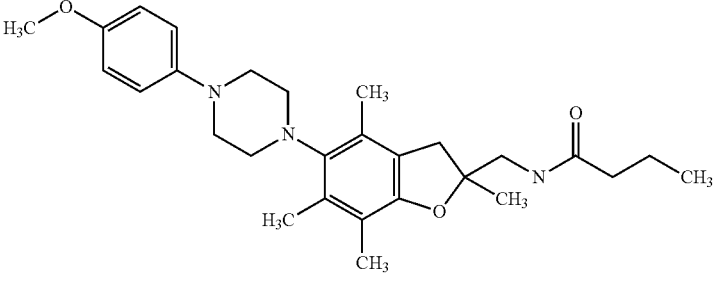 |
| 139 | 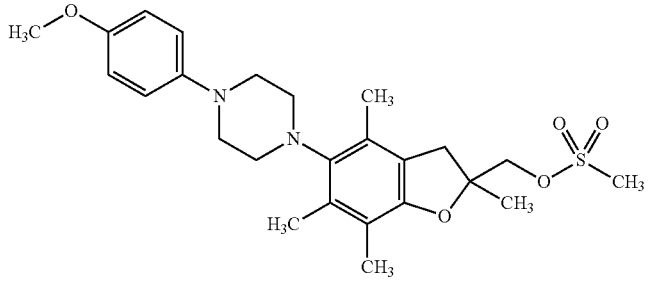 |
| 140 | 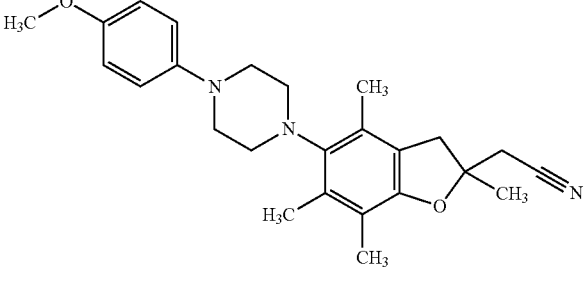 |

TABLE 8

| Example No. | structural formula |
|---|---|
| 141 | |
| 142 | |
| 143 | |
| 144 | |

Test Example 1

Activity of Promoting Neuronal Neogenesis in Rat Mixed Glial Culture

Test Method:

From a three-day old SD rat, hippocampus and cerebral cortex were removed. By using a kit of dispersion liquid for neuronal cells (MB-X9901, manufactured by SUMITOMO BAKELITE CO., LTD.), cell suspension was prepared and then seeded on a 96-well plate coated with collagen Type I (4860-010, manufactured by Asahi Techno Glass Co., Ltd.) to $10^5$ cells/well. Under the condition of 37° C. and 5% $CO_2$, the cells were cultured for four days in a growth medium (D-MEM/F12 with 10% FBS, comprising PS).

After culturing, the medium was exchanged with a medium for differentiation (D-MEM/F12, comprising PS), added with rhIGF-1 (R&D Systems, 291-G1-250, final concentration of 100 ng/ml) and the compound to 1 µM, followed by further culture for three days. Cultured cells were fixed with 4% paraformaldehyde-PBS (manufactured by MUTO PURE CHEMICALS CO., LTD.) and subjected to membrane penetration using 0.1% Triton X-100 PBS, followed by blocking with Block Ace solution (UK-B80, manufactured by Dainippon Sumitomo Pharma Co., Ltd.). As a primary antibody, Anti-neuron-specific class III beta-tubulin antibody (R&D Systems, MAB1195, clone Tuj-1) was used after 1000× dilution. As a secondary antibody, Anti-Mouse Ig, HRP-Linked F (ab') 2 Fragment Sheep (Amersham Biosciences, NA9310) was used after 10000× dilution. For washing process, the plate washer (BIO-TEK INSTRUMENTS ELX405) was used. For a chromogenic reaction, the reaction was carried out for 10 minutes using TMB Microwell Peroxidase Substrate System (Kirkegaard & Perry Laboratories, 50-76-00), followed by terminating the reaction according to the addition of 1M phosphoric acid. By using the plate reader (Labsystems Multiskan BICHROMATIC), absorbance at 450 nm was measured.

The absorbance for the case in which no compound is added (i.e., control, rhIGF-1 only) was 100%, and the increase ratio of the absorbance for the compound addition (i.e., compound+rhIGF-1) compared to the control was obtained as % control. Activity of the each compound for promoting neuronal differentiation that is measured according to the above method is summarized in Table 9 and Table 10.

TABLE 9

| Example No. | Increase Ratio of the Absorbance (% control) |
|---|---|
| 1 | 407 |
| 2 | 432 |
| 5 | 488 |
| 6 | >500 |
| 7 | 325 |
| 8 | 242 |
| 9 | 228 |
| 11 | 159 |
| 12 | 336 |
| 13 | 265 |
| 15 | 332 |
| 16 | 344 |
| 17 | 216 |
| 19 | 278 |
| 20 | 187 |
| 21 | 212 |
| 22 | 389 |
| 32 | >500 |
| 35 | 182 |
| 37 | >500 |
| 38 | 294 |
| 40 | 341 |
| 41 | >500 |

TABLE 10

| Example No. | Increase Ratio of the Absorbance (% control) |
|---|---|
| 45 | 205 |
| 46 | 221 |
| 47 | >500 |
| 48 | >500 |
| 55 | >500 |
| 56 | >500 |
| 59 | 478 |
| 61 | >500 |
| 62 | >500 |
| 65 | >500 |
| 87 | 256 |
| 90 | >500 |
| 92 | 457 |
| 95 | 405 |
| 97 | 439 |
| 101 | >500 |
| 102 | 347 |
| 108 | 282 |
| 116 | 276 |
| 117 | 100 |
| 133 | >500 |
| 137 | >500 |
| 143 | >500 |
| 144 | >500 |

Test Example 2

Activity of Inhibiting Akt Protein Degradation in Rat Mixed Glial Culture

Test Method:

The mixed glial cells used in the Test example 1 were seeded on a 6-well plate coated with collagen Type I (manufactured by Asahi Techno Glass Co., Ltd.) to $4 \times 10^6$ cells/well. Under the condition of 37° C. and 5% $CO_2$, the cells were cultured for four days in a growth medium (D-MEM/F12 with 10% FBS, comprising PS). After that, the medium was exchanged with a serum-free medium (D-MEM/F12, comprising PS) and the cells were subjected to starvation for 4 hours under the condition of 37° C. and 5% $CO_2$.

Next, rhIGF-1 (R&D Systems, 291-G1-250, final concentration 100 ng/ml) and the compound were added to obtain 1 μM and reacted in a water bath incubator at 37° C. for 10 minutes. Culture supernatant was aspirated off, 150 μL of RIPA (50 mM Tris-HCl pH7.5, 5 mM EDTA, 100 mM NaCl, 30 mM NaF, 5 mM sodium diphosphate, 137 mg/l pepstatin A, 2.5 KIU/l aprotinin, 1% NP-40, 6 mM sodium deoxycholate, 1 μM microcystinLR, 1 μM Z-Leu-Leu-Nva-H(aldehyde), 48 μM leupeptin, 96 μM 4-(2-aminoethyl)benzenesulfonyl fluoride-HCl, 1 mM sodium orthovanadate) was added thereto, and the reaction was terminated. After the termination of the reaction, the cell lysate was recovered by using a cell scraper on ice. Finally, the cell lysate was centrifuged for 30 minutes at 15000 rpm and the supernatant was taken as a cell extract.

Proteins were recovered from the cell extract by using trichloroacetic acid, and quantified according to Lowry method. Standard curve was established with bovine serum albumin. Based on the measured values, each cell extract was diluted with RIPA to prepare it in constant concentration (10 μg/lane). SDS-PAGE was carried out under reducing condition using 10% acrylamide (45 mA, 1.5 hours). After transferring to a PVDF membrane (0.13 A, 1 hour), reaction with an antibody was carried out. As a primary antibody, Akt (Cell Signaling, 9272) and ERK (Santa Cruz, sc-94) were used with the dilution ratio of 1000. As a secondary antibody, HRP-labeled anti-rabbit antibody (NA9340V, manufactured by Amersham) was used with the dilution ratio of 12500. Then, using ImmunoStar reagent (291-55203, manufactured by Wako Pure Chemical Industries, Ltd.), X-ray film detection was carried out. Quantification of the results was carried out by using GS-800 Calibrated Densitometer (manufactured by BioRad), and then the band strength was converted into the numerals by multiplying the absorbance originating from bands of Akt and ERK-1&2 by the area. Akt was calibrated with ERK to give the numeral values.

Inhibitory activity on Akt degradation was expressed as inhibition ratio. Specifically, the case in which neither the compound nor rhIGF-1 was added (no addition) is 100% and the case in which only rhIGF-1 was added is 0%, and then with the value measured from compound+rhIGF-1, the inhibition ratio was obtained.

Inhibition ratio(%)=[(compound+rhIGF-1)−(rhIGF-1)]÷[(no addition)−(rhIGF-1)]×100

Inhibitory activity of each compound on degradation of Akt protein, which had been measured by the method described above, is indicated in Table 11.

TABLE 11

| Example No. | Inhibition of Akt degradation (%) |
|---|---|
| 1 | 73.3 |
| 17 | 73.3 |
| 20 | 73.9 |
| 21 | 121.3 |
| 22 | 73.9 |
| 47 | 55.2 |
| 65 | 121.0 |

From the above results, it was found that the Compound (I) of the present invention has an activity of promoting neurogenesis and an activity of inhibiting degradation of Akt protein, indicating the activity of enhancing IGF-1 signal.

Test Example 3

Amelioration of Cognitive Function in Novel Object Recognition Test

Experimental Methods:

Female Tg2576 transgenic mice and wild-type littermates were used at 8-9 months old. All animals were housed in room maintained at 24±1° C. with a 12-h light/dark cycle. Lights on 7:00 a.m. Food chows (Oriental Yeast Co. Tokyo, Japan) and tap water were provided ad libitum.

Tg2576 mice were divided into treated and untreated groups in such a fashion that neither body weight nor blood glucose level differed significantly among the groups (n=11-15). The compounds (10 mg/kg/day) or vehicle (0.5% methylcellulose, Wako Pure Chemical Industries Limited, Osaka, Japan) was orally administered to the mice once a day for 3 weeks. After the gavages, the novel object recognition test was performed. The test procedure consisted of three sessions: habituation, training, and retention. In the training and retention sessions, observer was not informed of the group name or animal number (blind method). 4-5 mice were habituated to the box (30×30×30 high cm), with 30 minutes of exploration in the absence of objects (habituation session). During the training session, two objects were placed in the back corner of the box. A mouse was then placed at another corner of the box and the total time spent exploring the two objects was recorded for 5 minutes. During the retention session, animals were placed back into the same box 24 hours after the training session, in which one of the familiar objects used during training was replaced with a novel object. The animals were then allowed to explore freely for 5 minutes and the time spent exploring each object was recorded. Throughout the experiments, the objects were used in a counterbalanced manner in terms of an environmental effect, their physical complexity and emotional neutrality. A preference index (PI), a ratio of the amount of time spent exploring the novel object over the total time spent exploring both objects, was used to measure cognitive function. Furthermore, recovery ratio was calculated by following formula;

[Recovery ratio]=[[PI of Tg2576 mice treated by each compound]−[PI of Tg2576 mice treated by vehicle]]/[[PI of wild type mice]−[PI of Tg2576 mice treated by vehicle]]×100(%)

In the calculation, the animals, which did not explore both objects in training or retention sessions, were excluded. The results are shown in Table 12.

TABLE 12

| Case | Preference index (% recovery) |
|---|---|
| 17 | 70.9 |
| 22 | 76.9 |
| 47 | 82.2 |

INDUSTRIAL APPLICABILITY

Compound of the present invention, salts thereof or prodrugs thereof have an excellent activity of promoting neogenesis of neuronal cells, low light toxicity, and high transition to central nervous system. As such, they are useful as an agent for controlling IGF-1 signal, an agent for activating protein kinase B, and an agent for the prophylaxis and treatment of central nervous system disorders (e.g., Alzheimer's disease, etc.).

The invention claimed is:
1. 1-(4-Methoxyphenyl)-4-(2,2,4,6,7-pentamethyl-2,3-dihydro-1-benzofuran-5-yl)piperazine or a salt thereof.
2. A pharmaceutical composition comprising 1-(4 methoxyphenyl)-4-(2,2,4,6,7-pentamethyl-2,3-dihydro-1-benzofuran-5-yl)piperazine or a salt thereof and a pharmaceutically acceptable carrier.

* * * * *